US012577273B2

(12) United States Patent
Devlin et al.

(10) Patent No.: US 12,577,273 B2
(45) Date of Patent: Mar. 17, 2026

(54) SMALL MOLECULE MODULATORS OF GUT BACTERIAL BILE ACID METABOLISM

(71) Applicant: President and Fellows of Harvard College, Cambridge, MA (US)

(72) Inventors: Abigail Sloan Devlin, Cambridge, MA (US); Arijit Adhikari, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1042 days.

(21) Appl. No.: 17/610,037

(22) PCT Filed: May 8, 2020

(86) PCT No.: PCT/US2020/032016
§ 371 (c)(1),
(2) Date: Nov. 9, 2021

(87) PCT Pub. No.: WO2020/231776
PCT Pub. Date: Nov. 19, 2020

(65) Prior Publication Data

US 2022/0204548 A1 Jun. 30, 2022

Related U.S. Application Data

(60) Provisional application No. 62/962,048, filed on Jan. 16, 2020, provisional application No. 62/846,457, filed on May 10, 2019.

(51) Int. Cl.
*C07J 31/00* (2006.01)
*C07J 41/00* (2006.01)

(52) U.S. Cl.
CPC ......... *C07J 31/006* (2013.01); *C07J 41/0027* (2013.01); *C07J 41/005* (2013.01); *C07J 41/0055* (2013.01); *C07J 41/0094* (2013.01)

(58) Field of Classification Search
CPC .... C07J 31/006; C07J 41/0027; C07J 41/005; C07J 41/0055; C07J 41/0094; C07J 9/005; C07J 9/00; C07J 41/0005; A61P 1/00; A61P 1/16; A61P 3/04; A61P 29/00; A61P 31/04; A61P 35/00; A61K 31/575
See application file for complete search history.

(56) References Cited

U.S. PATENT DOCUMENTS

| | | | |
|---|---|---|---|
| 5,210,272 | A | 5/1993 | Palmer |
| 5,508,453 | A | 4/1996 | Arosio et al. |
| 5,695,738 | A | 12/1997 | Anderson et al. |
| 5,733,566 | A | 3/1998 | Lewis |
| 6,451,355 | B1 | 9/2002 | Reisner et al. |
| 9,345,715 | B2 | 5/2016 | Young et al. |
| 9,580,459 | B2 | 2/2017 | Dosa et al. |
| 12,186,329 | B2 | 1/2025 | Devlin et al. |
| 2007/0032464 | A1 | 2/2007 | Liao et al. |
| 2009/0118306 | A1 | 5/2009 | Husson et al. |
| 2010/0130426 | A1 | 5/2010 | Yung et al. |
| 2011/0059932 | A1 | 3/2011 | Peng et al. |
| 2012/0277198 | A1 | 11/2012 | Ling et al. |
| 2014/0206657 | A1 | 7/2014 | Yu et al. |
| 2014/0234256 | A1 | 8/2014 | March et al. |
| 2014/0323748 | A1 | 10/2014 | Dosa et al. |

(Continued)

FOREIGN PATENT DOCUMENTS

| | | | |
|---|---|---|---|
| CN | 106478759 | A | 3/2017 |
| DE | 19941764 | A1 | 3/2001 |

(Continued)

OTHER PUBLICATIONS

National Center for Biotechnology Information (2024). PubChem Compound Summary for CID 68236652. Retrieved Dec. 4, 2024 from https://pubchem.ncbi.nlm.nih.gov/compound/68236652. Date created: Nov. 30, 2012 (Year: 2012).*
Ensign LM, Cone R, Hanes J. Oral drug delivery with polymeric nanoparticles: the gastrointestinal mucus barriers. Adv Drug Deliv Rev. May 1, 2012;64(6):557-70. doi: 10.1016/j.addr.2011.12.009. PMID: 22212900; PMCID: PMC3322271. (Year: 2012).*
Adhikari, Arijit A.Seegar, Tom C.Ficarro, Scott B. McCurry, Megan D. Ramachandran, Deepti Yao, Lina Chaudhari, Snehal N. Ndousse-Fetter, Sula Banks, Alexander S. Marto, Jarrod A. Blacklow, Stephen C. Devlin, A, Development of a Covalent Inhibitor of Gut Bacterial Bile Salt Hydrolase Jan. 1, 2019 (Year: 2019).*
CAS registry No. 127895-27-6, which entered STN on Jun. 29, 1990 (Year: 1990).*
Bloom, S., Bume, D.D., Pitts, C.R. and Lectka, T. (2015), Site-Selective Approach to β-Fluorination: Photocatalyzed Ring Opening of Cyclopropanols. Chem. Eur. J., 21: 8060-8063. https://doi.org/10.1002/chem.201501081 (Year: 2015).*

(Continued)

*Primary Examiner* — Joseph K McKane
*Assistant Examiner* — Anna Grace Kuckla
(74) *Attorney, Agent, or Firm* — Wolf, Greenfield & Sacks, P.C.

(57) ABSTRACT

Described herein are methods and compositions related to inhibiting bile salt hydrolase (BSH) and uses thereof. Provided herein is a method for treating a metabolic disorder (e.g., diabetes, obesity), gastrointestinal disease (e.g., a gastrointestinal infection; inflammatory bowel disease (IBD); appendicitis; Crohn's disease (CD); ulcerative colitis (UC); gastritis; enteritis; esophagitis; pancreatitis; diabetes; hepatitis; liver diseases (e.g., Non-alcoholic Fatty Liver Disease (NAFLD); non-alcoholic steatohepatitis (NASH); hepatitis A; hepatitis B; hepatitis C; autoimmune hepatitis; and cirrhosis of the liver) gastroesophageal reflux disease (GERD); celiac disease; diverticulitis; food intolerance; ulcer; infectious colitis; irritable bowel syndrome; leaky gut; and cancer), cancer (e.g., cancer of the digestive system, liver cancer), or an inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, gastroesophageal reflux disease (GERD), psoriatic arthritis, psoriasis, and rheumatoid arthritis) in a subject in need thereof comprising administering to a subject a compound of Formulae (I)-(XVIII).

15 Claims, 45 Drawing Sheets

(56) References Cited

U.S. PATENT DOCUMENTS

| | | | |
|---|---|---|---|
| 2016/0184266 | A9 | 6/2016 | Szewczyk |
| 2018/0319836 | A1 | 11/2018 | Yu et al. |
| 2018/0340006 | A1 | 11/2018 | Weymouth-Wilson et al. |
| 2021/0315908 | A1 | 10/2021 | Devlin et al. |
| 2022/0016138 | A1 | 1/2022 | Devlin et al. |
| 2023/0174988 | A1 | 6/2023 | Devlin et al. |

FOREIGN PATENT DOCUMENTS

| | | | |
|---|---|---|---|
| EP | 0117570 | A1 | 9/1986 |
| EP | 548793 | A2 | 6/1993 |
| EP | 624593 | A2 | 11/1994 |
| EP | 2221313 | A1 | 8/2010 |
| GB | 1360354 | A | 7/1974 |
| JP | S49-095955 | A | 9/1974 |
| JP | S51-26870 | A | 3/1976 |
| JP | H07-017997 | A | 1/1995 |
| KR | 20170099940 | A | 9/2017 |
| RU | 2665685 | C1 | 9/2018 |
| TW | 201700447 | A | 1/2017 |
| WO | WO 94/00126 | A1 | 1/1994 |
| WO | WO 95/07089 | A1 | 3/1995 |
| WO | WO 97/18816 | A1 | 5/1997 |
| WO | WO 98/52585 | A1 | 11/1998 |
| WO | WO 2000/024761 | A1 | 5/2000 |
| WO | WO 2000/066611 | A1 | 11/2000 |
| WO | WO 2001/021642 | A1 | 3/2001 |
| WO | WO 2003/066657 | A1 | 8/2003 |
| WO | WO 2004/092193 | A1 | 10/2004 |
| WO | WO 2011/022838 | A1 | 3/2011 |
| WO | WO 2013/096771 | A1 | 6/2013 |
| WO | WO 2013/113680 | A1 | 8/2013 |
| WO | WO 2016/100619 | A2 | 6/2016 |
| WO | WO 2016/205475 | A2 | 12/2016 |
| WO | WO 2017/035501 | A1 | 3/2017 |
| WO | WO 2017/106818 | A1 | 6/2017 |
| WO | WO 2017/142895 | A1 | 8/2017 |
| WO | WO 2019/075365 | A1 | 4/2019 |
| WO | WO 2019/191637 | A1 | 10/2019 |
| WO | WO 2020/041673 | A1 | 2/2020 |
| WO | WO 2020/117945 | A1 | 6/2020 |

OTHER PUBLICATIONS

International Search Report and Written Opinion for Application No. PCT/US2019/047856, mailed Dec. 10, 2019.

International Preliminary Report on Patentability for Application No. PCT/US2019/047856, mailed Mar. 4, 2021.

Invitation to Pay Additional Fees for Application No. PCT/US2020/032016, mailed Jul. 16, 2020.

International Search Report and Written Opinion for Application No. PCT/US2020/032016, mailed Sep. 22, 2020.

International Search Report and Written Opinion for Application No. PCT/US2019/064488, mailed Apr. 9, 2020.

International Preliminary Report on Patentability for Application No. PCT/US2019/064488, mailed Jun. 17, 2021.

Invitation to Pay Additional Fees for Application No. PCT/US2021/031277, mailed Aug. 11, 2021.

International Search Report and Written Opinion for Application No. PCT/US2021/031277, mailed Oct. 14, 2021.

Genbank Submission. NCBI; Accession No. ABC26911, version ABC26911.1. bile salt hydrolase [*Bifidobacterium breve* DSM 20213 = JCM 1192]. Goswami et al.; Dec. 19, 2005.

Genbank Submission. NCBI; Accession No. ABC26910, version ABC26910.1. bile salt hydrolase [*Bifidobacterium bifidum*]. Goswami et al.; Dec. 19, 2005.

Genbank Submission. NCBI; Accession No. ACL98203, version ACL98203.1; bile salt hydrolase (plasmid) [Ligilactobacillus salivarius]. Fang et al.; Jul. 24, 2016.

Genbank Submission. NCBI; Accession No. AAS98803, version AAS98803.1; bile salt hydrolase [*Bifidobacterium animalis*]. Kim et al.; Aug. 25, 2008.

Genbank Submission. NCBI; Accession No. AKI55714, version AKI55714.1; bile salt hydrolase [*Listeria monocytogenes*]. Bergholz et al.; Jun. 3, 2015.

Genbank Submission. NCBI; Accession No. Accession: AAP20760, version AAP20760.1; bile salt hydrolase [*Enterococcus faecium*]. Wijaya et al.; Apr. 28, 2003.

Genbank Submission. NCBI; Accession No. Accession: NM_006143, version NM_006143.2; *Homo sapiens* G protein-coupled receptor 19 (GPR19), mRNA. Rao et al.; Nov. 11, 2018.

Genbank Submission. NCBI; Accession No. Accession: NP_006134, version NP_006134.1; probable G-protein coupled receptor 19 [*Homo sapiens*]. Yang et al.; Nov. 11, 2018.

Genbank Submission. NCBI; Accession No. Accession: NG_008731, version NG_008731.1; *Homo sapiens* vitamin D receptor (VDR), RefSeqGene on chromosome 12. Loughran et al.; Feb. 15, 2021.

Genbank Submission. NCBI; Accession No. Accession: NP_001017535, version NP_001017535.1; vitamin D3 receptor isoform VDRA [*Homo sapiens*]. Moosavi et al.; Apr. 19, 2021.

Genbank Submission. NCBI; Accession No. Accession: NP¬_001017536, version NP_001017536.1; vitamin D3 receptor isoform VDRB1 [*Homo sapiens*]. Moosavi et al.; Apr. 18, 2021.

Genbank Submission. NCBI; Accession No. Accession: NM_000376, version NM_000376.2; *Homo sapiens* vitamin D receptor (VDR), transcript variant 1, mRNA. Kirac et al.; May 28, 2019.

Genbank Submission. NCBI; Accession No. Accession: NG_016745, version NG_016745.1; *Homo sapiens* sulfotransferase family 2A member 1 (SULT2A1), RefSeqGene on chromosome 19. No Author Listed; Dec. 14, 2020.

Genbank Submission. NCBI; Accession No. Accession: NP_003158, version NP_003158.2; sulfotransferase 2A1 [*Homo sapiens*]. Luck et al.; Apr. 15, 2021.

Genbank Submission. NCBI; Accession No. Accession: NM_003167, version NM_003167.4; *Homo sapiens* sulfotransferase family 2A member 1 (SULT2A1), mRNA. Luck et al.; Apr. 15, 2021.

[No Author Listed] Chemical Abstracts STN Database Record for RN 1240039-42-2. Entered Sep. 7, 2020. 4 pages.

[No Author Listed], Pubchem Compound for CID 129820655. Sep. 13, 2017. 9 pages.

[No Author Listed], Pubchem Compound for CID 126738689. Apr. 22, 2017. 8 pages.

[No Author Listed], Supplementary Information. Harvard University. Dec. 2019. 62 pages.

Abbasi, Unveiling the "Magic" of Diabetes Remission After Weight-Loss Surgery. JAMA. Feb. 14, 2017;317(6):571-574. doi: 10.1001/jama.2017.0020.

Adachi et al., Selective activation of vitamin D receptor by lithocholic acid acetate, a bile acid derivative. J Lipid Res. Jan. 2005;46(1):46-57. doi: 10.1194/jlr.M400294-JLR200. Epub Oct. 16, 2004.

Adhikari et al., Development of a covalent inhibitor of gut bacterial bile salt hydrolases. Nat Chem Biol. Mar. 2020;16(3):318-326. doi: 10.1038/s41589-020-0467-3. Epub Feb. 10, 2020.

Afonine et al., Towards automated crystallographic structure refinement with phenix.refine. Acta Crystallogr D Biol Crystallogr. Apr. 2012;68(Pt 4):352-67. doi: 10.1107/S0907444912001308. Epub Mar. 19, 2012.

Alexander et al., multiplierz v2.0: A Python-based ecosystem for shared access and analysis of native mass spectrometry data. Proteomics. Aug. 2017;17(15-16). doi: 10.1002/pmic.201700091.

Alnouti, Bile Acid sulfation: a pathway of bile acid elimination and detoxification. Toxicol Sci. Apr. 2009;108(2):225-46. doi: 10.1093/toxsci/kfn268. Epub Jan. 8, 2009.

Angliker et al., The Synthesis of Lysylfluoromethanes and Their Properties as Inhibitors of Trypsin, Plasmin and Cathepsin B. Biochem. J. 1987; 241(3): 871-875.

Assimakopoulos et al., Altered intestinal tight junctions' expression in patients with liver cirrhosis: a pathogenetic mechanism of intestinal hyperpermeability. Eur J Clin Invest. Apr. 2012;42(4):439-46. doi: 10.1111/j.1365-2362.2011.02609.x. Epub Oct. 24, 2011.

Atarashi et al., Treg Induction by a Rationally Selected Mixture of Clostridia Strains From the Human Microbiota. Nature. Aug. 8, 2013; 500 (7461): 232-236.

(56) References Cited

OTHER PUBLICATIONS

Baba et al., Selective activity of several cholic acid derivatives against human immunodeficiency virus replication in vitro. J Acquir Immune Defic Syndr (1988). 1989;2(3):264-71.
Bäckhed et al., Mechanisms Underlying the Resistance to Diet-Induced Obesity in Germ-Free Mice. PNAS. 2007; 104(3):979-84.
Bandiera et al., A convenient procedure for the synthesis of ursodeoxycholic acid sulfated derivatives. Synthetic Communications. 1987; 17(9): 1111-17.
Barnes et al., Renal mechanisms influencing the bile acid composition of cholestatic urine. Bile Acid Metab. Health Dis., Proc. Bile Acid Meeting. 1977; 89-92.
Barnes et al., The role of tubular reabsorption in the renal excretion of bile acids. Biochem J. Jul. 15, 1977;166(1):65-73. doi: 10.1042/bj1660065.
Batterham et al., Mechanisms of Diabetes Improvement Following Bariatric/Metabolic Surgery. Diabetes Care. Jun. 2016;39(6):893-901. doi: 10.2337/dc16-0145.
Begley et al., Bile Salt Hydrolase Activity in Probiotics. Appl. Environ. Microbiol. 2006; 72(3): 1729-1738.
Bernier-Latmani et al., Intestinal lymphatic vasculature: structure, mechanisms and functions. Nat Rev Gastroenterol Hepatol. Sep. 2017;14(9):510-526. doi: 10.1038/nrgastro.2017.79. Epub Jun. 28, 2017.
Besnard et al., Is the ileal bile acid-binding protein (I-BABP) gene involved in cholesterol homeostasis ?. Med Sci (Paris). Jan. 2004;20(1):73-7. doi: 10.1051/medsci/200420173.
Bhutta et al., Effect of Roux-en-Y gastric bypass surgery on bile acid metabolism in normal and obese diabetic rats. PLoS One. Mar. 23, 2015;10(3):e0122273. doi: 10.1371/journal.pone.0122273. eCollection 2015.
Blosser et al., A method to assess target gene involvement in angiogenesis in vitro and in vivo using lentiviral vectors expressing shRNA. PLoS One. Apr. 23, 2014;9(4):e96036. doi: 10.1371/journal.pone.0096036. eCollection 2014.
Brighton et al., Bile Acids Trigger GLP-1 Release Predominantly by Accessing Basolaterally Located G Protein-Coupled Bile Acid Receptors. Endocrinology. Nov. 2015;156(11):3961-70. doi: 10.1210/en.2015-1321. Epub Aug. 17, 2015.
Bureeva et al., Selective inhibition of the interaction of C1q with immunoglobulins and the classical pathway of complement activation by steroids and triterpenoids sulfates. Bioorg Med Chem. May 15, 2007;15(10):3489-98. doi: 10.1016/j.bmc.2007.03.002. Epub Mar. 6, 2007.
Callahan et al., DADA2: High-resolution sample inference from Illumina amplicon data. Nat Methods. Jul. 2016;13(7):581-3. doi: 10.1038/nmeth.3869. Epub May 23, 2016.
Cao et al., Intestinally-targeted TGR5 agonists equipped with quaternary ammonium have an improved hypoglycemic effect and reduced gallbladder filling effect. Sci Rep. Jun. 24, 2016;6:28676. doi: 10.1038/srep28676.
Cao et al., Liposomes Coated with Isolated Macrophage Membrane Can Target Lung Metastasis of Breast Cancer. ACS Nano. Aug. 23, 2016;10(8):7738-48. doi: 10.1021/acsnano.6b03148. Epub Jul. 27, 2016.
Caporaso et al., QIIME allows analysis of high-throughput community sequencing data. Nat Methods. May 2010;7(5):335-6. doi: 10.1038/nmeth.f.303. Epub Apr. 11, 2010.
Castro-Perez et al., Attenuation of Slc27a5 gene expression followed by LC-MS measurement of bile acid reconjugation using metabolomics and a stable isotope tracer strategy. J Proteome Res. Oct. 7, 2011;10(10):4683-91. doi: 10.1021/pr200475g. Epub Aug. 26, 2011.
Chand et al., Structure and Function of a Highly Active Bile Salt Hydrolase (BSH) From Enterococcus Faecalis and Post-Translational Processing of BSH Enzymes. Biochim Biophys Acta Proteins Proteom. 2018; 1866(4): 507-518.
Chaudhari et al., A microbial metabolite remodels the gut-liver axis following bariatric surgery. Cell Host Microbe. Mar. 10, 2021;29(3):408-424.e7. doi: 10.1016/j.chom.2020.12.004. Epub Jan. 11, 2021.
Chaudhari et al., Bariatric surgery reveals a gut-restricted TGR5 agonist with anti-diabetic effects. Nat Chem Biol. Jan. 2021;17(1):20-29. doi: 10.1038/s41589-020-0604-z. Epub Aug. 3, 2020.
Chen et al., Design of Gut-Restricted Thiazolidine Agonists of G Protein-Coupled Bile Acid Receptor 1 (GPBAR1, TGR5). J Med Chem. Sep. 13, 2018;61(17):7589-7613. doi: 10.1021/acs.jmedchem.8b00308. Epub Aug. 24, 2018.
Chen et al., MolProbity: all-atom structure validation for macromolecular crystallography. Acta Crystallogr D Biol Crystallogr. Jan. 2010;66(Pt 1):12-21. doi: 10.1107/S0907444909042073. Epub Dec. 21, 2009.
Chiang, Recent Advances in Understanding Bile Acid Homeostasis. F1000Res. Nov. 20, 2017;6:2029. doi: 10.12688/f1000research.12449.1. eCollection 2017.
Cohen et al., Differing effects of nor-ursodeoxycholic or ursodeoxycholic acid on hepatic histology and bile acid metabolism in the rabbit. Gastroenterology. Jul. 1986;91(1):189-97. doi: 10.1016/0016-5085(86)90457-9.
Cohen et al., Solvolysis of chenodeoxycholic acid sulfates. Steroids. Jun. 1981;37(6):621-6. doi: 10.1016/s0039-128x(81)90149-5.
Cohen et al., Structural Bioinformatics-Based Design of Selective, Irreversible Kinase Inhibitors. Science. 2005; 308(5726):1318-1321.
Coleman et al., Cloning and Characterization of a Conjugated Bile Acid Hydrolase Gene From Clostridium Perfringens. Appl Environ Microbiol. 1995; 61(7): 2514-2520.
Compher et al., Vitamin D and the bariatric surgical patient: a review. Obes Surg. Feb. 2008;18(2):220-4. doi: 10.1007/s11695-007-9289-6. Epub Jan. 5, 2008.
Craddock et al., Expression and transport properties of the human ileal and renal sodiumdependent bile acid transporter. Am J Physiol. Jan. 1998;274(1):G157-69. doi: 10.1152/ajpgi.1998.274.1.G157.
Cross et al., The Isothiocyanate Class of Bioactive Nutrients Covalently Inhibit the MEKK1 Protein Kinase. BMC Cancer. 2007; 7(1): 183.
Czygan et al., Synthesis and excretion of bile acid sulfate esters in the isolated perfused rat kidney. Bile Acid Metab. Health Dis., Proc. Bile Acid Meet., 4th (1977), Meeting Date 1976, 83-7.
Dawson et al., Targeted deletion of the ileal bile acid transporter eliminates enterohepatic cycling of bile acids in mice. J Biol Chem. Sep. 5, 2003;278(36):33920-7. doi: 10.1074/jbc.M306370200. Epub Jun. 20, 2003.
Dawson, Roles of Ileal ASBT and OSTalpha-OSTbeta in Regulating Bile Acid Signaling. Dig Dis. 2017;35(3):261-266. doi: 10.1159/000450987. Epub Mar. 1, 2017.
De Witt et al., Effects of sulfation patterns on intestinal transport of bile salt sulfate esters. Am J Physiol. Jan. 1980;238(1):G34-9. doi: 10.1152/ajpgi.1980.238.1.G34.
Devlin, Gut Bacterial Modification of Bile Acids Alters Host Physiology. Harvard Chan Microbiome in Public Health Center Symposium. May 8, 2020. 55 pages.
Diaz et al., Normal Gut Microbiota Modulates Brain Development and Behavior. Proc. Natl. Acad. Sci. U.S.A. 2011; 108(7):3047-3052.
Ding et al., Vertical sleeve gastrectomy activates GPBAR-1/TGR5 to sustain weight loss, improve fatty liver, and remit insulin resistance in mice. Hepatology. Sep. 2016;64(3):760-73. doi: 10.1002/hep.28689. Epub Jul. 25, 2016.
Disibio et al., Metastatic patterns of cancers: results from a large autopsy study. Arch Pathol Lab Med. Jun. 2008;132(6):931-9. doi: 10.5858/2008-132-931-MPOCRF.
Dong et al., Bile Salt Hydrolases: Structure and Function, Substrate Preference, and Inhibitor Development. Protein Sci. 2018; 27(10): 1742-1754.
Donia et al., Human Microbiota. Small Molecules From the Human Microbiota. Science. 2015; 349(6246): 1254766.
Dosa et al., Synthesis and evaluation of water-soluble prodrugs of ursodeoxycholic acid (UDCA), an anti-apoptotic bile acid. ChemMedChem. Jun. 2013;8(6):1002-11. doi: 10.1002/cmdc.201300059. Epub May 2, 2013.
Duboc et al., The bile acid TGR5 membrane receptor: from basic research to clinical application. Dig Liver Dis. Apr. 2014;46(4):302-12. doi: 10.1016/j.dld.2013.10.021. Epub Jan. 9, 2014.

(56) References Cited

OTHER PUBLICATIONS

Eissele et al., Glucagon-like peptide-1 cells in the gastrointestinal tract and pancreas of rat, pig and man. Eur J Clin Invest. Apr. 1992;22(4):283-91. doi: 10.1111/j.1365-2362.1992.tb01464.x.
Eriksson et al., Occurrence of sulfated 5alpha-cholanoates in rat bile. J Lipid Res. Feb. 1978;19(2):177-86.
Eyssen et al., Sulfate bile acids in germ-free and conventional mice. Eur J Biochem. Jul. 15, 1976;66(3):507-14. doi: 10.1111/j.1432-1033.1976.tb10576.x.
Ferrell et al., Understanding Bile Acid Signaling in Diabetes: From Pathophysiology to Therapeutic Targets. Diabetes Metab J. Jun. 2019;43(3):257-272. doi: 10.4093/dmj.2019.0043.
Ferruzza et al., A protocol for differentiation of human intestinal Caco-2 cells in asymmetric serum-containing medium. Toxicol In Vitro. Dec. 2012;26(8):1252-5. doi: 10.1016/j.tiv.2012.01.008. Epub Jan. 15, 2012.
Ficarro et al., Improved electrospray ionization efficiency compensates for diminished chromatographic resolution and enables proteomics analysis of tyrosine signaling in embryonic stem cells. Anal Chem. May 1, 2009;81(9):3440-7. doi: 10.1021/ac802720e.
Ficarro et al., mzStudio: A Dynamic Digital Canvas for User-Driven Interrogation of Mass Spectrometry Data. Proteomes. Aug. 1, 2017;5(3):20. doi: 10.3390/proteomes5030020.
Fiorucci et al., Bile Acid-Activated Receptors, Intestinal Microbiota, and the Treatment of Metabolic Disorders. Trends Mol Med. 2015; 21(11): 702-714.
Frank et al., Molecular-Phylogenetic Characterization of Microbial Community Imbalances in Human Inflammatory Bowel Diseases. PNAS. 2007; 104 (34):13780-13785.
Franzone et al., [Pharmacokinetics and hepatic metabolism of ursulcholic acid (a soluble form of ursodeoxycholic acid in the rat]. Boll Chim Farm. Jul. 1987;126(7):289-93.
Franzone et al., [The pharmacologic activity of ursulcholic acid, a soluble form of ursodeoxycholic acid]. Boll Chim Farm. Jul. 1987; 126(7):282-8.
Fukui, Gut-liver axis in liver cirrhosis: How to manage leaky gut and endotoxemia. World J Hepatol. Mar. 27, 2015;7(3):425-42. doi: 10.4254/wjh.v7.i3.425.
Garland et al., Covalent Modifiers of Botulinum Neurotoxin Counteract Toxin Persistence. ACS Chem Biol. 2019; 14(1): 76-87.
Gartner et al., Transport of chenodeoxycholic acid and its 3-alpha-and 7-alpha-sulfates by isolated perfused rat liver. Hepatology. Oct. 1990; 12(4 Pt 1):738-42. doi: 10.1002/hep.1840120419.
Gehringer et al., Emerging and Re-Emerging Warheads for Targeted Covalent Inhibitors: Applications in Medicinal Chemistry and Chemical Biology. J Med Chem. 2019; 62:5673-5724.
Gehringer et al., Solution-Phase Parallel Synthesis of Ruxolitinib-Derived Janus Kinase Inhibitors via Copper-Catalyzed Azide-Alkyne Cycloaddition. ACS Comb Sci. 2015; 17(1): 5-10.
Ghosh et al., c-Fos mediates repression of the apical sodium-dependent bile acid transporter by fibroblast growth factor-19 in mice. Am J Physiol Gastrointest Liver Physiol. Jan. 2014;306(2):G163-71. doi: 10.1152/ajpgi.00276.2013. Epub Dec. 5, 2013.
Gloy et al., Bariatric surgery versus non-surgical treatment for obesity: a systematic review and meta-analysis of randomised controlled trials. BMJ. Oct. 22, 2013;347:f5934. doi: 10.1136/bmj.f5934.
Gonzalez et al., Putative irreversible inhibitors of the human sodium-dependent bile acid transporter (hASBT; SLC10A2) support the role of transmembrane domain 7 in substrate binding/translocation. Pharm Res. Jul. 2012;29(7):1821-31. doi: 10.1007/s11095-012-0706-8. Epub Feb. 22, 2012.
Goto et al., Separation of monosulfated bile acids by high-performance liquid chromatography. J Chromatogr. 1980;3(5): 645-55.
Goto et al., Studies on steroids. Part CCXXXII. Synthesis of disulfates of unconjugated and conjugated bile acids. Chem Pharm Bull (Tokyo). Nov. 1987;35(11):4562-7. doi: 10.1248/cpb.35.4562.
Goto et al., Studies on steroids. CCXXVII. Separation and determination of bile acid 7- and 12-sulphates in urine by high-performance liquid chromatography with fluorescence labelling. J Chromatogr. Mar. 20, 1987;415(1):45-52.
Goto et al., Studies on steroids. CCXXXIII. Separation and characterization of bile acid disulphates in human urine by high-performance liquid chromatography. J Chromatogr. Mar. 4, 1988;425(1):59-66. doi: 10.1016/0378-4347(88)80006-9.
Goto et al., Studies on steroids. CLXIII. Synthesis of monosulfates of cholic acid derivatives. Chem Pharm Bull. 1980; 28(11):3389-94.
Goto et al., Studies on steroids. CLXX. Separation and determination of bile acid 3-sulfates in human bile by high-performance liquid chromatography. J Chromatogr. Nov. 13, 1981;226(1):13-24.
Goto et al., Synthesis of monosulfates of unconjugated and conjugated bile acids. Chem Pharm Bull (Tokyo). Jun. 1979;27(6):1402-11. doi: 10.1248/cpb.27.1402.
Goto, [Chromatographic determination of bile acids in biological fluids with sensitive and selective detection]. Yakugaku Zasshi. Nov. 1990;110(11):807-21. doi: 10.1248/yakushi1947.110.11_807.
Goudarzi et al., An Integrated Multi-Omic Approach to Assess Radiation Injury on the Host-Microbiome Axis. Radiat Res. Sep. 2016;186(3):219-34. doi: 10.1667/RR14306.1. Epub Aug. 11, 2016.
Griffiths et al., Charge-remote fragmentation of sulfated and glucuronidated bile acids and their 2-aminoethanesulfonic acid derivatives. Rapid Commun Mass Spectrom. 1994; 8(3): 227-36.
Hamilton et al., Human Cecal Bile Acids: Concentration and Spectrum. Am. J. Physiol. Gastrointest. Liver Physiol. 2007; 293(1): G256-G263.
Harach et al., TGR5 potentiates GLP-1 secretion in response to anionic exchange resins. Sci Rep. 2012;2:430. doi: 10.1038/srep00430. Epub May 30, 2012.
Hasegawa et al., Effect of ursodeoxycholate-3,7-disulfate on biliary excretion of lithocholate-3-O-glucuronide in Eisai hyperbilirubinemic rat (EHBR). Hepatol Res. Aug. 2002;23(4):296-300. doi: 10.1016/s1386-6346(01)00188-7.
He et al., Gut microbiota as a potential target of metabolic syndrome: the role of probiotics and prebiotics. Cell Biosci. Oct. 25, 2017;7:54. doi: 10.1186/s13578-017-0183-1. eCollection 2017.
Henise et al., Irreversible Nek2 Kinase Inhibitors with Cellular Activity. Journal of Medicinal Chemistry. 2011; 54(12):4133-4146.
Hodge et al., Therapeutic potential of Takeda-G-protein-receptor-5 (TGR5) agonists. Hope or hype? Diabetes Obes Metab. May 2016;18(5):439-43. doi: 10.1111/dom.12636. Epub Mar. 17, 2016.
Hofmann, The Function of Bile Salts in Fat Absorption. the Solvent Properties of Dilute Micellar Solutions of Conjugated Bile Acids. Biochem J. 1963; 89(1): 57-68.
Huijghebaert et al., Influence of the Amino Acid Moiety on Deconjugation of Bile Acid Amidates by Cholylglycine Hydrolase or Human Fecal Cultures. J Lipid Res. 1986; 27(7): 742-752.
Huijghebaert et al., Specificity of bile salt sulfatase activity from Clostridium sp. strains S1. Appl Environ Microbiol. Nov. 1982;44(5):1030-4. doi: 10.1128/AEM.44.5.1030-1034.1982.
Iguchi et al., Effects of chemical modification of ursodeoxycholic acid on TGR5 activation. Biol Pharm Bull. 2011;34(1):1-7. doi: 10.1248/bpb.34.1.
Ivanov et al., Induction of Intestinal Th17 Cells by Segmented Filamentous Bacteria. Cell. 2009; 139(3): 485-98.
Jacobs et al., A Disease-Associated Microbial and Metabolomics State in Relatives of Pediatric Inflammatory Bowel Disease Patients. Cell Mol Gastroenterol Hepatol. Jul. 2, 2016;2(6):750-766. doi: 10.1016/j.jcmgh.2016.06.004. eCollection Nov. 2016.
Jahansouz et al., Antibiotic-induced Disruption ofIntestinal Microbiota Contributes to Failure of Vertical Sleeve Gastrectomy. Ann Surg. Jun. 2019;269(6):1092-1100. doi: 10.1097/SLA.0000000000002729.
Jarocki et al., A New Insight into the Physiological Role of Bile Salt Hydrolase among Intestinal Bacteria from the Genus Bifidobacterium. PLoS One. Dec. 3, 2014;9(12):e114379. doi: 10.1371/journal.pone.0114379. eCollection 2014.
Joyce et al., Bacterial bile salt hydrolase in host metabolism: Potential for influencing gastrointestinal microbe-host crosstalk. Gut Microbes. 2014;5(5):669-74. doi: 10.4161/19490976.2014.969986.
Joyce et al., Regulation of Host Weight Gain and Lipid Metabolism by Bacterial Bile Acid Modification in the Gut. Proc. Natl. Acad. Sci. U.S.A. 2014; 111(20): 7421-7426.

(56) References Cited

OTHER PUBLICATIONS

Kakizaki et al., Xenobiotic-sensing nuclear receptors CAR and PXR as drug targets in cholestatic liver disease. Curr Drug Targets. Nov. 2009;10(11):1156-1163. doi: 10.2174/138945009789735174.
Kaplan et al., Monitoring dynamic changes in lymph metabolome of fasting and fed rats by electrospray ionization-ion mobility mass spectrometry (ESI-IMMS). Anal Chem. Oct. 1, 2009;81(19):7944-53. doi: 10.1021/ac901030k.
Kaska et al., Improved glucose metabolism following bariatric surgery is associated with increased circulating bile acid concentrations and remodeling of the gut microbiome. World J Gastroenterol. Oct. 21, 2016;22(39):8698-8719. doi: 10.3748/wjg.v22.i39.8698.
Katsuma et al., Bile acids promote glucagon-like peptide-1 secretion through TGR5 in a murine enteroendocrine cell line STC-1. Biochem Biophys Res Commun. Apr. 1, 2005;329(1):386-90. doi: 10.1016/j.bbrc.2005.01.139.
Kawamoto et al., Purification and Characterization of a New Hydrolase for Conjugated Bile Acids, Chenodeoxycholyltaurine Hydrolase, From Bacteroides Vulgatus. J. Biochem. 1989; 106(6): 1049-1053.
Khorgami et al., Trends in utilization ofbariatric surgery, 2010-2014: sleeve gastrectomy dominates. Surg Obes Relat Dis. May 2017;13(5):774-778. doi: 10.1016/j.soard.2017.01.031. Epub Jan. 25, 2017.
Kraal et al., The Prevalence of Species and Strains in the Human Microbiome: a Resource for Experimental Efforts. PLOS ONE. 2014; 9(5): e97279.
Kuhre et al., Peptide production and secretion in GLUTag, NCI-H716, and STC-1 cells: a comparison to native L-cells. J Mol Endocrinol. Apr. 2016;56(3):201-11. doi: 10.1530/JME-15-0293. Epub Jan. 27, 2016.
Larraufie et al., Important Role of the GLP-1 Axis for Glucose Homeostasis after Bariatric Surgery. Cell Rep. Feb. 5, 2019;26(6):1399-1408.e6. doi: 10.1016/j.celrep.2019.01.047.
Lastya et al., The low level of glucagon-like peptide-1 (glp-1) is a risk factor of type 2 diabetes mellitus. BMC Res Notes. Nov. 26, 2014;7:849. doi: 10.1186/1756-0500-7-849.
Lebel et al., Boc-Protected Amines via a Mild and Efficient One-Pot Curtius Rearrangement. Org Lett. 2005; 7(19): 4107-4110.
Lepage et al., Separation of sulfated from non-sulfated serum bile acids without the use of Sephadex cols. J Lipid Res. May 1981;22(4):705-11.
Lespessailles et al., Vitamin D alteration associated with obesity and bariatric surgery. Exp Biol Med (Maywood). May 2017;242(10):1086-1094. doi: 10.1177/1535370216688567. Epub Jan. 1, 2017.
Lewis et al., Inactivation of Protein Tyrosine Phosphatases by Dietary Isothiocyanates. Bioorganic & Medicinal Chemistry Letters. 2015; 25(20):4549-52.
Li et al., Bile acids as metabolic regulators. Curr Opin Gastroenterol. Mar. 2015 ; 31(2): 159-165. doi:10.1097/MOG.0000000000000156.
Li et al., Microbiome Remodelling Leads to Inhibition of Intestinal Farnesoid X Receptor Signalling and Decreased Obesity. Nat Commun. 2013;4:2384. doi: 10.1038/ncomms3384.
Lianidou et al., Enzymic fluorimetric determination of sulphated and non-sulphated primary bile acids in urine using a rapid solvolysis technique. Analyst. Sep. 1988;113(9):1459-63. doi: 10.1039/an9881301459.
Liu et al., Developing Irreversible Inhibitors of the Protein Kinase Cysteinome. Chemistry & Biology. 2013; 20(2): 146-159.
Liu et al., Role of gut microbiota, bile acids and their cross-talk in the effects of bariatric surgery on obesity and type 2 diabetes. J Diabetes Investig. Jan. 2018;9(1):13-20. doi: 10.1111/jdi.12687. Epub Jun. 12, 2017.
Lööf, Enzymatic sulphation of bile salts in man. Bile salt sulphotransferase activity in human adrenal. Digestion. 1981;21(6):297-303. doi: 10.1159/000198580.
Lutz et al., M. The Use of Rat and Mouse Models in Bariatric Surgery Experiments. Front Nutr. Aug. 5, 2016;3:25. doi: 10.3389/fnut.2016.00025. eCollection 2016.
Ma et al., Gut Microbiome-Mediated Bile Acid Metabolism Regulates Liver Cancer via NKT Cells. Science. 2018; 360 (6391): eaan5931.
Madsbad, The role of glucagon-like peptide-1 impairment in obesity and potential therapeutic implications. Diabetes Obes Metab. Jan. 2014;16(1):9-21. doi: 10.1111/dom.12119. Epub May 26, 2013.
Magouliotis et al., Impact of Bariatric Surgery on Metabolic and Gut Microbiota Profile: a Systematic Review and Meta-analysis. Obes Surg. May 2017;27(5):1345-1357. doi: 10.1007/s11695-017-2595-8.
Mahowald et al., Characterizing a model human gut microbiota composed of members of its two dominant bacterial phyla. Proc Natl Acad Sci U S A. Apr. 7, 2009;106(14):5859-64. doi: 10.1073/pnas.0901529106. Epub Mar. 24, 2009.
Makishima et al., Vitamin D Receptor as an Intestinal Bile Acid Sensor. Science. May 17, 2002; 296 (5571): 1313-1316.
Manchanda et al., Vitamin D receptor and type 2 diabetes mellitus: Growing therapeutic opportunities. Indian J Hum Genet. Sep. 2012;18(3):274-5. doi: 10.4103/0971-6866.107975.
Marschall et al., The major metabolites of ursodeoxycholic acid in human urine are conjugated with N-acetylglucosamine. Hepatology. Oct. 1994;20(4 Pt 1):845-53. doi: 10.1002/hep.1840200412.
Martinez-Augustin et al., Intestinal bile acid physiology and pathophysiology. World J Gastroenterol. Oct. 7, 2008;14(37):5630-40. doi: 10.3748/wjg.14.5630.
Mccoy et al., Phaser crystallographic software. J Appl Crystallogr. Aug. 1, 2007;40(Pt 4):658-674. doi: 10.1107/S0021889807021206. Epub Jul. 13, 2007.
Mcdonald et al., Partitioning of polar fatty acids into lymph and portal vein after intestinal absorption in the rat. Q J Exp Physiol. Apr. 1987;72(2):153-9. doi: 10.1113/expphysiol.1987.sp003059.
Mcdonald et al., Portal venous transport of long-chain fatty acids absorbed from rat intestine. Am J Physiol. Sep. 1980;239(3):G141-50. doi: 10.1152/ajpgi.1980.239.3.G141.
Mcgavigan et al., TGR5 contributes to glucoregulatory improvements after vertical sleeve gastrectomy in mice. Gut. Feb. 2017;66(2):226-234. doi: 10.1136/gutjnl-2015-309871. Epub Oct. 28, 2015.
Medina et al., Distinct patterns in the gut microbiota after surgical or medical therapy in obese patients. PeerJ. Jun. 20, 2017;5:e3443. doi: 10.7717/peerj.3443. eCollection 2017.
Mertens et al., Bile Acid Signaling Pathways from the Enterohepatic Circulation to the Central Nervous System. Front Neurosci. Nov. 7, 2017;11:617. doi: 10.3389/fnins.2017.00617. eCollection 2017.
Mi et al., Covalent Binding to Tubulin by Isothiocyanates. a Mechanism of Cell Growth Arrest and Apoptosis. J Biol Chem. 2008; 283(32): 22136-22146.
Miller et al., Targeting Protein Kinases with Selective and Semipromiscuous Covalent Inhibitors. Meth Enzymol. 2014; 548: 93-116.
Miyata et al., Enterobacteria modulate intestinal bile acid transport and homeostasis through apical sodium-dependent bile acid transporter (SLC10A2) expression. J Pharmacol Exp Ther. Jan. 2011;336(1):188-96. doi: 10.1124/jpet.110.171736. Epub Sep. 30, 2010.
Modica et al., Deciphering the Nuclear Bile Acid Receptor FXR Paradigm. Nucl Recept Signal. 2010; 8:e005.
Moore et al., Intestinal Floras of Populations That Have a High Risk of Colon Cancer. Appl Environ Microbiol. 1995; 61(9): 3202-7.
Morin et al., Collaboration gets the most out of software. Elife. Sep. 10, 2013;2:e01456. doi: 10.7554/eLife.01456.
Moser et al., Bile Salt Hydrolase Activity and Resistance to Toxicity of Conjugated Bile Salts Are Unrelated Properties in Lactobacilli. Appl Environ Microbiol. Aug. 2001;67(8):3476-80. doi: 10.1128/AEM.67.8.3476-3480.2001.
Myronovych et al., Vertical sleeve gastrectomy reduces hepatic steatosis while increasing serum bile acids in a weight-loss-independent manner. Obesity (Silver Spring). Feb. 2014;22(2):390-400. doi: 10.1002/oby.20548. Epub Sep. 5, 2013.
Nair et al., The enzymatic cleavage of the carbon-nitrogen bond in 3-alpha, 7-alpha, 12-alpha-trihydroxy-5-beta-cholan-24-oylglycine. J Biol Chem. Jan. 10, 1967;242(1):7-11.
Nemati et al., Increased Bile Acids and FGF19 After Sleeve Gastrectomy and Roux-en-Y Gastric Bypass Correlate with Improve-

(56) References Cited

OTHER PUBLICATIONS ment in Type 2 Diabetes in a Randomized Trial. Obes Surg. Sep. 2018;28(9):2672-2686. doi: 10.1007/s11695-018-3216-x.
Nishida et al., Modulation of bile acid metabolism by lalphahydroxyvitamin D3 administration in mice. Drug Metab Dispos. Oct. 2009;37(10):2037-44. doi: 10.1124/dmd.109.027334. Epub Jul. 6, 2009.
Ogasawara et al., Biliary excretion of phenolphthalein glucuronide in the rat. Hepatol Res. Jun. 2001;20(2):221-231. doi: 10.1016/s1386-6346(00)00143-1.
Pageaux et al., Bile acid sulfates in serum bile acids determination. Steroids. Jul. 1979;34(1):73-88. doi: 10.1016/0039-128x(79)90127-2.
Park et al., Metabolism of fluorine-containing drugs. Annu Rev Pharmacol Toxicol. 2001;41:443-70. doi: 10.1146/annurev.pharmtox.41.1.443.
Parmentier et al., Cholic acid-7-sulfate, a major bile acid in the large intestine of the mouse. Adv. Bile Acid Res., Bile Acid Meet., 3rd (1975), Meeting Date 1974, 139-44.
Parmentier et al., Synthesis and characteristics of the specific monosulfates of chenodeoxycholate, deoxycholate and their taurine or glycine conjugates. Steroids. Nov. 1977;30(5):583-90. doi: 10.1016/0039-128x(77)90049-6.
Parmentier et al., Synthesis of the specific monosulfates of cholic acid. Steroids. Dec. 1975;26(6):721-9. doi: 10.1016/0039-128x(75)90105-1.
Parmentier et al., Thin-layer chromatography of bile salt sulfates. Journal of Chromatography. 1978; 152(1):285-9.
Patti et al., Serum bile acids are higher in humans with prior gastric bypass: potential contribution to improved glucose and lipid metabolism. Obesity (Silver Spring). Sep. 2009;17(9):1671-7. doi: 10.1038/oby.2009.102. Epub Apr. 9, 2009.
Peng et al., Liquid-liquid extraction combined with differential isotope dimethylaminophenacyl labeling for improved metabolomic profiling of organic acids. Anal Chim Acta. Nov. 25, 2013;803:97-105. doi: 10.1016/j.aca.2013.07.045. Epub Jul. 27, 2013.
Pols et al., Lithocholic Acid Controls Adaptive Immune Responses by Inhibition of Th1 Activation Through the Vitamin D Receptor. PLOS ONE. 2017; 12(5): e0176715.
Princen et al., One-step solvolysis of 3-, 7- and 12-sulfated free and conjugated bile acids. Clin Chim Acta. Nov. 15, 1990;192(1):77-83. doi: 10.1016/0009-8981(90)90274-v.
Quintás-Cardama et al., Kinase Inhibitors for the Treatment of Myeloproliferative Neoplasias and Beyond. Nature Reviews Drug Discovery. 2011; 10(2): 127-140.
Raedsch et al., Separation of individual sulfated bile acid conjugates as calcium complexes using reversed-phase partition thin-layer chromatography. J Lipid Res. Aug. 1979;20(6):789-95.
Rearick et al., Increase in cholesterol sulfotransferase activity during in vitro squamous differentiation of rabbit tracheal epithelial cells and its inhibition by retinoic acid. J Biol Chem. Sep. 25, 1987;262(27):13069-74.
Ridaura et al., Gut Microbiota From Twins Discordant for Obesity Modulate Metabolism in Mice. Science. 2013; 341(6150): 1241214.
Ridlon et al., Bile Salt Biotransformations by Human Intestinal Bacteria. J Lipid Res. 2006; 47(2): 241-259.
Rizzo et al., Functional characterization of the semisynthetic bile acid derivative INT-767, a dual farnesoid X receptor and TGR5 agonist. Mol Pharmacol. Oct. 2010;78(4):617-30. doi: 10.1124/mol.110.064501. Epub Jul. 14, 2010.
Robben et al., Formation of delta 2- and delta 3-cholenoic acids from bile acid 3-sulfates by a human intestinal Fusobacterium strain. Appl Environ Microbiol. Nov. 1989;55(11):2954-9. doi: 10.1128/AEM.55.11.2954-2959.1989.
Roberts et al., Development of a Gut Microbe-Targeted Nonlethal Therapeutic to Inhibit Thrombosis Potential. Nat. Med. 2018; 24(9): 1407-1417.
Roda et al., Quantitative aspects of the interaction of bile acids with human serum albumin. J Lipid Res. Mar. 1982;23(3):490-5.
Rodrigues et al., The site-specific delivery of ursodeoxycholic acid to the rat colon by sulfate conjugation. Gastroenterology. Dec. 1995;109(6):1835-44. doi: 10.1016/0016-5085(95)90750-5.
Rossocha et al., Conjugated Bile Acid Hydrolase Is a Tetrameric N-Terminal Thiol Hydrolase with Specific Recognition of Its Cholyl but Not of Its Tauryl Product. Biochem. 2005; 44(15): 5739-5748.
Runge-Morris et al., Regulation of the cytosolic sulfotransferases by nuclear receptors. Drug Metab Rev. Feb. 2013;45(1):15-33. doi: 10.3109/03602532.2012.748794.
Ryan et al., FXR is a molecular target for the effects of vertical sleeve gastrectomy. Nature. May 8, 2014;509(7499):183-8. doi: 10.1038/nature13135. Epub Mar. 26, 2014.
Sampson et al., Gut Microbiota Regulate Motor Deficits and Neuroinflammation in a Model of Parkinson's Disease. Cell. 2016; 167(6): 1469-80.
Sandler et al., Short-Term Benefit From Oral Vancomycin Treatment of Regressive-Onset Autism. Journal of Child Neurology. 2016; 15(7): 429-435.
Sano et al., Estradiol-17 beta-glucuronide-induced cholestasis. Effects of ursodeoxycholate-3- O-glucuronide and 3,7-disulfate. J Hepatol. Feb. 1993;17(2):241-6. doi: 10.1016/s0168-8278(05)80045-5.
Santhekadur et al., Preclinical models of non-alcoholic fatty liver disease. J Hepatol. Feb. 2018;68(2):230-237. doi: 10.1016/j.jhep.2017.10.031. Epub Nov. 9, 2017.
Sasaki et al., Separation of double conjugates of bile acids by two-dimensional high-performance thin-layer chromatography with tetra-n-butylammonium phosphate and methyl β-cyclodextrin. Chromatographia. 1999; 49(11/12): 681-685.
Sato et al., Novel Potent and Selective Bile Acid Derivatives as TGR5 Agonists: Biological Screening, Structure-Activity Relationships, and Molecular Modeling Studies. J Med Chem. Mar. 27, 2008;51(6):1831-41. doi: 10.1021/jm7015864. Epub Feb. 29, 2008.
Sayin et al., Gut Microbiota Regulates Bile Acid Metabolism by Reducing the Levels of Tauro-Beta-Muricholic Acid, a Naturally Occurring FXR Antagonist. Cell Metab. 2013; 17(2):225-235.
Schloss et al., Introducing mothur: open-source, platform-independent, community-supported software for describing and comparing microbial communities. Appl Environ Microbiol. Dec. 2009;75(23):7537-41. doi: 10.1128/AEM.01541-09. Epub Oct. 2, 2009.
Serafimova et al., Reversible Targeting of Noncatalytic Cysteines with Chemically Tuned Electrophiles. Nature Chemical Biology. 2012; 8(5): 471-476.
Setchell et al., General methods for the analysis of metabolic profiles of bile acids and related compounds in feces. J Lipid Res. 1983; 24: 1085-1100.
Setchell et al., Serum bile acid analysis. Clin Chim Acta. Jan. 7, 1983;127(1):1-17. doi: 10.1016/0009-8981(83)90070-0.
Setchell et al., Ursodeoxycholic acid-disulphate (SUDCA)-a potent chemopreventive agent against colon cancer in: Bile Acids: Biological Actions and Clinical Relevance. Falk Symposium 155. 2007; 194-200.
Shang et al., Colesevelam improves insulin resistance in a diet-induced obesity (F-DIO) rat model by increasing the release of GLP-1. Am J Physiol Gastrointest Liver Physiol. Mar. 2010;298(3):G419-24. doi: 10.1152/ajpgi.00362.2009. Epub Dec. 31, 2009.
Sisley et al., Hypothalamic Vitamin D Improves Glucose Homeostasis and Reduces Weight. Diabetes. Sep. 2016;65(9):2732-41. doi: 10.2337/db16-0309. Epub May 23, 2016.
Smith et al., Discovery of Bile Salt Hydrolase Inhibitors Using an Efficient High-Throughput Screening System. PLOS ONE. 2014; 9(1): e85344.
Solbach et al., BaiCD gene cluster abundance is negatively correlated with Clostridium difficile infection. PLoS One. May 8, 2018;13(5):e0196977. doi: 10.1371/journal.pone.0196977. eCollection 2018.
Song et al., Selective Activation of Liver X Receptor Alpha by 6alpha-Hydroxy Bile Acids and Analogs. Steroids. 2000; 65(8): 423-427.
Song et al., Taxonomic Profiling and Populational Patterns of Bacterial Bile Salt Hydrolase (BSH) Genes Based on Worldwide Human Gut Microbiome. Microbiome. 2019; 7(1): 9.

(56) References Cited

OTHER PUBLICATIONS

Spiljar et al., The Immune System Bridges the Gut Microbiota with Systemic Energy Homeostasis: Focus on TLRs, Mucosal Barrier, and SCFAs. Front Immunol. 2017; 8: 1353.
Staudinger et al., The Nuclear Receptor PXR Is a Lithocholic Acid Sensor That Protects Against Liver Toxicity. PNAS. 2001; 98(6):3369-3374.
Steinert et al., Intestinal GLP-1 and satiation: from man to rodents and back. Int J Obes (Lond). Feb. 2016;40(2):198-205. doi: 10.1038/ijo.2015.172. Epub Aug. 28, 2015.
Stellwag et al., Purification and Characterization of Bile Salt Hydrolase From Bacteroides Fragilis Subsp. Fragilis. Biochim Biophys Acta. Nov. 8, 1976;452(1):165-76. doi: 10.1016/0005-2744(76)90068-1.
Stoltz et al., Synthesis and Biological Evaluation of Bile Acid Analogues Inhibitory to Clostridium difficile Spore Germination. J Med Chem. Apr. 27, 2017;60(8):3451-3471. doi: 10.1021/acs.jmedchem.7b00295. Epub Apr. 12, 2017.
Strelow, A Perspective on the Kinetics of Covalent and Irreversible Inhibition. SLAS Discov. 2017; 22(1): 3-20.
Summerfield et al., Renal synthesis of bile acid sulphates: evidence from man and the isolated perfused rat kidney. Clinical Science and Molecular Medicine. 1976; 50(2): 25P-26P.
Summerfield et al., Synthesis of bile acid monosulphates by the isolated perfused rat kidney. Biochem J. May 15, 1976;156(2):339-45. doi: 10.1042/bj1560339.
Sun et al., Gut Microbiota and Intestinal FXR Mediate the Clinical Benefits of Metformin. Nat. Med. 2018; 24(12): 1919-1929.
Sun et al., Identification of functionally relevant residues of the rat ileal apical sodium-dependent bile acid cotransporter. J Biol Chem. Jun. 16, 2006;281(24):16410-8. doi: 10.1074/jbc.M600034200. Epub Apr. 11, 2006.
Takikawa et al., Binding of bile acids by glutathione S-transferases from rat liver. J Lipid Res. Sep. 1986;27(9):955-66.
Takikawa et al., Comparison of the affinities of newly identified human bile acid binder and cationic glutathione S-transferase for bile acids. J Lipid Res. Jun. 1986;27(6):652-7.
Takikawa et al., Effects of organic anions and bile acids on biliary lipid excretion in hyperbilirubinemic mutant Sprague-Dawley rats. J Hepatol. Feb. 1993;17(2):247-52. doi: 10.1016/s0168-8278(05)80046-7.
Takikawa et al., Effects of ursodeoxycholate and its conjugates on biliary glutathione excretion in rats. Dig Dis Sci. Oct. 1996;41(10):1953-8. doi: 10.1007/BF02093595.
Takikawa et al., Effects of ursodeoxycholate, its glucuronide and disulfate and beta-muricholate on biliary bicarbonate concentration and biliary lipid excretion. J Hepatol. May 1992;15(1-2):77-84. doi: 10.1016/0168-8278(92)90015-h.
Takikawa et al., Enhanced biliary excretion of lithocholate-3-sulfate by ursodeoxycholate- 3,7-disulfate infusion in Eisai hyperbilirubinemic rat (EHBR). Dig Dis Sci. Jan. 1998;43(1):188-92. doi: 10.1023/a:1018809028425.
Tan et al., A multi-chamber microfluidic intestinal barrier model using Caco-2 cells for drug transport studies. PLoS One. May 10, 2018;13(5):e0197101. doi: 10.1371/journal.pone.0197101. eCollection 2018.
Tanaka et al., Bile Salt Hydrolase of Bifidobacterium Longum-Biochemical and Genetic Characterization. Appl Environ Microbiol. 2000; 66(6): 2502-2512.
Thaiss et al., The Microbiome and Innate Immunity. Nature. 2016; 535 (7610): 65-74.
Tiscornia et al., A general method for gene knockdown in mice by using lentiviral vectors expressing small interfering RNA. Proc Natl Acad Sci U S A. Feb. 18, 2003;100(4):1844-8. doi: 10.1073/pnas.0437912100. Epub Jan. 27, 2003.
Tremaroli et al., Roux-en-Y Gastric Bypass and Vertical Banded Gastroplasty Induce Long-Term Changes on the Human Gut Microbiome Contributing to Fat Mass Regulation. Cell Metab. Aug. 4, 2015;22(2):228-38. doi: 10.1016/j.cmet.2015.07.009.
Tserng et al., Bile acid sulfates. III. Synthesis of 7- and 12-monosulfates of bile acids and their conjugates using a sulfur trioxide-triethylamine complex. Steroids. Feb. 1979;33(2):167-82. doi: 10.1016/0039-128x(79)90024-2.
Turnbaugh et al., An Obesity-Associated Gut Microbiome with Increased Capacity for Energy Harvest. Nature. 2006; 444(7122): 1027-31.
Uegaki et al., Effect of organic anions and bile acid conjugates on biliary excretion of taurine-conjugated bile acid sulfates in the rat. Steroids. Nov. 1999;64(11):790-5. doi: 10.1016/s0039-128x(99)00071-9.
Van De Laarschot et al., The role of bile salts in liver regeneration. Hepatol Int. Sep. 2016;10(5):733-40. doi: 10.1007/s12072-016-9723-8. Epub Apr. 5, 2016.
Vavassori et al., The Bile Acid Receptor FXR Is a Modulator of Intestinal Innate Immunity. J. Immunol. 2009; 183(10): 6251-6261.
Verhoeckx et al., Caco-2 Cell Line. The Impact of Food Bioactives on Health. 2015; 175:103-111.
Wahlstrom et al., Intestinal Crosstalk between Bile Acids and Microbiota and Its Impact on Host Metabolism. Cell Metab. Jul. 12, 20164(1):41-50. doi: 10.1016/j.cmet.2016.05.005. Epub Jun. 16, 2016.
Walker et al., Importance of sulfur-containing metabolites in discriminating fecal extracts between normal and type-2 diabetic mice. J Proteome Res. Oct. 3, 2014;13(10):4220-31. doi: 10.1021/pr500046b. Epub Sep. 2, 2014.
Wallace et al., Alleviating Cancer Drug Toxicity by Inhibiting a Bacterial Enzyme. Science. 2010; 330(6005): 831-835.
Wang et al., Identification and Characterization of a Bile Salt Hydrolase From Lactobacillus Salivarius for Development of Novel Alternatives to Antibiotic Growth Promoters. Appl. Environ. Microbiol. 2012; 78(24): 8795-8802.
Weber et al., Nephele: a cloud platform for simplified, standardized and reproducible microbiome data analysis. Bioinformatics. Apr. 15, 2018;34(8):1411-1413. doi: 10.1093/bioinformatics/btx617.
Weerapana et al., Tandem orthogonal proteolysis-activity-based protein profiling (Top-ABPP)—a general method for mapping sites of probe modification in proteomes. Nat Protoc. 2007;2(6):1414-25. doi: 10.1038/nprot.2007.194.
Wilson et al., Keap Calm, and Carry on Covalently. J Med Chem. Oct. 10, 2013;56(19):7463-76. doi: 10.1021/jm400224q. Epub Jul. 25, 2013.
Wrzosek et al. Transplantation of human microbiota into conventional mice durably reshapes the gut microbiota. Sci Rep. May 1, 2018;8(1):6854. doi: 10.1038/s41598-018-25300-3.
Wu et al., Vitamin D receptor negatively regulates bacterial-stimulated NF-kappaB activity in intestine. Am J Pathol. Aug. 2010;177(2):686-97. doi: 10.2353/ajpath.2010.090998. Epub Jun. 21, 2010.
Xie et al., An Intestinal Farnesoid X Receptor-Ceramide Signaling Axis Modulates Hepatic Gluconeogenesis in Mice. Diabetes. 2017; 66 (3): 613-626.
Xie et al., Pharmacological Targeting of the Pseudokinase Her3. Nature Chemical Biology. 2014; 10(12): 1006-1012.
Yang et al., MX1013, a Dipeptide Caspase Inhibitor with Potent in Vivo Antiapoptotic Activity. Br. J. Pharmacol. 2003; 140(2): 402-412.
Yao et al., A selective gut bacterial bile salt hydrolase alters host metabolism. Elife. Jul. 17, 2018;7:e37182. doi: 10.7554/eLife.37182.
Yao et al., Nontargeted analysis of the urine nonpolar sulfateome: a pathway to the nonpolar xenobiotic exposome. Rapid Commun Mass Spectrom. Nov. 15, 2016;30(21):2341-2350. doi: 10.1002/rcm.7726.
Yousef et al., Effect of complete sulfation of bile acids on bile formation: role of conjugation and No. of sulfate groups. Hepatology. Mar. 1992;15(3):438-45. doi: 10.1002/hep.1840150314.
Zhang et al., Effects of feeding bile acids and a bile acid sequestrant on hepatic bile acid composition in mice. J Lipid Res. Nov. 2010;51(11):3230-42. doi: 10.1194/jlr.M007641. Epub Jul. 29, 2010.
Zhang et al., Lake char (Salvelinus namaycush) olfactory neurons are highly sensitive and specific to bile acids. J Comp Physiol A

(56) References Cited

OTHER PUBLICATIONS

Neuroethol Sens Neural Behav Physiol. Feb. 2009;195(2):203-15. doi: 10.1007/s00359-008-0399-y. Epub Jan. 10, 2009.

Zybailov et al., Statistical analysis of membrane proteome expression changes in *Saccharomyces cerevisiae*. J Proteome. Sep. 2006;5(9):2339-47. doi: 10.1021/pr060161n.

Extended European Search Report for Application No. 20805532.7, mailed Jan. 5, 2023.

Adhikari et al., Development of a covalent inhibitor of gut bacterial bile salt hydrolases. BioRxiv. May 17, 2019. URL: https: //www.biorxiv.org/content/10.1101/640086v1.full/ [retrieved from the internet: Dec. 14, 2022].

Fried et al., The synthesis of diazo, halo, and sulfoxy bile acid derivatives: potential affinity labels. Steroids. Aug. 1979;34(2):171-87. doi: 10.1016/0039-128x(79)90046-1.

Ishihara, Uber Den Systematischen Abbau Der Chenodeoxycholsaure. Journal of Biochemistry. 1938; 27(2):265-277. DOI: 10.1093/oxfordjournals. jbchem.a125715.

International Preliminary Report on Patentability for Application No. PCT/US2020/032016, mailed Nov. 25, 2021.

Extended European Search Report for Application No. 19892790.7, mailed Aug. 18, 2022.

International Preliminary Report on Patentability for Application No. PCT/US2021/031277, mailed Nov. 17, 2022.

Adhikari et al., A Gut-Restricted Lithocholic Acid Analog as an Inhibitor of Gut Bacterial Bile Salt Hydrolases. ACS Chem Biol. Aug. 20, 2021;16(8):1401-1412. doi: 10.1021/acschembio. 1c00192. Epub Jul. 19, 2021.

D'Amore et al., Design, synthesis, and biological evaluation of potent dual agonists of nuclear and membrane bile acid receptors. J Med Chem. Feb. 13, 2014;57(3):937-54. doi: 10.1021/jm401873d. Epub Jan. 17, 2014.

Fader et al., 2,3,7,8-Tetrachlorodibenzo-p-dioxin (TCDD)-elicited effects on bile acid homeostasis: Alterations in biosynthesis, enterohepatic circulation, and microbial metabolism. Sci Rep. Jul. 19, 2017;7(1):5921. doi: 10.1038/s41598-017-05656-8.

Festa et al., Exploitation of cholane scaffold for the discovery of potent and selective farnesoid X receptor (FXR) and G-protein coupled bile acid receptor 1 (GP-BAR1) ligands. J Med Chem. Oct. 23, 2014;57(20):8477-95. doi: 10.1021/jm501273r. Epub Oct. 9, 2014.

Kurosawa et al., Synthesis of 3α,7α, 12α-trihydroxy- and 3α,7α-dihydroxy-5β-cholestan-26-oic acids by the use of β-ketosulfoxide. Steroids. Jul. 1995;60(7):439-44. doi: 10.1016/0039-128x(95)00033-m.

Kurosawa et al., Synthesis of diastereomers of 3 alpha, 7 alpha, 12 alpha, 24-tetrahydroxy- and 3 alpha, 7 alpha,24-trihydroxy-5 beta-cholestan-26-oic acids and their structures. Steroids. Jul. 1996;61(7):421-8. doi: 10.1016/0039-128x(96)00062-1.

Nakhi et al., 7-Methylation of Chenodeoxycholic Acid Derivatives Yields a Substantial Increase in TGR5 Receptor Potency. J Med Chem. Jul. 25, 2019;62(14):6824-6830. doi: 10.1021/acs.jmedchem. 9b00770. Epub Jul. 3, 2019.

Sepe et al., Modification on ursodeoxycholic acid (UDCA) scaffold. discovery of bile acid derivatives as selective agonists of cell-surface G-protein coupled bile acid receptor 1 (GP-BAR1). J Med Chem. Sep. 25, 2014;57(18):7687-701. doi: 10.1021/jm500889f. Epub Sep. 7, 2014.

Skyler et al., Differentiation of Diabetes by Pathophysiology, Natural History, and Prognosis. Diabetes. Feb. 2017;66(2):241-255. doi: 10.2337/db16-0806. Epub Dec. 15, 2016.

Barysevich et al., Palladium-Catalyzed 2-(Neopentylsulfinyl)aniline Directed C-H Acetoxylation and Alkenylation of Arylacetamides. Eur J Org Chem. 2020; 8(14): 937-943. https://doi.org/10.1002/ejoc.201901646.

Bukiya et al., Calcium- and voltage-gated potassium (BK) channel activators in the 5β-cholanic acid-3α-ol analogue series with modifications in the lateral chain. NIH Public Access Author Manuscript. ChemMedChem. Author manuscript; available in PMC Oct. 10, 2014. Published in final edited form as: ChemMedChem. Oct. 2012;7(10):1784-92. doi: 10.1002/cmdc.201200290. Epub Sep. 4, 2012.

CAPLUS Accession No. 2010:1369244. Steroid side chain construction using the Knoevenagel reaction. Khripach et al.

Cloutier et al., Drastic fluorine effect: complete reversal of the selectivity in the Au-catalyzed hydroalkoxylation reaction of fluorinated haloalkynes. Chem Commun (Camb). Jun. 4, 2020;56(44):5969-5972. doi: 10.1039/d0cc02009e. Epub Apr. 29, 2020.

Cloutier et al., Drastic fluorine effect: complete reversal of the selectivity in the Au-catalyzed hydroalkoxylation reaction of fluorinated haloalkynes. Chem Commun (Camb). 2020. Supplementary Information. 237 pages.

Harikandei et al., Synthesis, in-vitro antiprotozoal activity and molecular docking study of isothiocyanate derivatives. Bioorg Med Chem. Jan. 1, 2020;28(1):115185. doi: 10.1016/j.bmc.2019.115185. Epub Nov. 9, 2019.

James et al., Basic derivatives of cholane and norcholane. J Chem Soc. Aug. 1946:665-70. doi: 10.1039/jr9460000665.

Sharma et al., Bile acid toxicity structure-activity relationships: correlations between cell viability and lipophilicity in a panel of new and known bile acids using an oesophageal cell line (HET-1A). Bioorg Med Chem. Sep. 15, 2010;18(18):6886-95. doi: 10.1016/j.bmc.2010.07.030. Epub Jul. 19, 2010.

Sharma et al., Ursodeoxycholic acid amides as novel glucocorticoid receptor modulators. J Med Chem. Jan. 13, 2011;54(1):122-30. doi: 10.1021/jm100860s. Epub Dec. 15, 2010.

* cited by examiner

= electrophilic warhead

R = H, chenodeoxycholic acid core
R = OH, cholic acid acid

| analog | electrophilic warhead |
|---|---|
| 1, R = H |  |
| 2, R = H |  |
| 3, R = H |  |
| 4, R = H |  |
| 5, R = H |  |
| 6, R = H |  |
| 7, R = H |  |
| 8, R = H |  |
| 9, R = OH |  |

Riboflavin (10)

Caffeic acid phenethyl ester
(CAPE, 11)

inhibitor 1 inhibitor 7 inhibitor 9

3-sulfated-lithocholic acid-fluoromethyl ketone

3S-LCA-FMK

1, R = H
2, R = H
3, R = H
4, R = H
5, R = H
6, R = H
7, R = H
8, R = H
9, R = OH

7-$N_3$ (compound 12)

GR-7 (compound 13)

Inhibitor 7

Inhibitor 8

Inhibitor 9

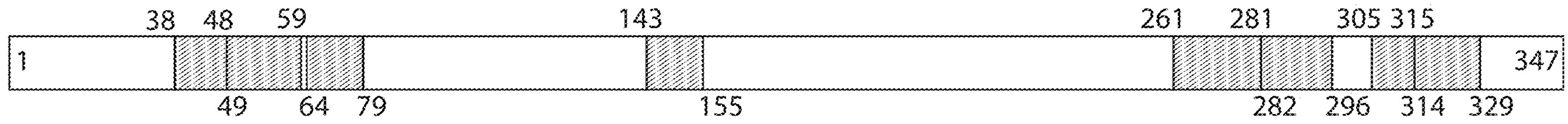

| | | | | | | | | | | |
|---|---|---|---|---|---|---|---|---|---|---|
| | 1 | 11 | 21 | 31 | 41 | 51 | 61 | 71 | 81 | 91 |
| 1 | MFIRRLKPWL | VQPSMRMMNA | PGQSNKGRKS | IMCTGVRFSD | EEGNMYFGRN | LDWSESYGES | ILATPRGYHY | DNVFGASGKA | TPNAVIGVGV | VMADRPMYFD |
| 101 | CANEHGLAIA | GLNFPGYAEF | VHEPVEGTDN | VATFEFPLWV | ARNFDSVDEV | EEALKNVTLV | SQIVPGQQES | LLHWIIGDSE | RSIVVEQMAD | GMHVHHDDVD |
| 201 | VLTNQPTFGF | HMENLRNYMC | VGNEMAEPAT | WGKASLSAWG | AGVSMHGIPG | DVSSPSRFVR | VAYANTHYPQ | QEGEAANVSR | LFHTLGSVQM | VDGMAKMGNG |
| 301 | QFERTLFTSG | YSSKTNTYYM | NTYDDPATRS | YAMADFDMDS | SELITAA | | | | | |

Figure 27E

SMALL MOLECULE MODULATORS OF GUT BACTERIAL BILE ACID METABOLISM

RELATED APPLICATIONS

The present application is a national stage filing under 35 U.S.C. § 371 of International PCT Application PCT/US2020/032016, filed May 8, 2020, which claims priority under 35 U.S.C. § 119(e) to U.S. provisional applications, U.S. Ser. No. 62/846,457, filed May 10, 2019, and U.S. Ser. No. 62/962,048, filed Jan. 16, 2020, each of which is incorporated herein by reference.

GOVERNMENT SUPPORT

This invention was made with government support under GM128618 and DK034854 awarded by the National Institutes of Health. The government has certain rights in the invention.

FIELD OF THE INVENTION

The technology described herein relates to compounds, compositions, and methods for inhibiting bile salt hydrolase (BSH).

BACKGROUND OF THE INVENTION

Bile salt hydrolase (BSH) enzymes are widely expressed by human gut bacteria and catalyze the gateway reaction that leads to the conversion of host-produced primary bile acids into bacterially modified secondary bile acids. Both primary and secondary bile acids regulate key metabolic and immune processes in the host by acting as ligands for host receptors. There is currently an unmet need for a potent and selective agent to inhibit BSH for the treatment of diseases such as cancer, inflammation, obesity, diabetes, and gastrointestinal diseases and to use as a tool to understand bile acid physiology in the host subject.

SUMMARY OF THE INVENTION

In one aspect, provided herein is a compound of Formula (I):

FORMULA (I)

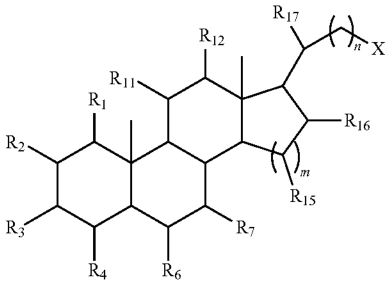

wherein:

n is 1, 2, 3, 4, 5, 6, 7, 8, 9, or 10;

m is 1, 2, 3, or 4;

X is an electrophilic group;

$R_1$, $R_2$, $R_3$, $R_4$, $R_6$, $R_7$, $R_{11}$, $R_{12}$, $R_{15}$, $R_{16}$ and $R_{17}$ are independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR_{18}$, $N(R_{18})_2$, $SR_{18}$, halogen, CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —NHC(O)$NHNH_2$;

each $R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a pharmaceutically acceptable salt thereof.

In one aspect, the compound of Formula (I) is of Formula (I'):

(I')

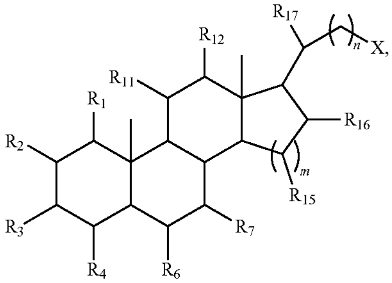

wherein:

n is 1, 2, 3, 4, 5, 6, 7, 8, 9 or 10;

m is 1, 2, 3 or 4;

X is an electrophilic group;

$R_1$, $R_2$, $R_3$, $R_4$, $R_6$, $R_7$, $R_{11}$, $R_{12}$, $R_{15}$, $R_{16}$ and $R_{17}$ are independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR_{18}$, $N(R_{18})_2$, $SR_{18}$, halogen, CN, —CHO, —$CO_2H$, —$CO_2R_{18}$, —$NO_2$, —$ONO_2$, —$SO_2Cl$, —$SO_3H$, —$OSO_3H$, —$NR_{18}SO_3H$, —$PO_3H_2$, —$OPO_3H_2$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —NHC(O)$NHNH_2$, wherein each $R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

or a pharmaceutically acceptable salt thereof.

In another aspect, provided herein is a pharmaceutical composition comprising a compound provided herein and a pharmaceutically acceptable carrier or excipient.

In another aspect, provided herein is a method for inhibiting a bile salt hydrolase (BSH), the method comprising contacting a BSH with a compound provided herein.

In another aspect, provided herein is a method of inhibiting bile acid deconjugation in a subject, the method comprising administering to a subject a therapeutically effective amount of a compound provided herein.

In another aspect, provided herein is a method of promoting bile acid conjugation in a subject, the method comprising administering to a subject a therapeutically effective amount of a compound provided herein.

In another aspect, provided herein is a method of modulating bile acids in a subject, the method comprising administering to the subject in need thereof a therapeutically effective amount of a compound provided herein. In another aspect, provided herein is a method for treating a metabolic disorder (e.g., diabetes, obesity), gastrointestinal disease (e.g., a gastrointestinal infection; inflammatory bowel disease (IBD); appendicitis; Crohn's disease (CD); ulcerative colitis (UC); gastritis; enteritis; esophagitis; pancreatitis; diabetes; hepatitis; liver disease (e.g., Non-alcoholic Fatty Liver Disease (NAFLD); non-alcoholic steatohepatitis (NASH); hepatitis A; hepatitis B; hepatitis C; autoimmune hepatitis; and cirrhosis of the liver); gastroesophageal reflux disease (GERD); celiac disease; diverticulitis; food intolerance; ulcer; infectious colitis; irritable bowel syndrome; leaky gut; and cancer), cancer (e.g., cancer of the digestive system; hepatic carcinoma; liver cancer; colon cancer; esophageal cancer; gastric cancer; hepatoma; kidney or renal cancer; oral cavity cancer; pancreatic cancer; prostate cancer; rectal cancer; stomach cancer; basal cell carcinoma, biliary tract cancer; lung cancer; bladder cancer; cervical cancer; endometrial cancer; uterine cancer; and cancer of the urinary system) e.g., or an inflammatory disease (e.g., Crohn's disease, inflammatory bowel disease, ulcerative colitis, pancreatitis, hepatitis, liver disease, biliary atresia, appendicitis, gastritis, diverticulitis, celiac disease, food intolerance, enteritis, ulcer, gastroesophageal reflux disease (GERD), psoriatic arthritis, psoriasis, rheumatoid arthritis), the method comprising administering to a subject in need thereof a compound of Formulae (I)-(XVIII). genetically engineered microorganism or population thereof, that secretes cholic acid 7-sulfate.

In another aspect, provided are compounds of Formulae (I)-XVIII), or pharmaceutically acceptable salts thereof, or pharmaceutical compositions comprising a compound of Formulae (I)-(XVIII), for use in treating a metabolic disorder (e.g., diabetes, obesity), gastrointestinal disease (e.g., a gastrointestinal infection; inflammatory bowel disease (IBD); appendicitis; Crohn's disease (CD); ulcerative colitis (UC); gastritis; enteritis; esophagitis; pancreatitis; diabetes; hepatitis; liver disease (e.g., Non-alcoholic Fatty Liver Disease (NAFLD); non-alcoholic steatohepatitis (NASH); hepatitis A; hepatitis B; hepatitis C; autoimmune hepatitis; and cirrhosis of the liver); gastroesophageal reflux disease (GERD); celiac disease; diverticulitis; food intolerance; ulcer; infectious colitis; irritable bowel syndrome; leaky gut; and cancer), cancer (e.g., cancer of the digestive system; hepatic carcinoma; liver cancer; colon cancer; esophageal cancer; gastric cancer; hepatoma; kidney or renal cancer; oral cavity cancer; pancreatic cancer; prostate cancer; rectal cancer; stomach cancer; basal cell carcinoma, biliary tract cancer; lung cancer; bladder cancer; cervical cancer; endometrial cancer; uterine cancer; and cancer of the urinary system) e.g., or an inflammatory disease (e.g., Crohn's disease, inflammatory bowel disease, ulcerative colitis, pancreatitis, hepatitis, liver disease, biliary atresia, appendicitis, gastritis, diverticulitis, celiac disease, food intolerance, enteritis, ulcer, gastroesophageal reflux disease (GERD), psoriatic arthritis, psoriasis, rheumatoid arthritis) in a subject in need thereof.

In another aspect, provided are kits comprising a compound of Formulae (I)-(XVIII), or a pharmaceutically acceptable salt thereof, or a pharmaceutical composition comprising a compound of Formulae (I)-(XVII). In certain embodiments, the kit further comprises instructions for administration (e.g., human administration) and/or use.

The details of certain embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE DRAWINGS

FIG. 1A shows that BSH are the gateway enzyme in the conversion of primary (host-produced) to secondary (bacterially produced) bile acids. Removal or inhibition of BSH should result in a decrease in deconjugated primary and secondary bile acids. FIG. 1B shows that certain primary and secondary bile acids are ligands for host nuclear hormone receptors (NhR) and G protein-coupled receptors (GPCRs). By acting as agonists or antagonists for these receptors, these bile acids affect host processes, including metabolic control and immune response.

FIG. 2A shows the mechanism of enzymatic amide bond cleavage by BSH. FIG. 2B shows a co-crystal structure of the BSH from the Gram positive gut bacterium *Clostridium perfringens* and deconjugated tauro-deoxycholic acid (TDCA) (PDB 2BJF) guided the inhibitor design. While hydrophobic interactions orient the bile acid core in the active site (magenta residues), the D-ring side chain and amino acid are exposed to solvent. FIG. 2C shows the representative mechanism of BSH inhibition by rationally designed inhibitors. Attack of the catalytic nucleophilic cysteine residue in the BSH active site can result in covalent binding to an inhibitor. FIG. 2D shows a library of synthesized inhibitors. Electrophilic warheads that had been successfully incorporated into the design of kinase and protease inhibitors were appended to the chenodeoxycholic acid bile core in order to create a broad-spectrum BSH inhibitor. FIG. 2E shows the most potent BSH inhibitors identified from a high-throughput screen, riboflavin and caffeic acid phenethyl ester (CAPE), that are were also included in this study.

FIG. 3A shows the screen of inhibitor library versus *B. theta* BSH showing % deconjugation at 2 and 21 hours. FIG. 3B shows the screen of compounds 1, 7, and CAPE versus *B. longum* BSH showing % deconjugation at 2 and 21 hours. Inhibitor (100 μM) was incubated with 200 nM rBSH for 30 mins followed by addition of taurine-conjugated bile acid substrates (TβMCA, TCA, TUDCA and TDCA, 25 μM each). Deconjugation of substrate was followed by UPLC-MS. Assays were performed in biological triplicate. Data are presented as mean±SEM.

FIG. 4A demonstrates that compound 7 inhibits BSH activity in live Gram negative (*B. theta* VPI 5482, *Bacteroides fragilis* ATCC 25285, and *Bacteroides* vulgatus ATCC 8482) and Gram positive (*Lactobacillus plantarum* WCFS1, *Clostridium perfringens* ATCC 13124, and *Bifidobacterium adolescentis* L2-32) bacteria. Inhibitor (100 μM of compound 7 or CAPE) and taurine-conjugated bile acid substrates (TβMCA, TCA, TUDCA and TDCA, 25 μM each) were added to bacterial cultures at $OD_{600}$ 0.1. Bacterial cultures were allowed to grow into stationary phase and percent deconjugation at 24 h was determined by UPLC-MS. Assays were performed in biological triplicate. Data are presented as mean±SEM. One-way ANOVA followed by Tukey's multiple comparisons test. *p<0.05, p<0.01, *p<0.0001, ****p<0.00001. No statistical analysis is presented for *B. vulgatus* because the replicates had a standard error of zero. FIG. 4B shows that compound 7 is not bactericidal. $OD_{600}$ of bacterial culture was measured at 24 hours. CAPE inhibited the growth of the Gram positive strains tested. Red downward arrows indicate percentage decrease compared to DMSO control. FIG. 4C shows that dose-response curves and calculated $IC_{50}$ values for compound 7 incubated with growing cultures of *B. theta* (Gram negative) and *B. adolescentis* (Gram positive) demonstrate that compound 7 is a potent broad-spectrum BSH inhibitor. FIG. 4D shows representative UPLC-MS traces showing that inhibitor structure determines BSH inhibitory activity against growing *B. theta* cultures. Compounds 1, 7 and 9 were tested at 1 and 10 μM concentrations. For simplicity, one substrate (GUDCA) was added to bacterial cultures and its deconjugation to UDCA was tracked by UPLC-MS. Inhibitor 9, which has a cholic acid (C12=OH) core and an α-FMK warhead, demonstrated significantly diminished activity to inhibit *B. theta* BSH.

FIGS. 5A to 5B show mass spectrometry revealed that compound 7 monolabels *B. theta* BSH. FIG. 5A shows mass spectra (left) and zero-charge mass spectra (right, overlayed) of BSH treated with DMSO (top, trace in red) or 10-fold excess of inhibitor compound 7 for 2 h (bottom, trace in green). A shift in mass of 388 Da is consistent with covalent modification of BSH with a loss of HF. FIG. 5B shows top-down MS of BSH treated with 10 fold excess of inhibitor compound 7. Ions of type c and z are indicated with red and green glyphs respectively. Ion c3 indicates that modification is on the N-terminus Cys2 residue. FIG. 5C shows X-ray co-crystal structure of compound 7 bound to *B. theta* BSH confirmed that compound 7 was covalently linked to active site Cys2 and not to Cys67, and that the C25 fluorine had been eliminated. C3 of the steroidal core was solvent-exposed, indicating this site can be amenable to modification.

FIG. 6A shows that Compound 7 is neither a farnesoid X receptor (FXR) agonist nor antagonist as determined by an FXR coactivator recruitment assay. FXR antagonist activity of compound 7 on FXR was evaluated in the presence of the known FXR agonist GW4064 at its $EC_{50}$ value (50 nM). n=4 biological replicates per concentration. Data are presented as mean±SEM. FIG. 6B shows that compound 7 is neither a G protein-coupled bile acid receptor (GPBAR1, also known as TGR5) agonist nor antagonist. Endogenous TGR5 agonist activity was measured by incubating Caco-2 cells with varying concentrations of compound 7 overnight. Endogenous TGR5 antagonist activity was evaluated in the presence of 10 μM of the TGR5 agonist LCA. n≥3 biological replicates per concentration. Data are presented as mean±SEM. One-way ANOVA followed by Dunnett's multiple comparisons test, ns=not significant. FIG. 6C shows that compound 7 did not display toxicity toward Caco-2 cells up to a concentration of 50 μM. n≥3 biological replicates per concentration. Data are presented as mean±SEM. One-way ANOVA followed by Dunnett's multiple comparisons test, *p<0.05.

FIG. 7A shows fecal BSH activity assay design. Freshly collected feces from conventional mice (1 mg/mL) were resuspended in PBS and incubated with 20 μM of inhibitor (Compound 1, 7, or CAPE) for 30 mins. Glycochenodeoxycholic acid-d4 (GCDCA-d4, 100 μM) was added as a substrate and deconjugation was determined by UPLC-MS after 18 hours. FIG. 7B shows that compound 7 effectively inhibited BSH activity in a fecal slurry, while CAPE displayed minimal inhibitory activity. Consistent with in vitro results, compound 1 displayed moderate BSH inhibition. Assays were performed in biological triplicate. Data are presented as mean±SEM. FIGS. 7C to 7E shows the treatment of conventional mice with a single dose of compound 7 resulted in recoverable inhibition of BSH activity and a shift toward deconjugated bile acids. n=4 mice per group, Welch's t test, *p<0.05, p<0.01, ns=not significant. FIG. 7C shows the design of in vivo BSH inhibition experiment. Male conventional C57BL/6 mice were gavaged with a single dose of compound 7 (10 mg/kg) or vehicle control. Feces were collected 1 day, 1.5 days, 2 days, and 2.5 days post-gavage. Bile acid profiling was performed 1-day post-gavage. FIG. 7D shows that BSH activity was significantly lower in the compound 7-treated group compared to the control group 1 day and 1.5 days post-gavage as determined by BSH activity in feces. BSH had recovered 2 days post-gavage. BSH activity was determined by resuspending fresh feces from inhibitor- or vehicle-treated groups with substrate (GCDCA-d4, 100 μM), incubating for 25 min, and quantifying deconjugation by UPLC-MS. FIG. 7E shows fecal bile acid composition 1 day post-gavage. Deconjugated bile acids, including the secondary bile acid deoxycholic acid (DCA), were decreased in the inhibitor-treated group. FIG. 7**F shows that microbial biomass did not differ between the inhibitor- and vehicle-treated groups 1 day or 2.5 days post-gavage. n=4 mice per group, Mann-Whitney test.

FIG. 8A shows the structure of 3-sulfated-lithocholic acid-fluoromethyl ketone (3S-LCA-FMK). FIG. 8B shows the design of in vivo BSH inhibition experiment. Male conventional C57Bl/6 mice were fed normal chow or 3S-LCA-FMK in chow (0.03% weight/weight) ad libitum for 7 days. Feces were collected pre-diet change and on days 3, 4, and 7 post-diet change. n=5 mice per group. FIG. 8C shows BSH activity was significantly reduced in the feces of mice fed 3S-LCA-FMK in chow. FIG. 8D shows that the concentration of 3S-LCA-FMK as measured in feces and cecal contents at sacrifice. No 3S-LCA-FMK was detectable in circulating plasma on day 4, indicating that the compound was gut-restricted.

FIG. 13A shows design of in vivo BSH inhibition experiment. Adult male C57BL/6 mice were gavaged with a single dose of compound 7 (10 mg/kg) or vehicle control. FIG. 13B shows BSH activity was measured in half-day increments starting 1 day post-gavage. Resuspended fresh feces from inhibitor- or vehicle-treated groups were incubated with substrate (GCDCA-d4, 100 PM) for 25 min and formation of product was quantified by UPLC-MS. n=4 mice per group, two-tailed Student's t test. FIG. 13C shows Fecal bile acid composition 1 day post-gavage. Deconjugated bile acids, including the secondary bile acid deoxycholic acid (DCA), were decreased in the inhibitor-treated group. n=4 mice per group, two-tailed Student's t test.

FIG. 15 shows identification of compound 7 as a potent broad-spectrum BSH inhibitor.

FIG. 17 shows compound structure affects BSH inhibitory activity against growing *B. theta* cultures.

tauro-cholic acid, TCA; tauro-ursodeoxycholic acid, TUDCA; and tauro-deoxycholic acid, TDCA) were added concomitantly to 200 nM rBSH with no preincubation period. Formation of deconjugated bile acid was measured using a UPLC-MS-based assay and reported as % conversion.

FIG. 21 shows compound 7 did not alter bile acid pools when incubated with *B. theta* BSH KO strain.

FIG. 23 shows mass spectrometry revealed that compound 7 monolabels *B. theta* BSH.

FIG. 25 shows compound 7 is neither an agonist nor an antagonist of FXR or TGR5 and not toxic to human cells.

FIG. 27E shows BSH derived tryptic peptides identified by LC-MS/MS analysis of in-gel digestion performed on bands indicated in FIG. 27D. Amino acids highlighted in red map to tryptic peptides identified at a ~1% FDR.

FIG. 29 shows compound 7 did not significantly affect bacterial community composition or microbial biomass in vivo.

FIG. 30 shows activity and in vivo effects of GR-7.

DEFINITIONS

Chemical Definitions

Figure 1A:
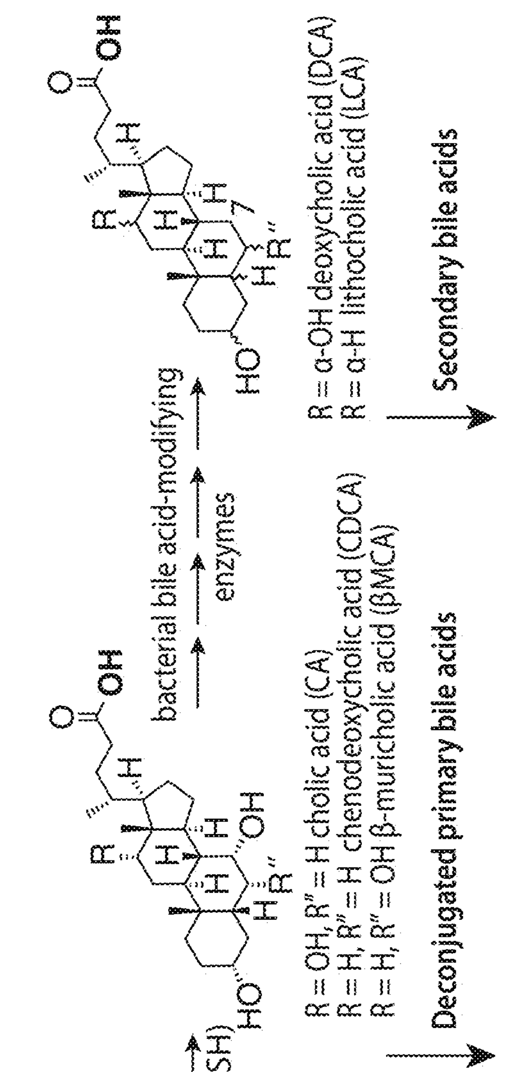
FIGS. 1A and 1B demonstrate chemical and biological effects of gut bacterial bile salt hydrolase (BSH).

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Definitions of common terms in immunology and molecular biology can be found in *The Merck Manual of Diagnosis and Therapy,* 19th Edition, published by Merck Sharp & Dohme Corp., 2011 (ISBN 978-0-911910-19-3); Robert S. Porter et al. (eds.), *The Encyclopedia of Molecular Cell Biology and Molecular Medicine*, published by Blackwell Science Ltd., 1999-2012 (ISBN 9783527600908); and Robert A. Meyers (ed.), *Molecular Biology and Biotechnology: a Comprehensive Desk Reference*, published by VCH Publishers, Inc., 1995 (ISBN 1-56081-569-8); *Immunology* by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); *Lewin's Genes XI,* published by Jones & Bartlett Publishers, 2014 (ISBN-1449659055); Michael Richard Green and Joseph Sambrook, *Molecular Cloning: A Laboratory Manual,* 4th ed., Cold Spring Harbor Laboratory Press, Cold Spring Harbor, N.Y., USA (2012) (ISBN 1936113414); Davis et al., *Basic Methods in Molecular Biology*, Elsevier Science Publishing, Inc., New York, USA (2012) (ISBN 044460149X); *Laboratory Methods in Enzymology: DNA*, Jon Lorsch (ed.) Elsevier, 2013 (ISBN 0124199542); *Current Protocols in Molecular Biology* (CPMB), Frederick M. Ausubel (ed.), John Wiley and Sons, 2014 (ISBN 047150338X, 9780471503385), *Current Protocols in Protein Science* (CPPS), John E. Coligan (ed.), John Wiley and Sons, Inc., 2005; and *Current Protocols in Immunology* (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Definitions of specific functional groups and chemical terms are described in more detail below. The chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Michael B. Smith, *March's Advanced Organic Chemistry,* 7$^{th}$ Edition, John Wiley & Sons, Inc., New York, 2013; Richard C. Larock, *Comprehensive Organic Transformations,* John Wiley & Sons, Inc., New York, 2018; and Carruthers, Some Modern Methods of Organic Synthesis, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, IN 1972). The disclosure additionally encompasses compounds as individual isomers substantially free of other isomers, and alternatively, as mixtures of various isomers.

The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). An alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred in the present invention. An alkylene is au uncyclized chain. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. A heteroalkyl is an uncyclized chain. The heteroatom(s) O, N, P, S, B, As, and Si may be placed at any interior position of the heteroalkyl group or at the position at which the alkyl group is attached to the remainder of the molecule. Examples include, but are not limited to: $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2$, $-S(O)-CH_3$, $-CH_2-CH_2-S(O)_2-CH_3$, $-CH{=}CHO-CH_3$, $-Si(CH_3)_3$, $-CH_2-CH{=}N-OCH_3$, $-CH{=}CH-N(CH_3)-CH_3$, $-O-CH_3$, $-O-CH_2-CH_3$, and $-CN$. Up to two or three heteroatoms may be consecutive, such as, for example, $-CH_2-NH-OCH_3$ and $-CH_2-O-Si(CH_3)_3$.

The term "heteroalkylene," by itself or as part of another substituent, means, unless otherwise stated, a divalent radical derived from heteroalkyl, as exemplified, but not limited by, $-CH_2-CH_2-S-CH_2-CH_2-$ and $-CH_2-S-CH_2-CH_2-NH-CH_2-$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $-C(O)_2R'-$ represents both $-C(O)_2R'-$ and $-R'C(O)_2-$. A heteroalkylene is an uncyclized chain. As described above, heteroalkyl groups, as used herein, include those groups that are attached to the remainder of the molecule through a heteroatom, such as $-C(O)R'$, $-C(O)NR'$, $-NR'R''$, $-OR'$, $-SR'$, and/or $-SO_2R'$. Where "heteroalkyl" is recited, followed by recitations of specific heteroalkyl groups, such as $-NR'R''$ or the like, it will be understood that the terms heteroalkyl and $-NR'R''$ are not redundant or mutually exclusive. Rather, the specific heteroalkyl groups are recited to add clarity. Thus, the term "heteroalkyl" should not be interpreted herein as excluding specific heteroalkyl groups, such as $-NR'R''$ or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. A cycloalkyl or heteroalkyl is not aromatic. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, $-C(O)R$ where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a $-O-$ bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substituents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, $—CF_3$, —CN, —OH, $—NH_2$, —COOH, $—CONH_2$, $—NO_2$, —SH, $—SO_2Cl$, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, $—OCF_3$, $—OCHF_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, $—CF_3$, —CN, —OH, $—NH_2$, —COOH, $—CONH_2$, $—NO_2$, —SH, $—SO_2Cl$, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, $—OCF_3$, $—OCHF_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, halogen, $—CF_3$, —CN, —OH, $—NH_2$, —COOH, $—CONH_2$, $—NO_2$, —SH, $—SO_2Cl$, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, $—OCF_3$, $—OCHF_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, $—CF_3$, —CN, —OH, $—NH_2$, —COOH, $—CONH_2$, $—NO_2$, —SH, $—SO_2Cl$, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, $—OCF_3$, $—OCHF_2$, unsubstituted alkyl, unsubstituted heteroalkyl, unsubstituted cycloalkyl, unsubstituted heterocycloalkyl, unsubstituted aryl, and unsubstituted heteroaryl.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

The term "silyl ether" as used herein, refers to a chemical compound containing a silicon atom covalently bonded to an alkoxy group generally having the structure $R^wR^xR^ySi—O—R^z$, wherein $R^w$, $R^x$, $R^y$, and $R^z$ are independently alkyl or aryl groups.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts," *Journal of Pharmaceutical Science,* 1977, 66, 1-19). Certain specific compounds of the present invention contain both basic and acidic functionalities that allow the compounds to be converted into either base or acid addition salts.

As used herein, the term "salt" refers to acid or base salts of the compounds used in the methods of the present invention. Illustrative examples of salts include mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. The term salt also refers to formation of a salt between two compounds.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY, or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

The term "obesity" refers to excess fat in the body. Obesity can be determined by any measure accepted and utilized by those of skill in the art. Currently, an accepted measure of obesity is body mass index (BMI), which is a measure of body weight in kilograms relative to the square of height in meters. Generally, for an adult over age 20, a BMI between about 18.5 and 24.9 is considered normal, a BMI between about 25.0 and 29.9 is considered overweight, a BMI at or above about 30.0 is considered obese, and a BMI at or above about 40 is considered morbidly obese. (See, e.g., Gallagher et al. (2000) Am J Clin Nutr 72:694-701.) These BMI ranges are based on the effect of body weight on increased risk for disease. Some common conditions related to high BMI and obesity include cardiovascular disease, high blood pressure (i.e., hypertension), osteoarthritis, cancer, and diabetes. Although BMI correlates with body fat, the relation between BMI and actual body fat differs with age and gender. For example, women are more likely to have a higher percent of body fat than men for the same BMI. Furthermore, the BMI threshold that separates normal, overweight, and obese can vary, e.g. with age, gender, ethnicity, fitness, and body type, amongst other factors. In some embodiments, a subject with obesity can be a subject with a body mass index of at least about 25 $kg/m^2$ prior to administration of a treatment as described herein. In some embodiments, a subject with obesity can be a subject with a body mass index of at least about 30 $kg/m^2$ prior to administration of a treatment, compound, or agent as described herein.

As used herein, the term "inflammation" or "inflamed" or "inflammatory" refers to activation or recruitment of the immune system or immune cells (e.g., T cells, B cells, macrophages). A tissue that has inflammation can become reddened, white, swollen, hot, painful, exhibit a loss of function, or have a film or mucus. Methods of identifying inflammation are well known in the art. Inflammation generally occurs following injury or infection by a microorganism. In some embodiments, the infection is caused by a bacteria selected from the group consisting of: *Staphylococcus; Helicobacter pylori; Escherichia coli; Salmonella; Campylobacter; Yersinia enterocolitica; Shigella; Clostridium; Bacteroides; Lactobacillus*; Parabacteroides; *Bifidobacterium; Listeria*; and *Streptococcus.*

As used herein the term "an inflammatory disease" refers to any disease that affects the immune system. The inflammatory disease can cause at least one symptom of the disease. These symptoms can include but are not limited to, diarrhea, vomiting, nausea, upset stomach, pain, swollen joints, malaise, fever, weight loss, weight gain, bleeding, any change in the consistency or frequency of a bowel movement or stool, or any other symptom associated with an inflammatory disease in a subject. In some embodiments, the inflammatory disease is an autoimmune disease.

In some embodiments of any of the aspects, the inflammatory disease is selected from the group consisting of: an infection; Crohn's disease, inflammatory bowel disease, ulcerative colitis, pancreatitis, hepatitis, liver disease, biliary atresia, appendicitis, gastritis, diverticulitis, celiac disease, food intolerance, enteritis, ulcer, gastroesophageal reflux disease (GERD), psoriatic arthritis, psoriasis, rheumatoid arthritis, or any other inflammatory disease known in the art.

As used herein, the term "gastrointestinal disease" refers to any disease that affects the gastrointestinal tract or gut. The gastrointestinal disease can cause at least one symptom of the disease. These symptoms can include but are not limited to, diarrhea, vomiting, nausea, upset stomach, pain, malaise, fever, weight loss, weight gain, bleeding, any change in the consistency or frequency of a bowel movement or stool, or any other symptom associated with a gastrointestinal disease in a subject. Non-limiting examples of gastrointestinal diseases include a gastrointestinal infection, inflammatory bowel disease (IBD), gastrointestinal injury, appendicitis, Crohn's disease (CD), ulcerative colitis (UC), gastritis, enteritis, esophagitis, gastroesophageal reflux disease (GERD), celiac disease, diverticulitis, food intolerance, ulcer, infectious colitis, irritable bowel syndrome, leaky gut, pancreatitis, diabetes, hepatitis, liver disease, and cancer.

As used herein, the term "liver disease" refers to any disease that affects the liver.

The liver disease can cause at least one symptom of the disease. These symptoms include but are not limited to bile acid dysbiosis, fatigue, weight loss, pain, yellowing of skin and/or eyes, or dark urine. Examples of liver diseases include but are not limited to Non-alcoholic Fatty Liver Disease (NAFLD); Non-alcoholic steatohepatitis (NASH); hepatitis A; hepatitis B; hepatitis C; autoimmune hepatitis; and cirrhosis of the liver.

As used herein, the term "cancer" refers to a hyperproliferation of cells that exhibit a loss of normal cellular control that results in unregulated growth, lack of differentiation, local tissue invasion, and metastasis. Cancer can be a solid tumor, leukemia, lymphoma, or multiple myeloma. As used herein, the term "tumor" refers to an abnormal growth of cells or tissues, e.g., of malignant type or benign type. Non-limiting examples of cancer include cancer of the digestive system; hepatic carcinoma; liver cancer; colon cancer; esophageal cancer; gastric cancer; hepatoma; kidney or renal cancer; oral cavity cancer; pancreatic cancer; prostate cancer; rectal cancer; stomach cancer; basal cell carcinoma, biliary tract cancer; lung cancer; bladder cancer; cervical cancer; endometrial cancer; uterine cancer; and cancer of the urinary system.

As used herein, a "subject" means a human or animal. Usually the animal is a vertebrate such as a primate, rodent, domestic animal or game animal. Primates include, for example, chimpanzees, cynomolgus monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease. The term "treating" includes reducing or alleviating at least one adverse effect or symptom of diabetes. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "small molecule" refers to a organic or inorganic molecule, either natural (i.e., found in nature) or non-natural (i.e., not found in nature), which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Examples of "small molecules" that occur in nature include, but are not limited to, taxol, dynemicin, and rapamycin. In certain other preferred embodiments, natural-product-like small molecules are utilized.

As used herein, a "compound" refers to any chemical, test chemical, drug, new chemical entity (NCE), or other moiety. For example, a compound can be any foreign chemical not normally present in a subject such as mammals including humans. A compound can also be an endogenous chemical that is normally present and synthesized in biological systems, such as mammals including humans. For example, a compound, such as a test compound, such as a drug, can reduce the deconjugation of primary and secondary bile acids as provided herein.

The term "derivative" as used herein means any chemical, conservative substitution, or structural modification of an agent. The derivative can improve characteristics of the agent or small molecule such as pharmacodynamics, pharmacokinetics, absorption, distribution, delivery, targeting to a specific receptor, or efficacy. For example, for a small molecule, the derivative can consist essentially of at least one chemical modification to about ten modifications. The derivative can also be the corresponding salt of the agent. The derivative can be the pro-drug of the small molecule as provided herein.

As used herein, the term "bile acid" refers to a steroid acid that aids digestion as emulsifiers of fat, and may also play a role in various systemic endocrine hormone-like functions. Bile acids in mammals are synthesized from cholesterol in the liver as primary bile acids and are metabolized by particular mammalian gut microbes to secondary bile acids. Bile acids are stored in the gallbladder and released into the duodenum upon the ingestion of food where they aid in absorption of lipids and fat-soluble vitamins. Over 95% of bile acids are reabsorbed in the ileum and recirculated to the liver. The remaining ~5% pass into the colon, where the majority of gut bacteria reside. Gut bacteria then enzymatically modify the primary bile acids, producing a group of molecules called secondary bile acids.

Bile acids in mammals regulate metabolic pathways by activation of farnesoid X receptor as well as the G-protein-coupled receptor (GPCRs) such as TGR5. Through activation of these diverse signaling pathways, bile acids can regulate their own enterohepatic circulation, but also triglyceride, cholesterol, energy, and glucose homeostasis. Non-limiting examples of bile acids include cholic acid, glycocholic acid, taurocholic acid, deoxycholic acid, chenodeoxycholic acid (CDCA), glycochenodeoxycholic acid, taurochenodeoxycholic acid (TCDA), lithocholic acid (LCA), ursodeoxycholic acid (UDCA), muricholic acids, obeticholic acid, and any other bile acid known in the art. The term "bile acid" or "bile salt" can further refer to salt forms of bile acids, sulfated bile acids, and other metabolites.

As used herein, "bile salt hydrolase" or "BSH" refers to an enzyme widely expressed by mammalian gut bacteria that converts host-produced primary bile acids into bacterially modified secondary bile acids. FIG. 1A provides an example of the deconjugation of primary and secondary bile acids by BSH and the conversion to secondary bile acids by bacterial bile acid modifying enzymes. Numerous amino acid sequences are known in the art for BSH of various bacterial species (e.g., NCBI Accession Nos. Accession: ABC26911.1; Accession: ABC26910.1; Accession: ACL98203.1; Accession: AAS98803.1; Accession: AKI55714.1; Accession: AAP20760.1). Without limitations, BSH can refer to any bacterial BSH enzyme. The keystone reaction in the conversion of primary into secondary bile acids is the hydrolysis of the C24-amide bond of conjugated primary bile acids (FIG. 1A) by gut bacterial BSH.

As used herein, an "appropriate control" refers to an untreated, otherwise identical cell or population (e.g., a subject who was not administered an agent provided herein, or was administered by only a subset of agents provided herein, as compared to a non-control cell). As used herein, the term "pharmaceutical composition" can include any material or substance that, when combined with an active ingredient (e.g. compound 7 or derivative thereof), allows the ingredient to retain biological activity and is non-reactive with the subject's immune system. Examples include, but are not limited to, any of the standard pharmaceutical carriers such as a phosphate buffered saline solution, emulsions such as oil/water emulsion, and various types of wetting agents. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

An "agent" as used herein is a chemical molecule of synthetic or biological origin. In the context of the present invention, an agent is generally a molecule that can be used in a pharmaceutical composition.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. The term "pharmaceutically acceptable carrier" excludes tissue culture media. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably. Non-limiting examples of pharmaceutical carriers include particle or polymer-based vehicles such as nanoparticles, microparticles, polymer microspheres, or polymer-drug conjugates.

As used herein, the term "restricts delivery of the composition to the gastrointestinal tract" refers to a formulation that permits or facilitates the delivery of the agent or pharmaceutical composition described herein to the colon, large intestine, or small intestine in viable form. Enteric coating or micro- or nano-particle formulations can facilitate such delivery as can, for example, buffer or other protective formulations.

The term "effective amount" is used interchangeably with the term "therapeutically effective amount" or "amount sufficient" and refers to the amount of at least one inhibitor of BSH e.g., any one of Formula (I)-(XVIII) or derivative thereof, of a pharmaceutical composition, at dosages and for periods of time necessary to achieve the desired therapeutic result, for example, to "attenuate", reduce or stop at least one symptom of diabetes, obesity, or an inflammatory disease. For example, an effective amount using the methods as disclosed herein would be considered as the amount sufficient to reduce one or more symptoms of diabetes, obesity, or an inflammatory disease by at least 10%. An effective amount as used herein would also include an amount sufficient to prevent or delay the development of such a symptom, alter the course of a symptom disease (for example but not limited to, slow the progression of a symptom of the disease), or reverse a symptom of the disease in a subject suffering from diabetes, prediabetes, hyperglycemia, obesity, or an inflammatory disease. Accordingly, the term "effective amount" or "therapeutically effective amount" as used herein refers to the amount of therapeutic agent (e.g. compound of Formula (I)-(XVIII) or derivative thereof) of a pharmaceutical composition to alleviate at least one symptom of a disease. Stated another way, "therapeutically effective amount" of an inhibitor of BSH as disclosed herein is the amount of an agonist which exerts a beneficial effect on, for example, the symptoms of the disease (e.g. an inflammatory disease, gastrointestinal disease, cancer, obesity, etc). The dosage administered, as single or multiple doses, to an individual will vary depending upon a variety of factors, including pharmacokinetic properties of the inhibitor, the route of administration, conditions and characteristics (sex, age, body weight, health, size) of subjects, extent of symptoms, concurrent treatments, frequency of treatment and the effect desired. A therapeutically effective amount is also one in which any toxic or detrimental effects of the therapeutic agent are outweighed by the therapeutically beneficial effects. The effective amount in each individual case can be determined empirically by a skilled artisan according to established methods in the art and without undue experimentation. In general, the phrases "therapeutically-effective" and "effective for the treatment, prevention, or inhibition", are intended to qualify agonist as disclosed herein which will achieve the goal of reduction in the severity of a diabetes, cancer, gastrointestinal disease, obesity, or an inflammatory disease or at one related symptom thereof.

The terms "co-administration" or the like, as used herein, are meant to encompass administration of the selected therapeutic agents to a single patient and are intended to include treatment regimens in which the agents are administered by the same or different route of administration or at the same or different time.

"Unit dosage form" as the term is used herein refers to a dosage suitable for one administration. By way of example, a unit dosage form can be an amount of therapeutic disposed in a delivery device, e.g., a syringe or intravenous drip bag. In one embodiment of any of the aspects, a unit dosage form is administered in a single administration. In another embodiment, more than one unit dosage form can be administered simultaneously.

The terms "administered" and "subjected" are used interchangeably in the context of treatment of a disease or disorder.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. Without limitations, oral administration can be in the form of solutions, suspensions, tablets, pills, capsules, sustained-release formulations, oral rinses, powders and the like.

As used herein, the term "modulates" refers to an effect including increasing or decreasing a given parameter as those terms are defined herein.

As used herein, the term "contacting" when used in reference to a cell or organ, encompasses both introducing or administering an agent, surface, hormone, etc. to the cell, tissue, or organ in a manner that permits physical contact of the cell with the agent, surface, hormone etc., and introducing an element, such as a genetic construct or vector, that permits the expression of an agent, such as a miRNA, polypeptide, or other expression product in the cell. It should be understood that a cell genetically modified to express an agent, is "contacted" with the agent, as are the cell's progeny that express the agent.

The term "statistically significant" or "significantly" refers to statistical significance and generally means a two standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

DETAILED DESCRIPTION OF CERTAIN EMBODIMENTS OF THE INVENTION

Human-associated bacteria play a vital role in health and disease. Microbial imbalance has been linked to a wide range of disease states. Studies in germ-free mice colonized with a single strain, multiple strains, or defined communities of bacteria have revealed the capacity of gut bacteria to affect host processes, including metabolism, immune function, and neurological responses. Compounds that selectively alter the levels of specific bacterial metabolites and proteins can be useful in evaluating how bacterial products affect host physiology in fully developed animals possessing complex microbial communities and be used as therapeutics for treating diseases, such as metabolic disorder (e.g., diabetes, obesity), gastrointestinal disease, cancer (e.g., liver cancer), or an inflammatory disease (e.g., Crohn's disease, inflammatory bowel disease, ulcerative colitis, pancreatitis, hepatitis, liver disease, biliary atresia, appendicitis, gastritis, diverticulitis, celiac disease, food intolerance, enteritis, ulcer, gastroesophageal reflux disease (GERD), psoriatic arthritis, psoriasis, rheumatoid arthritis).

The compositions and methods provided herein are related, in part, to the discovery of several compounds that inhibit bile salt hydrolase (BSH) and modulate the deconjugation of primary and secondary bile acids in a subject.

The compounds provided herein are selective, potently inhibit BSH in a broad spectrum of bacteria, do not have off-target effects in the host, can allow for restriction to the gut, and modulate the bile acids present in the host subject.

Compounds

In one aspect provided herein is a compound of Formula (I):

FORMULA (I)

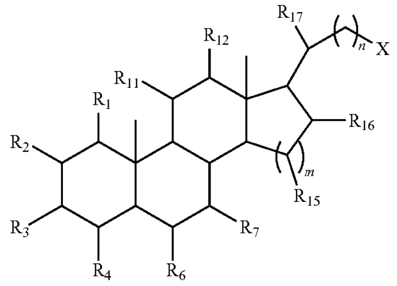

wherein:

n is 1, 2, 3, 4, 5, 6, 7, 8, 9 or 10;

m is 1, 2, 3 or 4;

X is an electrophilic group;

$R_1$, $R_2$, $R_3$, $R_4$, $R_6$, $R_7$, $R_{11}$, $R_{12}$, $R_{15}$, $R_{16}$ and $R_{17}$ are independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR_{18}$, $N(R_{18})_2$, $SR_{18}$, halogen, CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —NHC(O)$NHNH_2$, wherein each $R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

or a pharmaceutically acceptable salt thereof.

In certain embodiments, the compound of Formula (I) is of Formula (I'):

(I')

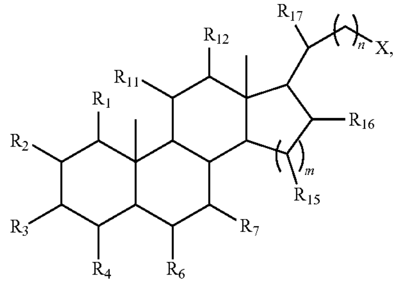

wherein:

n is 1, 2, 3, 4, 5, 6, 7, 8, 9 or 10;

m is 1, 2, 3 or 4;

X is an electrophilic group;

$R_1$, $R_2$, $R_3$, $R_4$, $R_6$, $R_7$, $R_{11}$, $R_{12}$, $R_{15}$, $R_{16}$ and $R_{17}$ are independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR_{18}$, $N(R_{18})_2$, $SR_{18}$, halogen, CN, —CHO, —$CO_2H$, —$CO_2R_{18}$, —$NO_2$, —$ONO_2$, —$SO_2Cl$, —$SO_3H$, —$OSO_3H$, —$NR_{18}SO_3H$, —$PO_3H_2$, —$OPO_3H_2$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —NHC(O)$NHNH_2$, wherein each $R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

or a pharmaceutically acceptable salt thereof.

In certain embodiments, the compound of Formula (I) is of the Formula (I-a):

(I-a)

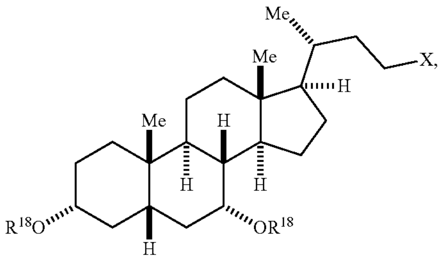

wherein:

each $R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a pharmaceutically acceptable salt thereof.

In certain embodiments, the compound of Formula (I-a) is of the Formula (I-a'):

(I-a')

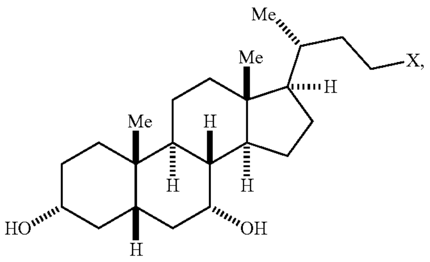

wherein:

each $R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a pharmaceutically acceptable salt thereof.

In certain embodiments, the compound of Formula (I) is of the Formula (I-b):

(I-b)

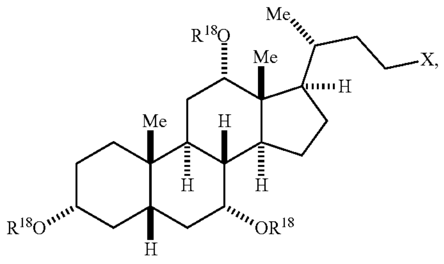

wherein:

each $R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a pharmaceutically acceptable salt thereof.

In certain embodiments, the compound of Formula (I-b) is of the Formula (I-b'):

(I-b')

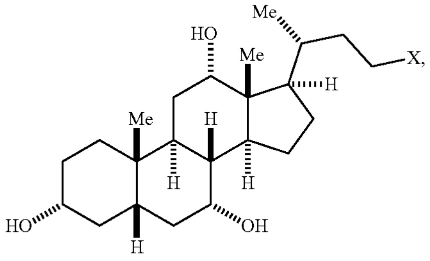

wherein:

each $R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a pharmaceutically acceptable salt thereof.

In certain embodiments, the compound of Formula (I) or Formula (I') is of the Formula (I-c):

(I-c)

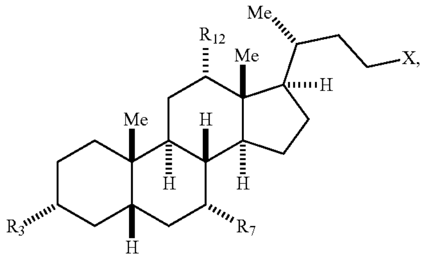

or a pharmaceutically acceptable salt thereof.

In certain embodiments, the compound of Formula (I) or Formula (I') is of the Formula (I-d):

(I-d)

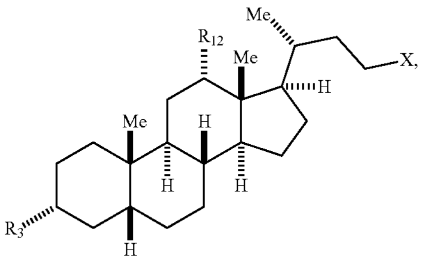

or a pharmaceutically acceptable salt thereof.

In certain embodiments, the compound of Formula (I) or Formula (I') is of the Formula (I-e):

(I-e)

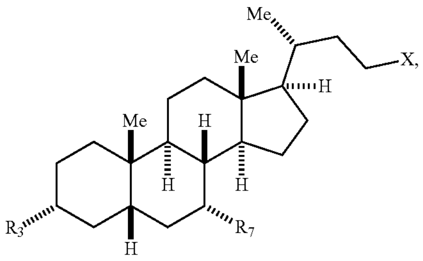

or a pharmaceutically acceptable salt thereof.

In certain embodiments, the compound of Formula (I) or Formula (I') is of the Formula (I-f):

(I-f)

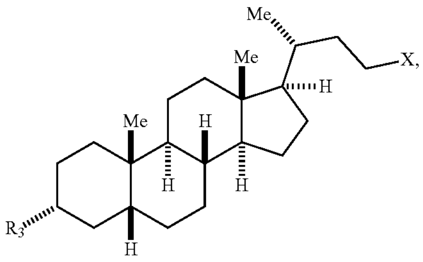

or a pharmaceutically acceptable salt thereof.

In certain embodiments, the compound of Formula (I) or Formula (I') is of the Formula (I-g):

(I-g)

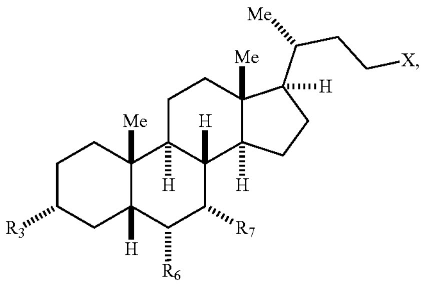

or a pharmaceutically acceptable salt thereof.

In certain embodiments, the compound of Formula (I) or Formula (I') is of the Formula (I-h):

(I-h)

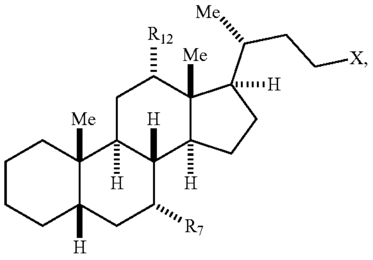

or a pharmaceutically acceptable salt thereof.

In certain embodiments, the compound of Formula (I) or Formula (I') is of the Formula (I-i):

(I-i)

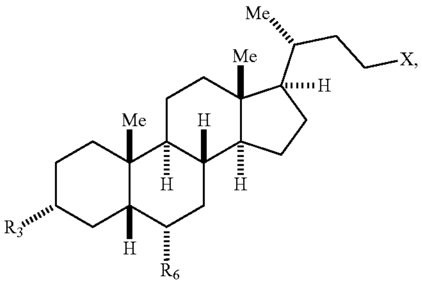

or a pharmaceutically acceptable salt thereof.

In certain embodiments, the compound of Formula (I) or Formula (I') is of the Formula (I-c'):

(I-c')

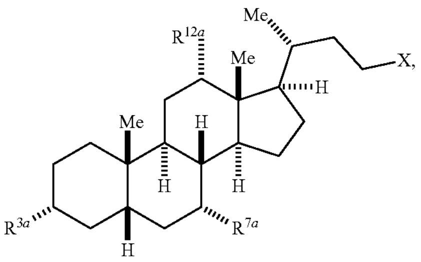

or a pharmaceutically acceptable salt thereof, wherein:

$R^{3a}$, $R^{7a}$, and $R^{12a}$ are independently selected from the group consisting of —$OR_{18}$, —$SO_3R_{18}$, —$OSO_3R_{18}$, —$PO_3(R_{18})_2$, —$OPO_3(R_{18})_2$, —$OSO_2R_{18}$, and —$SO_2N(R_{18})_2$, wherein each $R_{18}$ is independently H, or substituted or unsubstituted alkyl. In certain embodiments, $R^{3a}$, $R^{7a}$, and $R^{12a}$ are independently selected from the group consisting of —$OR_{18}$, —$SO_3H$, —$OSO_3H$, —$PO_3H_2$, —$OPO_3H_2$, —$OSO_2H$, and —$SO_2NH_2$, wherein each $R_{18}$ is independently H, or substituted or unsubstituted alkyl. In certain embodiments, $R^{3a}$, $R^{7a}$, and $R^{12a}$ are independently selected from the group consisting of —$OR_{18}$, —$SO_3H$, and —$OSO_3H$, wherein $R_{18}$ is H, or substituted or unsubstituted alkyl. In certain embodiments, $R^{3a}$, $R^{7a}$, and $R^{12a}$ are independently selected from the group consisting of —OH, and —$OSO_3H$.

In certain embodiments, the compound of Formula (I) or Formula (I') is of the Formula (I-d'):

(I-d')

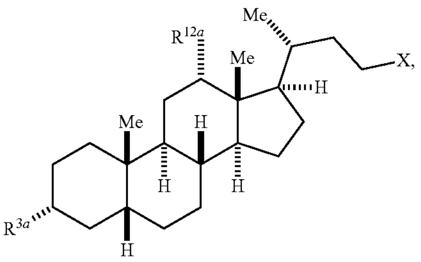

or a pharmaceutically acceptable salt thereof, wherein:

$R^{3a}$ and $R^{12a}$ are independently selected from the group consisting of —$OR_{18}$, —$SO_3R_{18}$, —$OSO_3R_{18}$, —$PO_3(R_{18})_2$, —$OPO_3(R_{18})_2$, —$OSO_2R_{18}$, and —$SO_2N(R_{18})_2$, wherein each $R_{18}$ is independently H, or substituted or unsubstituted alkyl. In certain embodiments, $R^{3a}$ and $R^{2a}$ are independently selected from the group consisting of —$OR_{18}$, —$SO_3H$, —$OSO_3H$, —$PO_3H_2$, —$OPO_3H_2$, —$OSO_2H$, and —$SO_2NH_2$, wherein $R_{18}$ is independently H, or substituted or unsubstituted alkyl. In certain embodiments, $R^{3a}$ and $R^{12a}$ are independently selected from the group consisting of —OH, and —$OSO_3H$. In certain embodiments, the compound of Formula (I) or Formula (I') is of the Formula (I-d"):

(I-d")

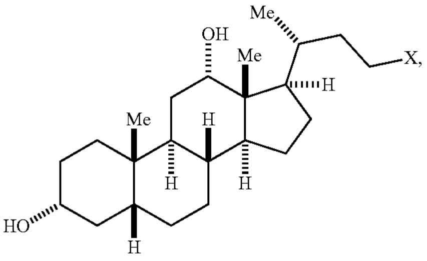

or a pharmaceutically acceptable salt thereof.

In certain embodiments, the compound of Formula (I) or Formula (I') is of the Formula (I-e'):

(I-e')

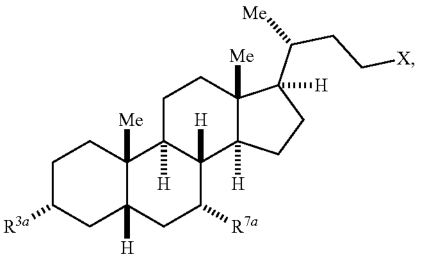

or a pharmaceutically acceptable salt thereof, wherein:

$R^{3a}$ and $R^{7a}$ are independently selected from the group consisting of —$OR_{18}$, —$SO_3R_{18}$, —$OSO_3R_{18}$, —$PO_3(R_{18})_2$, —$OPO_3(R_{18})_2$, —$OSO_2R_{18}$, and —$SO_2N(R_{18})_2$, wherein each $R_{18}$ is independently H, or substituted or unsubstituted alkyl. In certain embodiments, $R^{3a}$ and $R^{7a}$ are independently selected from the group consisting of —$OR_{18}$, —$SO_3H$, —$OSO_3H$, —$PO_3H_2$, —$OPO_3H_2$, —$OSO_2H$, and —$SO_2NH_2$, wherein $R_{18}$ is independently H, or substituted or unsubstituted alkyl. In certain embodiments, $R^{3a}$ and $R^{7a}$ are independently selected from the group consisting of —OH and —$OSO_3H$. In certain embodiments, $R^{3a}$ is —$OSO_3H$, and $R^{7a}$ is selected from the group consisting of —$OR_{18}$, —$SO_3H$, —$OSO_3H$, —$PO_3H_2$, —$OPO_3H_2$, —$OSO_2H$, and —$SO_2NH_2$, wherein $R_{18}$ is independently H, or substituted or unsubstituted alkyl. In certain embodiments, $R^{3a}$ is —OH, and $R^{7a}$ is selected from the group consisting of —$OR_{18}$, —$SO_3H$, —$OSO_3H$, —$PO_3H_2$, —$OPO_3H_2$, —$OSO_2H$, and —$SO_2NH_2$, wherein $R_{18}$ is independently H, or substituted or unsubstituted alkyl.

In certain embodiments, the compound of Formula (I-e) is of the Formula (I-e"):

(I-e″)

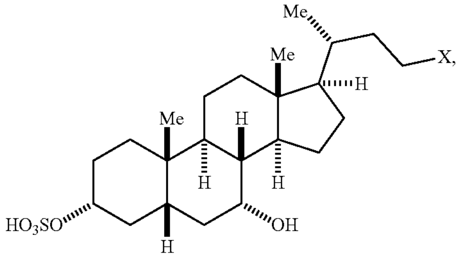

or a pharmaceutically acceptable salt thereof.

In certain embodiments, the compound of Formula (I-e") is of the formula:

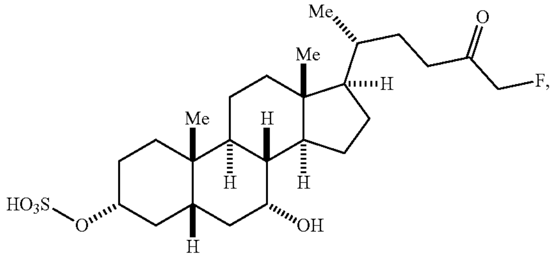

or a pharmaceutically acceptable salt thereof.

In certain embodiments, the compound of Formula (I) or Formula (I') is of the Formula (I-f'):

(I-f')

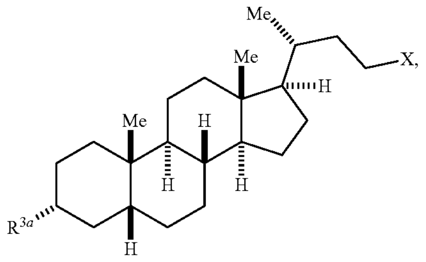

or a pharmaceutically acceptable salt thereof, wherein:

$R^{3a}$ is selected from the group consisting of —$OR_{18}$, —$SO_3R_{18}$, —$OSO_3R_{18}$, —$PO_3(R_{18})_2$, —$OPO_3(R_{18})_2$, —$OSO_2R_{18}$, and —$SO_2N(R_{18})_2$, wherein each $R_{18}$ is independently H, or substituted or unsubstituted alkyl. In certain embodiments, $R^{3a}$ is selected from the group consisting of —$OR_{18}$, —$SO_3H$, —$OSO_3H$, —$PO_3H_2$, —$OPO_3H_2$, —$OSO_2H$, and —$SO_2NH_2$, wherein $R_{18}$ is independently H, or substituted or unsubstituted alkyl. In certain embodiments, $R^{3a}$ is —$OSO_3H$. In certain embodiments, $R^{3a}$ is —OH.

In certain embodiments, the compound of Formula (I) or Formula (I') is of the Formula (I-f"):

(I-f″)

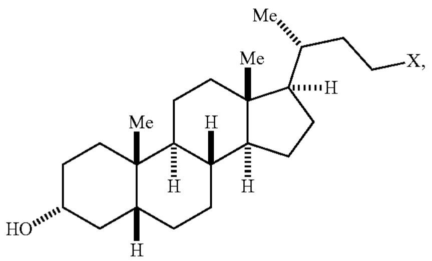

or a pharmaceutically acceptable salt thereof.

In certain embodiments, the compound of Formula (I-f') is of the Formula (I-f'"):

(I-f‴)

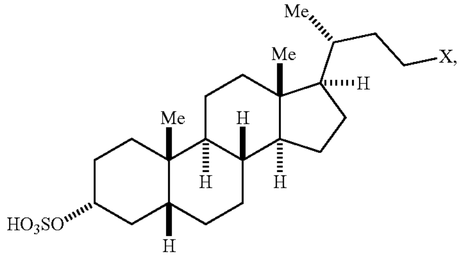

or a pharmaceutically acceptable salt thereof.

In certain embodiments, the compound of Formula (I-f'") is of the formula:

(3S-LCA-FMK)

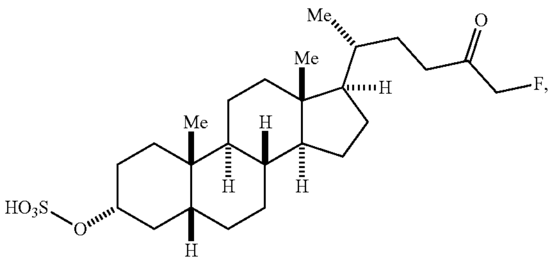

or a pharmaceutically acceptable salt thereof.

In certain embodiments, the compound of Formula (I) or Formula (I') is of the Formula (I-g'):

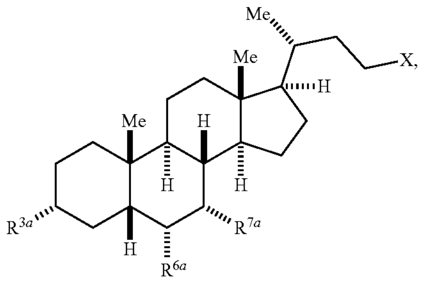

(I-g')

or a pharmaceutically acceptable salt thereof, wherein:

$R^{3a}$, $R^{6a}$, and $R^{7a}$ are independently selected from the group consisting of —$OR_{18}$, —$SO_3R_{18}$, —$OSO_3R_{18}$, —$PO_3(R_{18})_2$, —$OPO_3(R_{18})_2$, —$OSO_2R_{18}$, and —$SO_2N(R_{18})_2$, wherein each $R_{18}$ is independently H, or substituted or unsubstituted alkyl. In certain embodiments, $R^{3a}$, $R^{6a}$, and $R^{7a}$ are independently selected from the group consisting of —$OR_{18}$, —$SO_3H$, —$OSO_3H$, —$PO_3H_2$, —$OPO_3H_2$, —$OSO_2H$, and —$SO_2NH_2$, wherein $R_{18}$ is independently H, or substituted or unsubstituted alkyl. In certain embodiments, $R^{3a}$, $R^{6a}$, and $R^{7a}$ are independently selected from the group consisting of —OH and —$OSO_3H$.

In certain embodiments, the compound of Formula (I) or Formula (I') is of the Formula (I-g"):

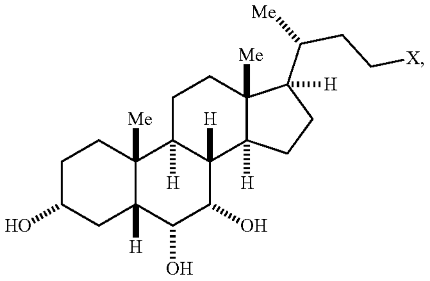

(I-g")

or a pharmaceutically acceptable salt thereof.

In certain embodiments, the compound of Formula (I) or Formula (I') is of the Formula (I-h'):

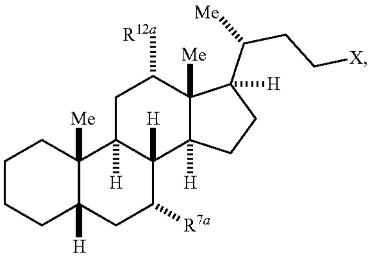

(I-h')

or a pharmaceutically acceptable salt thereof, wherein:

$R^{7a}$ and $R^{12a}$ are independently selected from the group consisting of —$OR_{18}$, —$SO_3R_{18}$, —$OSO_3R_{18}$, —$PO_3(R_{18})_2$, —$OPO_3(R_{18})_2$, —$OSO_2R_{18}$, and —$SO_2N(R_{18})_2$, wherein each $R_{18}$ is independently H, or substituted or unsubstituted alkyl. In certain embodiments, $R^{7a}$ and $R^{12a}$ are independently selected from the group consisting of —$OR_{18}$, —$SO_3H$, —$OSO_3H$, —$PO_3H_2$, —$OPO_3H_2$, —$OSO_2H$, and —$SO_2NH_2$, wherein $R_{18}$ is independently H, or substituted or unsubstituted alkyl. In certain embodiments, $R^{7a}$ and $R^{12a}$ are independently selected from the group consisting of —OH and —$OSO_3H$.

In certain embodiments, the compound of Formula (I) or Formula (I') is of the Formula (I-h"):

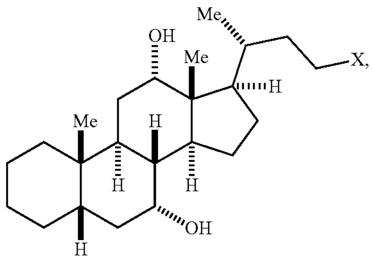

(I-h")

or a pharmaceutically acceptable salt thereof.

In certain embodiments, the compound of Formula (I) or Formula (I') is of the Formula (I-i'):

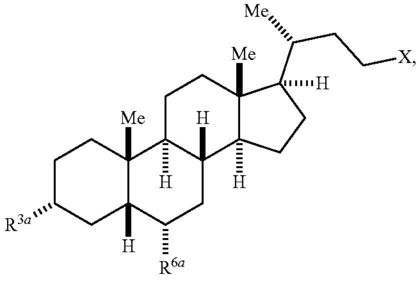

(I-i')

or a pharmaceutically acceptable salt thereof, wherein:

$R^{3a}$ and $R^{6a}$ are independently selected from the group consisting of —$OR_{18}$, —$SO_3R_{18}$, —$OSO_3R_{18}$, —$PO_3(R_{18})_2$, —$OPO_3(R_{18})_2$, —$OSO_2R_{18}$, and —$SO_2N(R_{18})_2$, wherein each $R_{18}$ is independently H, or substituted or unsubstituted alkyl. In certain embodiments, $R^{3a}$ and $R^{6a}$ are independently selected from the group consisting of —$OR_{18}$, —$SO_3H$, —$OSO_3H$, —$PO_3H_2$, —$OPO_3H_2$, —$OSO_2H$, and —$SO_2NH_2$, wherein $R_{18}$ is independently H, or substituted or unsubstituted alkyl. In certain embodiments, $R^{3a}$ and $R^{6a}$ are independently selected from the group consisting of —OH and —$OSO_3H$.

In certain embodiments, the compound of Formula (I) or Formula (I') is of the Formula (I-i'):

(I-i″)

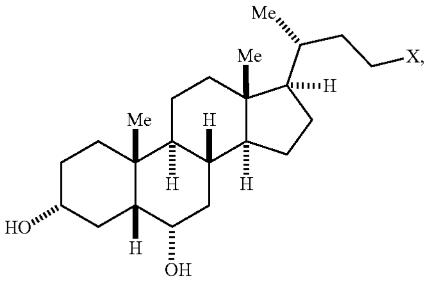

or a pharmaceutically acceptable salt thereof.

In certain embodiments, the compound of any one of Formulae (I-c'), (I-d'), (I-e'), (I-f'), (I-g'), (I-h'), or (I-i') may contain the substituent $R^{3a}$, $R^{6a}$, $R^{7a}$, or $R^{12a}$. In certain embodiments, $R^{3a}$, $R^{6a}$, $R^{7a}$, and $R^{12a}$ are independently selected from the group consisting of $—OR_{18}$, $—SO_3R_{18}$, $—OSO_3R_{18}$, $—PO_3(R_{18})_2$, $—OPO_3(R_{18})_2$, $—OSO_2R_{18}$, and $—SO_2N(R_{18})_2$, wherein each $R_{18}$ is independently H, or substituted or unsubstituted alkyl. In certain embodiments, at least one instance of $R^{3a}$, $R^{6a}$, $R^{7a}$, or $R^{12a}$ is independently $—OR_{18}$. In certain embodiments, at least one instance of $R^{3a}$, $R^{6a}$, $R^{7a}$, or $R^{12a}$ is independently $—SO_3R_{18}$. In certain embodiments, at least one instance of $R^{3a}$, $R^{6a}$, $R^{7a}$, or $R^{12a}$ is independently $—OSO_3R_{18}$. In certain embodiments, at least one instance of $R^{3a}$, $R^{6a}$, $R^{7a}$, or $R^{12a}$ is independently $—PO_3(R_{18})_2$. In certain embodiments, at least one instance of $R^{3a}$, $R^{6a}$, $R^{7a}$, or $R^{12a}$ is independently $—OPO_3(R_{18})_2$. In certain embodiments, at least one instance of $R^{3a}$, $R^{6a}$, $R^{7a}$, or $R^{12a}$ is independently $—OSO_2R_{18}$. In certain embodiments, at least one instance of $R^{3a}$, $R^{6a}$, $R^{7a}$, or $R^{12a}$ is independently $—SO_2N(R_{18})_2$. In certain embodiments, $R^{3a}$ is —OH, and $R^{6a}$, $R^{7a}$, and $R^{2a}$ are independently selected from the group consisting of —OH and $—OSO_3H$. In certain embodiments, $R^{3a}$ is $—OSO_3H$, and $R^{6a}$, $R^{7a}$, and $R^{12a}$ are independently selected from the group consisting of —OH and $—OSO_3H$.

In some embodiments of the various aspects disclosed herein, the compound of Formula (I) can be a compound of any one of Formula (II)-(XV):

FORMULA (II)

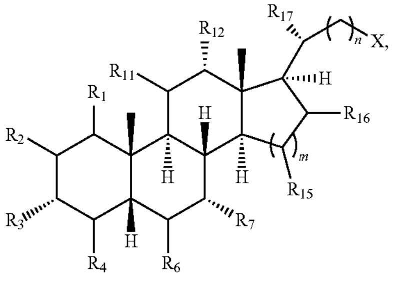

-continued

FORMULA (III)

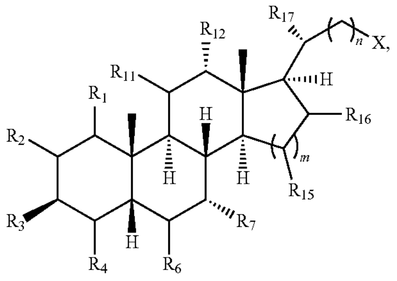

FORMULA (IV)

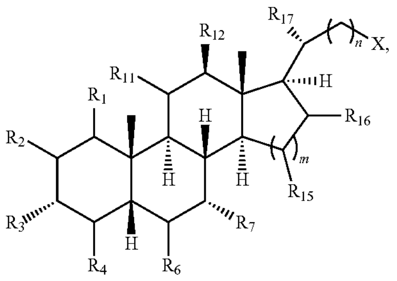

FORMULA (V)

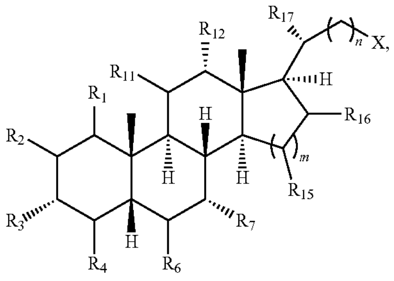

FORMULA (VI)

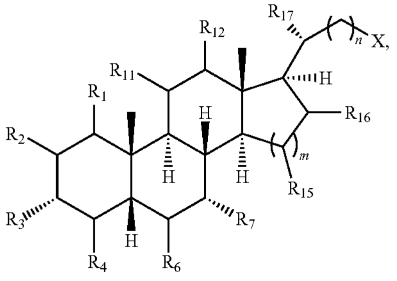

FORMULA (VII)

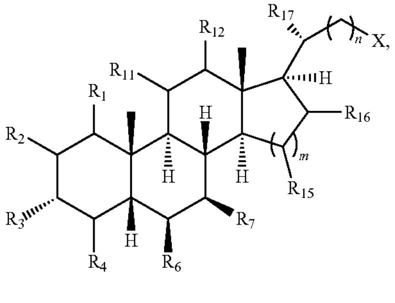

-continued

FORMULA (VIII)

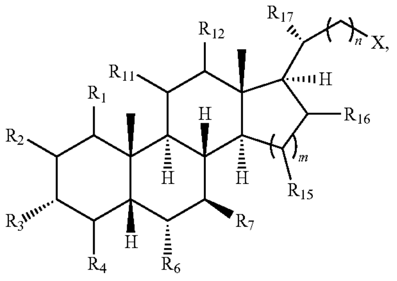

FORMULA (IX)

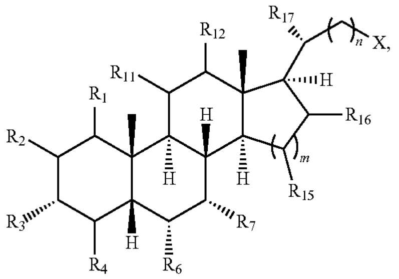

FORMULA (X)

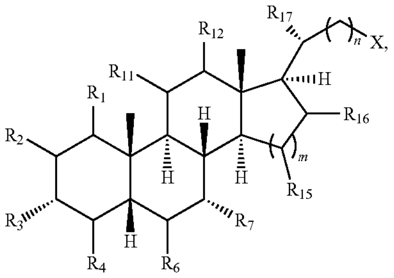

FORMULA (XI)

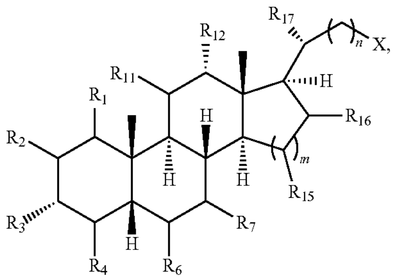

FORMULA (XII)

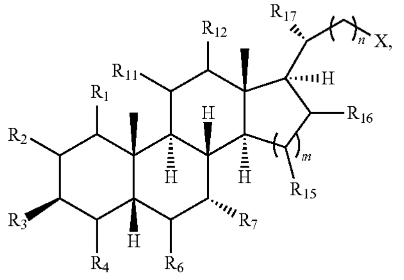

-continued

FORMULA (XIII)

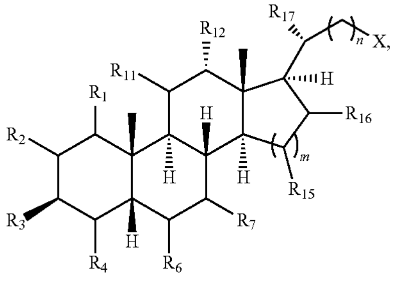

FORMULA (XIV)

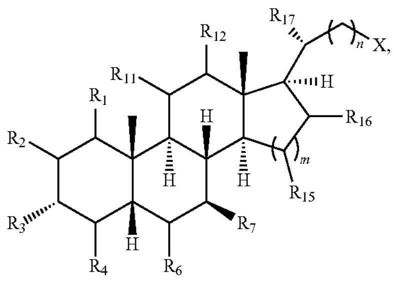

or

FORMULA (XV)

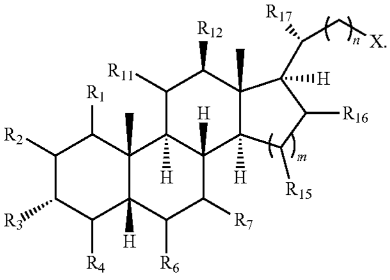

In compounds of Formula (I)-(XV), X is an electrophilic group. The terms "electrophile" and "electrophilic" refer to a functional group that is susceptible to nucleophilic attack, i.e., susceptible to reaction with an incoming nucleophilic group, e.g., thiol, amine. Generally, an electrophilic group is a grouping of atoms, one or more of which is electron deficient. Usually, the electrophilic group comprises an electron-withdrawing group. Examples of electron-withdrawing groups include, but are not limited to, a halo group, a nitro group, a cyano group, an ester group, an aldehyde group, a keto group, a sulfone group, or an amide group. The electron deficient atom(s) is referred to as the electrophilic center, representative examples of which include carbonyl, thiocarbonyl, phosphinyl, and thiophosphinyl. Exemplary electrophilic groups include, but are not limited to, acid halide, isothiocyanate, isocyanate, epoxy, and anhydride group.

In some embodiments of the various aspects disclosed herein, X is a thiol-reactive electrophilic group. The term "thiol-reactive electrophilic group" as used herein is any group that is susceptible to nucleophilic attack by the lone-pair electrons on the sulfur atom of the thiol group or by the thiolate anion. Examples of thiol-reactive electrophilic groups include groups that have good leaving groups. For example, an α-halocarbonyl group, isothiocyanate group, isocyanate group, an alkyl group having a halide or alkoxy group attached to it, and an electron-deficient vinyl group. In some embodiments, X is an α-halocarbonyl group or a isothiocyanate group.

In some embodiments of the various aspects disclosed herein, X is —C(O)$R_{19}$, —NCS, —NHC(O)$R_{19}$, —CH═C(CN)$CO_2R_{20}$, or —CN, where $R_{19}$ is alkyl, haloalkyl, alkenyl, or alkynyl, and $R_{20}$ is alkyl.

In certain embodiments, X is —C(O)$R_{19}$, wherein $R_{19}$ is alkyl, haloalkyl, alkenyl, or alkynyl. In certain embodiments, X is —C(O)$R_{19}$, wherein $R_{19}$ is —$CH_2F$. In certain embodiments, X is —NCS. In certain embodiments, X is —NHC(O)$R_{19}$, wherein $R_{19}$ is alkyl (e.g., Me, Et, Pr), haloalkyl (e.g., $CH_2F$), In certain embodiments, X is —CH═C(CN)$CO_2R_{20}$, wherein $R_{20}$ is alkyl. In certain embodiments, X is —CN.

In certain embodiments, X is an electrophilic group selected from the group consisting of

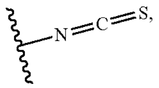, 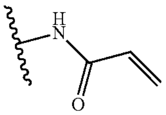, 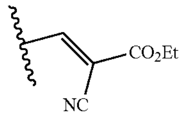, 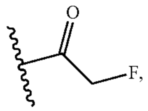, 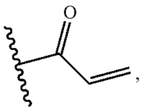, 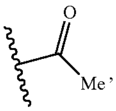, and 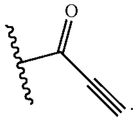

In certain embodiments, X is

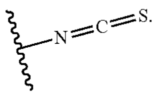 [SMILES: *N=C=S]

In certain embodiments, X is

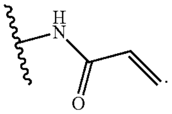 [SMILES: *NC(=O)C=C]

In certain embodiments, X is

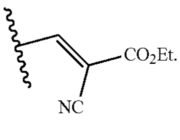 [SMILES: */C=C(\C#N)C(=O)OCC]

In certain embodiments, X is

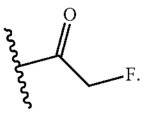 [SMILES: *C(=O)CF]

In certain embodiments, X is

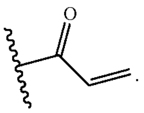 [SMILES: *C(=O)C=C]

In certain embodiments, X is

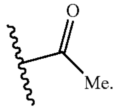 [SMILES: *C(C)=O]

In certain embodiments, X is

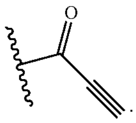 [SMILES: *C(=O)C#C]

In some embodiments, X is —C(O)$R_{19}$ or —NCS, wherein $R_{19}$ is haloalkyl. For example, X is —C(O)$CH_2F$ or —NCS.

In certain embodiments, $R_1$, $R_2$, $R_3$, $R_4$, $R_6$, $R_7$, $R_{11}$, $R_{12}$, $R_{15}$, $R_{16}$ and $R_{17}$ are independently H. In certain embodiments, $R_1$, $R_2$, $R_3$, $R_4$, $R_6$, $R_7$, $R_{11}$, $R_{12}$, $R_{15}$, $R_{16}$ and $R_{17}$ are independently substituted or unsubstituted alkyl. In certain embodiments, $R_1$, $R_2$, $R_3$, $R_4$, $R_6$, $R_7$, $R_{11}$, $R_{12}$, $R_{15}$, $R_{16}$ and $R_{17}$ are independently substituted or unsubstituted heteroalkyl. In certain embodiments, $R_1$, $R_2$, $R_3$, $R_4$, $R_6$, $R_7$, $R_{11}$, $R_{12}$, $R_{15}$, $R_{16}$ and $R_{17}$ are independently substituted or unsubstituted cycloalkyl. In certain embodiments, $R_1$, $R_2$, $R_3$, $R_4$, $R_6$, $R_7$, $R_{11}$, $R_{12}$, $R_{15}$, $R_{16}$ and $R_{17}$ are independently substituted or unsubstituted heterocycloalkyl. In certain embodiments, $R_1$, $R_2$, $R_3$, $R_4$, $R_6$, $R_7$, $R_{11}$, $R_{12}$, $R_{15}$, $R_{16}$ and $R_{17}$ are independently substituted or unsubstituted aryl. In certain embodiments, $R_1$, $R_2$, $R_3$, $R_4$, $R_6$, $R_7$, $R_{11}$, $R_{12}$, $R_{15}$, $R_{16}$ and $R_{17}$ are independently substituted or unsubstituted heteroaryl. In certain embodiments, $R_1$, $R_2$, $R_3$, $R_4$, $R_6$, $R_7$, $R_{11}$, $R_{12}$, $R_{15}$, $R_{16}$ and $R_{17}$ are independently $OR_{18}$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently $N(R_{18})_2$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently $SR_{18}$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently halogen. In certain embodiments, $R_1$, $R_2$, $R_3$, $R_4$, $R_6$, $R_7$, $R_{11}$, $R_{12}$, $R_{15}$, $R_{16}$ and $R_{17}$ are independently CN. In certain embodiments, $R_1$, $R_2$, $R_3$, $R_4$, $R_6$, $R_7$, $R_1$, $R_{12}$, $R_{15}$, $R_{16}$ and $R_{17}$ are independently —CHO. In certain embodiments, $R_1$, $R_2$, $R_3$, $R_4$, $R_6$, $R_7$, $R_{11}$, $R_{12}$, $R_{15}$, $R_{16}$ and $R_{17}$ are independently —$CO_2H$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently —$CO_2R_{18}$. In certain embodiments, $R_1$, $R_2$, $R_3$, $R_4$, $R_6$, $R_7$, $R_1$, $R_{12}$, $R_{15}$, $R_{16}$ and $R_{17}$ are independently —$NO_2$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently —$ONO_2$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently —$SO_2Cl$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently —$SO_3^-$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently —$OSO_3^-$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently —$NR_{18}SO_3^-$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently $-PO_{32}-$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently $-OPO_{32}-$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently $-OSO_2R_{18}$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently $-SO_2N(R_{18})_2$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently $-OSO_2N(R_{18})_2$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently $-NR_{18}SO_2R_{18}$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently $-SO_2N(R_{18})_2$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently $-NHNH_2$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently $-ONH_2$. In certain embodiments, $R_1$, $R_2$, $R_3$, $R_4$, $R_6$, $R_7$, $R_{11}$, $R_{12}$, $R_{15}$, $R_{16}$ and $R_{17}$ are independently $-NHC(O)NHNH_2$.

In certain embodiments, $R_{18}$ is H. In certain embodiments, $R_{18}$ is substituted or unsubstituted alkyl. In certain embodiments, $R_{18}$ is substituted or unsubstituted heteroalkyl. In certain embodiments, $R_{18}$ is substituted or unsubstituted cycloalkyl. In certain embodiments, $R_{18}$ is substituted or unsubstituted heterocycloalkyl. In certain embodiments, $R_{18}$ is substituted or unsubstituted aryl. In certain embodiments, $R_{18}$ is substituted or unsubstituted heteroaryl.

In compounds of Formula (I), at least one of $R_1$, $R_2$, $R_4$, $R_6$, $R_{11}$, $R_{15}$, and $R_{16}$ can be H. For example, one, two, three, four, five, six or all seven of $R_1$, $R_2$, $R_4$, $R_6$, $R_{11}$, $R_{15}$, and $R_{16}$ can be H. In some embodiments of the various aspects disclosed herein, all of $R_1$, $R_2$, $R_4$, $R_6$, $R_{11}$, $R_{15}$, and $R_{16}$ are H.

In some compounds of Formula (I) at least one of $R_3$, $R_7$ and $R_{12}$ can be $-OR_{18}$. For example, one, two or all three of $R_3$, $R_7$, and $R_{12}$ can be $-OR_{18}$. Accordingly, in some embodiments of the various aspects disclosed herein, $R_3$ is $-OR_{18}$. In some embodiments of the various aspects disclosed herein, $R_7$ is $-OR_{18}$. In some embodiments of the various aspects disclosed herein, $R_{12}$ is $-OR_{18}$. In some embodiments, $R_3$ and $R_7$ are $-OR_{18}$. In some embodiments, $R_3$ and $R_{12}$ are $-OR_{18}$. In some embodiments, $R_7$ and $R_{12}$ are $-OR_{18}$. In some embodiments, all of $R_3$, $R_7$, and $R_{12}$ can be $-OR_{18}$.

In some embodiments of the various aspects disclosed herein, at least one of $R_3$ and $R_7$ is $-OR_{18}$, and $R_{12}$ is H or $OR_{18}$. For example, at least one of $R_3$ and $R_7$ is $-OH$, and $R_{12}$ is H or $-OH$.

In some additional embodiments of the various aspects disclosed herein, $R_3$ and $R_7$ are $-OR_{18}$, and $R_{12}$ is H or $-OR_{18}$. For example, $R_3$ and $R_7$ are $-OH$, and $R_{12}$ is H or $-OH$.

In some compounds of Formula (I) at least one of $R_3$, $R_6$, $R_7$, and $R_{12}$ can be $-OSO_3^-$, $-NR_{18}SO_3^-$, or $-OPO_3^{2-}$. In some further embodiments of this at least one of $R_3$, $R_6$, $R_7$, and $R_{12}$ is $-OSO_3^-$. In some particular embodiments, $R_3$ is $-OSO_3^-$.

Exemplary $R_{18}$ groups include, but are not limited to H and $C_1$-$C_6$ alkyl. In some embodiments of the various aspects disclosed herein, $R_{18}$ is H.

In compounds of Formula (I), $R_{17}$ can $C_1$-$C_6$ alkyl. For example, $R_{17}$ can be methyl, ethyl, propyl, isopropyl, butyl, pentyl. In some embodiments of the various aspects disclosed herein, $R_{17}$ is methyl.

In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8. In certain embodiments, n is 9. In certain embodiments, n is 10.

In certain embodiments, m is 1. In certain embodiments, m is 2. In certain embodiments, m is 3. In certain embodiments, m is 4.

In compounds of Formula (I), n can be 1 or 2. In some exemplary compounds of Formula (I)-(XVIII), n is 2.

In compounds of Formula (I), m can be 1, 2 or 3. In some exemplary compounds of Formula (I)-(XVIII), m is 1.

In some embodiments of the various aspects described herein, the compound of Formula (I) is of Formula (XVI):

FORMULA (XVI)

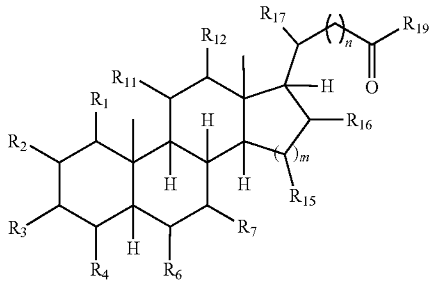

wherein $R_{19}$ is haloalkyl; $R_1$, $R_2$, $R_3$, $R_4$, $R_6$, $R_7$, $R_{11}$, $R_{12}$, $R_{15}$, $R_{16}$, $R_{17}$, n, and m are as defined for Formula (I). In some exemplary compounds of Formula (XVI), m is 1 or 2; n is 1 or 2; $R_1$, $R_2$, $R_4$, $R_6$, $R_{11}$, $R_{15}$, $R_{16}$ are H; $R_3$ and $R_7$ are OH; $R_{12}$ is H or $-OH$; $R_{17}$ is methyl; and $R_{19}$ is haloalkyl, e.g., $-CH_2F$. In some other exemplary compounds of Formula (XVI), m is 1 or 2; n is 1 or 2; $R_1$, $R_2$, $R_4$, $R_6$, $R_{11}$, $R_{15}$, $R_{16}$ are H; $R_3$ is $-OSO_3^-$; $R_7$ is OH; $R_{12}$ is H or $-OH$; $R_{17}$ is methyl; and $R_{19}$ is haloalkyl, e.g., $-CH_2F$.

In some embodiments of the various aspects described herein, the compound of Formula (I) is of Formula (XVII):

FORMULA (XVII)

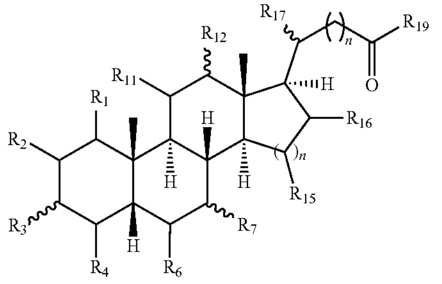

wherein $R_{19}$ is haloalkyl; $R_1$, $R_2$, $R_3$, $R_4$, $R_6$, $R_7$, $R_1$, $R_{12}$, $R_{15}$, $R_{16}$, $R_{17}$, n and m are as defined for Formula (I). In some exemplary compounds of Formula (XVII), m is 1 or 2; n is 1 or 2; $R_1$, $R_2$, $R_4$, $R_6$, $R_{11}$, $R_{15}$, $R_{16}$ are H; $R_3$ and $R_7$ are OH; $R_{12}$ is H or OH; $R_{17}$ is methyl; and $R_{19}$ is haloalkyl. In some other exemplary compounds of Formula (XVII), m is 1 or 2; n is 1 or 2; $R_1$, $R_2$, $R_4$, $R_6$, $R_{11}$, $R_{15}$, $R_{16}$ are H; $R_3$ is $-OSO_3^-$; $R_{17}$ is OH; $R_{12}$ is H or $-OH$; $R_{17}$ is methyl; and $R_{19}$ is haloalkyl, e.g., $-CH_2F$.

In some embodiments of the various aspects described herein, the compound of Formula (I) is of Formula (XVIII):

FORMULA (XVIII)

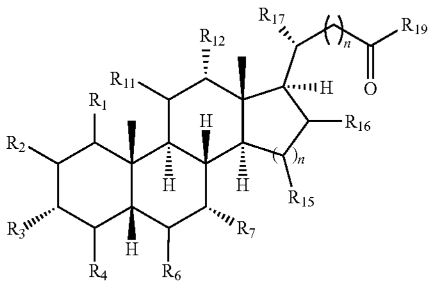

wherein $R_{19}$ is haloalkyl; $R_1$, $R_2$, $R_3$, $R_4$, $R_6$, $R_7$, $R_{11}$, $R_{12}$, $R_{15}$, $R_{16}$, $R_{17}$, n and m are as defined for Formula (I). In some exemplary compounds of Formula (XVIII), m is 1 or 2; n is 1 or 2; $R_1$, $R_2$, $R_4$, $R_6$, $R_{11}$, $R_{15}$, $R_{16}$ are H; $R_3$ and $R_7$ are OH; $R_{12}$ is H or OH; $R_{17}$ is methyl; and $R_{19}$ is haloalkyl, e.g., $-CH_2F$. In some other exemplary compounds of Formula (XVIII), m is 1 or 2; n is 1 or 2; $R_1$, $R_2$, $R_4$, $R_6$, $R_{11}$, $R_{15}$, $R_{16}$ are H; $R_3$ is $-OSO_3^-$; $R_7$ is OH; $R_{12}$ is H or OH; $R_{17}$ is methyl; and $R_{19}$ is haloalkyl, e.g., $-CH_2F$.

In certain embodiments, the compound of Formula (XVIII) is of the Formula (XVIII-a):

(XVIII-a)

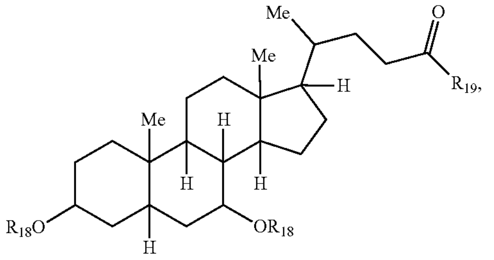

wherein:

$R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R_{19}$ is alkyl, haloalkyl, alkenyl, or alkynyl, or a pharmaceutically acceptable salt thereof. In certain embodiments, $R_{18}$ is H and $R_{19}$ is haloalkyl (e.g., $-CH_2F$).

In certain embodiments, the compound of Formula (XVIII-a) is of the Formula (XVIII-a'):

(XVIII-a')

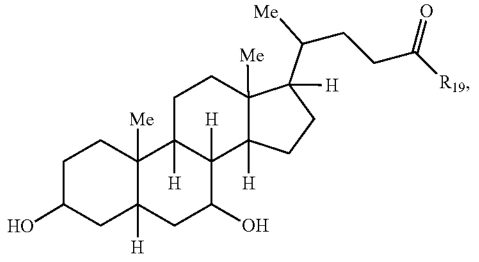

wherein:

$R_{19}$ is alkyl, haloalkyl, alkenyl, or alkynyl, or a pharmaceutically acceptable salt thereof. In certain embodiments, $R_{19}$ is haloalkyl (e.g., $-CH_2F$).

In certain embodiments, the compound of Formula (XVIII) is of the Formula (XVIII-b):

(XVIII-b)

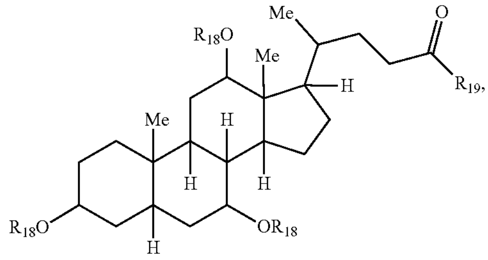

wherein:

$R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R_{19}$ is alkyl, haloalkyl, alkenyl, or alkynyl, or a pharmaceutically acceptable salt thereof. In certain embodiments, $R_{18}$ is H and $R_{19}$ is haloalkyl (e.g., $-CH_2F$).

In certain embodiments, the compound of Formula (XVIII-b) is of the Formula (XVIII-b'):

(XVIII-b')

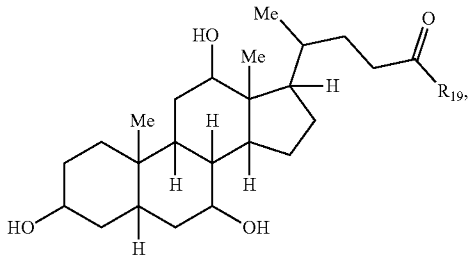

wherein:

$R_{19}$ is alkyl, haloalkyl, alkenyl, or alkynyl, or a pharmaceutically acceptable salt thereof. In certain embodiments, $R_{19}$ is haloalkyl (e.g., $-CH_2F$).

In certain embodiments, the compound of Formula (XVIII) is of the Formula (XVIII-c):

(XVIII-c)

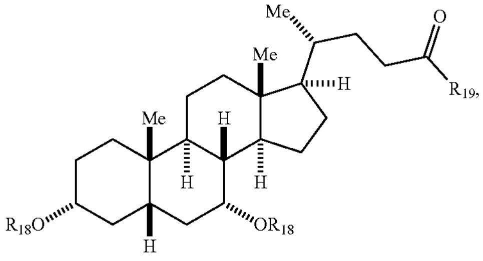

wherein:

$R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R_{19}$ is alkyl, haloalkyl, alkenyl, or alkynyl, or a pharmaceutically acceptable salt thereof. In certain embodiments, $R_{18}$ is H and $R_{19}$ is haloalkyl (e.g., —$CH_2F$).

In certain embodiments, the compound of Formula (XVIII-c) is of the Formula (XVIII-c'):

(XVIII-c')

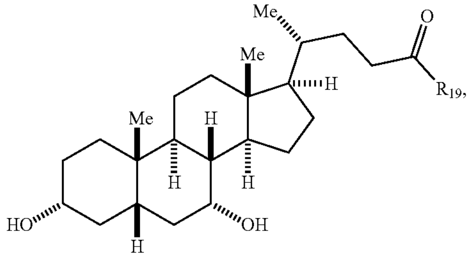

wherein:

$R_{19}$ is alkyl, haloalkyl, alkenyl, or alkynyl, or a pharmaceutically acceptable salt thereof. In certain embodiments, $R_{19}$ is haloalkyl (e.g., —$CH_2F$).

In certain embodiments, the compound of Formula (XVIII) is of the Formula (XVIII-d):

(XVIII-d)

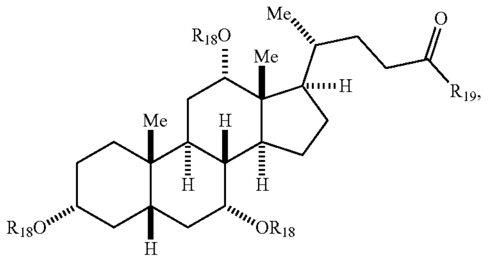

wherein:

$R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R_{19}$ is alkyl, haloalkyl, alkenyl, or alkynyl, or a pharmaceutically acceptable salt thereof. In certain embodiments, $R_{18}$ is H and $R_{19}$ is haloalkyl (e.g., —$CH_2F$).

In certain embodiments, the compound of Formula (XVIII-d) is of the Formula (XVIII-d'):

(XVIII-d')

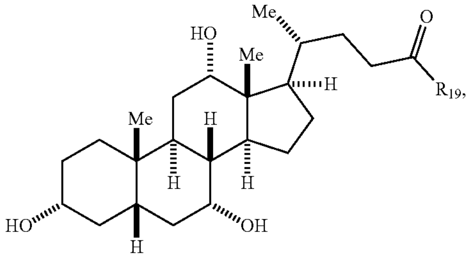

wherein:

$R_{19}$ is alkyl, haloalkyl, alkenyl, or alkynyl, or a pharmaceutically acceptable salt thereof. In certain embodiments, $R_{19}$ is haloalkyl (e.g., —$CH_2F$).

In some embodiments of the various aspects disclosed herein, m is 1; n is 2; X is —C(O)$CH_2F$, —NCS, —C(O)CH═$CH_2$, —C(O)C≡CH, —NHC(O)CH═$CH_2$, —CN, —CH═C(CN)$CO_2$Et, or —C(O)$CH_3$; $R_1$, $R_2$, $R_4$, $R_{16}$, $R_{11}$, $R_{15}$ and $R_{16}$ are H; $R_3$ is —OH or —$OSO_3^-$; $R_7$ is —OH; and $R_{12}$ is H or —OH.

In some embodiments of the various aspects disclosed herein, m is 1; n is 2; X is —C(O)$CH_2F$, —NCS, —C(O)CH═$CH_2$, —C(O)C≡CH, —NHC(O)CH═$CH_2$, —CN, —CH═C(CN)$CO_2$Et, or —C(O)$CH_3$; $R_1$, $R_2$, $R_4$, $R_{16}$, $R_{11}$, $R_{15}$ and $R_{16}$ are H; $R_3$ is —OH or —$OSO_3$H; $R_7$ is —OH; and $R_{12}$ is H or —OH.

In some embodiments of the various aspects disclosed herein, m is 1; n is 2; X is —C(O)$CH_2F$ or —NCS; $R_1$, $R_2$, $R_4$, $R_{16}$, $R_{11}$, $R_{15}$ and $R_{16}$ are H; $R_3$ is —OH or —$OSO_3^-$; $R_7$ is —OH; and $R_{12}$ is H or —OH.

In some embodiments of the various aspects disclosed herein, m is 1; n is 2; X is —C(O)$CH_2F$ or —NCS; $R_1$, $R_2$, $R_4$, $R_{16}$, $R_{11}$, $R_{15}$ and $R_{16}$ are H; $R_3$ is —OH or —$OSO_3$H; $R_7$ is —OH; and $R_{12}$ is H or —OH.

In some embodiments of the various aspects disclosed herein, m is 1; n is 2; X is —C(O)$CH_2F$; $R_1$, $R_2$, $R_4$, $R_{16}$, $R_{11}$, $R_{15}$ and $R_{16}$ are H; $R_3$ is —OH or —$OSO_3^-$; $R_7$ is —OH; and $R_{12}$ is H or —OH.

In some embodiments of the various aspects disclosed herein, m is 1; n is 2; X is —C(O)$CH_2F$; $R_1$, $R_2$, $R_4$, $R_{16}$, $R_{11}$, $R_{15}$ and $R_{16}$ are H; $R_3$ is —OH or —$OSO_3$H; $R_7$ is —OH; and $R_{12}$ is H or —OH.

In some embodiments of the various aspects disclosed herein, m is 1; n is 2; X is —C(O)$CH_2F$; $R_1$, $R_2$, $R_4$, $R_{16}$, $R_{18}$, $R_{15}$ and $R_{16}$ are H; $R_3$ is —OH and $R_7$ are OH; and $R_{12}$ is H or —OH.

In some embodiments of the various aspects disclosed herein, m is 1; n is 2; X is —C(O)$CH_2F$; $R_1$, $R_2$, $R_4$, $R_{16}$, $R_{11}$, $R_{15}$ and $R_{16}$ are H; $R_3$ is —$OSO_3^-$; and $R_7$ is —OH; and $R_{12}$ is H.

In some embodiments of the various aspects disclosed herein, m is 1; n is 2; X is —C(O)$CH_2F$; $R_1$, $R_2$, $R_4$, $R_{16}$, $R_{11}$, $R_{15}$ and $R_{16}$ are H; $R_3$ is —$OSO_3$H; and $R_7$ is —OH; and $R_{12}$ is H.

In embodiments of the various aspects disclosed herein, compounds of Formula (I) do not modulate activity of TGR5. In other words, compounds of Formula (I) are neither agonists nor antagonists of TGR5.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NR$SO_2$R', —NR'NR"R'", —ONR'R", —NR'C=(O)NR"NR'"R"", —CN, —$NO_2$, —NR'$SO_2$R", —NR'C=(O)R", —NR'C(O)—OR", —NR'OR", in a number ranging from zero to (2m'+1), where m' is the total number of carbon atoms in such radical. R', R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR"R")—NR'", —S(O)R', —S(O)$_2$R', —S(O)$_2$NR'R", —NR$SO_2$R', —NR'NR"R'", —ONR'R", —NR'C=(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, —NR'$SO_2$R", —NR'C=(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In some embodiments of any of the aspects, the ring-forming substituents are attached to adjacent members of the base structure. For example, two ring-forming substituents attached to adjacent members of a cyclic base structure create a fused ring structure. In another embodiment of any of the aspects, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'—, r a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where r and d are independently integers of from 0 to 3, and X' is —O—, —NR'—, —S—, —S(O)—, —S(O)$_2$—, or —S(O)$_2$NR'—. The substituents R', R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In certain embodiments, the compound of Formula (I) is of the formula:
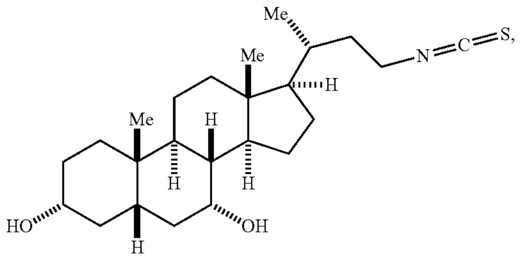
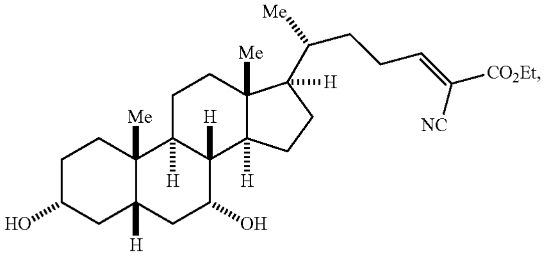
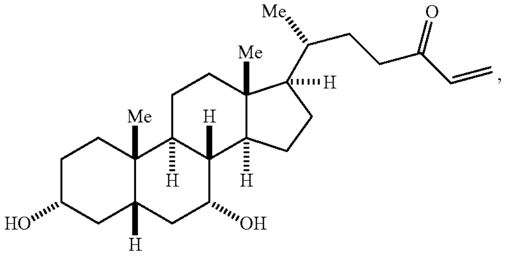
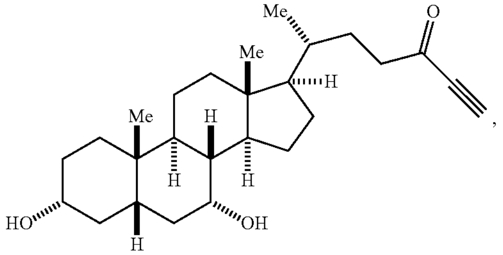
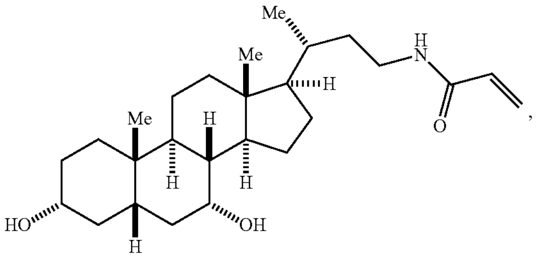
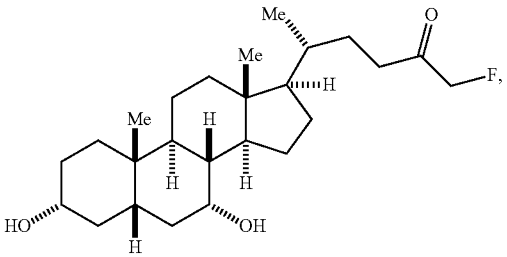
-continued
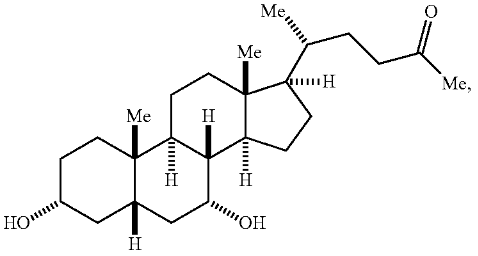
or
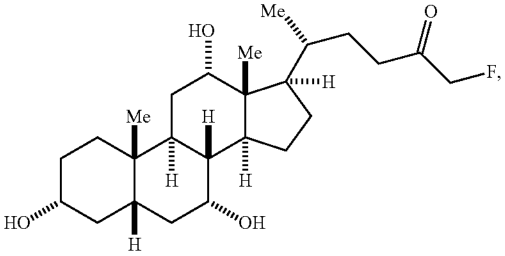
or a pharmaceutically acceptable salt thereof.
In certain embodiments, the compound of Formula (I) is of the formula:
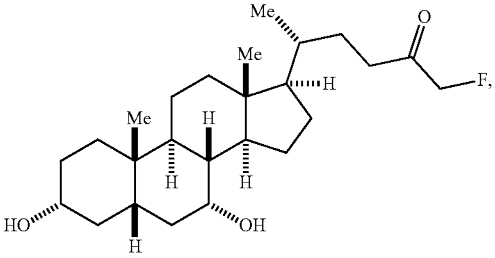
or
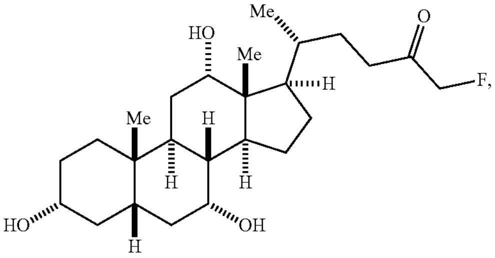
or a pharmaceutically acceptable salt thereof.
In certain embodiments, the compound of Formula (I) is of the formula:
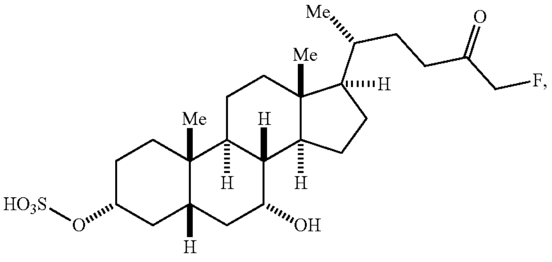
or a pharmaceutically acceptable salt thereof.

In certain embodiments, the compound of Formula (I) is of the formula:

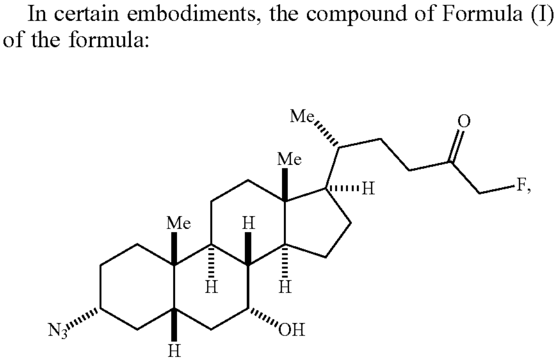

or a pharmaceutically acceptable salt thereof.

In certain embodiments, the compound of Formula (I) is not of the formula:

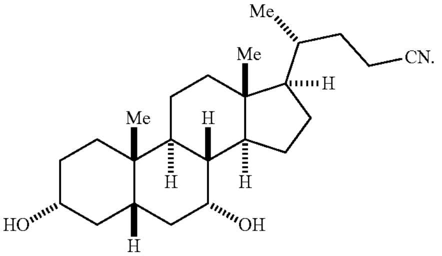

In certain embodiments, the compound of Formula (I) is not of the formula:

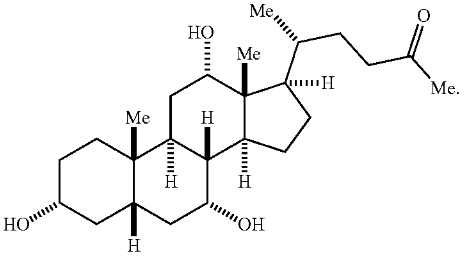

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium (3H), iodine-125 ($^{125}I$), or carbon-14 ($^{14}C$). All isotopic variations of the compounds of the present invention, whether radioactive or not, are encompassed within the scope of the present invention.

Pharmaceutical Compositions, Kits, and Administration

In still another aspect, provided herein is a pharmaceutical composition comprising a compound of Formula (I)-(XVIII) and a pharmaceutically acceptable carrier or excipient.

In some embodiments of any of the aspects, the agents or compounds as provided herein is formulated with a pharmaceutical composition. In another embodiment of any of the aspects, the pharmaceutical composition is formulated to treat a disease (e.g., a metabolic disorder (e.g., diabetes, obesity), a gastrointestinal disease (e.g., a gastrointestinal infection; inflammatory bowel disease (IBD); appendicitis; Crohn's disease (CD); ulcerative colitis (UC); gastritis; enteritis; esophagitis; pancreatitis; diabetes; hepatitis; liver disease (e.g., Non-alcoholic Fatty Liver Disease (NAFLD); non-alcoholic steatohepatitis (NASH); hepatitis A; hepatitis B; hepatitis C; autoimmune hepatitis; and cirrhosis of the liver); gastroesophageal reflux disease (GERD); celiac disease; diverticulitis; food intolerance; ulcer; infectious colitis; irritable bowel syndrome; leaky gut; and cancer), cancer (e.g., cancer of the digestive system; hepatic carcinoma; liver cancer; colon cancer; esophageal cancer; gastric cancer; hepatoma; kidney or renal cancer; oral cavity cancer; pancreatic cancer; prostate cancer; rectal cancer; stomach cancer; basal cell carcinoma, biliary tract cancer; lung cancer; bladder cancer; cervical cancer; endometrial cancer; uterine cancer; and cancer of the urinary system)e.g., or an inflammatory disease (e.g., Crohn's disease, inflammatory bowel disease, ulcerative colitis, pancreatitis, hepatitis, liver disease, biliary atresia, appendicitis, gastritis, diverticulitis, celiac disease, food intolerance, enteritis, ulcer, gastroesophageal reflux disease (GERD), psoriatic arthritis, psoriasis, rheumatoid arthritis)).

In another aspect of any of the embodiments, provided herein is a composition comprising an agent that inhibits bile salt hydrolase (BSH) in a subject.

In another embodiment of any of the aspects, the composition further comprises a pharmaceutically acceptable carrier or excipient.

The present disclosure provides pharmaceutical compositions comprising a compound of Formulae (I)-(XVIII), or a pharmaceutically acceptable salt thereof, and optionally a pharmaceutically acceptable excipient. In certain embodiments, the pharmaceutical composition described herein comprises a compound of Formulae (I)-(XVIII), or a pharmaceutically acceptable salt thereof, and a pharmaceutically acceptable excipient.

In some embodiments, the pharmaceutical composition is a liquid dosage form or solid dosage form. Liquid dosage forms for oral administration include, but are not limited to, pharmaceutically acceptable emulsions, microemulsions, solutions, suspensions, syrups and elixirs. In addition to the compound of any of Formulas (I)-(XVIII), the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the compound of any of Formula (I)-(XVIII), are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcelhdose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols, and the like. The solid dosage forms of tablets, dragées, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polyethylene glycols, and the like.

The compound of any of Formula (I)-(XVIII) can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical formulating art. In such solid dosage forms, the compound of any of Formula (I)-(XVIII) can be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

In some embodiments, the carrier or excipient restricts delivery of the composition to the gastrointestinal tract. In some embodiments, the composition provided herein is restricted to the gastrointestinal tract by the addition of a sulfate group or a polar group to the compounds.

In some embodiments, the carrier or excipient is an enteric coating or enteric-coated drug delivery device. As used herein, the terms "enteric coating" or "enteric-coated drug delivery device" refers to any drug delivery method that can be administered orally but is not degraded or activated until the device enters the intestines. Such methods can utilize a coating or encapsulation that is degraded using e.g., pH dependent means, permitting protection of the delivery device and the agent to be administered or transplanted throughout the gastrointestinal tract until the device reaches the alkaline pH of the intestines (e.g. cecum or colon).

An enteric coating can control the location of where an agent is released in the digestive system. Thus, an enteric coating can be used such that a pharmaceutical composition does not dissolve and release the agent in the stomach, but rather travels to the intestine, where it dissolves and releases the agent in an environment that is most beneficial for inhibiting BSH (e.g. targeting bacteria located in the cecum, ileum, large intestine, or colon). An enteric coating can be stable at low pH (such as in the stomach) and can dissolve at higher pH (for example, in the intestine). Material that can be used in enteric coatings includes, for example, alginic acid, cellulose acetate phthalate, plastics, waxes, shellac, and fatty acids (e.g., stearic acid, palmitic acid). Enteric coatings are described, for example, in U.S. Pat. Nos. 5,225,202, 5,733,575, 6,139,875, 6,420,473, 6,455,052, and 6,569,457, all of which are herein incorporated by reference in their entirety. The enteric coating can be an aqueous enteric coating. Examples of polymers that can be used in enteric coatings include, for example, shellac (trade name EmCoat 120 N, Marcoat 125); cellulose acetate phthalate (trade names AQUACOAT™, AQUACOAT ECD™, SEPIFILM™, KLUCEL™, and METOLOSE™); polyvinylacetate phthalate (trade name SURETERIC™); and methacrylic acid (trade names EUDRAGIT™, EUDRAGIT L 100-55™ from Evonik Industries, Germany).

Another example of methods known in the art that allow for restriction of pharmaceutical compositions to the intestines, include enteric magnesium micromotors (EMgMs). EMgMs are described in the art, for example, in Li et al., ACS NANO, (2016).

Pharmaceutical compositions include formulations suitable for oral administration may be provided as discrete units, such as tablets, capsules, cachets, syrups, elixirs, prepared food items, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

Accordingly, formulations suitable for rectal administration include gels, creams, lotions, aqueous or oily suspensions, dispersible powders or granules, emulsions, dissolvable solid materials, douches, and the like can be used. The formulations are preferably provided as unit-dose suppositories comprising the active ingredient in one or more solid carriers forming the suppository base, for example, cocoa butter. Suitable carriers for such formulations include petroleum jelly, lanolin, polyethyleneglycols, alcohols, and combinations thereof. Alternatively, colonic washes with the rapid recolonization deployment agent of the present disclosure can be formulated for colonic or rectal administration.

In certain embodiments, the compound or pharmaceutical composition is a solid. In certain embodiments, the compound or pharmaceutical composition is a powder. In certain embodiments, the compound or pharmaceutical composition can be dissolved in a liquid to make a solution. In certain embodiments, the compound or pharmaceutical composition is dissolved in water to make an aqueous solution. In certain embodiments, the pharmaceutical composition is a liquid for parental injection. In certain embodiments, the pharmaceutical composition is a liquid for oral administration (e.g., ingestion). In certain embodiments, the pharmaceutical composition is a liquid (e.g., aqueous solution) for intravenous injection. In certain embodiments, the pharmaceutical composition is a liquid (e.g., aqueous solution) for subcutaneous injection.

After formulation with an appropriate pharmaceutically acceptable excipient in a desired dosage, the pharmaceutical compositions of this disclosure can be administered to humans and other animals orally, parenterally, intracisternally, intraperitoneally, topically, bucally, or the like, depending on the disease or condition being treated.

In certain embodiments, a pharmaceutical composition comprising a compound of Formula (I)-(XVIII) is administered, orally or parenterally, at dosage levels of each pharmaceutical composition sufficient to deliver from about 0.001 mg/kg to about 200 mg/kg in one or more dose administrations for one or several days (depending on the mode of administration). In certain embodiments, the effective amount per dose varies from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, of subject body weight per day, one or more times a day, to obtain the desired therapeutic and/or prophylactic effect. In certain embodiments, the compounds described herein may be at dosage levels sufficient to deliver from about 0.001 mg/kg to about 200 mg/kg, from about 0.001 mg/kg to about 100 mg/kg, from about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In certain embodiments, the composition described herein is administered at a dose that is below the dose at which the compound or agent causes non-specific effects.

In certain embodiments, the pharmaceutical composition is administered at a dose of about 0.001 mg to about 1000 mg per unit dose. In certain embodiments, the pharmaceutical composition is administered at a dose of about 0.01 mg to about 200 mg per unit dose. In certain embodiments, the pharmaceutical composition is administered at a dose of about 0.01 mg to about 100 mg per unit dose. In certain embodiments, pharmaceutical composition is administered at a dose of about 0.01 mg to about 50 mg per unit dose. In certain embodiments, the pharmaceutical composition is administered at a dose of about 0.01 mg to about 10 mg per unit dose. In certain embodiments, the pharmaceutical composition is administered at a dose of about 0.1 mg to about 10 mg per unit dose.

Pharmaceutical compositions described herein can be prepared by any method known in the art of pharmacology. In general, such preparatory methods include the steps of bringing the composition comprising a compound of Formula (I)-(XVIII) into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the disclosure will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazelnut, hyssop, isopropyl myristate, jojoba, kukui nut, lavandin, lavender, lemon, *Litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents, such as CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragées, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active agents can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this disclosure. Additionally, the present disclosure contemplates the use of transdermal patches, which have the added advantage of providing controlled delivery of an agent to the body. Such dosage forms can be made by dissolving or dispensing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., quids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound of formulae (I)-(XVI), or pharmaceutical composition described herein. In certain embodiments, the kits are useful for treating a disease (e.g., a metabolic disorder (e.g., diabetes, obesity), a gastrointestinal disease (e.g., a gastrointestinal infection; inflammatory bowel disease (IBD); appendicitis; Crohn's disease (CD); ulcerative colitis (UC); gastritis; enteritis; esophagitis; pancreatitis; diabetes; hepatitis; liver disease (e.g., Non-alcoholic Fatty Liver Disease (NAFLD); non-alcoholic steatohepatitis (NASH); hepatitis A; hepatitis B; hepatitis C; autoimmune hepatitis; and cirrhosis of the liver); gastroesophageal reflux disease (GERD); celiac disease; diverticulitis; food intolerance; ulcer; infectious colitis; irritable bowel syndrome; leaky gut; and cancer), cancer (e.g., cancer of the digestive system; hepatic carcinoma; liver cancer; colon cancer; esophageal cancer; gastric cancer; hepatoma; kidney or renal cancer; oral cavity cancer; pancreatic cancer; prostate cancer; rectal cancer; stomach cancer; basal cell carcinoma, biliary tract cancer; lung cancer; bladder cancer; cervical cancer; endometrial cancer; uterine cancer; and cancer of the urinary system), inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis) in a subject in need thereof. In certain embodiments, the kits are useful for preventing a disease (e.g., a metabolic disorder (e.g., diabetes, obesity), gastrointestinal disease (e.g., a gastrointestinal infection; inflammatory bowel disease (IBD); appendicitis; Crohn's disease (CD); ulcerative colitis (UC); gastritis; enteritis; esophagitis; pancreatitis; diabetes; hepatitis; liver disease (e.g., Non-alcoholic Fatty Liver Disease (NAFLD); non-alcoholic steatohepatitis (NASH); hepatitis A; hepatitis B; hepatitis C; autoimmune hepatitis; and cirrhosis of the liver); gastroesophageal reflux disease (GERD); celiac disease; diverticulitis; food intolerance; ulcer; infectious colitis; irritable bowel syndrome; leaky gut; and cancer), cancer (e.g., cancer of the digestive system; hepatic carcinoma; liver cancer; colon cancer; esophageal cancer; gastric cancer; hepatoma; kidney or renal cancer; oral cavity cancer; pancreatic cancer; prostate cancer; rectal cancer; stomach cancer; basal cell carcinoma, biliary tract cancer; lung cancer; bladder cancer; cervical cancer; endometrial cancer; uterine cancer; and cancer of the urinary system), inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis) in a subject in need thereof. In certain embodiments, the kits are useful for reducing the risk of developing a disease (e.g., a metabolic disorder (e.g., diabetes, obesity), gastrointestinal disease, cancer, inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis) in a subject in need thereof.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., a metabolic disorder (e.g., diabetes, obesity), inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis) in a subject in need thereof. In certain embodiments, the kits and instructions provide for preventing a disease (e.g., metabolic disorder (e.g., diabetes, obesity), gastrointestinal disease (e.g., a gastrointestinal infection; inflammatory bowel disease (IBD); appendicitis; Crohn's disease (CD); ulcerative colitis (UC); gastritis; enteritis; esophagitis; pancreatitis; diabetes; hepatitis; liver disease (e.g., Non-alcoholic Fatty Liver Disease (NAFLD); non-alcoholic steatohepatitis (NASH); hepatitis A; hepatitis B; hepatitis C; autoimmune hepatitis; and cirrhosis of the liver); gastroesophageal reflux disease (GERD); celiac disease; diverticulitis; food intolerance; ulcer; infectious colitis; irritable bowel syndrome; leaky gut; and cancer), cancer (e.g., cancer of the digestive system; hepatic carcinoma; liver cancer; colon cancer; esophageal cancer; gastric cancer; hepatoma; kidney or renal cancer; oral cavity cancer; pancreatic cancer; prostate cancer; rectal cancer; stomach cancer; basal cell carcinoma, biliary tract cancer; lung cancer; bladder cancer; cervical cancer; endometrial cancer; uterine cancer; and cancer of the urinary system) e.g., or an inflammatory disease (e.g., Crohn's disease, inflammatory bowel disease, ulcerative colitis, pancreatitis, hepatitis, liver disease, biliary atresia, appendicitis, gastritis, diverticulitis, celiac disease, food intolerance, enteritis, ulcer, gastroesophageal reflux disease (GERD), psoriatic arthritis, psoriasis, rheumatoid arthritis) in a subject in need thereof. In certain embodiments, the kits and instructions provide for reducing the risk of developing a disease (e.g., metabolic disorder (e.g., diabetes, obesity), gastrointestinal disease, cancer (e.g., liver cancer), or an inflammatory disease (e.g., Crohn's disease, inflammatory bowel disease, ulcerative colitis, pancreatitis, hepatitis, liver disease, biliary atresia, appendicitis, gastritis, diverticulitis, celiac disease, food intolerance, enteritis, ulcer, gastroesophageal reflux disease (GERD), psoriatic arthritis, psoriasis, rheumatoid arthritis) in a subject in need thereof. A kit described herein may include one or more additional pharmaceutical compounds described herein in a separate composition.

Methods of Treatment

In one aspect, provided herein is a method of modulating bile acids in a subject. In another aspect, provided herein is a method of inhibiting bile acid deconjugation in a subject. In yet another aspect, provided herein is a method of promoting bile acid conjugation in a subject.

In one aspect of any of the embodiments, provided herein is a method of modulating bile acids in a subject, the method comprises: administering to the subject in need thereof a therapeutically effective amount of a compound of any one of Formulas I-XVIII, derivative thereof, or a pharmaceutical composition provided herein.

In some embodiments of any of the aspects, the agent is an inhibitor of BSH. In some embodiments of any of the aspects, the agent is an inhibitor of bacterial BSH present in a host subject.

In another embodiment any of the aspects, the agent or inhibitor is the compound of Formula (I)-(XVIII) or derivative thereof; compounds 1-9 or derivative thereof; riboflavin; or caffeic acid phenethyl ester (CAPE). Compounds 1-9 are also shown in FIG. 2D.

In another embodiment any of the aspects, the inhibitor is selected from the group consisting of a small molecule, an antibody, a peptide, a genome editing system, an antisense oligonucleotide, shRNA, and an siRNA.

In some embodiments of any of the aspects, the agent that inhibits BSH is an RNAi, siRNA, or shRNA. The term "RNAi" or "siRNA" or "shRNA" as used herein refers to interfering RNA or RNA interference. RNAi refers to a means of selective post-transcriptional gene silencing by destruction of specific mRNA by molecules that bind and inhibit the processing of mRNA, for example inhibit mRNA translation or result in mRNA degradation. As used herein, the term "RNAi" refers to any type of interfering RNA, including but are not limited to, siRNA, shRNA, endogenous microRNA and artificial microRNA. For instance, it includes sequences previously identified as siRNA, regardless of the mechanism of down-stream processing of the RNA.

In some embodiments of any of the aspects, the agent that inhibits BSH is an antisense oligonucleotide. As used herein, an "antisense oligonucleotide" refers to a synthesized nucleic acid sequence that is complementary to a DNA or mRNA sequence, such as that of a microRNA. Antisense oligonucleotides are typically designed to block expression of a DNA or RNA target by binding to the target and halting expression at the level of transcription, translation, or splicing. Antisense oligonucleotides as described herein are complementary nucleic acid sequences designed to hybridize under cellular conditions to a gene. Thus, oligonucleotides are chosen that are sufficiently complementary to the target, i.e., that hybridize sufficiently well and with sufficient specificity in the context of the cellular environment, to give the desired effect. For example, an antisense oligonucleotide that inhibits BSH levels or activity directly or indirectly may comprise at least 5, at least 10, at least 15, at least 20, at least 25, at least 30, or more bases complementary to a portion of the coding sequence of a bacterial BSH. Furthermore, the antisense oligonucleotide can target transcription factors that regulate the expression of bacterial BSH.

In some embodiments, the agent that inhibits BSH is an antibody. As used herein, the term "antibody" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include broadly neutralizing antibodies, midibodies, nanobodies, humanized antibodies, chimeric antibodies, and the like.

In other embodiments, the agent that inhibits BSH is a polypeptide. As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues provided herein are preferred to be in the "L" isomeric form. However, residues in the "D" isomeric form may be substituted for any L-amino acid residue provided the desired properties of the polypeptide are retained.

In another embodiment of any of the aspects, BSH is inhibited in a bacterial cell genome using any genome editing system including, but not limited to, zinc finger nucleases, TALENS, meganucleases, and CRISPR/Cas systems. In some embodiments of any of the aspects, the genomic editing system used to incorporate the nucleic acid encoding one or more guide RNAs into the cell's genome is not a CRISPR/Cas system; this can prevent undesirable cell death in cells that retain a small amount of Cas enzyme/protein. It is also contemplated herein that either the Cas enzyme or the sgRNAs are each expressed under the control of a different inducible promoter, thereby allowing temporal expression of each to prevent such interference. The gene editing system can directly or indirectly modulate levels or activity of BSH or expression.

In one aspect of any of the embodiments, provided herein is a method for inhibiting a bile salt hydrolase (BSH), the method comprises contacting a BSH with a compound provided herein.

In some embodiments of any of the aspects, the agent is an inhibitor of bile salt hydrolase (BSH). In another embodiment of any of the aspects, the agent is a compound of any one of Formulas I-XVIII or 3-sulfated-lithocholic acid-fluoromethyl ketone (3S-LCA-FMK). In another embodiment of any of the aspects, the agent is a derivative of any one of Formulas I-XVIII or 3-sulfated-lithocholic acid-fluoromethyl ketone (3S-LCA-FMK). In another embodiment of any of the aspects, the agent is a bile acid or derivative thereof. In another embodiment of any of the aspects, the agent is chenodeoxycholic acid (CDCA) or derivative thereof.

In some embodiments, inhibition of BSH results in a reduction in secondary bile acids. In other embodiments, inhibition of BSH promotes conjugation of bile acids. In another embodiment, inhibition of BSH reduces deconjugation of bile acids. The activity of BSH can be determined by the presence or absence of deconjugated bile acids.

In some embodiments of any of the aspects, the activity or levels of BSH is inhibited by at least 50%, at least 60%, at least 70%, at least 80%, at least 90%, or more as compared to an appropriate control.

Imbalances in bile acid homeostasis are can play causal roles in the pathophysiology of diseases including hypercholesterolemia, obesity, diabetes, cancer, gastrointestinal disease, and formation of gallstones, further highlighting the biological importance of these metabolites.

In some embodiments of any of the aspects, the subject is at risk of having, or has a gastrointestinal disease. (e.g., a gastrointestinal infection; inflammatory bowel disease (IBD); appendicitis; Crohn's disease (CD); ulcerative colitis (UC); gastritis; enteritis; esophagitis; pancreatitis; diabetes; hepatitis; liver disease (e.g., Non-alcoholic Fatty Liver Disease (NAFLD); non-alcoholic steatohepatitis (NASH); hepatitis A; hepatitis B; hepatitis C; autoimmune hepatitis; and cirrhosis of the liver); gastroesophageal reflux disease (GERD); celiac disease; diverticulitis; food intolerance; ulcer; infectious colitis; irritable bowel syndrome; leaky gut; and cancer).

In some embodiments of any of the aspects, the disease is a gastrointestinal disease. In certain embodiments, the gastrointestinal disease a gastrointestinal infection. In certain embodiments, the gastrointestinal infection is an infection caused by a bacteria selected from the group consisting *Staphylococcus; Helicobacter pylori; Escherichia coli; Salmonella; Campylobacter; Yersinia enterocolitica; Shigella; Clostridium; Bacteroides; Lactobacillus*; Parabacteroides; *Bifidobacterium; Listeria*; and *Streptococcus*. In certain embodiments, the gastrointestinal disease is inflammatory bowel disease (IBD). In certain embodiments, the gastrointestinal disease is appendicitis. In certain embodiments, the gastrointestinal disease is Crohn's disease (CD). In certain embodiments, the gastrointestinal disease is ulcerative colitis (UC). In certain embodiments, the gastrointestinal disease is gastritis. In certain embodiments, the gastrointestinal disease is enteritis. In certain embodiments, the gastrointestinal disease is esophagitis. In certain embodiments, the gastrointestinal disease is pancreatitis. In certain embodiments, the gastrointestinal disease is diabetes. In certain embodiments, the gastrointestinal disease is hepatitis. In certain embodiments, the gastrointestinal disease is liver disease (e.g., Non-alcoholic Fatty Liver Disease (NAFLD); non-alcoholic steatohepatitis (NASH); hepatitis A; hepatitis B; hepatitis C; autoimmune hepatitis; and cirrhosis of the liver). In certain embodiments, the gastrointestinal disease is gastroesophageal reflux disease (GERD). In certain embodiments, the gastrointestinal disease is celiac disease. In certain embodiments, the gastrointestinal disease is diverticulitis. In certain embodiments, the gastrointestinal disease is food intolerance. In certain embodiments, the gastrointestinal disease is an ulcer. In certain embodiments, the gastrointestinal disease is infectious colitis. In certain embodiments, the gastrointestinal disease is irritable bowel syndrome. In certain embodiments, the gastrointestinal disease is leaky gut. In certain embodiments, the gastrointestinal disease is cancer.

In another embodiment of any of the aspects, the gastrointestinal disease is a liver disease. In certain embodiments, the liver disease is Non-alcoholic Fatty Liver Disease (NAFLD). In certain embodiments, the liver disease is non-alcoholic steatohepatitis (NASH). In certain embodiments, the liver disease is hepatitis A. In certain embodiments, the liver disease is hepatitis B. In certain embodiments, the liver disease is hepatitis C. In certain embodiments, the liver disease is autoimmune hepatitis. In certain embodiments, the liver disease is cirrhosis of the liver.

In another embodiment of any of the aspects, the subject is at risk of having, or has obesity. As used herein, the term "obesity" refers to excess fat in the body.

In some embodiments of any of the aspects, a subject with obesity can be a subject with a body mass index of at least about 25 $kg/m^2$ prior to administration of a treatment as described herein. In some embodiments, a subject with obesity can be a subject with a body mass index of at least about 30 $kg/m^2$ prior to administration of a treatment, compound, or agent as described herein.

In another embodiment of any of the aspects, the subject is at risk of having, or has and inflammatory disease (e.g., Crohn's disease, inflammatory bowel disease, ulcerative colitis, pancreatitis, hepatitis, liver disease, biliary atresia, appendicitis, gastritis, diverticulitis, celiac disease, food intolerance, enteritis, ulcer, gastroesophageal reflux disease (GERD), psoriatic arthritis, psoriasis, rheumatoid arthritis).

In one aspect, provided herein is a method of treating diabetes in a subject.

In some embodiments, the diabetes is type I diabetes, type II diabetes, neonatal diabetes, maturity onset diabetes in the young, or gestational diabetes.

In some embodiments, the diabetes is caused by obesity. In one aspect, provided herein is a method of treating obesity in a subject.

In certain embodiments, the disease is cancer. In certain embodiments, the cancer is cancer of the digestive system. In certain embodiments, the cancer is hepatic carcinoma. In certain embodiments, the cancer is liver cancer. In certain embodiments, the cancer is colon cancer. In certain embodiments, the cancer is esophageal cancer. In certain embodiments, the cancer is gastric cancer. In certain embodiments, the cancer is hepatoma. In certain embodiments, the cancer is kidney or renal cancer. In certain embodiments, the cancer is oral cavity cancer. In certain embodiments, the cancer is pancreatic cancer. In certain embodiments, the cancer is prostate cancer. In certain embodiments, the cancer is rectal cancer. In certain embodiments, the cancer is stomach cancer. In certain embodiments, the cancer is basal cell carcinoma. In certain embodiments, the cancer is biliary tract cancer. In certain embodiments, the cancer is lung cancer. In certain embodiments, the cancer is bladder cancer. In certain embodiments, the cancer is cervical cancer. In certain embodiments, the cancer is endometrial cancer. In certain embodiments, the cancer is uterine cancer. In certain embodiments, the cancer is cancer of the urinary system.

In some embodiments, the inflammatory disease is selected from the group consisting of: Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis. In some embodiments, the inflammatory disease is Crohn's disease. In some embodiments, the inflammatory disease is inflammatory bowel disease. In some embodiments, the inflammatory disease is ulcerative colitis. In some embodiments, the inflammatory disease is pancreatitis, hepatitis. In some embodiments, the inflammatory disease is appendicitis. In some embodiments, the inflammatory disease is gastritis. In some embodiments, the inflammatory disease is diverticulitis. In some embodiments, the inflammatory disease is celiac disease. In some embodiments, the inflammatory disease is food intolerance. In some embodiments, the inflammatory disease is enteritis. In some embodiments, the inflammatory disease is ulcer. In some embodiments, the inflammatory disease is gastroesophageal reflux disease (GERD). In some embodiments, the inflammatory disease is psoriatic arthritis. In some embodiments, the inflammatory disease is psoriasis. In some embodiments, the inflammatory disease is rheumatoid arthritis.

In certain embodiments, the subject being treated is an animal. The animal may be of either sex and may be at any stage of development. In certain embodiments, the subject is a mammal. In certain embodiments, the subject being treated is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal.

In another embodiment of any of the aspects, the subject is at risk of having, or has cancer. The conversion of primary to secondary bile acids can lead to a decrease in a tumor-suppressors in the liver. It is contemplated that this mechanism can be extended to other types of cancers. See for example, Ma et al. *Science* (2018), which is incorporated herein by reference in its entirety.

The methods and compositions provided herein can further be applied to treat or prevent prediabetes in a subject. A subject can also be one who is suffering from or at risk of developing diabetes or a pre-diabetic condition. The cause of diabetes can be due to a genetic mutation, inherited diabetes, obesity, lifestyle, or idiopathic.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of use or administration utilized.

The effective dose can be estimated initially from cell culture assays. A dose can be formulated in animals. Generally, the compositions are administered so that a compound of the disclosure herein is used or given at a dose from 1 μg/kg to 1000 mg/kg; 1 μg/kg to 500 mg/kg; 1 μg/kg to 150 mg/kg, 1 μg/kg to 100 mg/kg, 1 μg/kg to 50 mg/kg, 1 μg/kg to 20 mg/kg, 1 μg/kg to 10 mg/kg, 1 μg/kg to 1 mg/kg, 100 μg/kg to 100 mg/kg, 100 μg/kg to 50 mg/kg, 100 μg/kg to 20 mg/kg, 100 μg/kg to 10 mg/kg, 100 μg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. Further contemplated is a dose (either as a bolus or continuous infusion) of about 0.1 mg/kg to about 10 mg/kg, about 0.3 mg/kg to about 5 mg/kg, or 0.5 mg/kg to about 3 mg/kg. It is to be further understood that the ranges intermediate to those given above are also within the scope of this disclosure, for example, in the range 1 mg/kg to 10 mg/kg, for example use or dose ranges such as 2 mg/kg to 8 mg/kg, 3 mg/kg to 7 mg/kg, 4 mg/kg to 6 mg/kg, and the like.

The compounds described herein can be administered at once, or can be divided into a number of smaller doses to be administered at intervals of time. It is understood that the precise dosage and duration of treatment will be a function of the location of where the composition is parenterally administered, the carrier and other variables that can be determined empirically using known testing protocols or by extrapolation from in vivo or in vitro test data. It is to be noted that concentrations and dosage values can also vary with the age of the individual treated. It is to be further understood that for any particular subject, specific dosage regimens can need to be adjusted over time according to the individual need and the professional judgment of the person administering or supervising the administration of the formulations. Hence, the concentration ranges set forth herein are intended to be exemplary and are not intended to limit the scope or practice of the claimed formulations.

In one embodiment of any of the aspects, the agent, compound, or composition is administered continuously (e.g., at constant levels over a period of time). Continuous administration of an agent or compound can be achieved, e.g., by epidermal patches, continuous release formulations, or on-body injectors.

The compound can be administered as a single bolus or multiple boluses, as a continuous infusion, or a combination thereof. For example, the compound can be administered as a single bolus initially, and then administered as a continuous infusion following the bolus. The rate of the infusion can be any desired rate. Some contemplated infusion rates include from 1 μg/kg/min to 100 mg/kg/min, or from 1 μg/kg/hr to 1000 mg/kg/hr. Rates of infusion can include 0.2 to 1.5 mg/kg/min, or more specifically 0.25 to 1 mg/kg/min, or even more specifically 0.25 to 0.5 mg/kg/min. It will be appreciated that the rate of infusion can be determined based upon the dose necessary to maintain effective plasma concentration and the rate of elimination of the compound, such that the compound is administered via infusion at a rate sufficient to safely maintain a sufficient effective plasma concentration of compound in the bloodstream.

The dosage of the agent or compound as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further agents, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

In one embodiment of any of the aspects, the agent, compound, or compositions described herein are used as a monotherapy. In another embodiment of any of the aspects, the agents or compounds described herein can be used in combination with other known agents and therapies for diabetes. Administered "in combination," as used herein, means that two (or more) different treatments are delivered to the subject during the course of the subject's affliction with the disorder, e.g., the two or more treatments are delivered after the subject has been diagnosed with the disorder (e.g. diabetes) and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery."

In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The compounds and agents described herein and the at least one additional therapy can be administered simultaneously, in the same or in separate compositions, or sequentially. For sequential administration, the agent described herein can be administered first, and the additional agent can be administered second, or the order of administration can be reversed. The agent and/or other therapeutic agents, procedures or modalities can be administered during periods of active disorder, or during a period of remission or less active disease. The agent can be administered before another treatment, concurrently with the treatment, post-treatment, or during remission of the disorder.

Therapeutics currently used to treat or prevent gastrointestinal diseases, inflammatory diseases, liver disease, and metabolic disorders (e.g., obesity) include, but are not limited to, insulin therapy, sulfonylureas (e.g. glyburide), meglitinides (e.g. nataglinide), SGLT2 inhibitors (e.g. canaglifozin), bile acid sequesterants (e.g. colesevelam), dopamine-2-agonists (e.g. bromocriptine), biguanides (e.g. metformin), DPP-4 inhibitors (e.g. alogliptin, linagliptin, etc.), alpha-glucosidase inhibitors (e.g. acarbose and miglitol), thiazolidinediones (e.g. rosiglitazone), antibiotics (e.g. aminosalicylic acid, norflaxacin, penicillin, cephalosporin), antivirals (e.g. zanamivir, oseltamivir), vaccines, corticosteroids (e.g. hydrocortisone, prednisone, prednisolone, budesonide), analgesics (e.g. acetaminophen, ibuprofen), non-steroidal anti-inflammatory drugs (e.g. mesalamine), anti-inflammatory drugs (e.g. sulfasalazine), immunosuppressants (e.g. infliximab, azathioprine, adalimumab, mercaptopurine), dietary supplements (e.g. iron), surgeries (e.g. colostomy, ileostomy, colectomy, proctocolectomy, gastric bypass), ursodeoxycholic acid (UDCA, also known as ursodiol, INN, NAN, AAN, or USAN), cholestyramine, stanozolol, naltrexone, rifampicin, pioglitazone, metformin, rosiglitazone, lobeglitazone, retinol ester, vitamin A, liver dialysis, or liver transplant, IV fluids, enemas, other treatments are known in the art.

In addition to the treatments for the diseases above chemotherapeutics can also be administered. Non-limiting examples of treatments for cancer (e.g., liver cancer), include nucleoside analogues (e.g., Tegafur), antifolates, anthracyclines, podophyllotoxins, taxanes, alkaloids, alkylating agents, platinum compounds, antibodies, retinoids, histone deacetylase inhibitors, arsenic trioxide, kinase inhibitors (e.g, Sorafenib), surgery, or any other chemotherapeutic known in the art. One of skill in the art can readily identify a chemotherapeutic agent of use (e.g. see Slapak and Kufe, Principles of Cancer Therapy, Chapter 86 in *Harrison's Principles of Internal Medicine,* 14th edition; Perry et al., Chemotherapy, Ch. 17 in Abeloff, Clinical Oncology 2nd ed. 2000 Churchill Livingstone, Inc; Baltzer L, Berkery R (eds): *Oncology Pocket Guide to Chemotherapy,* 2nd ed. St. Louis, Mosby-Year Book, 1995; Fischer D S, Knobf M F, Durivage H J (eds): *The Cancer Chemotherapy Handbook,* 4th ed. St. Louis, Mosby-Year Book, 1993).

In addition to the treatments for the diseases above chemotherapeutics can also be administered. Non-limiting examples of treatments for cancer (e.g., liver cancer), include nucleoside analogues (e.g., Tegafur), antifolates, anthracyclines, podophyllotoxins, taxanes, alkaloids, alkylating agents, platinum compounds, antibodies, retinoids, histone deacetylase inhibitors, arsenic trioxide, kinase inhibitors (e.g, Sorafenib), surgery, or any other chemotherapeutic known in the art. One of skill in the art can readily identify a chemotherapeutic agent of use (see, e.g., Slapak and Kufe, Principles of Cancer Therapy, Chapter 86 in Harrison's *Principles of Internal Medicine,* 14th edition; Perry et al., Chemotherapy, Ch. 17 in Abeloff, Clinical Oncology 2nd ed. 2000 Churchill Livingstone, Inc; Baltzer L, Berkery R (eds): *Oncology Pocket Guide to Chemotherapy,* 2nd ed. St. Louis, Mosby-Year Book, 1995; Fischer D S, Knobf M F, Durivage H J (eds): *The Cancer Chemotherapy Handbook,* 4th ed. St. Louis, Mosby-Year Book, 1993).

When administered in combination, the agent or composition and the additional agent (e.g., second or third agent), or all, can be administered in an amount or dose that is higher, lower or the same as the amount or dosage of each agent used individually, e.g., as a monotherapy. In certain embodiments, the administered amount or dosage of the agent, the additional agent (e.g., second or third agent), or all, is lower (e.g., at least 20%, at least 30%, at least 40%, or at least 50%) than the amount or dosage of each agent used individually. In other embodiments, the amount or dosage of agent, the additional agent (e.g., second or third agent), or all, that results in a desired effect (e.g., treatment of diabetes) is lower (e.g., at least 20%, at least 30%, at least 40%, or at least 50% lower) than the amount or dosage of each agent individually required to achieve the same therapeutic effect.

Administration

In some embodiments of any of the aspects, the agent is administered by direct injection, subcutaneous injection, muscular injection, oral administration, or nasal administration. In some embodiments, administering of the agent or pharmaceutical composition provided herein reduces glucose levels in the serum of a subject.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In certain preferred embodiments, the compositions are administered orally. some embodiments, the agents or compositions provided herein are directly injected into the portal vein. For example, injection into the portal vein can limit systemic side effects of the agent or pharmaceutical composition. In some embodiments, the compositions provided herein are implanted into the portal vein for sustained release. In some embodiments, the compositions are administered via an injection port.

Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments of any of the aspects, described herein is an agent or pharmaceutical composition that is administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of Formula (I)'s onset of action, duration of action, plasma levels within the therapeutic window, and peak blood levels. In particular, controlled- or extended-release dosage forms or formulations can be used to ensure that the maximum effectiveness of an agent is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with any agent described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, DUOLITE® A568 and DUOLITE® AP143 (Rohm&Haas, Spring House, Pa. USA).

Efficacy

The efficacy of an agents described herein, e.g., for the treatment of a disease, can be determined by the skilled practitioner. However, a treatment is considered "effective treatment," as the term is used herein, if one or more of the signs or symptoms of diabetes, obesity, gastrointestinal disease, cancer, or an inflammatory disease are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g., glucose levels or glucose tolerance. Efficacy can also be measured by a failure of an individual to worsen as assessed by hospitalization, or need for medical interventions (i.e., progression of the symptoms). Methods of measuring these indicators are known to those of skill in the art and/or are described herein.

Efficacy can be assessed in animal models of a condition described herein, for example, a mouse model or an appropriate animal model of the diseases provided herein, as the case may be. When using an experimental animal model, efficacy of treatment is evidenced when a statistically significant change in a marker is observed, e.g., reduced blood glucose levels in a model of diabetes.

It should be understood that this disclosure is not limited to the particular methodology, protocols, and reagents, etc., provided herein and as such may vary. The terminology used herein is for the purpose of describing particular embodiments only, and is not intended to limit the scope of the present disclosure, which is defined solely by the claims.

In certain embodiments, provided herein are methods of treating a metabolic disorder (e.g., diabetes, obesity), a gastrointestinal disease (e.g., a gastrointestinal infection; inflammatory bowel disease (IBD); appendicitis; Crohn's disease (CD); ulcerative colitis (UC); gastritis; enteritis; esophagitis; pancreatitis; diabetes; hepatitis; liver disease (e.g., Non-alcoholic Fatty Liver Disease (NAFLD); non-alcoholic steatohepatitis (NASH); hepatitis A; hepatitis B; hepatitis C; autoimmune hepatitis; and cirrhosis of the liver); gastroesophageal reflux disease (GERD); celiac disease; diverticulitis; food intolerance; ulcer; infectious colitis; irritable bowel syndrome; leaky gut; and cancer), cancer (e.g., cancer of the digestive system; hepatic carcinoma; liver cancer; colon cancer; esophageal cancer; gastric cancer; hepatoma; kidney or renal cancer; oral cavity cancer; pancreatic cancer; prostate cancer; rectal cancer; stomach cancer; basal cell carcinoma, biliary tract cancer; lung cancer; bladder cancer; cervical cancer; endometrial cancer; uterine cancer; and cancer of the urinary system), or an inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, gastroesophageal reflux disease (GERD), psoriatic arthritis, psoriasis, and rheumatoid arthritis) in a subject in need thereof.

In certain embodiments, provided herein are methods of preventing a metabolic disorder (e.g., diabetes, obesity), a gastrointestinal disease (e.g., a gastrointestinal infection; inflammatory bowel disease (IBD); appendicitis; Crohn's disease (CD); ulcerative colitis (UC); gastritis; enteritis; esophagitis; pancreatitis; diabetes; hepatitis; liver disease (e.g., Non-alcoholic Fatty Liver Disease (NAFLD); non-alcoholic steatohepatitis (NASH); hepatitis A; hepatitis B; hepatitis C; autoimmune hepatitis; and cirrhosis of the liver); gastroesophageal reflux disease (GERD); celiac disease; diverticulitis; food intolerance; ulcer; infectious colitis; irritable bowel syndrome; leaky gut; and cancer), cancer (e.g., cancer of the digestive system; hepatic carcinoma; liver cancer; colon cancer; esophageal cancer; gastric cancer; hepatoma; kidney or renal cancer; oral cavity cancer; pancreatic cancer; prostate cancer; rectal cancer; stomach cancer; basal cell carcinoma, biliary tract cancer; lung cancer; bladder cancer; cervical cancer; endometrial cancer; uterine cancer; and cancer of the urinary system), or an inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, gastroesophageal reflux disease (GERD), psoriatic arthritis, psoriasis, and rheumatoid arthritis) in a subject in need thereof.

The present disclosure also provides compounds of Formulae (I)-(XVIII), or a pharmaceutically acceptable salt thereof, for use in the treatment of a metabolic disorder (e.g., diabetes, obesity), a gastrointestinal disease (e.g., a gastrointestinal infection; inflammatory bowel disease (IBD); appendicitis; Crohn's disease (CD); ulcerative colitis (UC); gastritis; enteritis; esophagitis; pancreatitis; diabetes; hepatitis; liver disease (e.g., Non-alcoholic Fatty Liver Disease (NAFLD); non-alcoholic steatohepatitis (NASH); hepatitis A; hepatitis B; hepatitis C; autoimmune hepatitis; and cirrhosis of the liver); gastroesophageal reflux disease (GERD); celiac disease; diverticulitis; food intolerance; ulcer; infectious colitis; irritable bowel syndrome; leaky gut; and cancer), cancer (e.g., cancer of the digestive system; hepatic carcinoma; liver cancer; colon cancer; esophageal cancer; gastric cancer; hepatoma; kidney or renal cancer; oral cavity cancer; pancreatic cancer; prostate cancer; rectal cancer; stomach cancer; basal cell carcinoma, biliary tract cancer; lung cancer; bladder cancer; cervical cancer; endometrial cancer; uterine cancer; and cancer of the urinary system), or an inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, gastroesophageal reflux disease (GERD), psoriatic arthritis, psoriasis, and rheumatoid arthritis).

The present disclosure also provides compounds of Formulae (I)-(XVIII), or a pharmaceutically acceptable salt thereof, for use in the manufacture of a medicament for the treatment of a metabolic disorder (e.g., diabetes, obesity), a gastrointestinal disease (e.g., a gastrointestinal infection; inflammatory bowel disease (IBD); appendicitis; Crohn's disease (CD); ulcerative colitis (UC); gastritis; enteritis; esophagitis; pancreatitis; diabetes; hepatitis; liver disease (e.g., Non-alcoholic Fatty Liver Disease (NAFLD); non-alcoholic steatohepatitis (NASH); hepatitis A; hepatitis B; hepatitis C; autoimmune hepatitis; and cirrhosis of the liver); gastroesophageal reflux disease (GERD); celiac disease; diverticulitis; food intolerance; ulcer; infectious colitis; irritable bowel syndrome; leaky gut; and cancer), cancer (e.g., cancer of the digestive system; hepatic carcinoma; liver cancer; colon cancer; esophageal cancer; gastric cancer; hepatoma; kidney or renal cancer; oral cavity cancer; pancreatic cancer; prostate cancer; rectal cancer; stomach cancer; basal cell carcinoma, biliary tract cancer; lung cancer; bladder cancer; cervical cancer; endometrial cancer; uterine cancer; and cancer of the urinary system), or an inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis).

In certain embodiments, the disease is a metabolic disorder. In certain embodiments, the metabolic disorder is diabetes. In certain embodiments, the diabetes is type I diabetes. In certain embodiments, the diabetes is type II diabetes. In certain embodiments, the metabolic disorder is obesity.

In certain embodiments, the disease is an inflammatory disease. In certain embodiments, the inflammatory disease is Crohn's disease. In certain embodiments, the inflammatory disease is inflammatory bowel disease. In certain embodiments, the inflammatory disease is ulcerative colitis. In certain embodiments, the inflammatory disease is pancreatitis hepatitis. In certain embodiments, the inflammatory disease is appendicitis. In certain embodiments, the inflammatory disease is gastritis diverticulitis. In certain embodiments, the inflammatory disease is celiac disease. In certain embodiments, the inflammatory disease is food intolerance. In certain embodiments, the inflammatory disease is enteritis ulcer gastroesophageal reflux disease (GERD). In certain embodiments, the inflammatory disease is psoriatic arthritis. In certain embodiments, the inflammatory disease is psoriasis. In certain embodiments, the inflammatory disease is rheumatoid arthritis.

In certain embodiments, the methods of the disclosure comprise administering to the subject an effective amount of a compound of Formula (I)-(XVIII), or a pharmaceutically acceptable salt thereof. In some embodiments, the effective amount is a therapeutically effective amount. In some embodiments, the effective amount is a prophylactically effective amount.

Certain methods described herein may comprise administering one or more additional pharmaceutical agent(s) in combination with the compounds described herein. The additional pharmaceutical agent(s) may be administered at the same time as a compound of Formulae (I)-(XVIII), or at different times than the compound of Formulae (I)-(XVII). For example, the compound of Formulae (I)-(XVIII) and any additional pharmaceutical agent(s) may be on the same dosing schedule or different dosing schedules. All or some doses of the compound of Formulae (I)-(XVIII) may be administered before all or some doses of an additional pharmaceutical agent, after all or some does an additional pharmaceutical agent, within a dosing schedule of an additional pharmaceutical agent, or a combination thereof. The timing of administration of the compound of Formulae (I)-(XVIII) and additional pharmaceutical agents may be different for different additional pharmaceutical agents.

EXAMPLES

Assay Protocols

Bacterial Culturing. All bacterial strains were cultured at 37° C. in Cullen-Haiser Gut (CHG) media (which consists of brain heart infusion media (Bacto™ BHI, BD) supplemented with 1% BBL vitamin $K_1$-hemin solution (BD), 1% trace minerals solution (ATCC), 1% trace vitamins solution (ATCC), 5% fetal bovine serum (Hyclone), 1 g/L cellubiose, 1 g/L maltose, and 1 g/L fructose) or $BHI^+$ (Bacto™ BHI, BD, supplemented with 5 mg/L hemin, and 2.5 uL/L Vitamin $K_1$). All strains were grown under anaerobic conditions in a anaerobic chamber (Coy Lab Products Airlock) with a gas mix of 5% hydrogen and 20% carbon dioxide nitrogen. *Escherichia coli* was grown aerobically at 37° C. in LB medium supplemented with ampicillin to select for the pET21b plasmid.

UPLC-MS Analysis. Bile acid profiling by UPLC-MS was performed using a published method.[16] Correction factors for extraction efficiency were used and were determined by extraction of known concentrations of relevant bile acids from buffer or bacterial media and comparison to standard curves. The limits of detection for individual bile acids were determined using commercially available standards/synthesized compounds solubilized in 1:1 MeOH/water and are as follows: OMCA, 0.03 picomol/μL; TβMCA, 0.01 picomol/μL; CA, 0.04 picomol/μL; TCA, 0.01 picomol/μL; UDCA, 0.04 picomol/μL; TUDCA, 0.01 picomol/μL; DCA, 0.04 picomol/μL; TDCA, 0.05 picomol/μL; GCDCA-d4, 0.1 picomol/μL; CDCA-d4, 0.1 picomol/μL; 7-oxo-CA, 0.5 picomol/μL; 7, 1.0 picomol/μL; GR-7, 0.05 picomol/μL.

Protein Expression and Purification.

B. thetaiotaomicron rBSH. The gene encoding BT_2086 (without the leader sequence) was codon-optimized for *E. coli* and cloned into pET-21b(+) vector containing a C-terminal His6 tag (see Table 2 for primers). The expression plasmid was then transformed into BL21(DE3)pLysS *Escherichia coli* (New England Biolabs) cells under ampicillin selection. Overnight cultures grown in LB media with ampicillin (50 μg/mL) were diluted 1:1000 in fresh LB media with ampicillin and grown at 37° C. Expression was induced at an $OD_{600}$ of 0.6-0.7 by the addition of 1 mM isopropyl-1-thio-D-galactopyranoside (IPTG) and further incubated at 18° C. overnight. The cells were pelleted by centrifugation at 7,000 g for 20 mins at 4° C. The pelleted cells were then resuspended in PBS buffer (with 5% glycerol) containing 20 mM imidazole, 1 mM phenylmethylsulfonyl fluoride (PMSF), and 0.25 mM tris(2-carboxyethyl) phosphine hydrochloride (TCEP). The resuspended cells were sonicated and pelleted by centrifugation at 16,000 g for 20 mins at 4° C. The supernatant was then mixed with pre-formed Ni-NTA for 45 mins at 4° C. The nickel-bound protein was eluted with gradually increasing concentration of imidazole in PBS buffer (with 0.25 mM TCEP and 5% glycerol). Collected fractions were tested for purity by SDS-PAGE. The pure fractions were combined and concentrated followed by dialysis using the storage buffer (PBS at pH 7.5 with 0.25 mM TCEP and 5% glycerol).

For crystallization purposes, the protein was further purified using S200 size exclusion column (from GE) on a BioRad FPLC in 50 mM tris(hydroxymethyl)aminomethane buffer with 300 mM NaCl, 0.25 mM TCEP and 5% glycerol at pH 7.5.

*B. longum* rBSH. Recombinant BSH from *B. longum* SBT2928 was expressed and purified as above, except 0.25 mM IPTG was used for protein expression and 1 mM TCEP for protein purification.

Enzyme Kinetics. The enzyme was characterized using a modified BSH activity assay.[26] To 144.8 µL PBS buffer (containing 10 mM TCEP and 5% glycerol), 35.2 µL of rBSH was added to afford a final concentration of 6.2 µM and 7.0 µM for *B. theta* BSH and *B. longum* BSH, respectively. This solution was preheated to 37° C. in a water bath. 20 µL of a conjugated bile acid in DMSO at appropriate concentration was preheated to 37° C. in a water bath and added to the above solution. At every time interval, 15 µL of the mixture was quenched with 15 µL of 15% trichloroacetic acid. The cloudy solution was centrifuged at 4,200 g for 15 mins. 10 µL of the supernatant was added to 190 µL of ninhydrin mix (15 mL of 1% [wt/vol] ninhydrin in 0.5 M sodium citrate at pH 5.5, 36 mL glycerol and 6 mL 0.5 M sodium citrate buffer at pH 5.5) and the mixture was heated to 100° C. in a BioRad thermocycler for 18 mins. The obtained solution was cooled at 4° C. for 20 mins and absorbance was measured at 570 nm using a spectrophotometer (Molecular Devices).

Inhibitor Screen Using rBSHs. 200 nM rBSH was incubated with 100 µM inhibitor at 37° C. for 30 mins in 3 mL PBS buffer containing 0.25 mM TCEP and 5% glycerol at pH 7.5. Bile acid pool (100 µM) was added to the above solution and incubated at 37° C. At timepoint intervals, 1 mL of the above buffer solution was acidified to pH=1 using 6M HCl and extracted twice with 1 mL ethyl acetate. The combined organic layers were then dried using a Biotage TurboVap LV. The dried extracts were resuspended in 1:1 methanol:water and transferred to mass spec vials. Samples were analyzed as per the method described in "UPLC-MS analysis". The obtained concentrations of bile acids were used to determine % deconjugation.

Equation for Calculating % Deconjugation.

% deconjugation=concentration of deconjugated bile acids detected/(concentration of deconjugated bile acids detected+concentration of conjugated bile acids detected)*100.

Compound 7 Kinetic Studies. Assay was run in PBS buffer (containing 0.25 mM TCEP and 5% glycerol) and all reactants were incubated at 37° C. before reaction start time. *B. theta* BSH (200 nM) was added to a pool of 100 µM bile acid pool and 100 µM 7. 500 µL aliquots were removed at indicated time points and flash frozen in liquid nitrogen. After thawing the solution was acidified to pH=1 using 6M HCl and then processed as per the method described in "Inhibitor Screen Using rBSHs". Procedure was repeated with 8.2 mM TUDCA.

Determination of $IC_{50}$ Values of Compound 7 against recombinant proteins. 200 nM rBSH was incubated with increasing concentrations of 7 at 37° C. for 1 h in 1 mL PBS buffer containing 0.25 mM TCEP and 5% glycerol at pH 7.5. 100 µM bile acid (TUDCA for *B. theta* BSH and TDCA for *B. longum* BSH) was added to the above solution and incubated at 37° C. for 2 h. The solution was acidified to pH=1 using 6M HCl and then processed as per the method described in "Inhibitor Screen Using rBSHs".

Inhibitor Screen in Bacteria. Bacterial cultures were diluted to $OD_{600}$ of 0.1 in 4 mL $BHI^+$, containing 100 µM taurine conjugated bile acid pool 100 µM inhibitors. These cultures were then grown anaerobically at 37° C. After 21 h, serial dilutions were plated on $BHI^+$ agar to determine cell viability (CFU/mL). 1 mL of the entire bacterial culture was acidified to pH=1 using 6M HCl followed by addition of 2 mL ethyl acetate and vortexed. The cultures were spun down in a centrifuge at 2,500 g for 5 mins to obtain better separation. The organic layer was then removed and the aqueous layer was extracted again using 2 mL of ethyl acetate. The dried organic extracts were resuspended in 1:1 methanol:water and transferred to mass spec vials and analyzed as per the method described in "UPLC-MS Analysis". The obtained concentrations of bile acids were used to determine % deconjugation.

Determination of $IC_{50}$ Values of Compound 7 in Bacterial Cultures. Note that due to slow growth of *B. longum, B. adolescentis* was used for studies in growing bacteria. Overnight cultures of *B. theta* and *B. adolescentis* were diluted to an $OD_{600}$ of 0.1 in 2 mL fresh CHG media (see "Bacterial Culturing") containing 100 µM TUDCA or TDCA, respectively, and inhibitor 7 at increasing concentrations. *B. theta* and *B. adolescentis* deconjugated TUDCA and TDCA, respectively, to the greatest extent of any of the conjugated substrates in the Inhibitor Screen in Bacteria assay, and therefore these substrates were used to determine $IC_{50}$ values. Cultures were then grown anaerobically at 37° C. for 24 h (*B. adolescentis*) or 48 h (*B. theta*). Longer incubation time was required for *B. theta* because for this bacterium, significant BSH activity was only observed during stationary phase. Cultures were extracted and analyzed as per the method described in "Inhibitor Screen in Bacteria".

Screen of Inhibitors in Conventional Mouse Feces. BSH activity in fecal pellets were quantified using a modified version of a published method.[45] Fecal pellets (approximately 10-20 mg) were broken into fine particles in buffer (10% PBS, 90% sodium acetate at pH 5.2) to obtain a concentration of 1 mg/mL. Indicated concentration of inhibitors were added to the fecal slurry and the mixture was incubated at 37° C. for 30 mins. 100 µM glycochenodeoxycholic acid-d4 (GCDCA-d4) was added to the mixture and incubated at 37° C. for 18 h. The tubes were then frozen in dry ice for 5 mins and upon thawing were diluted with an equal volume of methanol. The slurry was centrifuged at 12,500 g for 10 mins. The supernatant was removed into a clean eppendorf tube and centrifuged again. The supernatant was transferred to MS vials and samples were analyzed as per the method described in "UPLC-MS Analysis". The concentration of product detected from these assays was reported directly.

Crystallization, Data Collection, and Structure Determination. Crystals of BSH and BSH in complex with 7 were grown in 24-well format hanging drops at room temperature. BSH crystals (5.0 mg/mL) grew from micro seeding after 3 days in 42% tacimate 100 mM Tris pH 7.4. The BSH-7 complex (5.0 mg/mL) crystals grew after 5 d in 21% PEG 3350 and 100 mM X Sodium citrate tribasic dihydrate pH 5.0. Crystals were cryoprotected by supplementing the mother liquor with 10% 2-methyl-2,4-pentanediol (v/v). Data collection was performed at Advanced Photon Source NE-CAT beamline 24 ID-C at 100 K using a wavelength of 0.979 Å. Diffraction images were processed and scaled using XDS. To obtain phases for the apo BSH structure, molecular replacement was performed in Phenix with Phaser[46] using 3HBC as the search model. Iterative model building and reciprocal space refinement was performed in COOT and phenix.refine,[47] respectively. The BSH-7 structure was phased using molecular replacement with apo BSH as a search model. Iterative model building and refinement for the BSH-7 grouped atomic B-factors and used an applied twinlaw of k h-l. Model quality for both structures was evaluated using composite omit density maps. In final cycles of model building, NCS restraints were removed. Final model quality was assessed using MolProbity.[48] For 6UFY, 97% of residues were in favored regions of the Ramachandran plot, 3% were in allowed regions, and none were in outlier regions; for 6UH4, 89.3% of residues were in favored regions, 10.3% were in allowed regions, and 0.4% were outliers. All crystallographic data processing, refinement, and analysis software was compiled and supported by the SBGrid Consortium.[49] Figures were prepared using Pymol (Schrödinger).

Mass Spectrometry Analysis for Identifying Labeled Residue on BSH. BSH protein was incubated with DMSO or a 10-fold molar excess of inhibitor 7 for 2 h at room temperature. Reactions were then analyzed by LC-MS using a Shimadzu LC and autosampler system (Shimadzu, Marlborough, MA) interfaced to an LTQ ion trap mass spectrometer (ThermoFisher Scientific, San Jose, CA).

To determine the site of modification, compound 7 modified protein was analyzed as described above, except that the LC system was interfaced to an Orbitrap Lumos Mass Spectrometer (ThermoFisher Scientific). The mass spectrometer was programmed to perform continuous cycles consisting of 1 MS scan (m/z 300-2000, profile mode, electron multiplier detection) followed by ETD MS/MS scans targeting the +41 charge state precursor of compound 7 modified protein (ETD reagent target=200 ms, image current detection at 60K resolution, target value=2E6, ETD reaction time=100 or 200 ms). Ion assignments were performed using mzStudio software.[50]

Effect of 7 on FXR. LanthaScreen TR-FRET Coactivator Assay (Invitrogen, Carlsbad, CA) was used to test the effect of 7 on FXR according to the manufacturer's instructions. Known FXR agonist GW4064 (Sigma, G5172) was used as a positive control (agonism assay) or added at its $EC_{50}$ (50.3 nM, measured in this assay) (antagonism assay). Following 1 h incubation at room temperature, the 520/495 TR-FRET ratio was measured with a PerkinElmer Envision fluorescent plate reader using the following filter set: excitation 340 nm, emission 495 nm, and emission 520 nm. A 100 psec delay followed by a 200 psec integration time was used to collect the time-resolved signal.

Cell Culture. Caco-2 cells and NCI-H716 cells were obtained from American Type Culture Collection (Manassas, VA). Caco-2 cells were maintained in Minimum Essential Medium (MEM) supplemented with GlutaMAX and Earle's Salts, while NCI-H76 cells were maintained in Roswell Park Memorial Institute (RPMI) media (Gibco, Life Technologies, UK). All cell culture media were supplemented with 10% fetal bovine serum (FBS), 100 units/ml penicillin, and 100 µg/ml streptomycin (GenClone). Cells were grown in FBS—and antibiotic-supplemented 'complete' media at 37° C. in an atmosphere of 5% $CO_2$.

Plasmids and Transient Transfections. For luciferase reporter assays, vectors expressing human reporter constructs were used. The pGL4.29[luc2P/CRE/Hygro] plasmid (Promega Corporation) was transiently transfected in Caco-2 cells at a concentration of 2 µg/ml of media each for studying TGR5 activation respectively. The pGL4.74[hRluc/CMV] plasmid (Promega Corporation) was used as a transfection efficiency control at a concentration of 0.05 µg/ml of media. All plasmids were transfected using Opti-MEM (Gibco) and Lipofectamine 2000 (Invitrogen, Life Technologies, Grand Island, NY, USA) according to manufacturer's instructions. Plasmid transfections were performed in antibiotic-free MEM media with 10% FBS. After overnight incubation, 7 and/or bile acids were added in complete media. 7 and/or bile acids were diluted in DMSO and the concentration of DMSO was kept constant. 10 µM of LCA was added along with 7 to study TGR5 antagonism and incubated overnight. Cells were harvested the next day for luciferase assay.

Luciferase Reporter Assay. Luminescence was measured using the Dual-Luciferase Reporter Assay System (Promega Corporation) according to manufacturer's instructions. Cells were washed gently with PBS and lysed in PLB from the kit. Luminescence was measured using a SpectraMax M5 plate reader (Molecular Devices, San Jose, CA) at the ICCB-Longwood Screening Facility at HMS. Luminescence was normalized to *Renilla* luciferase activity and percentage relative luminescence was calculated compared to DMSO control.

Cell Viability Assay. Caco-2 and NCI-H716-cells were treated with indicated compounds diluted in DMSO in complete MEM and RPMI media respectively. The concentration of DMSO was kept constant and used as a negative control. Cells were incubated with compound overnight at 37° C. in an atmosphere of 5% $CO_2$. The next day, cells were treated with 0.25% trypsin in HBSS (GenClone) for 10 min at 37° C. Cell viability was measured in Countess II automated cell counter (Invitrogen). Percentage relative viability was calculated compared to DMSO control.

Epithelial Permeability Assay. Undifferentiated Caco-2 cells were seeded in 24-well plate transwells (0.4 uM pore size, Costar) at 200,000 cells per transwell. Media was changed on days 4, 8, 12, 16, and 18 to differentiate Caco-2 cells in vitro.[51] On day 21, fully differentiated and polarized cells were used for FITC-dextran permeability assay. Briefly, 7 and GR-7 were added in PBS at indicated concentrations to the apical chamber of the transwells containing differentiated Caco-2 cells and incubated for 6 or 12 h. The apical chamber of the transwells contained a volume of 100 ul PBS with compounds or DMSO control, while the basolateral chamber contained 500 µL of PBS. Caco-2 epithelial integrity was assayed by measuring passive diffusion of 4 kDa FITC-Dextran (Sigma Aldrich) added at a concentration of 5 uM to the apical chamber. Diffusion from the apical to basolateral side was measured by fluorescence reading in PBS on the basolateral side of the transwell system using a SpectraMax M5 plate reader (Molecular Devices, San Jose, CA) at the ICCB-Longwood Screening Facility at HMS. Fluorescence reading was normalized to the DMSO control.

Target Validation and Off-target Profiling in *B. adolescentis* using 7-$N_3$. Pilot studies with 7-$N_3$ were performed using *B. adolescentis* (Gram positive) and *B. theta* (Gram negative). We chose to use *B. adolescentis* due to the stronger total fluorescent signal detected by-in gel fluorescence. *B. adolescentis* cultures were diluted to an $OD_{600}$ of 0.1 in 6 mL fresh CHG media containing 100 μM taurine-conjugated bile acid pool. Cultures were allowed to grow anaerobically at 37° C. for 21 h. 10 μM 7-$N_3$ (10 mM stock in DMSO) or 6 FL DMSO (to control tubes) was then added to the cultures and incubated anaerobically at 37° C. for 1 h. The cultures were centrifuged at 2,500 g at 4° C. for 15 mins. The media was decanted and cells were resuspended in PBS containing 1 mM TCEP and 1 mM PMSF and centrifuged 4,200 rpm at 4° C. for 15 mins. The buffer was decanted and the cells were suspended in 300 μL of fresh buffer and transferred to homogenizing tubes (Precellys lysing kit tough micro-organism lysing VK05 tubes) with ceramic beads. The suspension was then homogenized (5000 speed for 90 s*2, 6500 speed for 60 s) and spun down for 20 min at 15,000 g at 4° C. The supernatant was removed and the concentration of proteins in the lysate was quantified by Bradford assay. The lysates were then subjected to click reaction as per "Click Chemistry for In-gel Fluorescence Imaging" for fluorescence imaging and "Click Chemistry for MS/MS on Bacterial Lysate" for mass spectrophotometer-based quantification and identification.

Dose-dependent Labeling of BSH in *B. adolescentis* via competition of 7 and 7-$N_3$. *B. adolescentis* cultures were diluted to an $OD_{600}$ of 0.1 in 6 ml, fresh CHG containing 100 μM taurine-conjugated bile acid pool. Cultures were allowed to grow anaerobically at 37° C. for 21 h. Decreasing concentrations of 7 were added to different tubes and the cultures were incubated anaerobically at 37° C. for 1 h. 10 μM 7-$N_3$ was then added to the cultures and incubated anaerobically at 37° C. for an additional hour. The cultures were further processed as per the reported method in "Target Validation and Off-target Profiling in *B. adolescentis* using 7-$N_3$" and "Click Chemistry for In-gel Fluorescence Imaging".

Off-Target profiling in Mammalian Cells using 7-$N_3$. The human epithelial cell line NCI-H716 was used to study interactions with mammalian proteins. 10 μM 7-$N_3$ (10 mM stock in DMSO) or 1 uL DMSO (for control) were added to ~$8\times10^6$ cells in 1 ml DPBS (HiMedia) and incubated for 1 h. Cells were collected in 15 ml Falcon tubes and washed 2 times in 15 ml DBPS by centrifugation at 500 g for 5 mins. A 3rd wash by centrifugation was performed in 1 mM solution of cOmplete™ Protease Inhibitor Cocktail (Roche, Switzerland) in DPBS. Cells were resuspended in 250 ul of DPBS with 1 mM cOmplete™ Protease Inhibitor Cocktail and sonicated at 50% amplitude for 2 secs followed by 30 secs on ice for 3 cycles. The lysate was centrifuged at 15,000 g for 15 mins at 4° C. The supernatant was removed and protein concentration was measured by Bradford assay. The lysates were then subjected to click reaction as per "Click Chemistry for In-gel Fluorescence Imaging" for in-gel fluorescence and "Click Chemistry for MS/MS on Mammalian Lysate" for mass spectrophotometer-based quantification and identification.

Click Chemistry for In-gel Fluorescence Imaging. Click reactions were performed on 25 μL scale. Lysates (normalized to 1.5 mg/mL for both bacterial and mammalian cells) pretreated with 10 μM Compound 7-$N_3$ were incubated with 100 μM fluor 488-alkyne (10 mM stock in DMSO), 100 μM CuBr (5 mM stock in DMSO), and 100 μM Tris[(1-benzyl-1H-1,2,3-triazol-4-yl)methyl]amine (5 mM stock in 4:1 t-BuOH:DMSO) for 1 h at 37° C. in the dark. 10 μL of 2×Laemmli buffer (containing 5% β-mercaptoethanol) was added to the reactions and the tubes were heated at 95° C. for 10 mins. 15 μL of the protein samples were then resolved by 10% SDS-PAGE. The ladder was diluted 100-fold and 10 μL was loaded. Gels were destained for 30 mins using 40% methanol, 50% acetic acid, 10% water and visualized using Bio-Rad ChemiDoc MP Imaging System. Gels were stained for 20 mins in Coomassie blue and destained for 2 h prior to imaging.

Click Chemistry for MS/MS on Bacterial Lysate. Click reactions were performed on 100 μL scale. Lysates (normalized to 1.3 mg/mL) pretreated with 10 μM 7-$N_3$ were incubated with 100 μM desthiobiotin-PEG4-alkyne (10 mM stock in DMSO), 1 mM CuBr (50 mM stock in DMSO), and 1 mM Tris[(1-benzyl-1H-1,2,3-triazol-4-yl)methyl]amine (50 mM stock in 4:1 t-BuOH:DMSO) for 1 h at 37° C. The samples were then processed for further analysis as per "Proteomic Analysis of Click-Tagged Proteins".

Click Chemistry for MS/MS on Mammalian Lysate. Click reactions were performed on 100 μL scale. Lysates (1.5 mg/mL for mammalian cells) pretreated with 10 μM 7-$N_3$ were incubated with 100 μM desthiobiotin-PEG4-alkyne (10 mM stock in DMSO), 100 μM CuBr (5 mM stock in DMSO), and 100 μM Tris[(1-benzyl-1H-1,2,3-triazol-4-yl)methyl]amine (5 mM stock in 4:1 t-BuOH:DMSO) for 1 h at 37° C. The samples were then processed for further analysis as per "Proteomic Analysis of Click-Tagged Proteins".

Proteomic Analysis of Click-Tagged Proteins. Pulldown of desthiobiotinylated proteins and on bead digestion was performed similar to a previously described protocol.[52] After resuspending tryptic peptides in 5% acetonitrile with 0.1% formic acid, peptides were analyzed by nanoflow LC-MS/MS as described.[53] Raw data were converted to .mgf using multiplierz[54] and searched using Mascot 2.6.2 against forward reversed databases of either human or *bifidobacterium adolescentis* proteins (uniprot). Search results were downloaded from Mascot, converted to xls, and filtered to 1% FDR using multiplierz scripts. Normalized spectral abundance factors were derived as described.[55] Data were filtered for proteins with more than 5 spectral counts (averaged across biological triplicates) for 7-$N_3$ treated samples. In separate experiments, clicked bacterial lysate proteins were subjected to avidin enrichment and washed as described above. Proteins were then eluted with LDS loading buffer and subjected to SDS-PAGE and silver staining. Indicated bands were excised, subjected to in-gel digestion, and extracted peptides analyzed by nanoflow LC-MS/MS as described.[53]

Animal Studies. C57BL/6 mice obtained from Jackson laboratories were maintained under a strict 12 h/12 h light/dark cycle and a constant temperature (21±1° C.) and humidity (55-65%). All experiments were conducted on 8-9 week old male mice.

Single Gavage of 7. Based on the efficacy of 7 at 10 μM to 100 μM in in vitro assays, our goal concentration of 7 in vivo was ~50 uM: (0.00005 M)×(~10 mL volume/1 mouse GI tract)×(1 mmol compound 7/408 mg)=0.2 mg/mouse×(1 mouse/~0.02 kg)=10 mg/kg.

Mice were maintained on a standard chow diet (LabDiet, catalog no. 5053) for the duration of the experiment. Mice were split into two groups of four mice each and were gavaged with either 200 μL of corn oil containing 5% DMSO (vehicle group) or with 200 μL of corn oil containing 7 at a concentration of 1.25 mg/mL (experimental group). For the fecal pellet collection, each mouse was transferred to a temporary cardboard cage for a few minutes until it defecated.

Feeding of GR-7 in Chow for One Day. Mice were fed powdered standard chow diet (LabDiet, catalog no. 5053) for the duration of the experiment. Mice were split into two groups of ten mice each and were maintained on powdered chow (control group) or fed powdered chow containing 0.09% (w/w) GR-7 (experimental group). Feces from these mice were collected as described above at 8 h. Mice were euthanized after 30 hours of access to the powdered chow with or without GR-7 using carbon dioxide. Blood samples were collected by cardiac puncture and placed in EDTA-coated tubes on ice. The liver and cecal contents were then collected from each mouse, snap frozen in liquid nitrogen, and stored at −80° C. until further analysis. The blood samples were then centrifuged at 2500 g for 15 minutes at 4° C. The resulting supernatant (plasma) was collected and stored at −80° C. until analysis.

BSH Activity in Feces. BSH activity in fecal pellets were quantified using a modified version of a published method.[45] Fecal pellets (approximately 10-20 mg) were suspended in buffer (10% PBS, 90% sodium acetate at pH 5.2) containing 100 μM (GCDCA-d4) to obtain a concentration of 20 mg/mL. The fecal pellets were broken into fine particles and the mixture was incubated at 37° C. for 25 mins. Samples were processed and analyzed as per the method described in "Screen of Inhibitors in Conventional Mouse Feces". The concentration of product detected from these assays were reported directly.

Quantification of Bile Acids in Tissues and Plasma. Bile acids from tissues and plasma that were collected from mouse experiments were extracted using a previously published method.[16]

Determination of Microbial Biomass by Plating. Frozen fecal pellets were used to determine colony forming units (CFU/g). Feces were suspended in PBS buffer in an anaerobic chamber. Serial dilutions were plated on CHG agar plates (see "Bacterial Culturing") and incubated at 37° C.

Isolation of Fecal Bacterial Microbiota and 16S rRNA Gene Sequencing Analysis. Mouse fecal microbiota DNA was isolated by using ZymoBIOMICS 96 DNA Kit (ZymoBIOMICS™) according to the manufacturer's instructions. The variable region 4 of the 16S rRNA genes was amplified using primers: Forward 5'-TATGGTAATTGTGTGCCAGCMGCCGCGGTAA-3'

Reverse 5'-AGTCAGTCAGCCGGACTACHVGGGTWTCTAAT-3'. PCR products were quantified using Quant-IT dsDNA high sensitivity assay (Invitrogen) according to the manufacturer's instructions. Gel electrophoresis was used to check the success of PCR amplification. The concentration of the PCR product was measured by the Quan-IT dsDNA high sensitivity assay. ~120 ng of DNA of each PCR product was pooled together to generate an aggregated library for downstream processing. PCR DNA amplicons between 300-500 bp were selected from the aggregated library on a targeted size selection platform (pippin prep 1.5% agarose cassette from Sage Sciences) according to the manufacturer's instructions. The size of DNA amplicons was characterized on an Agilent Technologies 2100 bioanalyzer trace. DNA concentration of the aggregated library was measured by the Quant-IT dsDNA high sensitivity assay. The DNA in the library was denatured by NaOH and diluted to 7.5 pM with HT buffer provided in the Illumina kit. 600 ul of the denatured and diluted library with 20% phiX spike-in (120 ul, 7.5 pM of phiX) was loaded onto the MiSeq V2 reagent cartridge (Illumina) and was sequenced with paired-end 250 bp reads using the custom primers described above. After MiSeq running, demultiplexed fastq files were generated by the Illumina MiSeq control software using default parameters and quality control was done by the pipeline at the Massachusetts Host-Microbiome Center. The resulting FASTQ sequences were then quality-filtered and analyzed by following QIIME_mothur_DADA2.[56-59] Operational Taxonomic Units (OTUs) were picked with 97% sequence similarity. The phylogenetic affiliation of each OTUs were aligned to the Greengenes reference database and 99% ID.

Quantification of bacterial 16S rDNA copy number. Bacterial DNA was isolated from mouse cecal contents using AllPrep Bact. DNA/RNA/Protein Kit (QIAGEN). The 16S rDNA was then amplified using 10 μM of the following pair of primers: Forward 5'-AGAGTTTGATCCTGGCTCAG-3', Reverse 5'-CTGCTGCCTYCCGTA-3'. Amplification was performed using LightCycler 480 SYBR Green I Master on a QuantStudio 7 Flex Real-Time PCR System according to the provided qPCR protocol. The cycle threshold of each sample was compared to a standard curve, obtained from serial dilution of *B. theta* genomic DNA.[60]

Example 1. Development of a Broad-Spectrum., Covalent Inhibitor of Gut Bacterial Bile Salt Hydrolases Development of a Broad-Spectrum, Covalent Inhibitor of Gut Bacterial Bile Salt Hydrolases Described herein is the development of a broad-spectrum, covalent inhibitor of gut bacterial BSH. Using a rational design strategy, a small library of potential BSH inhibitors were generated. A lead inhibitor bearing an alpha-fluoromethyl ketone warhead was identified by testing these compounds against purified BSH proteins and growing cultures of gut bacteria. Another BSH inhibitor, caffeic acid phenethyl ester (CAPE) was determined to inhibit the growth of Gram negative gut bacteria but lacked the same broad spectrum activity as other BSH inhibitors described herein. Mass spectrometry and X-ray crystallography confirmed covalent mono-labeling of the protein by the inhibitor at the catalytic cysteine residue. Strikingly, the lead inhibitor completely abolished BSH activity in conventional mice feces. Conventional mice gavaged with a single dose of the lead inhibitor displayed a loss of BSH activity in feces and a decrease in deconjugated bile acids. Overall, these studies demonstrate the potential of a covalent BSH inhibitor to act as chemical tools that modulate bile acid composition in vivo.

INTRODUCTION

Human-associated bacteria play a vital role in health and disease. Microbial imbalance has been linked to a wide range of disease states, including inflammatory bowel disease,[1] cancer,[2] autism,[3] and obesity.[4] However, the ways in which the bacterial guests affect the human host at a molecular level are poorly understood. Studies in germ-free mice colonized with a single strain, multiple strains, or defined communities of bacteria have revealed the capacity of gut bacteria to affect host processes, including metabolism,[5] immune function,[6,7] and neurological responses.[8] While germ-free mice are a useful tool, they display physiological differences compared to conventional animals, including altered processing of food for energy,[9] defects in immune cell balance, especially in the gut,[10,11] and altered stress response behavior.[12] These differences can complicate the determination of whether effects observed in germ-free animals can be extrapolated to conventional animals and humans. Chemical tools that selectively alter the levels of specific bacterial metabolites and proteins can allow researchers to investigate how these bacterial products affect host physiology in fully developed animals possessing complex microbial communities. The use of small molecules as chemical tools can also present therapeutic opportunities. Indeed, small molecule inhibitors of gut bacterial beta-glucuronidases have been shown to reduce dose-limiting diarrhea caused by the colon cancer chemotherapeutic CPT-11 in mice.[13] In recent work, small molecule inhibitors of the gut bacterial enzyme cutC have been shown to reduce the levels of the pro-thrombotic metabolite trimethylamine N-oxide (TMAO) in vivo.[14] These studies demonstrate the power of non-bactericidal agents that target specific bacterial enzymes to beneficially alter host physiology.

Bacteria in the GI tract are inundated with molecules from the host, including both dietary compounds and products of host metabolism. Bacteria then chemically modify these compounds to produce new metabolite classes that can then act as signaling molecules between the bacteria and host.[15] One important example of a class of host-produced, bacterially modified signaling molecules is bile acids.[16] Primary bile acids are produced in the liver from cholesterol and conjugated to taurine or glycine to produce primary conjugated bile acids (FIG. 1A). These molecules are then stored in the gallbladder and released into the duodenum upon ingestion of food where they aid in absorption of lipids and fat-soluble vitamins. Over 95% of bile acids are reabsorbed in the ileum and recirculated the liver. The remaining ~5% pass into the colon, where the majority of gut bacteria reside. Gut bacteria then enzymatically modify these primary bile acids, producing a group of molecules called secondary bile acids (FIG. 1A). On the order of 50 secondary bile acids have been detected in human feces. Due to the high concentration of bile acids released into the small intestine, the resultant concentration of these molecules in the lower gut is still in the low millimolar range.[7] As a result, even less abundant secondary bile acids are present at physiologically relevant concentrations.

Figure 1B:
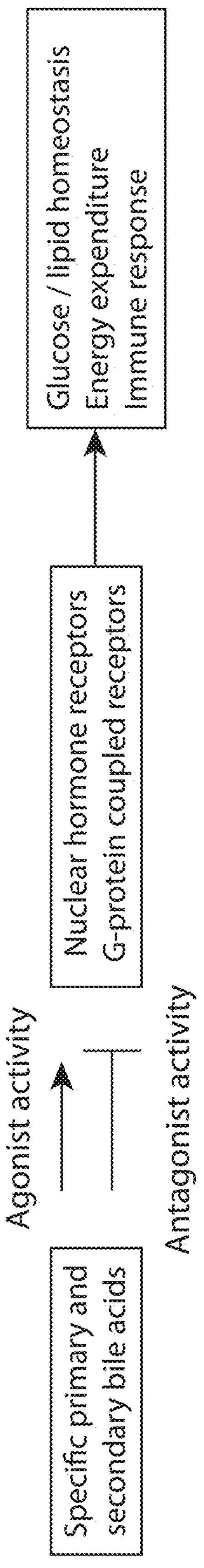

While bile acids were initially studied due to their detergent properties, it was later recognized that these compounds can act as signaling molecules by binding to host receptors, including nuclear hormone receptors (NhR) and G-protein coupled receptors (GPCRs) (FIG. 1B). By acting as either agonists or antagonists for these receptors, including the farnesoid X receptor (FXR), the liver X receptor (LXR), the pregnane X receptor (PXR), the G-protein coupled bile acid receptor 1 (GPBAR1, also known as TGR5), muscarinic receptors 2 and 3, and sphingosine 1 phosphate receptor 2, primary and secondary bile acids affect host processes.[18-22] In particular, by engaging host receptors, bile acids regulate host metabolism, including energy expenditure and glucose and lipid homeostatis,[18,23] and host immune response, including both innate and adaptive immunity.[24,25] In addition, bile acids tightly regulate their own biosynthesis through a negative feedback loop controlled by FXR.[23] Finally, imbalances in bile acid homeostasis are thought to play causal roles in the pathophysiology of diseases including hypercholesterolemia, obesity, diabetes, cancer, and formation of gallstones,[18,26,27] further highlighting the biological importance of these metabolites.

Importantly, individual primary and secondary bile acids possess different binding affinities for host receptors, suggesting that the specific composition of the in vivo bile acid pool determines downstream signaling events in the host.[18,28] The keystone reaction in the conversion of primary into secondary bile acids is the hydrolysis of the C24-amide bond of conjugated primary bile acids (FIG. 1A). This reaction is performed by gut bacterial bile salt hydrolase (BSH) enzymes.[16] BSH (EC 3.5.1.24) are widespread in human gut bacteria. A recent study identified BSH in gut species from 117 genera and 12 phyla, including the two dominant gut phyla, Bacteroidetes and Firmicutes, as well as Actinobacteria and Proteobacteria.[29] Moreover, this study identified BSH in human microbiomes from 11 different populations across 6 continents, including an indigenous population in Tanzania. These results suggest that BSH activity is a conserved function of human gut metagenomes. Thus, a broad-spectrum, non-toxic small molecule inhibitor of gut bacterial BSH can limit BSH activity across a variety of both Gram negative and Gram positive strains without significantly affecting the growth of these bacteria. Further, the use of such an inhibitor in vivo can result in a shift of the bile acid pool toward conjugated bile acids and away from deconjugated bile acids and secondary bile acids (FIG. 1A). These compounds as described herein can be used to study how bacterially produced secondary bile acids affect physiology in a fully colonized host.

The development of a broad-spectrum, covalent inhibitor of bacterial BSH is described herein and was determined by using a rational design approach. Importantly, the compounds described herein can significantly inhibit BSH activity in conventional mouse feces, demonstrating their activity as broad-spectrum inhibitors of BSH.

Experimental Results

Rational Design and Synthesis of Covalent Small Molecule Inhibitors of Bile Salt Hydrolases In order to achieve the goal of generating potent, long-lasting inhibitors of BSH, covalent inhibitors of these gut bacterial enzymes were developed and described herein. Covalent inhibitors have gained widespread interest in the field of drug discovery due to their ability to inactivate their protein target with a high degree of potency and selectivity even in the presence of large concentrations of native substrate.[30] The substrates for BSH, conjugated bile acids, are found in high concentrations in the colon (1-10 mM),[17] suggesting that covalent inhibition can be an effective strategy for targeting these enzymes. In addition, the recently developed inhibitors of bacterial cutC are irreversible and both block production of trimethylamine in vivo and display minimal off-target effects.[14] This work demonstrates that covalent inhibitors of bacterial enzymes can be effective in the gut, thus further validating the present approach.

Figure 2A:
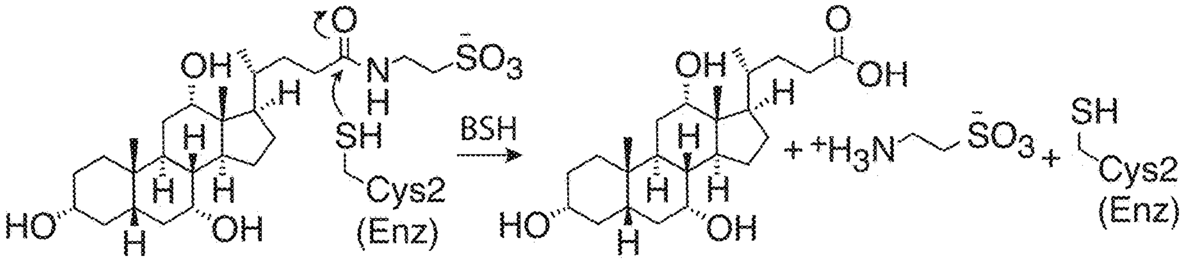
FIG. 2A to FIG. 2E demonstrate the rational design of small molecule, broad-spectrum BSH inhibitors.
Figure 2B:
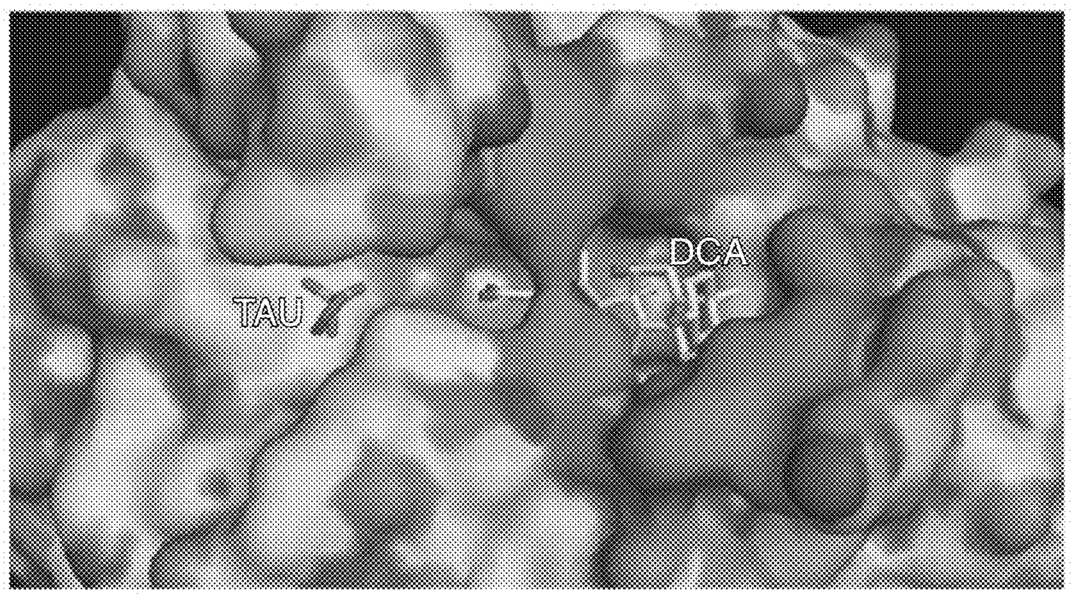

While there is significant divergence in BSH protein sequence across gut strains, all BSH possess a conserved active site comprised of five amino acids: cysteine 2 (Cys2), arginine 18 (Arg18), aspartic acid 21 (Asp21), asparagine 175 (Asn175), and arginine 228 (Arg228).[16,29] Cys2 performs the nucleophilic attack on the substrate carbonyl, resulting in amide bond cleavage (FIG. 2A). By designing compounds that targeted this highly conserved Cys residue, broad-spectrum BSH inhibitors were developed. Structural data and biochemical information from the Gram positive species *Clostridium perfringens* aided in the design plan. A co-crystal structure of *C. perfringens* BSH and the substrate taurodeoxycholic acid (TDCA) showed that while hydrophobic interactions held the bile acid core in place and oriented the amide bond toward the conserved cysteine, the amino acid was solvent-exposed (FIG. 2B).[31] Furthermore, purified *C. perfringens* BSH tolerates a large degree of variability in the amino acid side chain, including longer chain conjugates.[32] These results suggested that the bile acid D-ring side chain was a possible site for incorporation of electrophilic groups into the inhibitors.

Figure 2C:
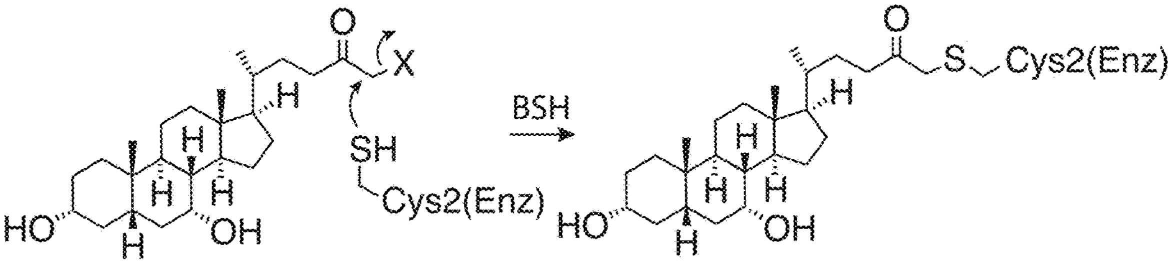
Figure 2D:
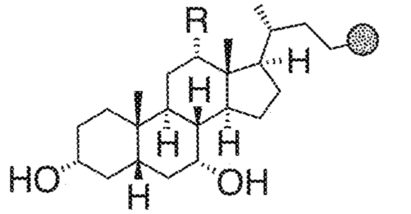
Figure 2D:
Figure 2D:
Figure 2D:
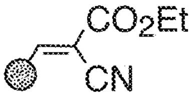
Figure 2D:
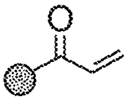
Figure 2D:
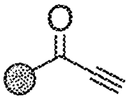
Figure 2D:
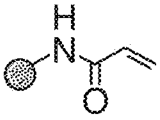
Figure 2D:
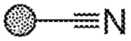
Figure 2D:
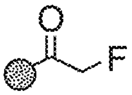
Figure 2D:
Figure 2D:
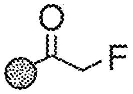

Next, a small library of potential inhibitors were designed containing both a bile acid core motif to selectively target BSH and a pendant electrophilic warhead to irreversibly bind the inhibitor to the enzyme (FIG. 2C). While previous literature suggested that BSH hydrolzye the amide bond cleavage of all conjugated bile acids regardless of the steroidal core,[16,26] it was recently determined that species from the abundant Gram negative gut bacterial phylum Bacteroidetes cleave C12=H but not C12=OH primary bile acids (FIG. 1A).[33] As the goal was to develop BSH inhibitors that target both Gram negative and Gram positive strains, the steroidal portion of the human primary bile acid chenodeoxycholic acid (CDCA, C12=H) was used as the scaffold for the inhibitors described herein (FIG. 2C).

For the electrophilic trapping groups, warheads that have been successfully deployed in the development of selective and potent protease and kinase inhibitors were selected,[34,35] including isothiocyanate (1),[36-38] cyanoacrylate (2),[39-40] α,β-unsaturated systems (3 and 4),[41] acrylamide (5),[42] and nitrile (6).[43,44] An inhibitor with an α-fluoromethyl ketone warhead (FMK) (7) was chosen in the library. Covalent inhibitors with this warhead have been shown to display high potency and selectivity.[45-47] In contrast to the more electrophilic α-iodo-, α-bromo- and α-chloromethyl ketone warheads, the weak leaving group ability of fluorine renders the FMK warhead less reactive and hence, more selective.[45,47-48] As a result, FMK-based inhibitors have been shown to elicit minimal off-target effects.[45-49]

All of the compounds in the library were accessed from the commercially available bile acid chenodeoxycholic acid (CDCA, 12) (Scheme 1) in 3-9 steps. Isothiocyanate (1) and acrylamide (5) were synthesized from CDCA over 3 steps utilizing a modified one-pot Curtius rearrangement to install the C23-substituted primary amine (Scheme S1).[50] Synthesis of the cyanoacrylate (2), α,β-unsaturated systems (3 and 4), and the nitrile (6) compounds proceeded rapidly in 2-3 steps from bis-methoxymethyl ether (MOM) protected, C24-aldehydic CDCA via either Grigard additions or condensation reactions (Scheme S1). To access compound 7, bis-MOM protected CDCA (13) was coupled with magnesium benzyl fluoromalonate, providing the β-keto-α-fluoro benzylester product 14 in 66% yield.[51] Hydrogenation followed by deprotection afforded target compound 7.

Scheme 1: Synthesis of compound 7, which contains an α-fluoromethyl ketone warhead on a chenodeoxycholic acid core.

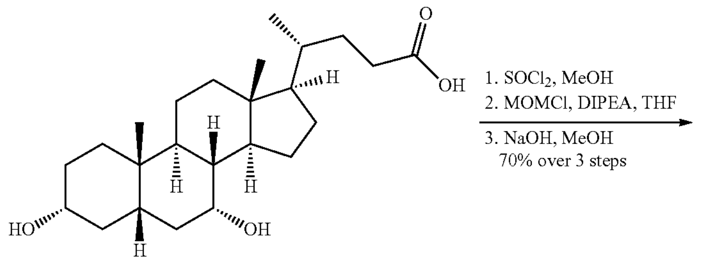

Chenodeoxycholic acid (CDCA, 12)

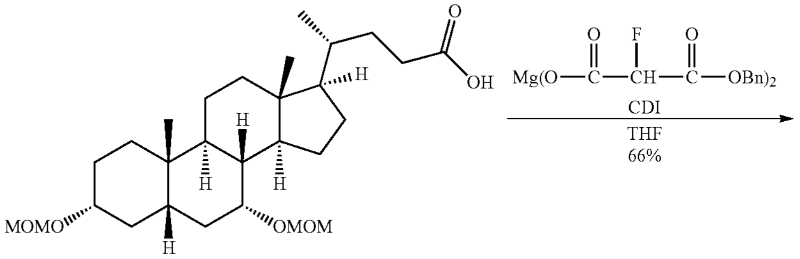

13

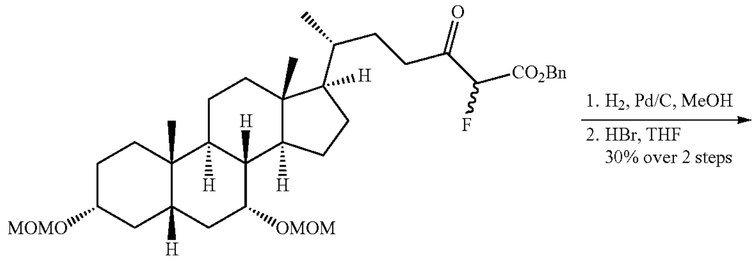

14

-continued

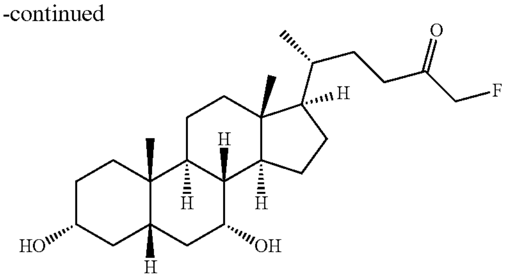

Compound 7

Abbreviations: $SOCl_2$, thionyl chloride; DIPEA, N,N-diisopropylethylamine; MOMCl, methoxymethyl chloride; THF, tetrahydrofuran; CDI, 1,1′-carbonyldiimidazole; Pd/C, palladium on carbon; R = methoxymethyl ether.

Biochemical Characterization of BSH

With inhibitors 1-9 in hand, the next goal was to evaluate the activity of these compounds biochemically against both Gram negative and Gram positive BSH. In particular, these compounds were tested against a selective *Bacteroides* BSH, reasoning that the more limited substrate scope of this enzyme can make it more difficult to target. To date, biochemical characterization has been largely limited to BSH from Gram positive bacteria,[16,26,52] including the genera *Lactobacillus,*[53] *Bifidobacterium,*[54] *Clostridium,*[31] and *Enterococcus.*[55] Among Gram negative bacteria, only the BSH from *Bacteroides* vulgatus and *Bacteroides fragilis* have been biochemically characterized, and the corresponding genes were not identified.[56,57] Moreover, these strains do not possess selective BSH selectivity.[33] Recently, BT2086 was identified as the gene responsible for selective BSH activity in the gut bacterium *Bacteroides* thetaiotaomicron VPI-5482 (*B. theta*).[33] In order to test the compounds against this selective BSH, the heterologously expressed, and purified the enzyme encoded by BT2086 was molecularly cloned. Because this enzyme had not been characterized previously, kinetic parameters were established for its hydrolysis of conjugated primary and secondary bile acids (primary, taurocholic acid, TCA, and taurochenodeoxycholic acid, TCDCA; secondary, tauroursodeoxycholic acid, TUDCA, and taurodeoxycholic acid, TDCA) using a ninhydrin-based assay.[58] Taurine-conjugated substrates were chosen because taurine conjugates are present in both mice and humans whereas glyco-bile acids are largely absent from mice.[28] Consistent with previous results from *B. theta* cultures, purified *B. theta* BSH displayed a preference for TDCA deconjugation and did not deconjugate TCA (Table 1).[33] These results suggest that the enzymatic selectively observed in *B. theta* whole cell culture was due to inherent biochemical properties of the BSH, not to differences in transport or the accessibility of the substrates to the enzyme.

In order to test the potency of inhibitors against Gram positive BSH, the known *Bifidobacterium longum* SBT2928 BSH[54] was cloned and expressed and the kinetic parameters of this enzyme were determined using the same panel of taurine-conjugated bile acid substrates (Table 1). Notably the $K_m$ values for all of the recognized substrates are in the low millimolar range, which is approximately the concentration of these bile acids in the gut. The $K_m$ values for *B. longum* established here are higher than those previously reported.[54] This difference may be a result of the conditions under which the assays were performed, that is, physiological pH in this work (7.5) versus pH optimized for activity (6) in the previous study. Overall, both enzymes displayed kinetic parameters that are comparable to those of previously characterized BSH.[53,54,56]

TABLE 1

Kinetic characterization of Gram negative *Bactereroides thetaiotaomicron* (*B. theta*) BSH and Gram positive *Bifidobacterium longum* (*B. longum*) BSH.

| BSH source [a] | Substrate[b] | $K_{cat}$ ($min^{-1}$) | $K_m$ (mM) | $K_{cat}/K_m$ ($min^{-1}mM^{-1}$) |
|---|---|---|---|---|
| *B. Theta* | TCA | — | — | — |
| *B. Theta* | TUDCA | 108.4 | 8.23 | 13.17 |
| *B. Theta* | TDCA | 100.9 | 3.35 | 30.11 |
| *B. Theta* | TCDCA | 101.4 | 2.86 | 35.45 |
| *B. longum* | TCA | 109.2 | 8.30 | 13.15 |
| *B. longum* | TUDCA | 96.49 | 4.14 | 23.30 |
| *B. longum* | TDCA | 101.7 | 2.28 | 44.60 |
| *B. longum* | TCDCA | 108.4 | 7.75 | 13.98 |

[a] Characterization was performed using ninhydrin reagent and experiments were performed in PBS buffer at pH 7.5 and 37° C.

[b]Conjugated primary and secondary bile acid used as substrates were taurocholic acid (TCA), tauroursodeoxycholic acid (TUDCA), taurodeoxycholic acid (TDCA), taurochenodeoxycholic acid (TCDCA).

Biochemical Evaluation Identifies α-FMK Compound 7 as Lead Inhibitor

Figure 2E:
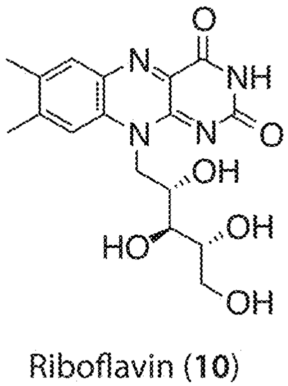
Figure 2E:
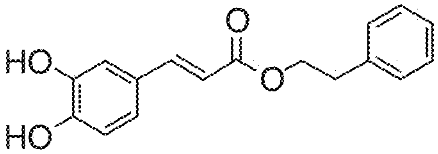

Next, the ability of the compounds in the library to inhibit *B. theta* and *B. longum* BSH were evaluated. Two additional compounds were included in the assays, riboflavin (10) and caffeic acid phenethyl ester (CAPE, 11) (FIG. 2E). These molecules had been previously identified as BSH inhibitors through a high throughput screen against the BSH from a *Lactobacillus salivarius* chicken gut isolate.[59] To determine the BSH inhibitory activity of these compounds, *B. theta* BSH was incubated with each inhibitor (100 μM) for 30 minutes and then added equimolar amounts of four conjugated bile acids (TβMCA, TCA, TUDCA and TDCA, 100 μM total).

Figure 3A:
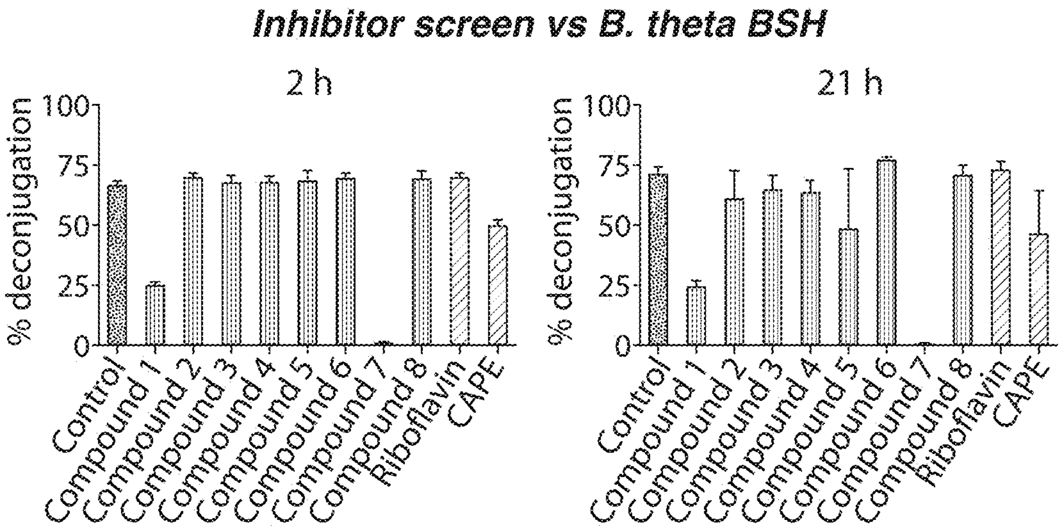
FIGS. 3A to 3B demonstrate that a screen identifies inhibitor 7 as a potent, long-lasting inhibitor of recombinant BSH.

Conversion of conjugated to deconjugated bile acids was monitored by Ultra Performance Liquid Chromatography-Mass Spectrometry (UPLC-MS) over a total of 21 hours (FIG. 3). Among the synthesized inhibitors, isothiocyanate (1) displayed modest inhibition over the course of experiment. Other compounds containing Michael acceptor warheads (inhibitors 2-6) did not inhibit deconjugation (FIG. 3A). In contrast, incubation with the α-fluoromethyl ketone-based inhibitor 7 resulted in almost complete inhibition of the *B. theta* BSH activity for 21 hours (>98%, FIG. 3A). In order to validate that the inhibitory activity of compound 7 was due to the presence of fluorine as a leaving group, a methyl ketone analog lacking the fluorine atom was synthesized (8).[49] This analog did not display BSH inhibition, indicating that the α-fluorine group was necessary for activity. The previously identified BSH inhibitor riboflavin did not display any inhibitory activity, while CAPE provided only moderate inhibition of *B. theta* BSH.

Figure 3B:
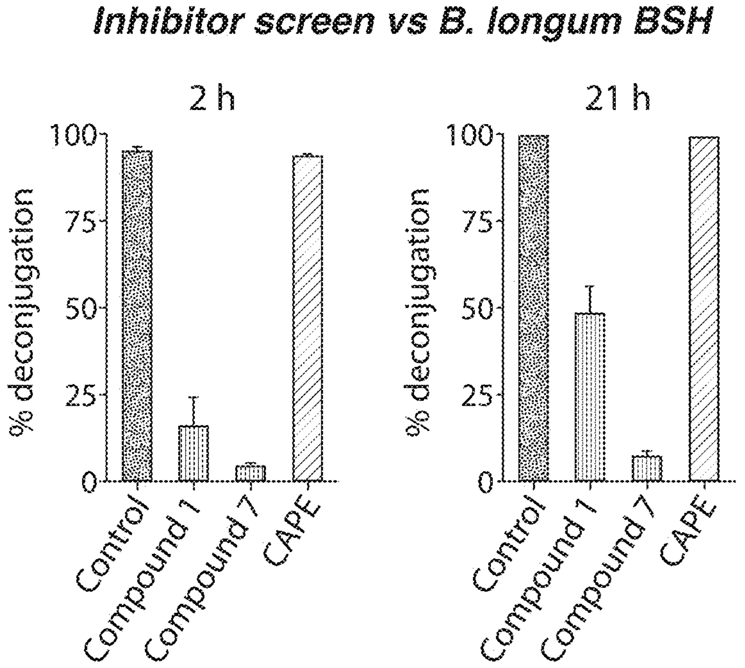

Next, the activity of the two most potent inhibitors against *B. theta* BSH were evaluated. Compounds 1 and 7 were tested, as well as CAPE, against the BSH from the Gram positive species *B. longum* (FIG. 3B). These compounds displayed the same differential effectiveness against *B. longum* BSH as was observed against *B. theta* BSH. Compound 7 was the most potent inhibitor at 2 h, 5 h, and 21 h timepoints, compound 1 displayed modest inhibition, and CAPE was ineffective at inhibiting deconjugation by *B. longum* BSH at all of the timepoints. These data indicate that compound 7 is a potent inhibitor of purified BSH protein from both a Gram negative and a Gram positive bacterial strain. In addition, because the activities of CAPE and riboflavin against genera other than *Lactobacillus* were not determined,[59] these results suggest that these molecules may not be effective broad-spectrum inhibitors.

Compound 7 Inhibits BSH Activity in Growing Cultures of Gut Bacteria

Given that compound 7 displayed activity against purified BSH from *B. theta* and *B. longum*, the potency of this inhibitor in growing bacterial cultures was evaluated. In order to test the scope of BSH inhibition, three Gram negative and three Gram positive strains of human gut bacteria known to possess BSH activity (Gram negative, *B. theta, Bacteroides fragilis* ATCC 25285, and *Bacteroides* vulgatus ATCC 8482; Gram positive, *Lactobacillus plantarum* WCFS1, *Clostridium perfringens* ATCC 13124, and *Bifidobacterium adolescentis* L2-32) were tested in this screen.[16,33]

Figure 4A:
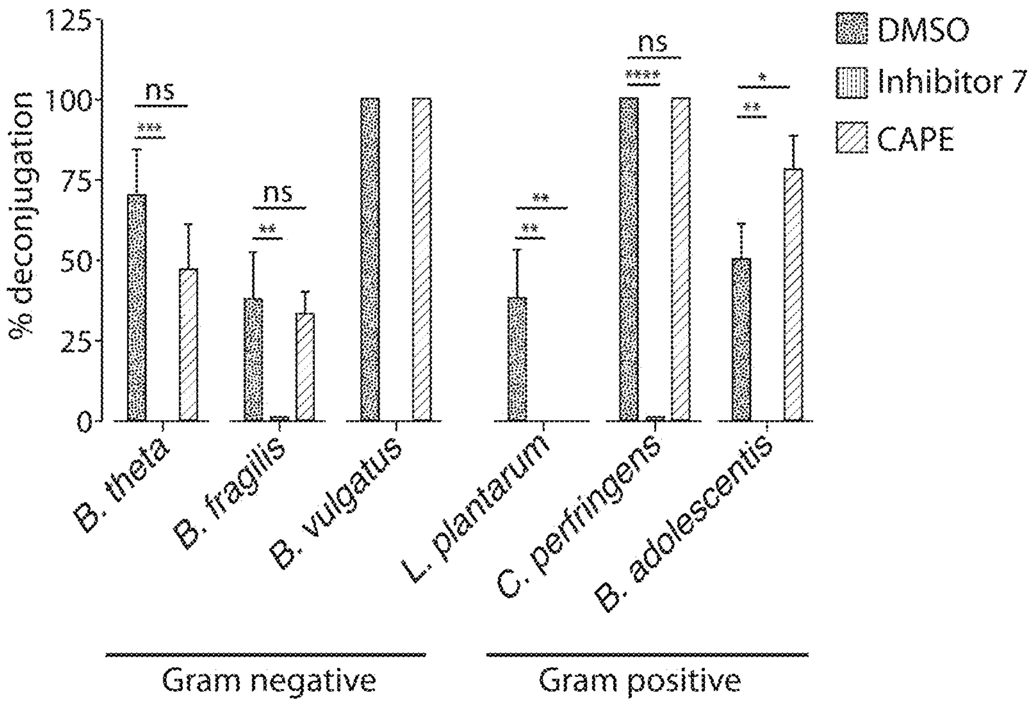
FIGS. 4A to 4D show that compound 7 is a potent, non-toxic inhibitor of BSH in growing cultures of Gram positive and Gram negative gut bacteria.
Figure 4B:
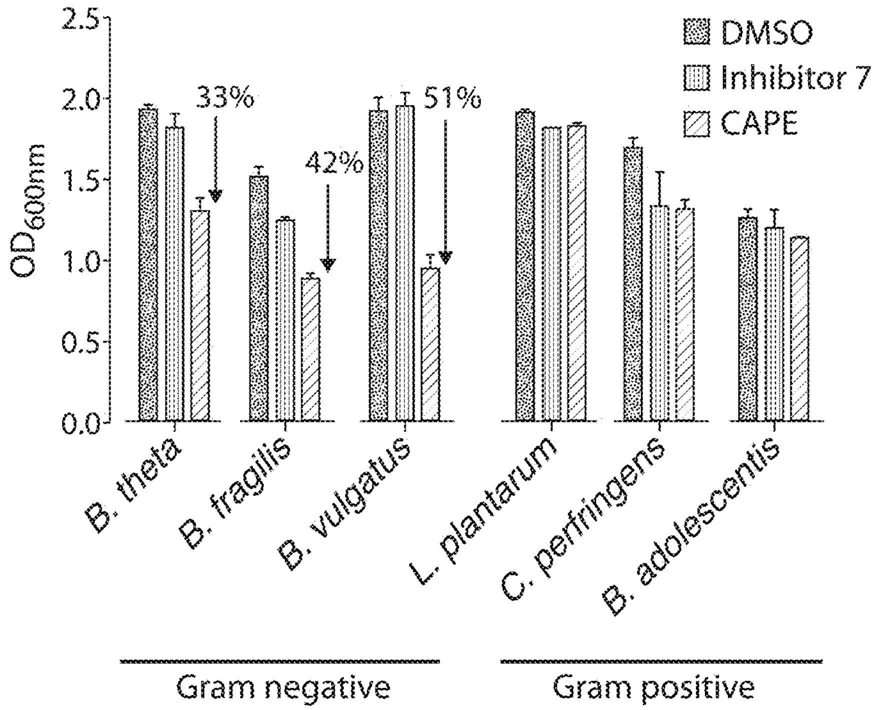
Figure 4C:
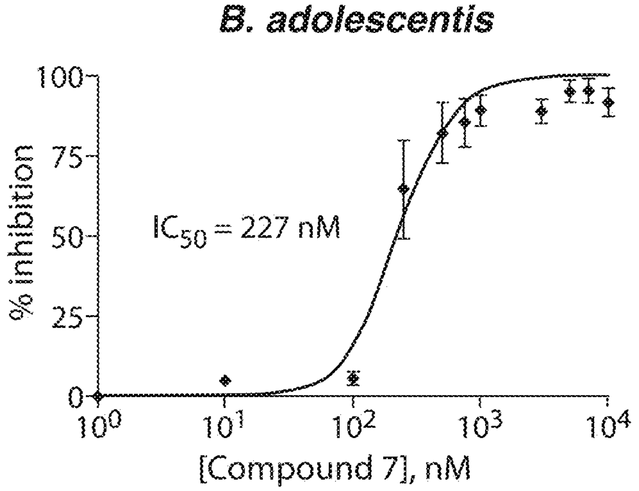

Bacterial cultures were diluted in pre-log phase and both inhibitor (100 μM) and a mixture of conjugated bile acids (100 μM final concentration; TCA, TβMCA, TDCA, and TUDCA) were added simultaneously. Deconjugation was monitored over 24 hours using UPLC-MS. Strikingly, while all six bacterial strains deconjugated bile acids in the presence of vehicle control, almost no detectable deconjugation was observed in any of the cultures grown in the presence of compound 7. These results suggest that compound 7 displays potent BSH inhibition of both Gram negative and Gram positive bacteria (FIG. 4A). Compound 7 did not significantly impact the growth of any of the tested strains (FIG. 4B), indicating that the BSH inhibition observed was not due to bacteriostatic activity. To quantify the potency of compound 7, the $IC_{50}$ values of this inhibitor against the Gram negative strain *B. theta* and the Gram positive strain *B. adolescentis* were determined to be 913 nM and 227 nM, respectively (FIG. 4C). Taken together, these results indicate that compound 7 is a potent, broad-spectrum inhibitor of BSH.

In contrast, no inhibition of deconjugation was observed over the course of 21 hours in five out of the six bacterial strains grown in the presence of CAPE (100 PM) (FIG. 4A). CAPE was found to inhibit deconjugation in *L. plantarum*, a result that is consistent with the hypothesis that this compound inhibits BSH from Lactobacilli but is not a broad-spectrum BSH inhibitor. Moreover, in contrast to inhibitor 7, CAPE inhibited the growth of all three Gram negative bacterial strains tested (FIG. 4B). These results suggest that the dominant effect of CAPE on Gram negative bacteria is not inhibition of BSH activity but rather inhibition of growth.

Figure 4D:
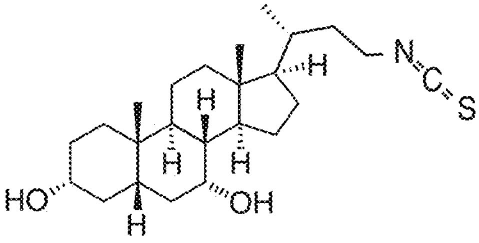
Figure 4D:
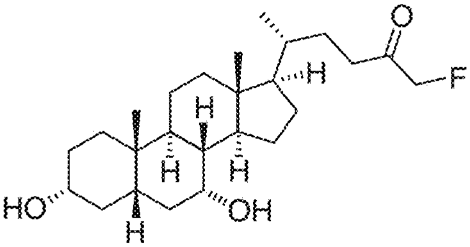
Figure 4D:
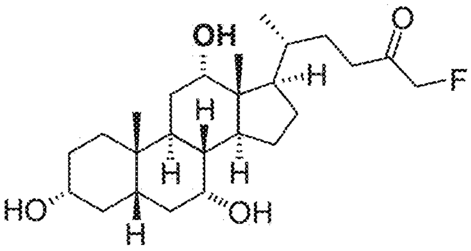
Figure 4D:
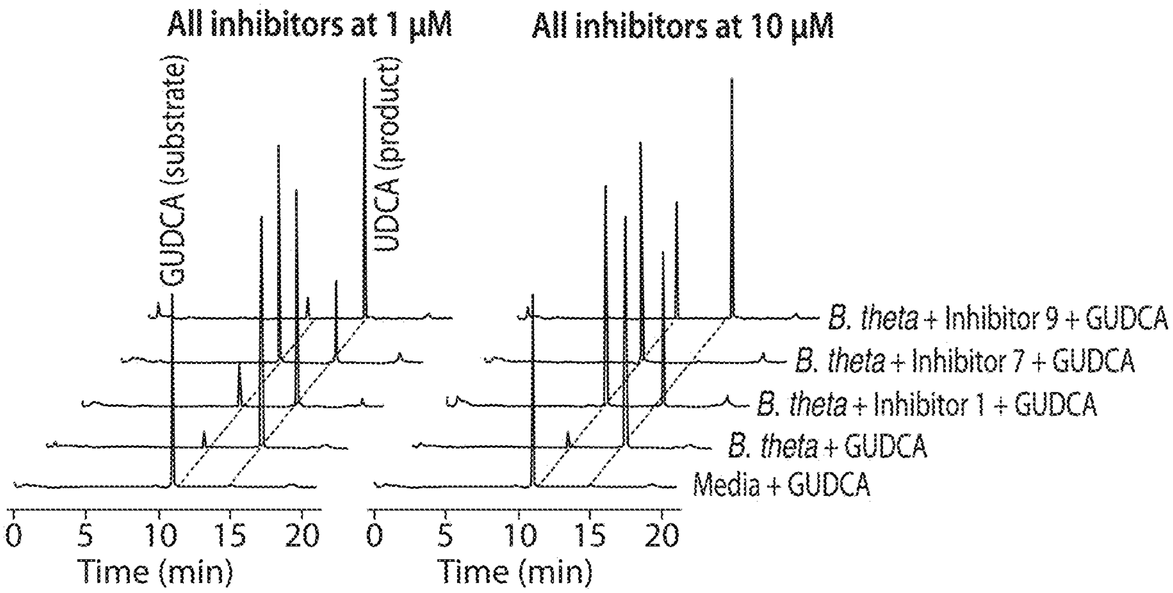

In order to evaluate the hypothesis that C12=OH compounds would not be effective inhibitors broad-spectrum inhibitors because they would not inhibit *B. theta* BSH activity, an inhibitor was synthesized where the α-fluoromethyl ketone warhead was appended from the most potent inhibitor, compound 7, to a C12=OH bile acid core, cholic acid (compound 9, FIG. 2D). Next, growing cultures of *B. theta* were incubated with compound 9 (1 μM or 10 μM) and conjugated bile acid substrate (GUDCA, 100 PM), and monitored deconjugation using UPLC-MS. While incubation with 10 μM of compound 7 resulted in nearly complete inhibition of deconjugation, significant deconjugation was observed in the presence of the same concentration of compound 9 (FIG. 4D). These results support the hypothesis that bile acid core structure, specifically C12 substitution, affects the ability of the probes to act as broad-spectrum inhibitors. In addition, these results suggest that the α-fluoromethyl ketone warhead is not broadly reactive but rather requires suitable positioning within the active site, that can be further tested using mass spectrometry and crystallography studies.

Compound 7 Covalently Binds to the Catalytic Cysteine Residue of BSH

Figure 5A:
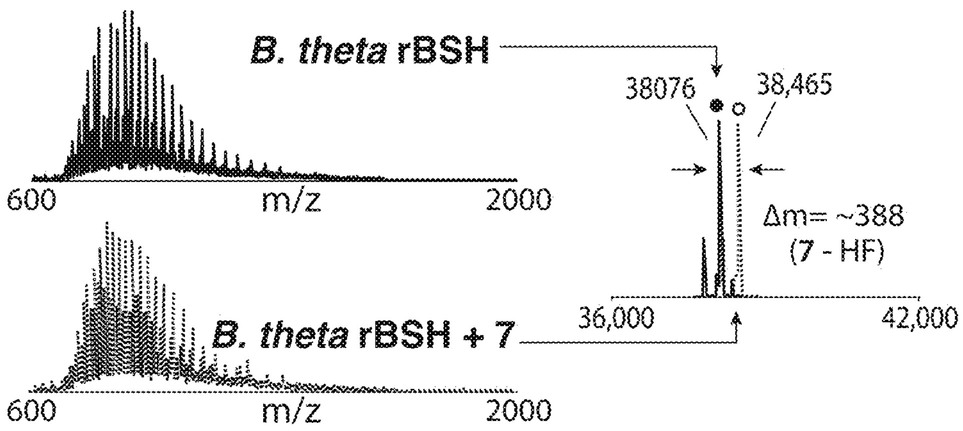
FIGS. 5A to 5C demonstrate that Compound 7 covalently modifies *B. theta* BSH at the active site cysteine residue.
Figure 5B:
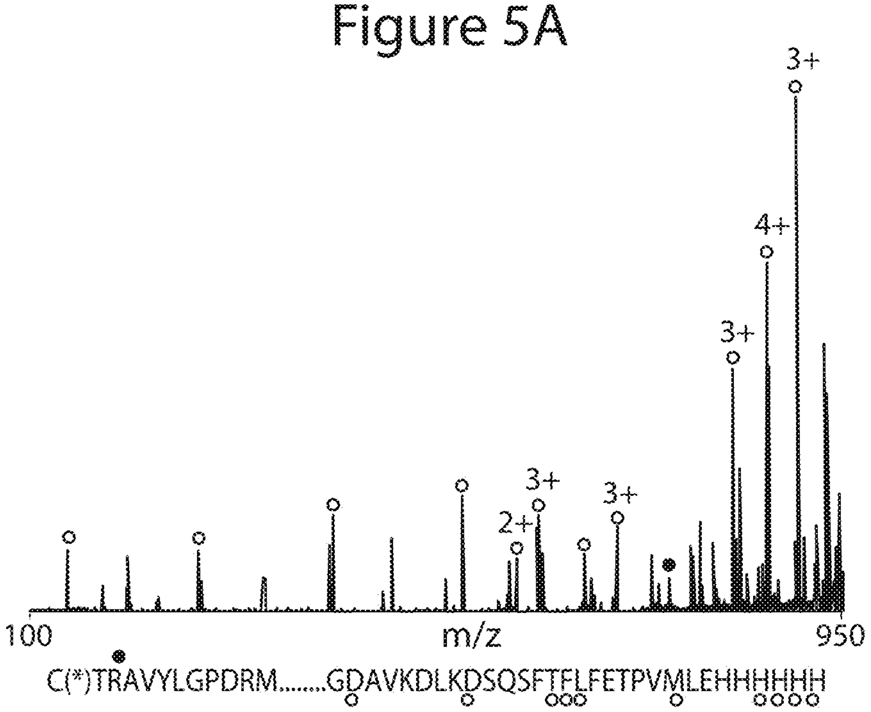

With the potency of compound 7 established, the mechanism of its inhibition was investigated. To confirm that compound 7 is a covalent inhibitor and that it modifies Cys2, the catalytic cysteine residue, mass spectrometry experiments were performed. The *B. theta* BSH contains two cysteine residues, Cys2 and Cys67. Analysis of the apo crystal structure of this enzyme revealed that both the cysteine residues are pointed towards the active site, indicating either residue can be a potential binding site for compound 7 (PDB 3HBC). It was discovered that reincubation of *B. theta* BSH with compound 7 resulted in a shift in the intact mass of the protein by 388 mass units. This mass shift is consistent with the addition of a single equivalent of the inhibitor to the protein (FIG. 5A). While digestion with Trypsin or Lys-C did not identify the peptide being labelled, a top-down approach revealed Cys2 as the modified residue as indicated by the c3 ions (FIG. 5B).

In order to understand the spatial arrangement of the inhibitor in the binding pocket and to guide further inhibitor design, the co-crystal structure of *B. theta* BSH covalently bound to compound 7 was determined at 3.4 Å resolution. Consistent with the mass spectrometry data, the co-crystal structure revealed that Cys2 was bound to the C25-methylene of the bile acid structure and that the fluorine atom had been eliminated. Taken together, these data indicate that compound 7 selectively labels the *B. theta* BSH at the nucleophilic cysteine residue in the active site of the protein. Furthermore, the co-crystal structure reveals that the C3-hydroxyl group is solvent-exposed, suggesting that this site might be amenable to further modification.

Compound 7 Displays Minimal Off-Target Effects

Figure 6A:
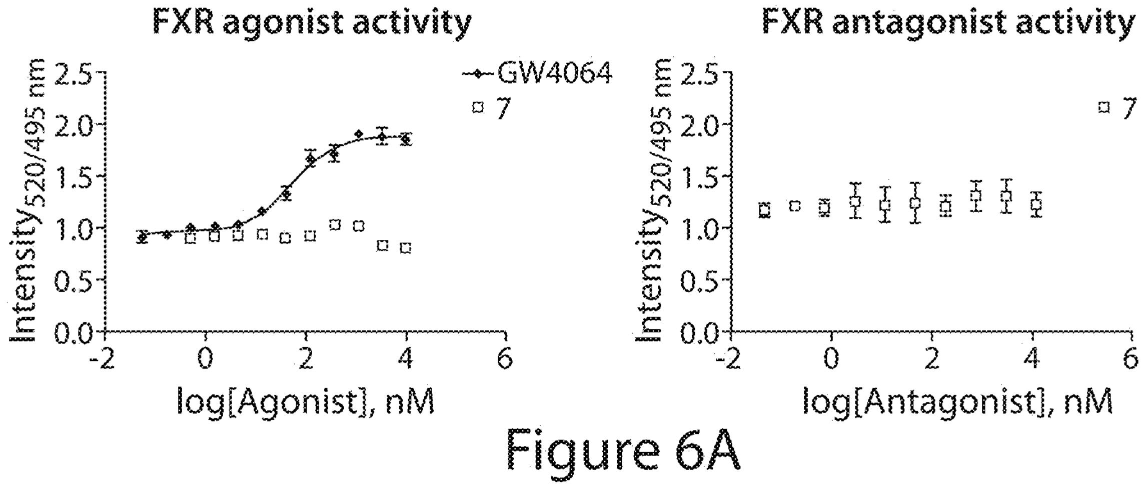
FIGS. 6A to 6C demonstrate that compound 7 exhibits minimal off-target effects.
Figure 6B:
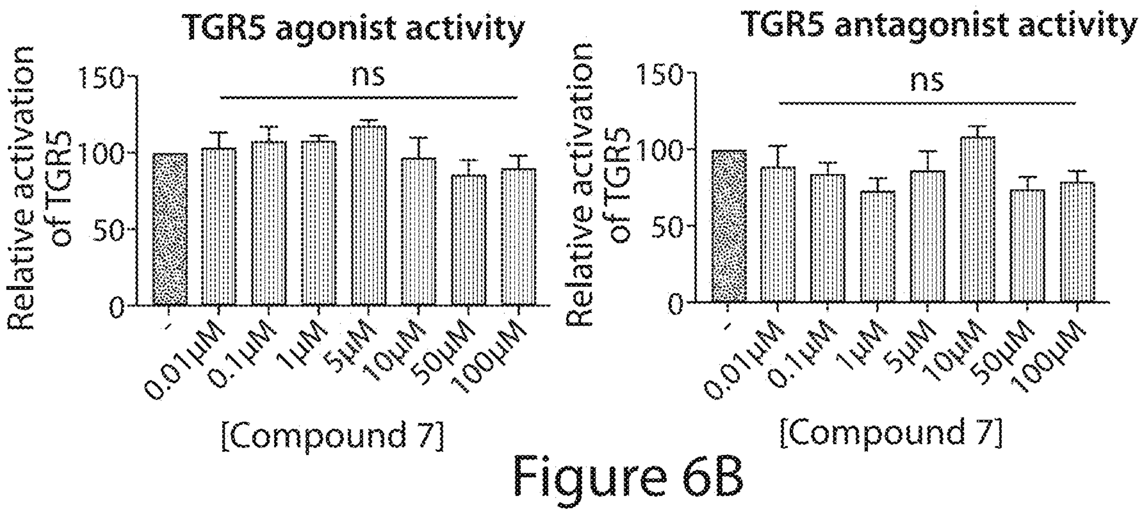

While covalent inhibitors have been shown to be highly potent, concerns have been raised that non-specific reactivity of these compounds can result in acute toxicity.[30] The inhibitors described herein were designed to contain a bile acid core in order to increase selectivity of these compounds for BSH. However, bile acids are known to be ligands for host nuclear hormone receptors (NhR) and G protein-couple receptors (GPCR).[18] It is possible, then, that the lead inhibitor can bind to these receptors and induce off-target effects in the host. In particular, binding of certain bile acids to FXR and GPBAR1/TGR5 affects core host metabolic and immune processes.[18] In order to determine whether compound 7 can act as a ligand for FXR, an in vitro coactivator recruitment assay was performed (FIG. 6A).[28] This assay measures the ability of a compound to enhance the binding of a recombinant FXR ligand-binding domain (LBD) to a co-activator peptide (SRC2-2) as measured by an increase in time-resolved fluorescence resonance energy transfer (TR-FRET) signal. While the known FXR agonist GW4064 showed a clear dose-dependent increase in the binding of SRC2-2 to FXR ($EC_{50}$=50 nM), the binding of SRC2-2 to FXR did not increase in the presence of compound 7, suggesting that this inhibitor does not activate FXR. In the presence of GW4064 at its $EC_{50}$ concentration, compound 7 did not display a dose-dependent curve, indicating that compound 7 does not possess FXR antagonist activity at physiologically relevant concentrations. Next, the effect of compound 7 on TGR5 activation was evaluated in a human intestinal cell line (Caco-2). Compound 7 did not agonize TGR5 over the range of concentrations tested. In addition, compound 7 did not antagonize TGR5 in the presence of known TGR5 agonist LCA (10 μM) (FIG. 6B). These results suggest that inhibitor 7 will not induce off-target effects via binding to either of these critical host receptors.

Figure 6C:
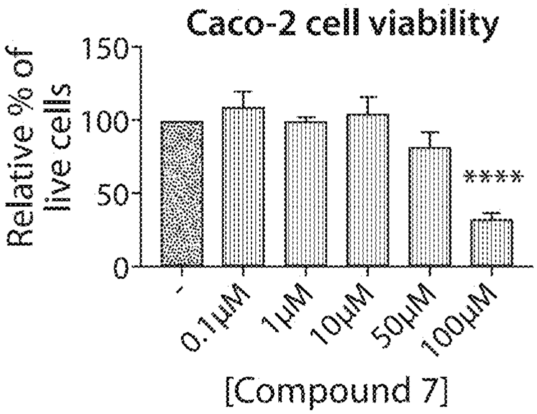

In addition to their effects on host receptors, bile acids are known to be toxic to cells due to their detergent properties.[16,60] Because the expected in vivo area of action of inhibitor 7 is the lower gut, the toxicity of this compound against human intestinal cells (Caco-2) was tested. No resultant toxicity was observed when these cells were incubated with up to 50 μM of compound 7 (FIG. 6C). Because the $IC_{50}$ values of compound 7 against bacterial BSH from 227 nM to 913 nM, these results suggest that it should be possible to achieve an effective in vivo dose at a concentration that will not result in toxicity to intestinal cells. Taken together, these results suggest that inhibitor 7 is both non-toxic and selective for bacterial BSH over potential host targets.

Compound 7 Inhibits BSH Activity in Conventional Mouse Feces

Figure 7A:
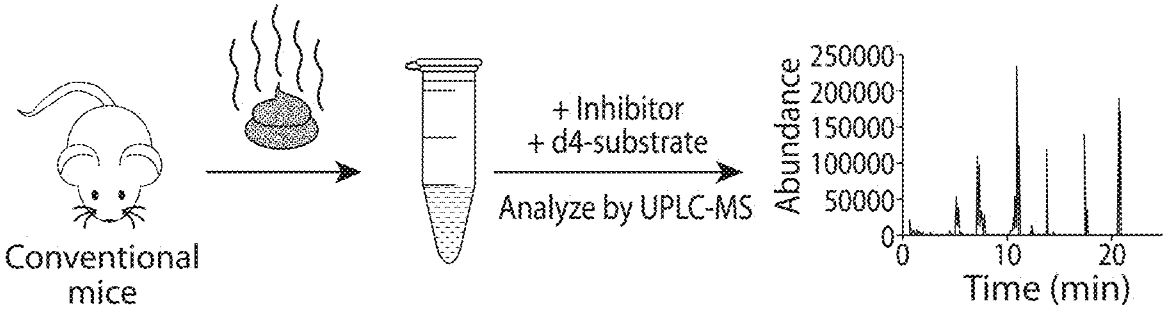
FIGS. 7A to 7F demonstrate that compound 7 inhibits BSH activity ex vivo and in vivo.
Figure 7B:
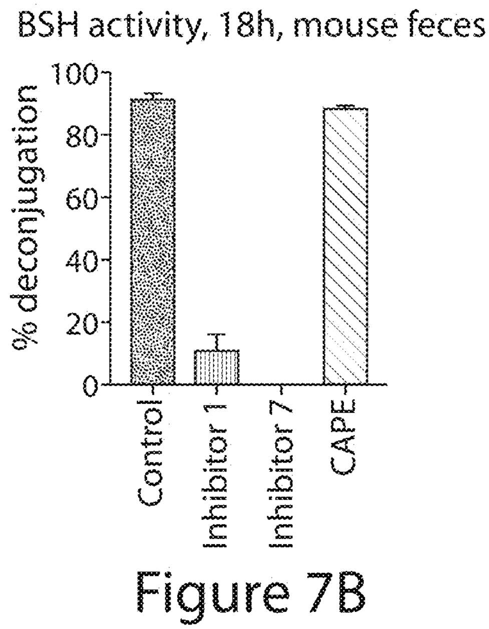

While the experimental results demonstrate the potency of inhibitor 7 against growing cultures of six different strains of gut bacteria, there are hundreds of bacterial species in the human gut.[61] Previous literature had reported significant BSH activity in mouse feces.[62] In order to further bolster the finding that compound 7 is a broad-spectrum BSH inhibitor, the activity of compound 7 in resuspended feces from conventional (i.e., fully colonized) mice was tested. Compounds 1, 7, and CAPE (20 μM) were added to a fecal suspension in buffer. After 30 minutes, the deuterated substrate GCDCA-d4 was added, and deconjugation was determined by quantifying the formation of CDCA-d4 after 18 hours using UPLC-MS (FIG. 7A). Strikingly, it was observed that while incubation with compound 1 resulted in decreased deconjugation, incubation with compound 7 completely inhibited the BSH activity in feces (FIG. 7B). Consistent with the in vitro results, CAPE provided no inhibition of BSH in conventional mouse feces. These results further demonstrate that the lead inhibitor, compound 7, is a potent, broad-spectrum inhibitor of gut bacterial BSH activity.

Single Dose of Compound 7 Inhibits BSH Activity in Conventional Mice

Figure 7C:
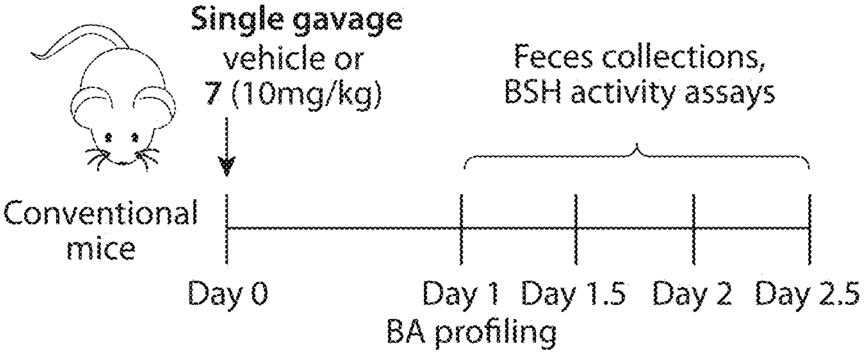

Having established the potency of compound 7 in vitro, the activity of this inhibitor was evaluated in conventional mice. C57Bl/6 mice were gavaged with one dose of either compound 7 (10 mg/kg) or vehicle control, and BSH activity was monitored in half-daily increments until 2.5 days post-gavage (FIG. 7C). While not being bound by a particular theory, it was contemplated that if compound 7 was active in vivo, an initial decrease in BSH activity would be observed followed by a recovery in BSH activity. This expected effect was observed.

Figure 7D:
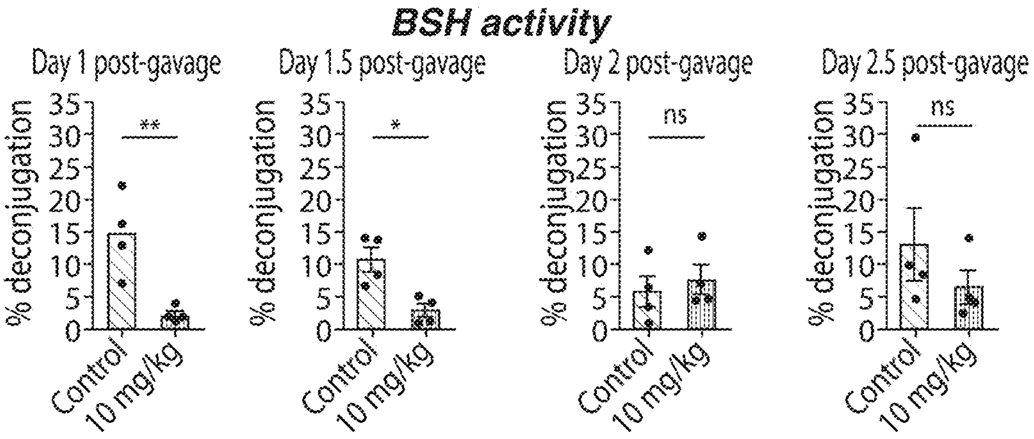
Figure 7E:
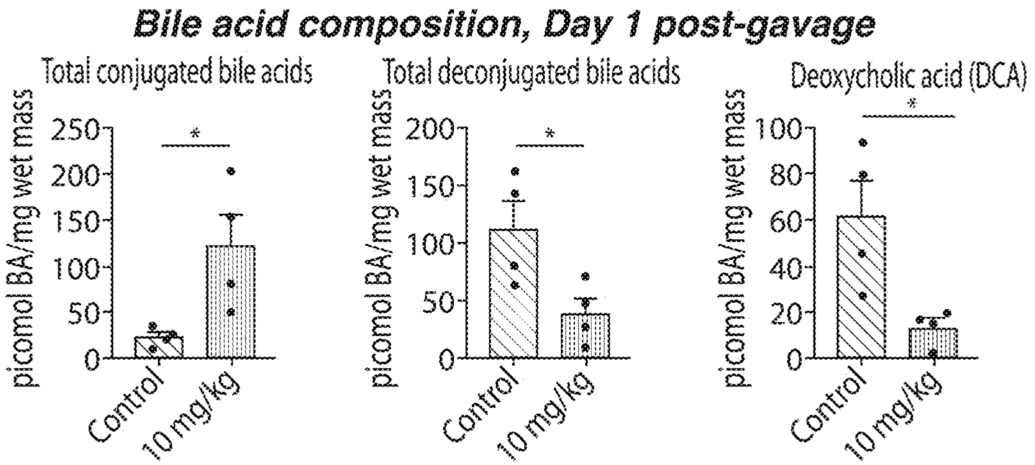

One day and 1.5 days post-gavage, a significant decrease in BSH activity in feces was noted, while at subsequent timepoints (2 days and 2.5 days post-gavage), a recovery of activity was observed (FIG. 7D). Based on the initial hypothesis (FIG. 1A), and not to be bound by a particular theory, it was contemplated that a change in the bile acid pool following BSH inhibition should be observed. A significant decrease in conjugated bile acids and in increase in deconjugated bile acids 1 day-post gavage was observed. Notably, a decrease in the deconjugated secondary bile acid deoxycholic acid (DCA) was observed at this timepoint (FIG. 7E).

Figure 7F:
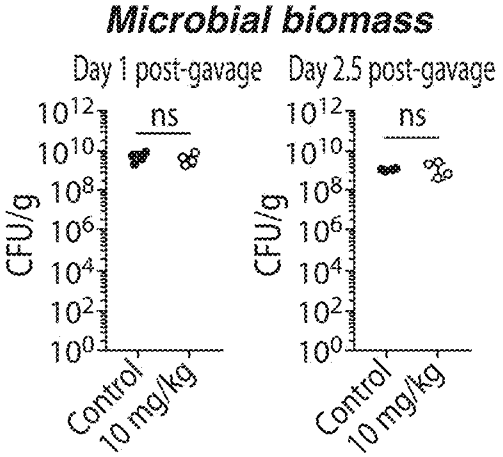

The bacterial culture results indicated that compound 7 did not significantly inhibit bacterial growth. Consistent with this result, a significant decrease in bacterial biomass at any timepoint following initial gavage was not observed (FIG. 7F). Taken together, these results suggest that compound 7 inhibits gut bacterial BSH activity in vivo in the mouse GI tract while not significantly inhibiting overall growth of the gut bacterial community.

Figure 8A:
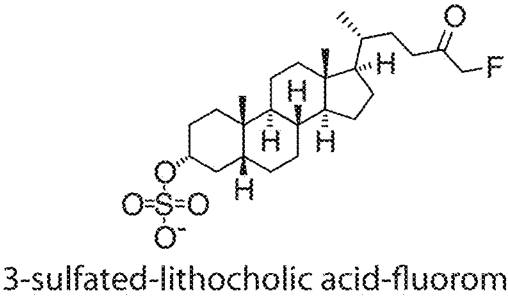
FIGS. 8A to 8D demonstrate the administration of a gut-restricted derivative of compound 7, 3-sulfated-lithocholic acid-fluoromethyl ketone (3S-LCA-FMK), resulted in significant reduction of BSH activity over 1 week when fed in chow.
Figure 8B:
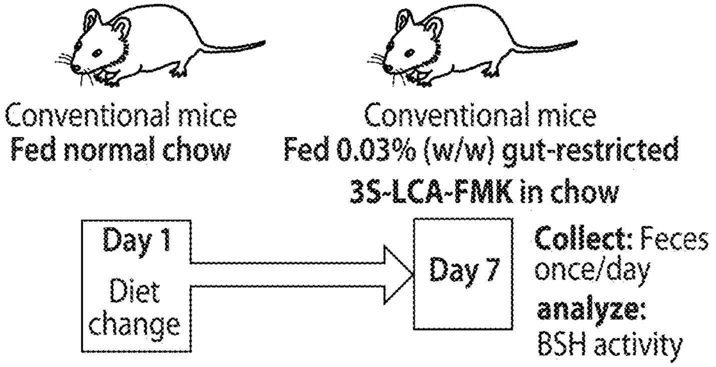
Figure 8C:
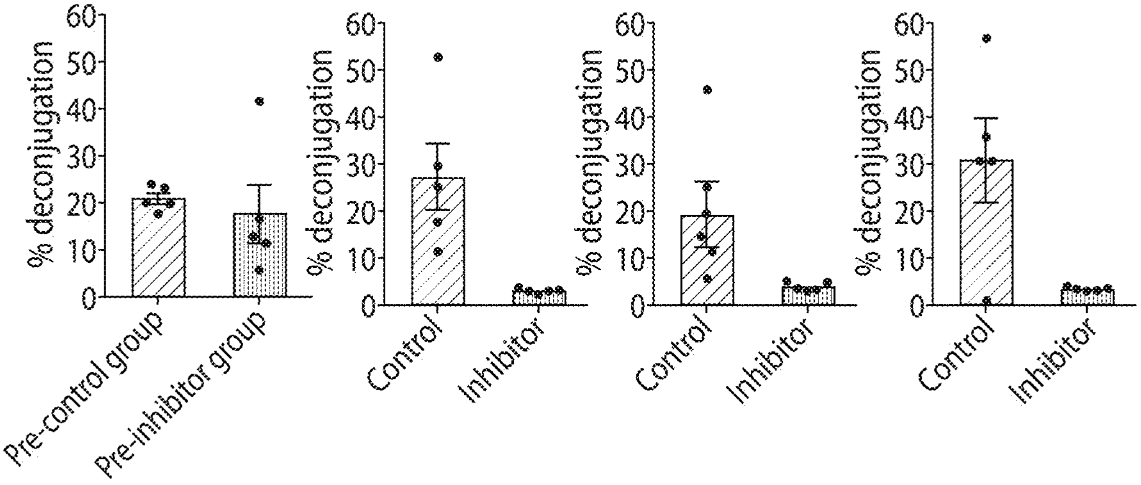
Figure 8D:
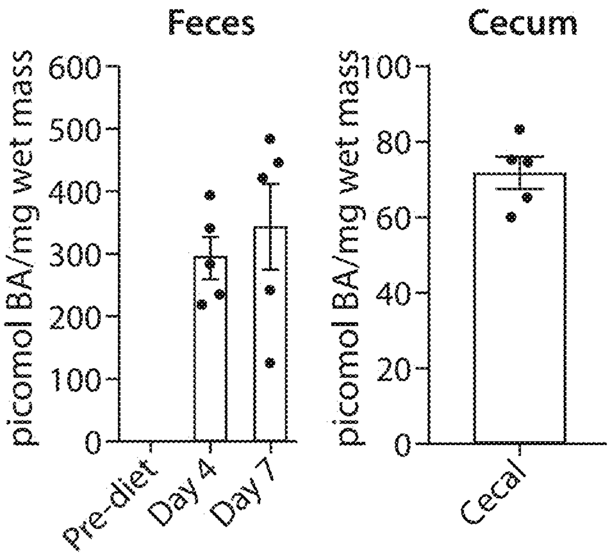
Figure 31:
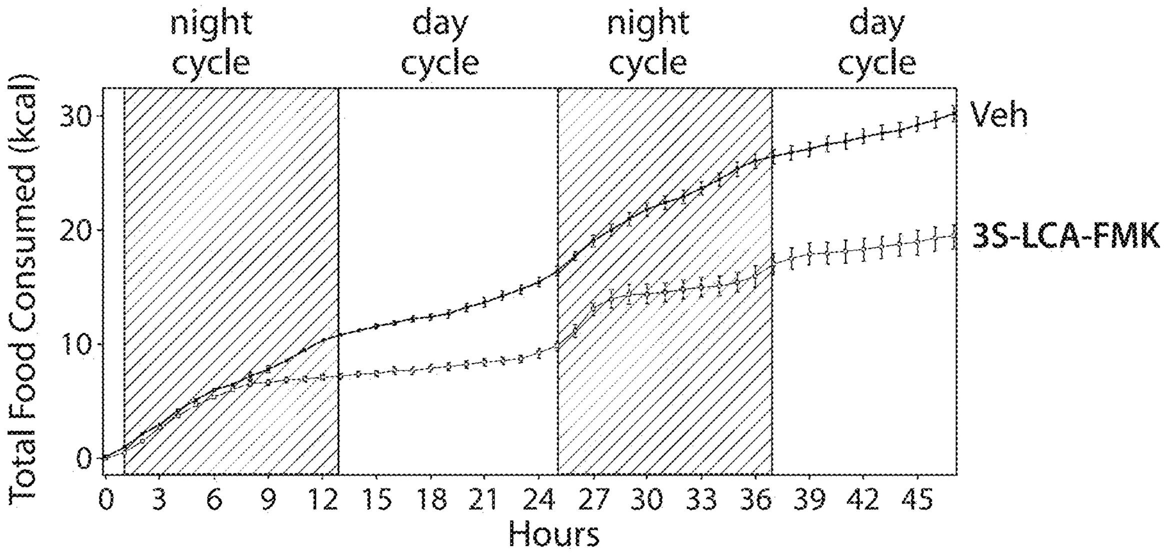
FIG. 31 shows 3S-LCA-FMK reduces food intake in conventional mice compared to mice dosed with vehicle (n=8 mice per group).

A derivative of compound 7, 3-sulfated-lithocholic acid-fluoromethyl ketone (3S-LCA-FMK), was generated to restrict delivery of the BSH inhibitor to the gut (FIG. 8A). Male conventional C57Bl/6 mice were fed normal chow or 3S-LCA-FMK in chow (0.03% weight/weight) ad libitum for 7 days. Feces were collected pre-diet change and on days 3, 4, and 7 post-diet change. n=5 mice per group (FIG. 8B). It was discovered that BSH activity was significantly reduced in the feces of mice fed 3S-LCA-FMK in chow and 3S-LCA-FMK was not detectable in circulating plasma on day 4 (FIGS. 8C-8D). Taken together, these results confirm that the 3S-LCA-FMK compound was gut-restricted and maintains the inhibition of bile acid deconjugation in the animal model. 3S-LCA-FMK has also been shown to reduce food intake in conventional mice compared to mice dosed with vehicle (n=8 mice per group). Mice dosed with 3S-LCA-FMK displayed inhibited BSH activity and a significant decrease in food consumption (FIG. 31).

SUMMARY

Described herein is the development of such a chemical tool, a potent, selective, broad-spectrum inhibitor of gut bacterial BSH. A lead inhibitor, compound 7, was identified that effectively inhibits deconjugation by purified BSH protein, growing cultures of both BSH-containing Gram negative and Gram positive human gut strains, and resuspended conventional mouse feces. It was also shown that a single dose of compound 7 administered to conventional mice reduces BSH activity and predictably shifts the in vivo bile acid pool. Importantly, compound 7 does not significantly affect the growth of these bacteria.

These results suggest that compound 7 or derivatives thereof can be used as tools to study the biological effects of primary and secondary bile acids in fully colonized animals. For example, previous research suggested that bacterial BSH activity affects host metabolism. There have been conflicting reports, however, about how altering BSH activity in vivo affects host metabolic responses.

One study found that increasing the BSH activity in conventional mice via the introduction of an *E. coli* strain engineered to express a *L. salivarius* BSH resulted in reduced weight gain and lower serum and liver lipid levels.[63] Introduction into the gut of an exogenous bacterial strain overexpressing a protein from a different bacterial source is a significant perturbation of the natural ecosystem, however, complicating interpretations of how BSH function in the native system. Another study found that treating conventional mice with the antioxidant compound TEMPOL (4-hydroxy-2,2,6,6-tetramethylpiperidin-1-oxyl) resulted in decreased *Lactobacillus* BSH activity and reduced weight gain.[62] However, TEMPOL has not been shown to act directly as a BSH inhibitor, and it may exert metabolic effects via a BSH-independent mechanism.

Furthermore, in recent work, it was shown that deleting the BSH-encoding gene from the Gram negative gut commensal strain *B. theta* resulted in decreased weight gain, lower liver and blood lipid levels, and a decreased respiratory exchange ratio in mice colonized with this bacterium compared to the *B. theta* wild-type strain.[33] However, these experiments were performed in monocolonized germ-free mice and do not reveal how limiting activity of all BSH will affect the metabolism of conventional animals. To not be bound by a particular theory, it was hypothesized that the reduced weight gain phenotype in *B. theta* BSH knock-out (KO)-colonized mice was due to reduced food intake. Administration of a chemical inhibitor such as compound 7 to mice in metabolic cages can determine the origin of the metabolic effects of inhibiting both individual BSH in monocolonized mice and all BSH in conventional mice.

In addition to facilitating the study of the effects of bile acids on host metabolism, a selective BSH inhibitor can also enable the investigation how primary and secondary bile acids affect host immune response, specifically in the context of liver cancer. A recent study proposed a causal connection between bacterial bile acid metabolism, in particular the conversion of primary to secondary bile acids, and a decrease in a tumor-suppressive environment in the liver.[64] Through bile acid feeding, treatment with antibiotics, and colonization of mice with bile acid-metabolizing bacteria, these researchers gathered support for a model in which secondary bile acids reverse beneficial NKT cell accumulation and inhibition of liver tumor growth promoted by primary bile acids. Use of a BSH inhibitor in mouse models of liver cancer can further test this hypothesis by shifting the endogenous in vivo bile acid pool toward primary bile acids without significantly perturbing the enterohepatic system and the microbial community. If such a shift in the bile acid pool limits liver tumor growth, bacterial BSH inhibitors can be developed as novel cancer therapeutic agents.

Finally, while developing BSH inhibitors, riboflavin and CAPE, two molecules previously identified through a high-throughput screen as inhibitors of BSH from a *Lactobacillus salivarius* chicken gut isolate were also evaluated.[59] In contrast to compound 7, neither riboflavin nor CAPE displayed significant inhibitory activity against any of the Gram negative strains and only one of the three Gram positive strains of gut bacteria, which was also from the genus *Lactobacillus*. In addition, while compound 7 (20 μM) almost completely inhibited BSH activity in resuspended mouse feces, CAPE did not noticeably reduce deconjugation in this assay at either 20 μM or 100 μM concentrations. CAPE significantly inhibits the growth of the strains of Gram negative gut bacteria tested. Use of CAPE to inhibit BSH in mice and thereby study how a shift toward a more FXR-antagonistic bile acid pool affects host metabolism, and in particular, hepatic gluconeogenesis, has been reported.[65] In light of these results, especially the finding that CAPE possesses antibiotic qualities, the conclusions of previous in vivo results obtained using CAPE should be reexamined, or at least viewed with caution.[66] The use of a selective BSH inhibitor such as compound 7 allows for the evaluation of bacterial bile acid metabolism and the effects on host physiology.

Covalent inhibitors can inactivate their protein target with a high degree of potency and selectivity even in the presence of large concentrations of native substrate.[11] The substrates for BSHs, conjugated bile acids, are found in high concentrations in the colon (1-10 mM).[4] In addition, recent work has demonstrated that irreversible inhibitors of bacterial enzymes can be effective in the gut.[12]

Figure 9A:
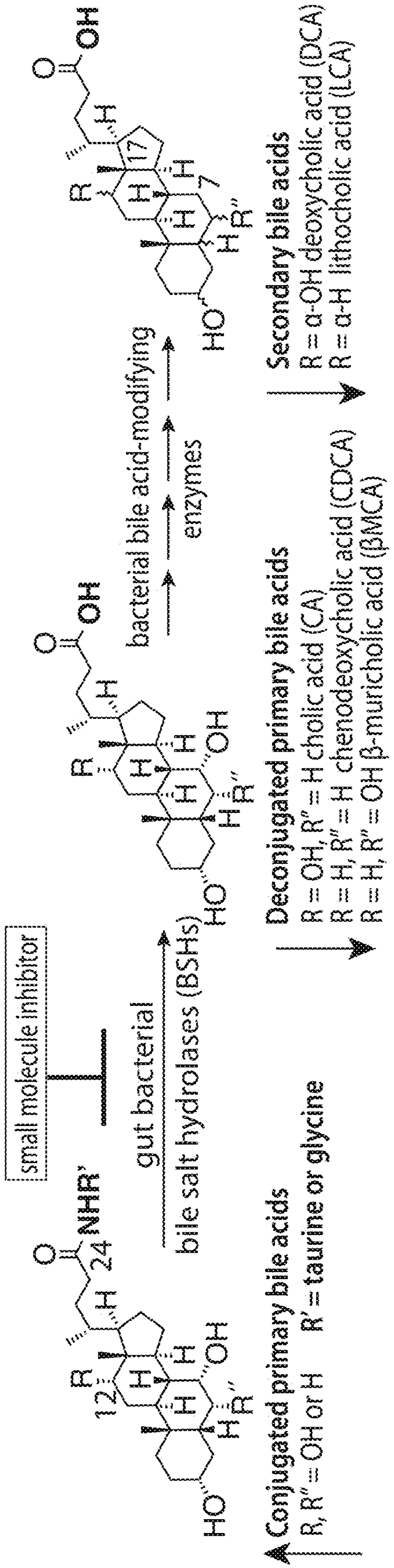
FIG. 9A shows the key reaction in the conversion of primary into secondary bile acids is the hydrolysis (deconjugation) of the C24-amide bond of conjugated primary bile acids.
Figure 9B:
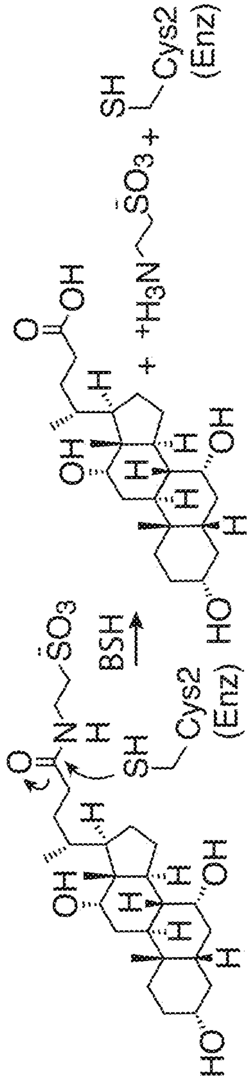
FIG. 9B shows that while there is significant divergence in BSH protein sequence across gut strains, all BSHs possess a conserved active site that includes a catalytic cysteine (Cys2).
Figure 9C:
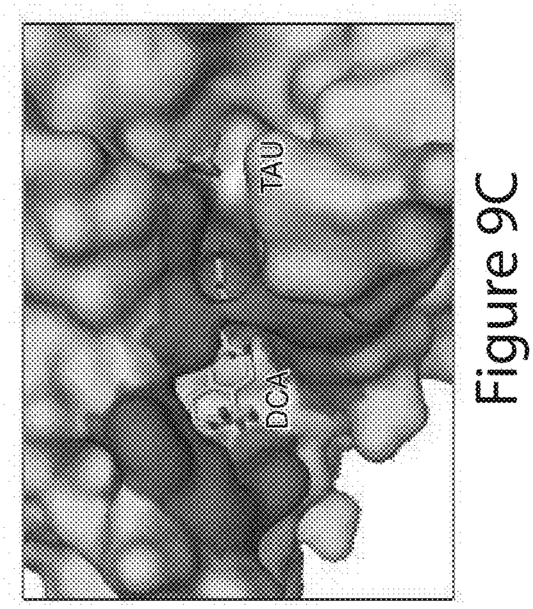
FIG. 9C shows a co-crystal structure of the *Clostridium perfringens* BSH and the substrate taurodeoxycholic acid, which showed that hydrophobic interactions engaged the bile acid core and oriented the amide toward Cys2, leaving the amino acid solvent-exposed.

While there is significant divergence in BSH protein sequence across gut strains, all BSHs possess a conserved active site that includes a catalytic cysteine (Cys2) (FIG. 9*b*).[1,10] Thus, compounds that targeted this conserved residue, may be effective pan-BSH inhibitors. A co-crystal structure of the *Clostridium perfringens* BSH and the substrate taurodeoxycholic acid showed that hydrophobic interactions engaged the bile acid core and oriented the amide toward Cys2, leaving the amino acid solvent-exposed (FIG. 9*c*).[13] Furthermore, *C. perfringens* BSH tolerates a large degree of variability in the amino acid side chain, including longer chain conjugates.[14]

A small library of potential inhibitors containing both a bile acid core motif and a pendant electrophilic warhead (FIG. 9*d*) was developed. Without wishing to be bound by any particular theory, previous literature indicated that conjugated amino acid identity may largely drive BSH specificity,[1] while sterol core configuration also affects BSH reactivity.[15] Additionally, some Bacteroidetes species cleave C12=H but not C12=OH primary bile acids (FIG. 9*a*).[16]

Several electrophilic trapping groups were chosen,[17] including isothiocyanate (1),[18] cyanoacrylate (2),[19] α,β-unsaturated systems (3 and 4),[20] acrylamide (5),[21] and nitrile (6).[22] An inhibitor with an α-fluoromethyl ketone warhead (FMK) (7) was also synthesized. In contrast to the more electrophilic α-iodo-, α-bromo- and α-chloromethyl ketone warheads, the weak leaving group ability of fluorine renders the FMK warhead less reactive and hence more selective.[23,24] FMK-based inhibitors have been shown to result in minimal off-target effects.[23,25]

Example 2. Biochemical Characterization of BSHs

The activity of inhibitors 1-9 against both Gram negative and Gram positive BSHs was then evaluated using a selective *Bacteroides* BSH for inhibitor optimization. Accordingly, the selective BSH (BT_2086) was heterologously expressed and purified (Table 2 and FIG. 14).[16]

TABLE 2

Primers for BSH gene amplification.

| Protein | Primer | Sequence |
|---|---|---|
| *B. theta* BSH | Bt_BSH_F | ATA GCT AGC ATG TGT ACG CGG GCG GTT TAC |
| *B. theta* BSH | Bt_BSH_R | ATC GCT CGA GCA TGA CTG GCG TTT CAA AC |
| *B. longum* BSH | BI_BSH_F | GAT TGG CTA GCA TGT GCA CCG GCG TTC GT |
| *B. longum* BSH | BI_BSH_R | GGG CTC GAG ACG TGC CAC TGA GAT TAA TTC |

Kinetic parameters using a ninhydrin-based assay were determined.[26] Purified *B. theta* BSH displayed a preference for tauro-ursodeoxycholic acid (TUDCA) deconjugation and did not deconjugate tauro-cholic acid (TCA) (Table 3 and FIG. 14).[16]

TABLE 3

Kinetic parameters for BSHs from *Bactereroides thetaiotaomicron* (*B. theta*) and *Bifidobacterium longum* (*B. longum*).

| BSH source[a] | Substrate[b] | $k_{cat}$ ($min^{-1}$) | $K_m$ (mM) | $k_{cat}/K_m$ ($min^{-1}mM^{-1}$) |
|---|---|---|---|---|
| *B. theta* | TCA[c] | — | — | — |
| | TUDCA | 15.3 ± 0.8 | 8.2 ± 1.0 | 1.9 ± 0.3 |
| | TDCA | 12.9 ± 0.6 | 3.4 ± 0.6 | 3.8 ± 0.7 |
| | TCDCA | 4.3 ± 0.6 | 2.9 ± 1.8 | 4.3 ± 0.9 |
| *B. longum* | TCA | 6.9 ± 0.9 | 8.3 ± 2.5 | 0.8 ± 0.3 |
| | TUDCA | 0.9 ± 0.2 | 4.1 ± 2.5 | 0.2 ± 0.1 |
| | TDCA | 3.5 ± 0.1 | 2.3 ± 0.3 | 1.5 ± 0.2 |
| | TCDCA | 4.6 ± 0.6 | 7.0 ± 2.3 | 0.6 ± 0.2 |

[a]Characterization was performed using ninhydrin reagent and experiments were performed in PBS buffer at pH 7.5 and 37° C.
[b]Conjugated primary and secondary bile acid used as substrates were taurocholic acid (TCA), tauroursodeoxycholic acid (TUDCA), taurodeoxycholic acid (TDCA), taurochenodeoxycholic acid (TCDCA).
[c]*B. theta* did not deconjugate TCA. n = 3 biological replicates per condition. All data are presented as mean ± SEM.

BSH from the Gram positive strain *Bifidobacterium longum* SBT2928 BSH[27] was also cloned, expressed, and the kinetic parameters determined (Table 3 and FIG. 14). The $K_m$ values for all of the recognized substrates are in the low millimolar range, which is approximately the concentration of these bile acids in the gut. While the $k_{cat}$ values are lower than the $k_{cat}$ reported for the *Lactobacillus salivarius* BSH, the $K_m$ values for these enzymes are similar to those of previously characterized BSHs.[27-29] Example 3. α-FMK compound 7 as lead inhibitor inhibits recombinant BSHs The ability of the compounds in our library to inhibit *B. theta* and *B. longum* BSHs was also evaluated. Riboflavin (10) and caffeic acid phenethyl ester (CAPE, 11), compounds that had been previously identified in a high-throughput screen for inhibition of a BSH from a *Lactobacillus salivarius* chicken gut isolate were also tested (FIG. 14).[30] BSH inhibitory activity, was determined by pre-incubating the *B. theta* BSH with each inhibitor (100 μM) for 30 minutes and then adding a mixture of conjugated bile acids (100 μM final concentration).

Because BSHs display varying reactivities toward different conjugated bile acids, an equimolar combination of two primary and two secondary conjugated bile acids that are predominant in the gallbladder and small intestine of conventional mice as our substrate mixture (tauro-β-muricholic acid (T β MC), TCA, TUDCA, and tauro-deoxycholic acid (TDCA)) was used.[31] Deconjugation of bile acids was monitored by Ultra Performance Liquid Chromatography-Mass Spectrometry (UPLC-MS) over 21 hours. Among the synthesized inhibitors, isothiocyanate (1) displayed modest inhibition. Other compounds containing Michael acceptor warheads (2-6) did not inhibit deconjugation. In contrast, incubation with α-FMK-based 7 resulted in almost complete inhibition of *B. theta* BSH activity for 21 hours (>98%, FIG. 10*a*, 15, 16, and Table 4).

TABLE 4

% deconjugation of each bile acid determined in experiments with a pool of four tauro conjugated bile acids.

Figure 21A:
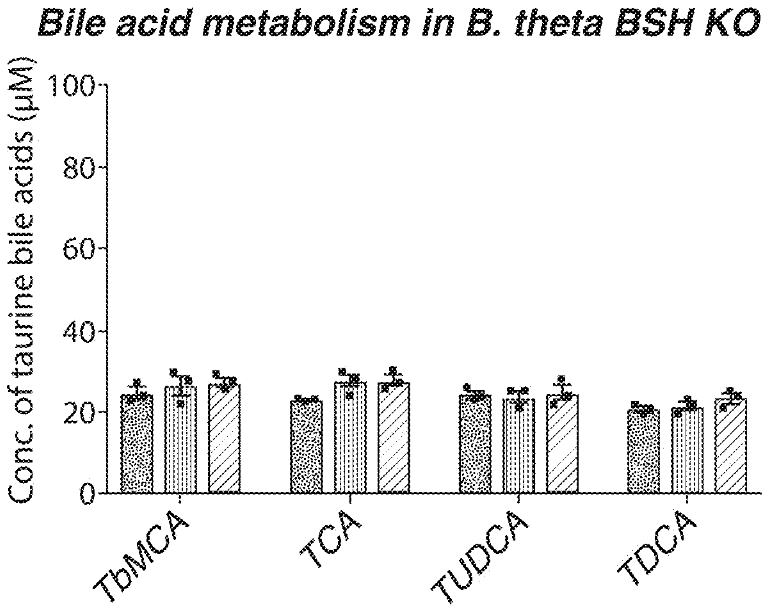
(FIG. 21A) 100 μM of a pool of taurine conjugated bile acids (TCA, TβMCA, TUDCA and TDCA, 25 μM each) and 100 μM inhibitor (compound 7 or CAPE) or DMSO were added to growing *B. theta*. Cultures were incubated for 24 h and bile acid profiling was then performing using UPLC-MS. No bile acids other than the starting materials (TCA, TβMCA, TUDCA and TDCA) were detected in any of the cultures.
Figure 21B:
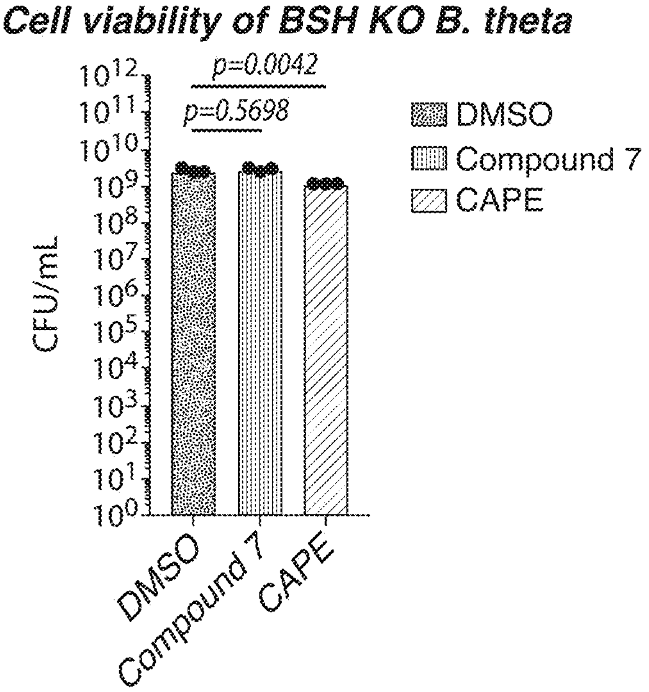
(FIG. 21B) Colony forming units (CFUs) were determined from the assay in panel (FIG. 21A) after 24 h. Compound 7 was not found to be bactericidal to BSH-deleted *B. theta* while CAPE was found to significantly affect the growth of this bacteria.

| | % deconjugation of TCA | | | % deconjugation of TβMCA | | | % deconjugation of TUDCA | | | % deconjugation of TDCA | | |
|---|---|---|---|---|---|---|---|---|---|---|---|---|
| | replicate 1 | replicate 2 | replicate 3 | replicate 1 | replicate 2 | replicate 3 | replicate 1 | replicate 2 | replicate 3 | replicate 1 | replicate 2 | replicate 3 |
| FIG. 2a, 2 hours | | | | | | | | | | | | |
| Control | 1.19 | 1.10 | 0.26 | 33.70 | 31.31 | 29.69 | 96.16 | 95.42 | 95.73 | 98.25 | 98.71 | 98.15 |
| Compound 1 | 0.12 | 0.17 | 0.29 | 3.72 | 3.29 | 3.28 | 37.96 | 35.92 | 33.34 | 51.40 | 46.10 | 43.43 |
| Compound 2 | 0.90 | 22.25 | 0.48 | 34.64 | 0.98 | 30.95 | 95.53 | 94.77 | 93.56 | 98.39 | 97.77 | 97.37 |
| Compound 3 | 0.67 | 1.01 | 0.09 | 34.08 | 27.93 | 27.02 | 95.01 | 94.06 | 91.94 | 97.76 | 97.25 | 96.55 |
| Compound 4 | 0.47 | 1.15 | 0.30 | 32.07 | 29.34 | 22.69 | 94.07 | 91.62 | 89.81 | 97.26 | 96.13 | 94.56 |
| Compound 5 | 0.95 | 0.92 | 1.05 | 32.80 | 36.63 | 9.44 | 96.13 | 96.16 | 95.10 | 98.42 | 98.52 | 98.57 |
| Compound 6 | 0.92 | 1.25 | 0.59 | 35.60 | 34.07 | 42.48 | 96.03 | 93.99 | 93.59 | 98.74 | 97.53 | 97.40 |
| Compound 7 | 0.00 | 0.06 | 0.07 | 0.00 | 0.00 | 0.00 | 1.77 | 1.53 | 1.45 | 2.16 | 1.98 | 2.01 |
| Compound 8 | 1.15 | 0.59 | 2.07 | 14.58 | 29.59 | 38.71 | 97.82 | 95.09 | 96.63 | 99.29 | 98.31 | 99.01 |
| Riboflavin | 1.37 | 0.06 | 0.69 | 37.87 | 30.51 | 33.21 | 99.21 | 94.73 | 94.97 | 99.69 | 97.30 | 97.98 |
| CAPE | 0.36 | 0.08 | 0.06 | 14.25 | 12.45 | 10.19 | 76.05 | 74.21 | 70.00 | 76.46 | 75.12 | 72.52 |
| FIG. 2a, 21 hours | | | | | | | | | | | | |
| Control | 2.93 | 3.44 | 1.16 | 61.21 | 71.43 | 55.90 | 99.06 | 99.21 | 99.02 | 97.10 | 97.36 | 94.86 |
| Compound 1 | 0.12 | 0.17 | 0.15 | 3.18 | 4.28 | 3.11 | 34.40 | 41.24 | 37.45 | 45.18 | 51.87 | 45.19 |
| Compound 2 | 0.21 | 2.67 | 2.13 | 27.46 | 61.90 | 51.76 | 96.86 | 99.36 | 98.17 | 93.10 | 98.34 | 96.06 |
| Compound 3 | 1.08 | 1.44 | 2.82 | 38.49 | 45.51 | 59.04 | 97.70 | 99.19 | 99.48 | 93.30 | 97.89 | 97.49 |
| Compound 4 | 1.50 | 0.85 | 1.80 | 47.65 | 32.41 | 43.47 | 98.54 | 97.31 | 97.80 | 95.87 | 95.61 | 96.21 |
| Compound 5 | 4.41 | 3.75 | 3.05 | 70.08 | 68.59 | 63.03 | 99.58 | 99.62 | 99.25 | 98.66 | 99.29 | 97.94 |
| Compound 6 | 2.57 | 0.00 | 1.90 | 64.01 | 0.30 | 61.81 | 99.32 | 53.74 | 99.44 | 98.26 | 62.13 | 98.29 |
| Compound 7 | 0.00 | 0.09 | 0.00 | 0.00 | 0.00 | 0.00 | 0.32 | 1.81 | 1.09 | 0.45 | 2.25 | 0.53 |
| Compound 8 | 1.90 | 3.94 | 2.71 | 60.01 | 69.30 | 60.40 | 99.39 | 99.62 | 99.58 | 97.93 | 99.68 | 98.41 |
| Riboflavin | 2.39 | 3.55 | 3.41 | 54.39 | 65.09 | 67.26 | 98.88 | 99.48 | 99.59 | 94.28 | 97.99 | 96.89 |
| CAPE | 0.74 | 0.09 | 1.11 | 25.75 | 3.08 | 37.00 | 93.76 | 59.73 | 96.84 | 91.61 | 54.27 | 94.84 |
| FIG. 2b, 2 hours | | | | | | | | | | | | |
| Control | 84.30 | 86.35 | 57.07 | 3.17 | 3.22 | 1.58 | 37.34 | 39.53 | 32.17 | 98.75 | 99.15 | 98.88 |
| Compound 1 | 0.10 | 0.89 | 0.43 | 2.49 | 0.05 | 0.03 | 2.12 | 1.09 | 0.61 | 7.25 | 4.34 | 2.20 |
| Compound 7 | 0.03 | 0.98 | 1.05 | 0.49 | 0.06 | 0.04 | 1.05 | 1.39 | 1.43 | 0.15 | 0.19 | 0.24 |
| CAPE | 68.68 | 55.04 | 54.30 | 2.05 | 1.81 | 1.50 | 26.95 | 25.15 | 24.35 | 93.93 | 93.63 | 93.26 |

TABLE 4-continued

% deconjugation of each bile acid determined in experiments with a pool of four tauro conjugated bile acids.

Figure 5C:
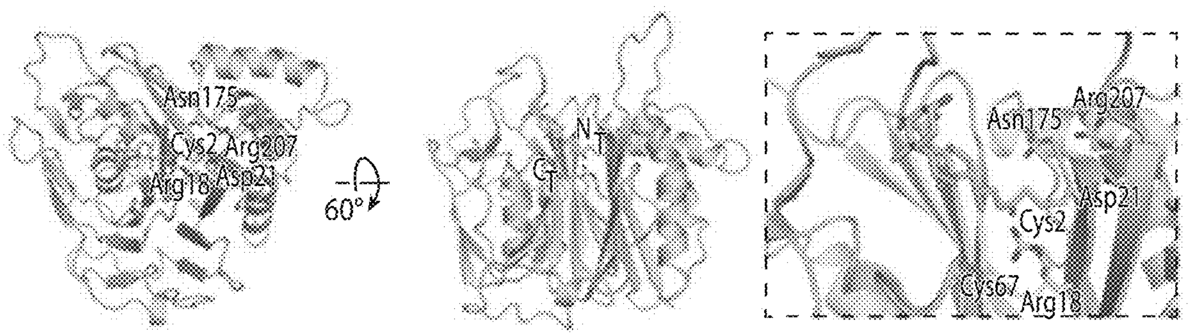

| | | % deconjugation of TCA | | | % deconjugation of TβMCA | | | % deconjugation of TUDCA | | | % deconjugation of TDCA | | |
|---|---|---|---|---|---|---|---|---|---|---|---|---|---|
| | | replicate 1 | replicate 2 | replicate 3 | replicate 1 | replicate 2 | replicate 3 | replicate 1 | replicate 2 | replicate 3 | replicate 1 | replicate 2 | replicate 3 |
| FIG. 2b, 21 hours | | | | | | | | | | | | | |
| Control | | 96.43 | 99.43 | 99.10 | 33.36 | 35.07 | 30.92 | 96.65 | 97.65 | 97.19 | 98.12 | 99.24 | 98.84 |
| Compound 1 | | 9.02 | 3.00 | 8.03 | 0.21 | 0.13 | 0.28 | 4.57 | 2.48 | 3.66 | 23.33 | 14.91 | 20.42 |
| Compound 7 | | 1.61 | 1.00 | 1.61 | 0.11 | 0.08 | 0.11 | 2.11 | 1.54 | 2.36 | 0.37 | 0.22 | 0.39 |
| CAPE | | 98.46 | 97.65 | 98.90 | 25.75 | 19.28 | 23.96 | 93.63 | 92.01 | 93.28 | 97.84 | 98.03 | 97.42 |
| Supplementary FIG. 3a, 5 hours | | | | | | | | | | | | | |
| Control | | 0.09 | 2.13 | 2.50 | 53.21 | 51.95 | 55.87 | 99.76 | 99.80 | 99.71 | 99.92 | 99.94 | 99.94 |
| Compound 1 | | 0.25 | 0.00 | 0.21 | 4.42 | 4.47 | 3.37 | 38.73 | 40.02 | 35.99 | 52.56 | 51.54 | 45.63 |
| Compound 2 | | 0.38 | 1.34 | 1.77 | 43.58 | 51.12 | 45.91 | 99.47 | 99.51 | 99.47 | 99.85 | 99.91 | 99.57 |
| Compound 3 | | 0.85 | 2.89 | 1.97 | 46.39 | 56.31 | 44.08 | 99.39 | 99.60 | 99.06 | 99.83 | 99.91 | 99.75 |
| Compound 4 | | 0.40 | 1.92 | 1.29 | 26.17 | 45.65 | 37.57 | 98.43 | 98.54 | 97.17 | 99.59 | 99.50 | 99.01 |
| Compound 5 | | 2.33 | 3.50 | 1.92 | 54.06 | 53.97 | 50.71 | 99.64 | 99.74 | 96.67 | 99.94 | 99.95 | 99.86 |
| Compound 6 | | 0.55 | 1.62 | 2.39 | 44.48 | 50.02 | 51.09 | 99.61 | 99.41 | 99.67 | 97.07 | 99.88 | 99.89 |
| Compound 7 | | 0.00 | 0.00 | 0.00 | 0.00 | 0.00 | 0.00 | 1.27 | 1.43 | 1.05 | 1.60 | 2.00 | 1.32 |
| Compound 8 | | 2.91 | 2.99 | 2.29 | 60.02 | 57.01 | 54.60 | 99.94 | 99.79 | 99.79 | 99.96 | 99.96 | 99.91 |
| Riboflavin | | 0.90 | 1.95 | 0.21 | 41.18 | 50.96 | 47.55 | 99.58 | 99.54 | 99.43 | 99.91 | 99.87 | 99.69 |
| CAPE | | 0.29 | 0.77 | 0.05 | 23.21 | 24.76 | 20.62 | 89.91 | 91.34 | 88.49 | 90.81 | 91.46 | 89.67 |
| Supplementary FIG. 3b, 5 hours | | | | | | | | | | | | | |
| Control | | 100.00 | 97.74 | 100.00 | 7.67 | 8.47 | 7.83 | 63.76 | 67.92 | 64.49 | 99.80 | 99.86 | 99.77 |
| Compound 1 | | 4.13 | 4.57 | 4.31 | 0.10 | 0.11 | 0.11 | 2.44 | 2.49 | 2.64 | 9.85 | 11.26 | 11.96 |
| Compound 7 | | 0.88 | 1.09 | 1.15 | 0.05 | 0.04 | 0.04 | 1.39 | 1.34 | 1.51 | 0.15 | 0.17 | 0.17 |
| CAPE | | 90.99 | 93.66 | 93.73 | 4.55 | 5.27 | 5.06 | 48.74 | 50.94 | 49.29 | 99.78 | 99.73 | 99.81 |
| FIG. 2c | | | | | | | | | | | | | |
| *B. theta* | DMSO | 0.16 | 0.16 | 0.00 | 0.66 | 0.39 | 0.66 | 14.79 | 14.73 | 11.85 | 29.18 | 27.70 | 26.58 |
| | compound 7 | 0.26 | 0.24 | 0.00 | 0.63 | 0.17 | 0.00 | 1.55 | 0.96 | 0.87 | 0.33 | 0.00 | 0.20 |
| | CAPE | 0.42 | 0.72 | 0.52 | 0.64 | 0.28 | 0.16 | 5.36 | 2.32 | 2.31 | 2.06 | 0.90 | 0.81 |
| *B. fragilis* | DMSO | 100.00 | 100.00 | 100.00 | 100.00 | 100.00 | 100.00 | 99.00 | 99.38 | 99.50 | 99.05 | 99.39 | 99.31 |
| | compound 7 | 1.14 | 1.51 | 1.11 | 4.96 | 4.15 | 2.69 | 10.78 | 9.04 | 6.33 | 9.74 | 8.92 | 5.67 |
| | CAPE | 88.33 | 85.35 | 84.93 | 98.64 | 98.42 | 99.12 | 98.65 | 99.13 | 98.66 | 98.95 | 98.93 | 99.13 |
| *B. vulgatus* | DMSO | 1.01 | 1.76 | 46.37 | 99.70 | 97.40 | 60.67 | 99.86 | 98.38 | 99.93 | 28.89 | 19.69 | 17.88 |
| | compound 7 | 0.68 | 0.64 | 0.47 | 1.58 | 0.41 | 0.65 | 3.62 | 0.80 | 1.90 | 0.90 | 0.17 | 0.81 |
| | CAPE | 1.46 | 1.06 | 0.00 | 88.92 | 78.15 | 71.86 | 94.25 | 87.91 | 82.37 | 5.47 | 3.03 | 1.28 |
| *L. plantarum* | DMSO | 10.32 | 15.55 | 24.03 | 0.10 | 0.42 | 0.09 | 1.48 | 2.75 | 3.77 | 52.77 | 53.89 | 74.27 |
| | compound 7 | 0.77 | 0.93 | 1.02 | 0.15 | 0.49 | 0.62 | 0.97 | 1.32 | 1.46 | 3.22 | 0.62 | 0.64 |
| | CAPE | 10.67 | 33.19 | 53.29 | 0.06 | 0.59 | 0.95 | 1.73 | 3.54 | 6.80 | 47.57 | 82.98 | 93.57 |
| *C. perfingens* | DMSO | 100.00 | 100.00 | 100.00 | 100.00 | 100.00 | 100.00 | 99.02 | 99.09 | 99.21 | 100.00 | 99.49 | 99.50 |
| | compound 7 | 19.18 | 14.04 | 7.40 | 7.40 | 4.72 | 4.84 | 18.06 | 15.54 | 9.84 | 78.88 | 69.68 | 54.57 |
| | CAPE | 100.00 | 100.00 | 100.00 | 100.00 | 100.00 | 100.00 | 98.62 | 98.71 | 98.92 | 99.71 | 99.30 | 99.38 |
| *B. adolescentis* | DMSO | 100.00 | 100.00 | 100.00 | 87.65 | 87.58 | 88.64 | 100.00 | 99.37 | 99.16 | 100.00 | 99.79 | 99.45 |
| | compound 7 | 2.88 | 3.09 | 2.93 | 0.34 | 0.37 | 0.73 | 1.26 | 1.21 | 1.54 | 10.43 | 6.05 | 7.35 |
| | CAPE | 100.00 | 100.00 | 100.00 | 100.00 | 100.00 | 100.00 | 99.43 | 100.00 | 99.43 | 99.85 | 100.00 | 99.71 |

Figure 10A:
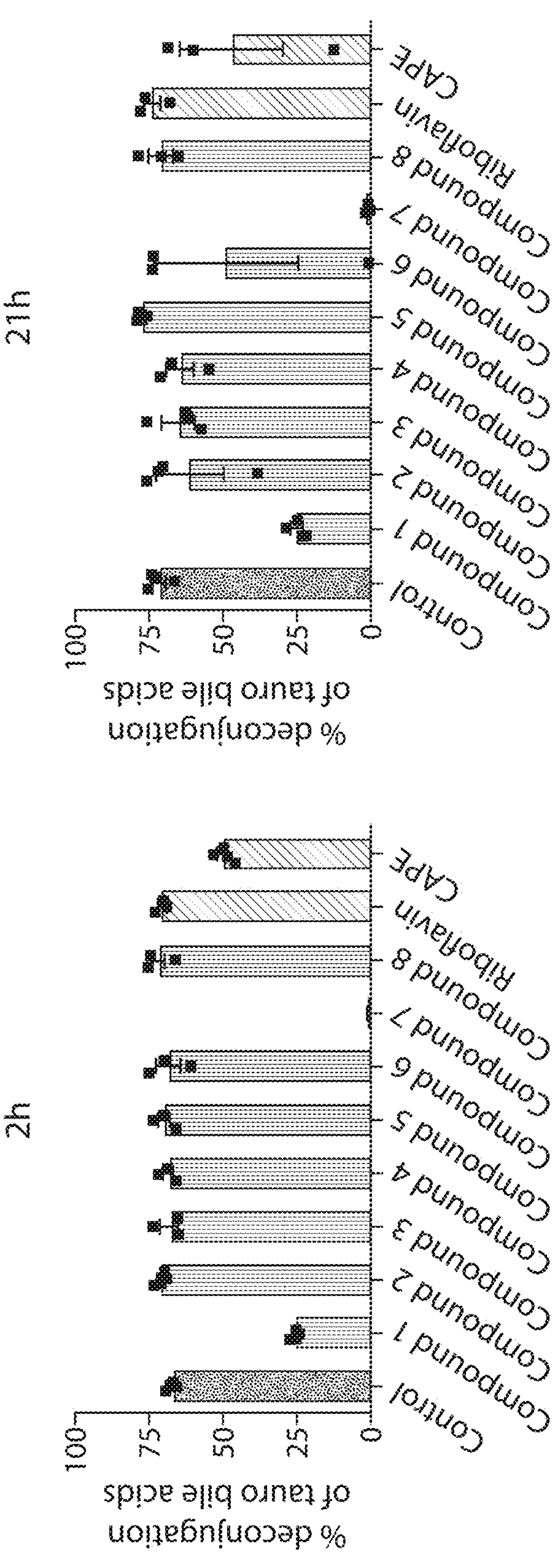
FIG. 10 shows screen of inhibitors versus *B. theta* BSH (FIG. 10A) and *B. longum* BSH (FIG. 10B) showing % deconjugation of tauro bile acids at 2 and 21 hours. Bacterial strains were incubated with 100 μM of conjugated bile acid and plated at 21 h to assess strain viability (FIG. 10C). Compound 7 is not bactericidal (FIG. 10D). CAPE decreased the cell viability of the Gram negative strains tested. Red downward arrows indicate fold decrease compared to DMSO control. For (FIG. 10C) and (FIG. 10D), one-way ANOVA followed by Dunnett's multiple comparisons test.
(FIG. 10E) Compound 7 inhibited BSH activity in a fecal slurry. All assays were performed in biological triplicate, and data are presented as mean±SEM.

In order to validate that the inhibitory activity of 7 was due to the presence of fluorine as a leaving group, the methyl ketone analog (8) was synthesized.[25] This analog did not display BSH inhibition against either recombinant protein or *B. theta* cultures, indicating that the α-fluoro group was necessary for activity (FIG. 10*a*, FIG. 17, and Table 4). Riboflavin did not display any inhibitory activity, while CAPE provided only moderate inhibition of *B. theta* BSH.

Figure 10C:
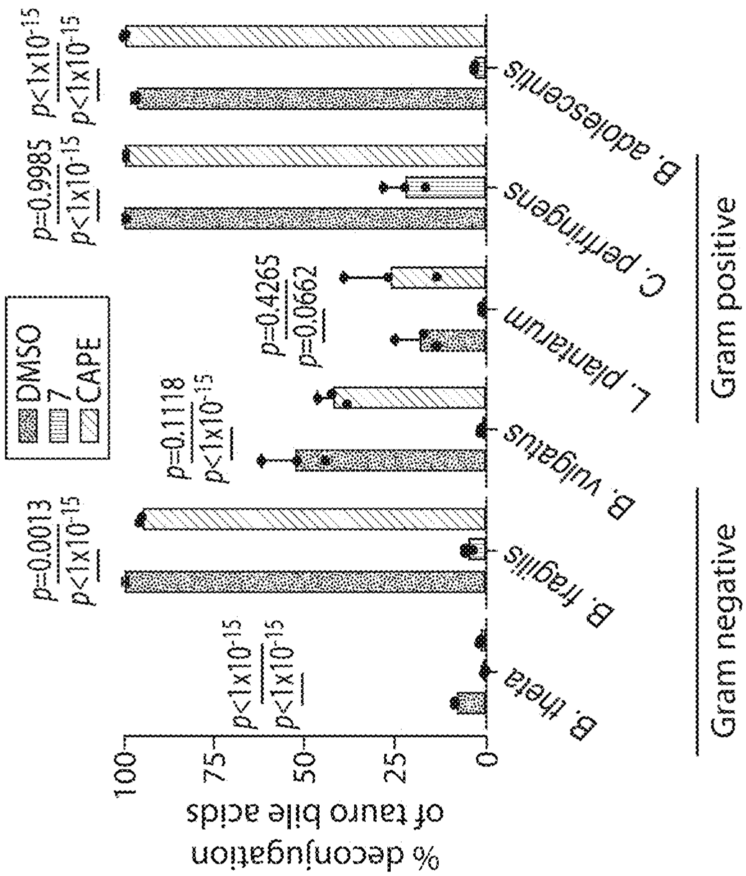
Figure 10B:
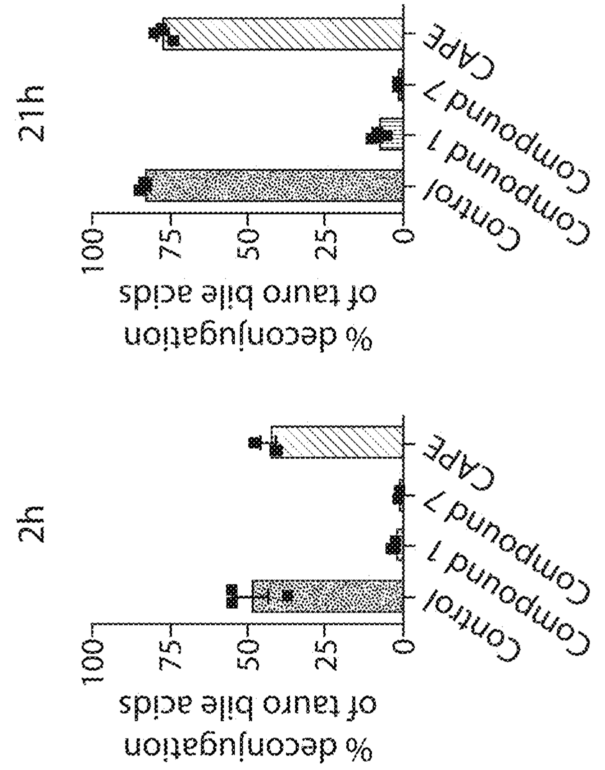
Figure 15B:
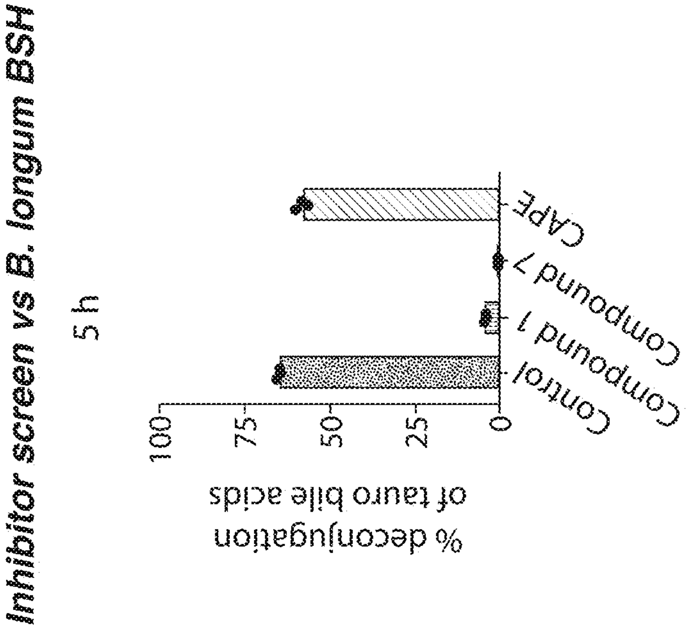
FIG. 15A-B show screen of inhibitors versus *B. theta* BSH (FIG. 15A) and *B. longum* BSH (FIG. 15B) showing % deconjugation of tauro bile acids at 5 hours. Inhibitor (100 μM) was incubated with 200 nM rBSH for 30 mins followed by addition of taurine-conjugated bile acid substrates (tauro-β-muricholic acid, TβMCA; tauro-cholic acid, TCA; tauro-ursodeoxycholic acid, TUDCA; and tauro-deoxycholic acid, TDCA, 25 μM each). Deconjugation of substrate was followed by UPLC-MS. Assays were performed in biological triplicate, and all data are presented as mean±SEM.
Figure 15A:
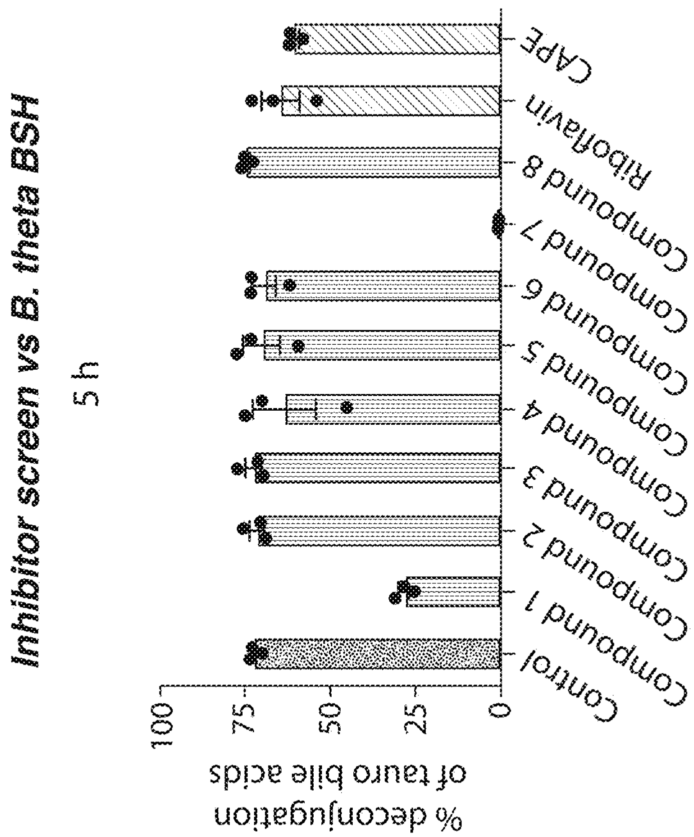
Figure 16A:
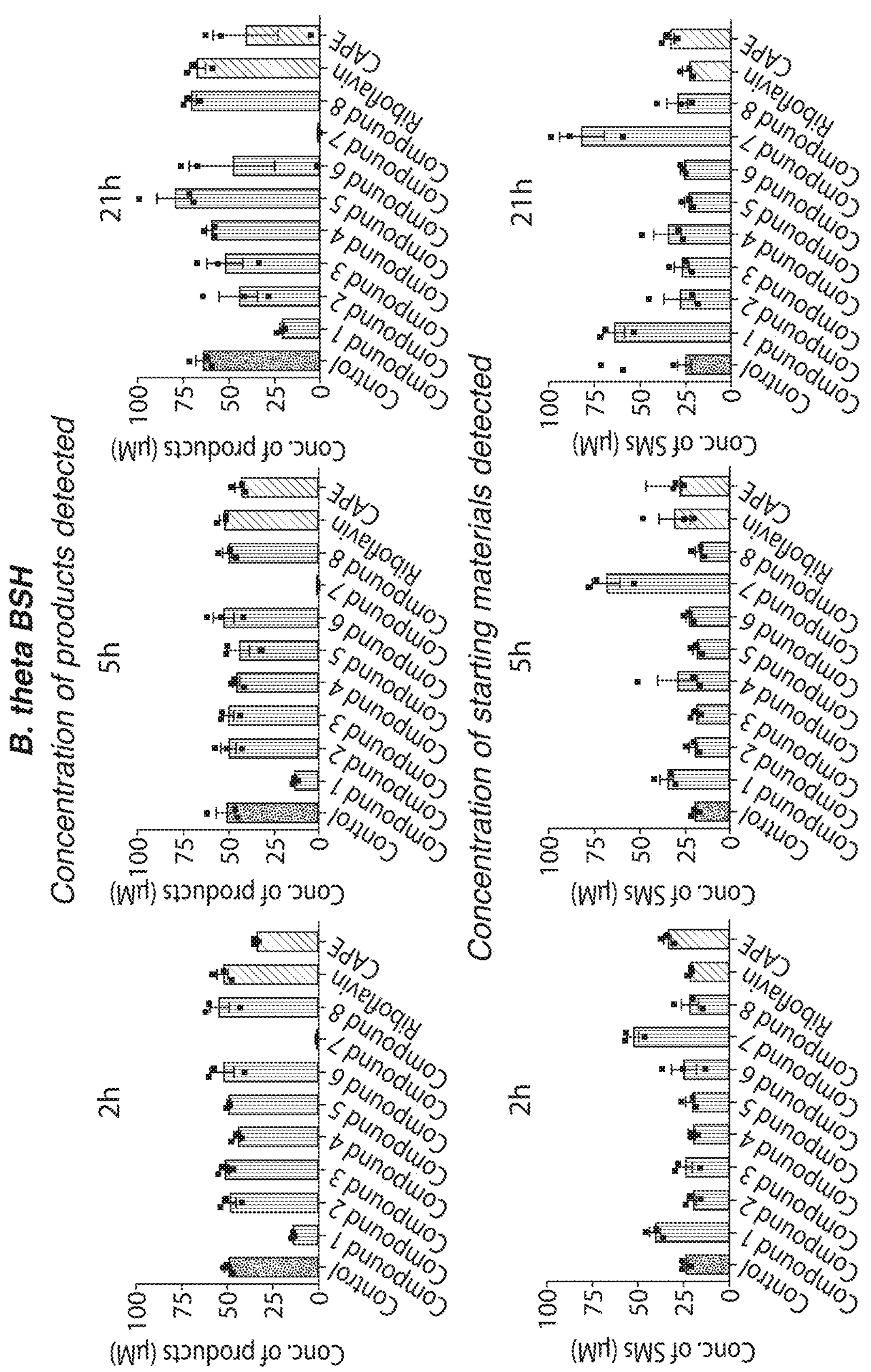
FIG. 16 shows bile acid quantification for reporting % deconjugation, purified BSH proteins. Concentration of products formed (deconjugated bile acids) and unreacted starting materials (SMs) at each time point were determined for both *B. theta* BSH (FIG. 16A) and *B. longum* BSH (FIG. 16B) using UPLC-MS. % deconjugation for each sample was then determined using the following equation: % deconjugation=Concentration of products/(Concentration of products+Concentration of starting materials)*100.
Figure 16B:
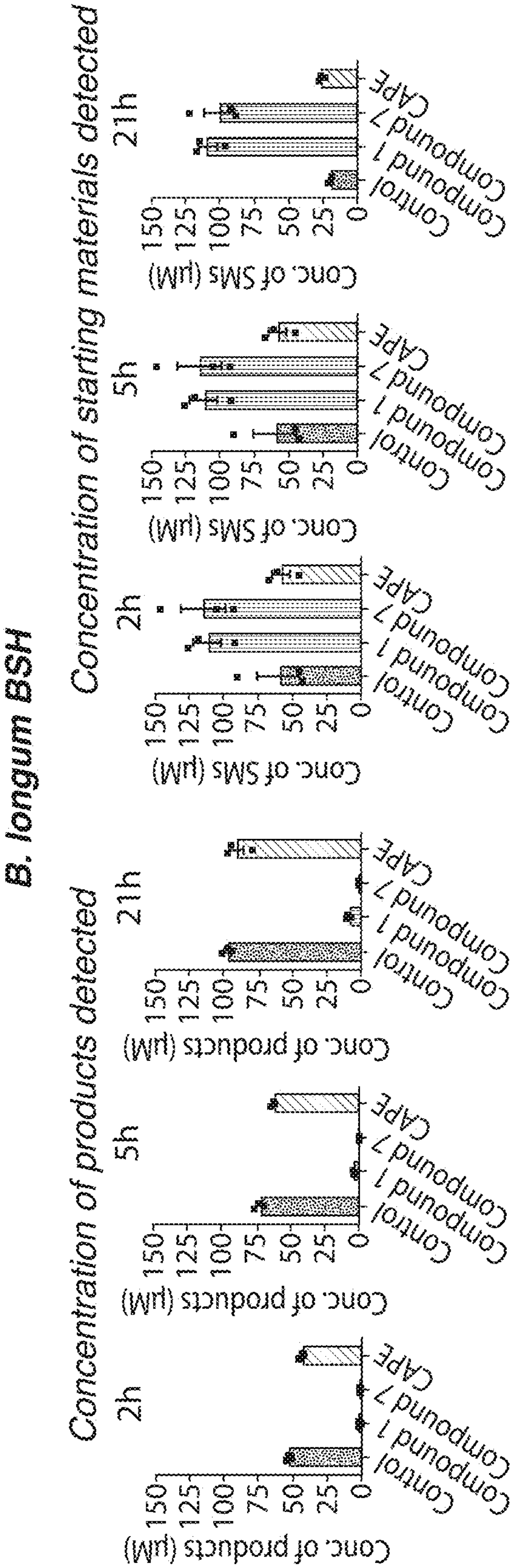
Figure 17A:
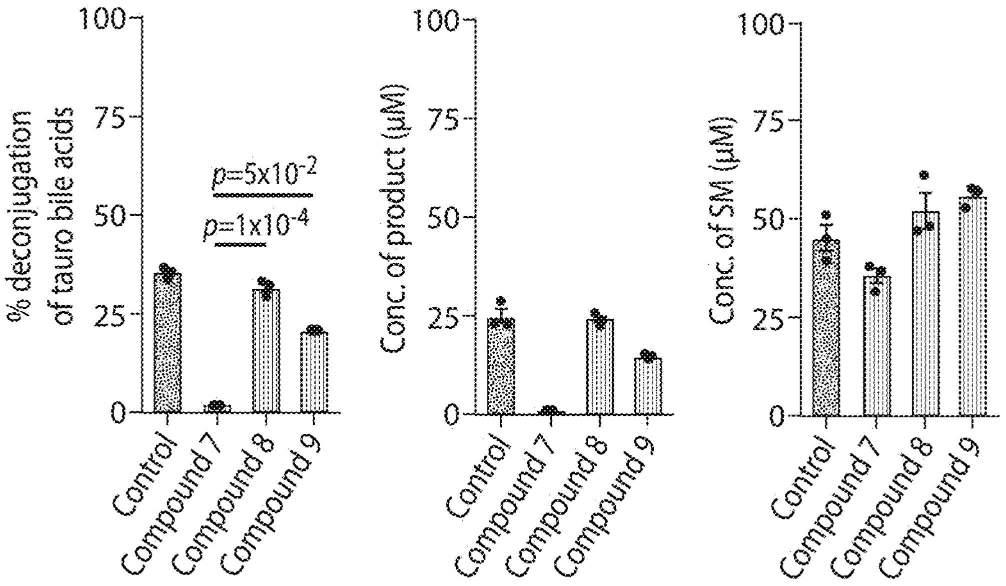
(FIG. 17A) Compounds 8 and 9 are less potent inhibitors of *B. theta* BSH than compound 7. Inhibitor (10 μM of compound 7, 8, or 9) and 100 μM TUDCA were added to *B. theta* cultures at OD 6000.1.
Figure 17B:
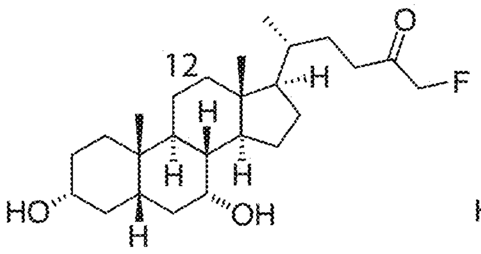
(FIG. 17B) Structural comparison of compounds 7, 8, and 9. Compound 8 lacks the α-FMK warhead, and compound 9 possesses a C12=OH hydroxyl group.
Figure 17B:
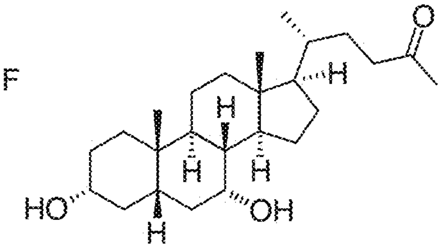
Figure 17B:
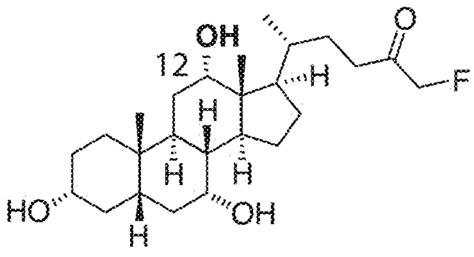
Figure 18A:
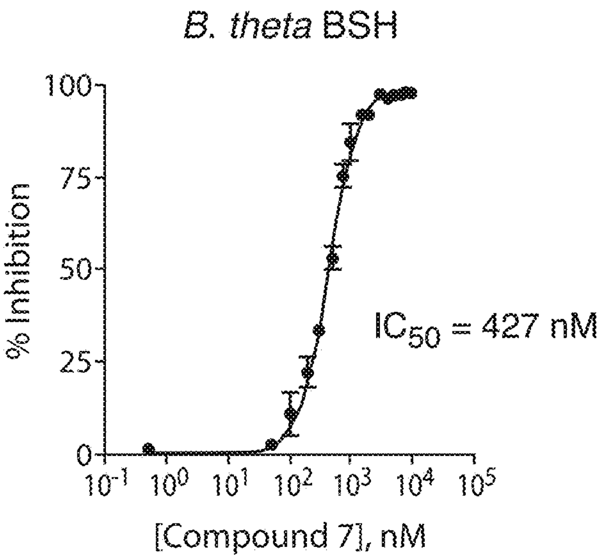
FIG. 18 shows compound 7 is a potent inhibitor of recombinant BSHs. Dose-response curves and calculated IC values for compound 7. 200 nM recombinant *B. theta* BSH (FIG. 18A, Gram negative) or *B. adolescentis* BSH (FIG. 18B, Gram positive) were pre-incubated with varying concentrations of compound 7 for 60 mins followed by the addition of conjugated bile acid substrate TUDCA and TDCA respectively.
Figure 18B:
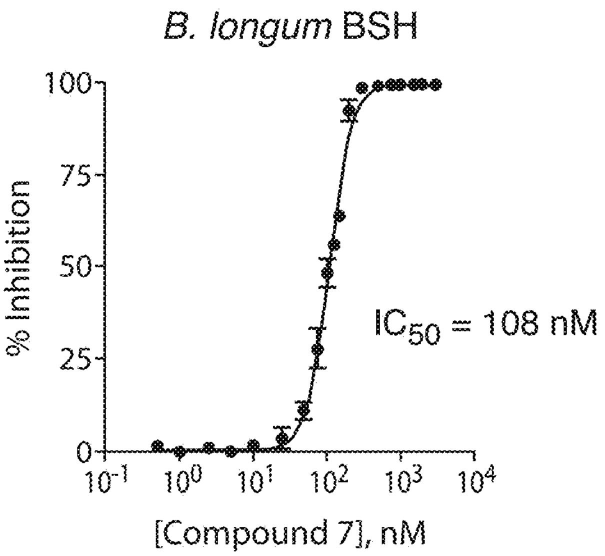

The activity of compounds 1, 7, and CAPE against the BSH from *B. longum* was also evaluated. Compound 7 was again the most active inhibitor, while CAPE was ineffective at inhibiting *B. longum* BSH at all timepoints (FIGS. 10*b*, 15-16, and Table 3). Compound 7 inhibited both *B. theta* and *B. longum* BSHs in a dose-dependent fashion ($IC_{50}$ values of 427 nM and 108 nM respectively, FIG. 18). Taken together, these data indicate that compound 7 is a potent inhibitor of purified BSH protein from both a Gram negative and a Gram positive bacterial strain.

Figure 19A:
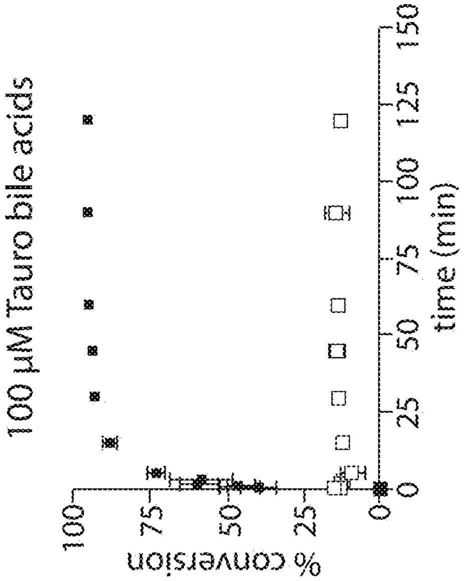
FIG. 19A shows the time required for complete inhibition of *B. theta* BSH. 100 μM compound 7 and conjugated bile acids (25 μM each of tauro-β-muricholic acid, TβMCA.
Figure 19B:
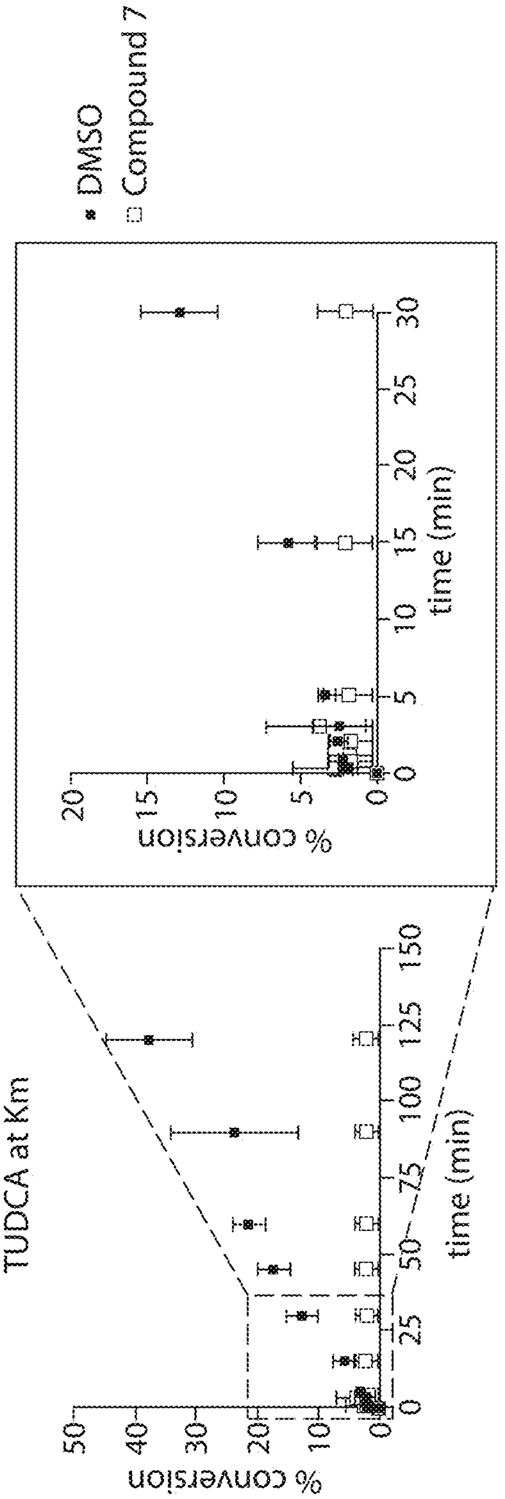
FIG. 19B shows that in the presence of compound 7, no increase in product formation was observed after 15 secs, indicating that enzyme activity was inhibited.

Compound 7 completely inhibited *B. theta* BSH, the more catalytically efficient of the two enzymes (Table 2), within 15 seconds at a concentration equimolar to substrate and without any preincubation of inhibitor with enzyme (FIG. 19). In the presence of a large excess (~80-fold) of substrate, 7 entirely inhibited *B. theta* BSH activity within 15 minutes, the earliest measurable timepoint for product formation under these conditions. These results indicate that 7 is a kinetically efficient inhibitor of BSH activity.

Example 4. Compound 7 Inhibits BSHs in Gut Bacterial Cultures

The potency of 7 in growing bacterial cultures was also evaluated. To test the scope of BSH inhibition, three Gram negative and three Gram positive strains of BSH-containing human gut bacteria (Gram negative, *B. theta, Bacteroides fragilis* ATCC 25285, and *Bacteroides* vulgatus ATCC 8482; Gram positive, *Lactobacillus plantarum* WCFS1,

*Clostridium perfringens* ATCC 13124, and *Bifidobacterium adolescentis* L2-32) were used.[1,16]

Figure 20A:
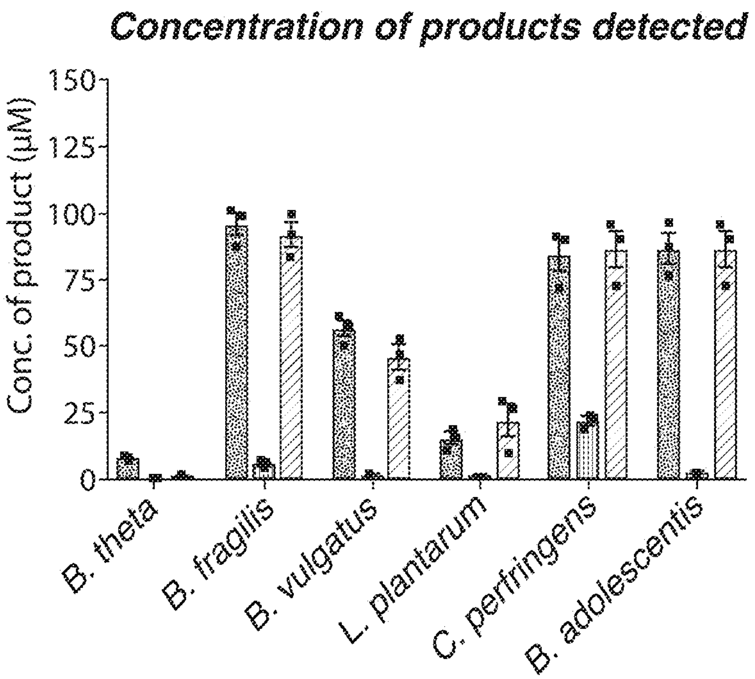
FIG. 20 shows bile acid quantification for reporting % deconjugation, bacterial cultures. Concentration of products formed (deconjugated bile acids) (FIG. 20A) and unreacted starting materials (SMs) (FIG. 20B) in each culture were determined using UPLC-MS. % deconjugation for each sample was then determined using the following equation: % deconjugation=Concentration of products/(Concentration of products+Concentration of starting materials)*100.
Figure 20B:
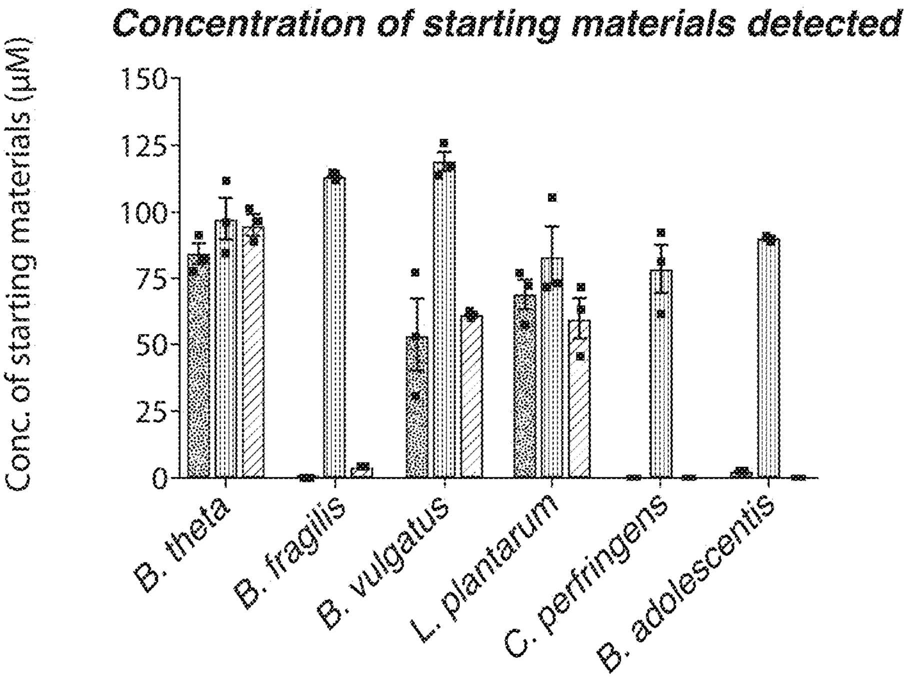
Figure 22A:
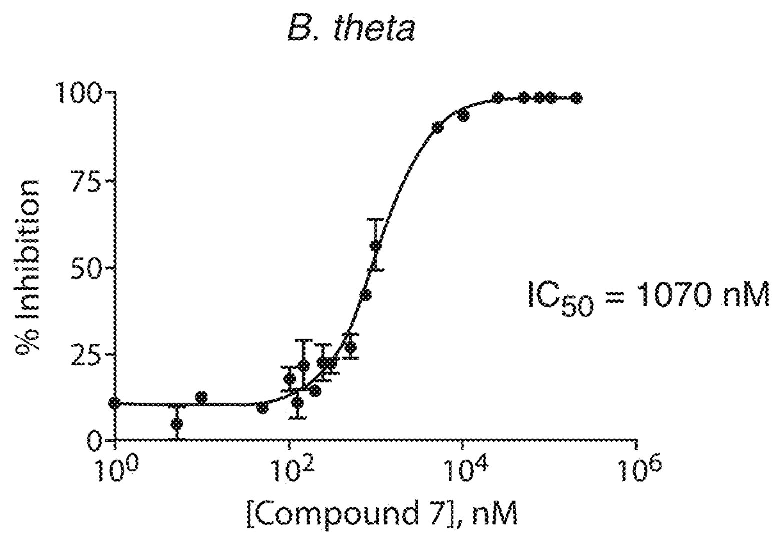
FIG. 22 shows compound 7 is a potent BSH inhibitor in growing bacterial cultures. Dose-response curves and calculated IC values for compound 7. Pre-log phase cultures of *B. theta* (FIG. 22A, Gram negative) and *B. adolescentis* (FIG. 22B, Gram positive) were incubated with conjugated substrate (TUDCA or TDCA) and allowed to grow anaerobically for 48 h and 24 h, respectively.
Figure 22B:
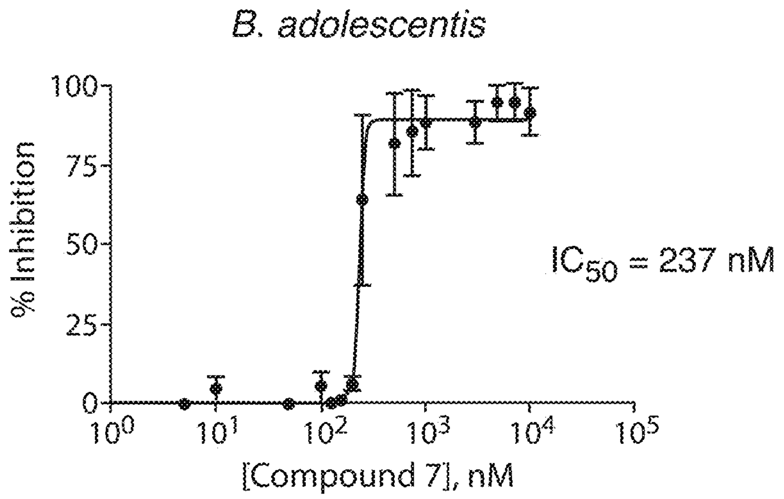

Bacterial cultures were diluted to pre-log phase and both inhibitor (100 μM) and a mixture of conjugated bile acids (100 μM final concentration) were added simultaneously. Deconjugation was monitored over 21 hours using UPLC-MS. Strikingly, while all six bacterial strains deconjugated bile acids in the presence of vehicle control, almost no deconjugation in any of the cultures grown in the presence of 7 was observed (FIG. 10*c*, 20, and Table 3). An isogenic BSH-deleted *B. theta* strain[16] was then incubated with either DMSO, 7, or CAPE. Under all three conditions, taurine-conjugated bile acids were recovered unmetabolized (FIG. 21). These results suggest that BSH inhibition by 7 is not due to the effects of this inhibitor on other bile acid-utilizing processes. Compound 7 did not significantly affect the cell viability of the majority of the tested strains (FIG. 10*d*), indicating that the BSH inhibition observed was not due to bactericidal activity. The $IC_{50}$ values of this inhibitor against *B. theta* and *B. adolescentis* were determined to be 1070 nM and 237 nM, respectively (FIG. 22). These results indicate that 7 is a potent, broad-spectrum inhibitor of BSHs.

Figure 10E:
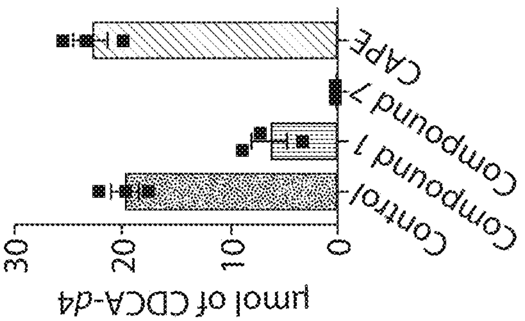
Figure 10D:
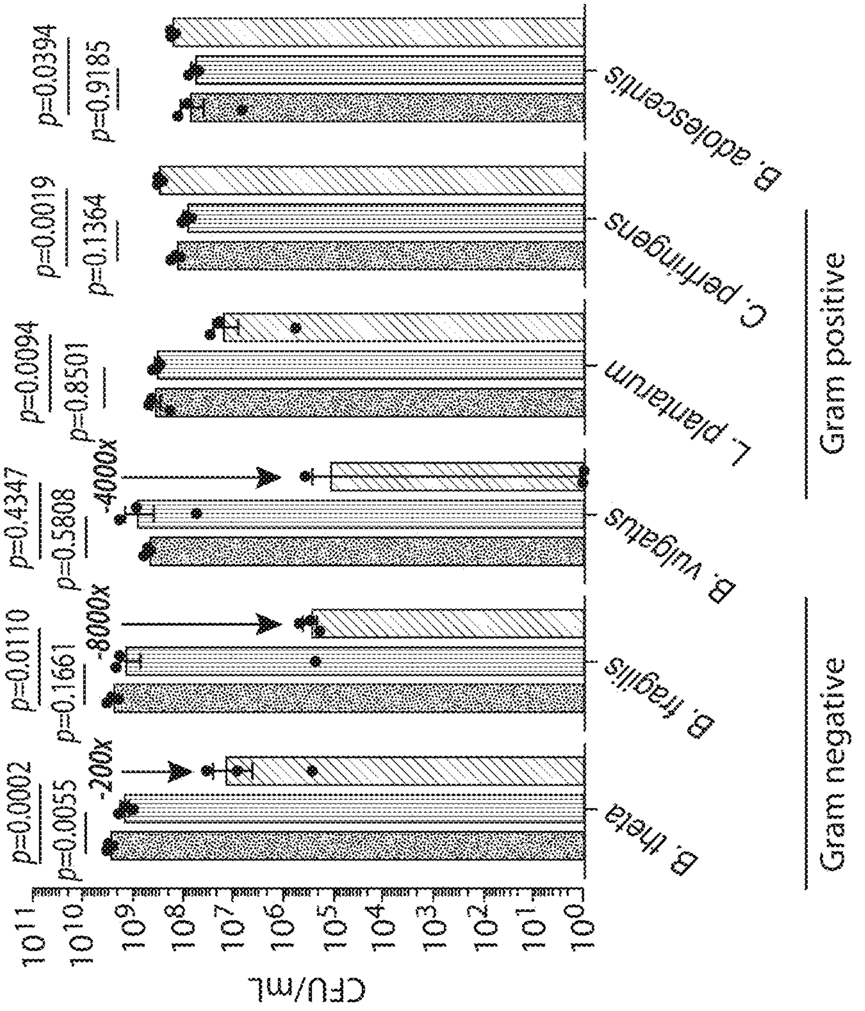

No BSH inhibition in five out of the six bacterial strains grown in the presence of CAPE (FIG. 10*c*) was observed. Moreover, CAPE inhibited the cell viability of all three Gram negative bacterial strains tested (FIG. 10*d*). These results suggest that the dominant effect of CAPE on Gram negative bacteria is not inhibition of BSH activity but rather inhibition of growth.

Figure 9D:
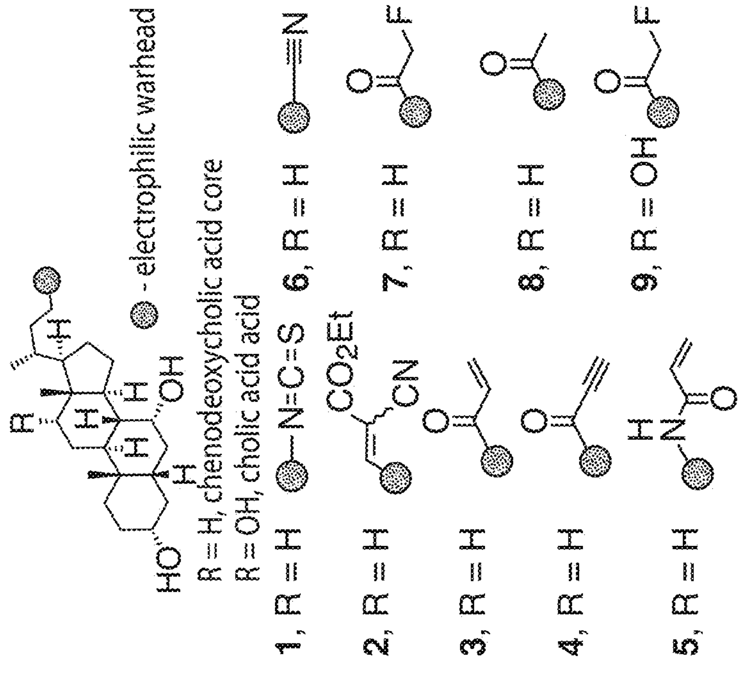
FIG. 9D shows compounds of the disclosure.

Finally, to evaluate whether C12=OH compounds would not be effective broad-spectrum inhibitors, a compound with an appended α-FMK warhead to a C12=OH bile acid core, cholic acid was synthesized (compound 9, FIG. 9*d*). Compound 9 displayed significantly reduced ability to inhibit BSH deconjugation in *B. theta* cultures compared to 7 (FIG. 17). Thus, the bile acid core structure, specifically C12 substitution, affects the ability of our probes to selectively inhibit BSH. In addition, these results show that the α-FMK warhead is not broadly reactive but rather requires suitable positioning within the active site.

Example 5. Compound 7 Inhibits BSH Activity in Mouse Feces

The previous literature had reported significant BSH activity in mouse feces.[32] To further assess whether 7 is a pan-inhibitor of BSH, its activity in resuspended feces from conventional mice was tested. This fecal slurry should contain BSHs from nearly the entire bacterial community of the distal colon. Compounds 1, 7, and CAPE (20 PM) were added to a fecal suspension in buffer. After 30 minutes, the deuterated substrate glycochenodeoxycholic acid-d4 (GCDCA-d4) was added, and formation of deconjugated product was quantified after 18 hours using UPLC-MS. Strikingly, incubation with 7 completely inhibited BSH activity in feces (FIG. 10*e*). CAPE provided no inhibition of BSH activity in feces. These results demonstrate that 7 is a potent pan-inhibitor of BSH activity.

Example 6. Compound 7 Covalently Modifies Catalytic Cys2 Residue

Figure 23A:
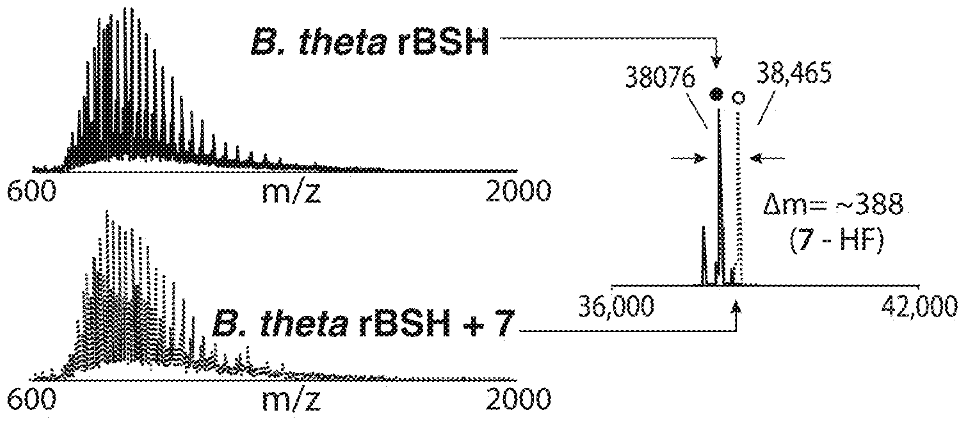
(FIG. 23A) Mass spectra (left) and zero-charge mass spectra (right) of BSH treated with DMSO (top, trace in red) or 10-fold excess of compound 7 for 2 h (bottom, trace in green). A shift in mass of 388 Da is consistent with covalent modification of BSH with a loss of HF. Two independent labeling reactions yielded similar results.
Figure 23B:
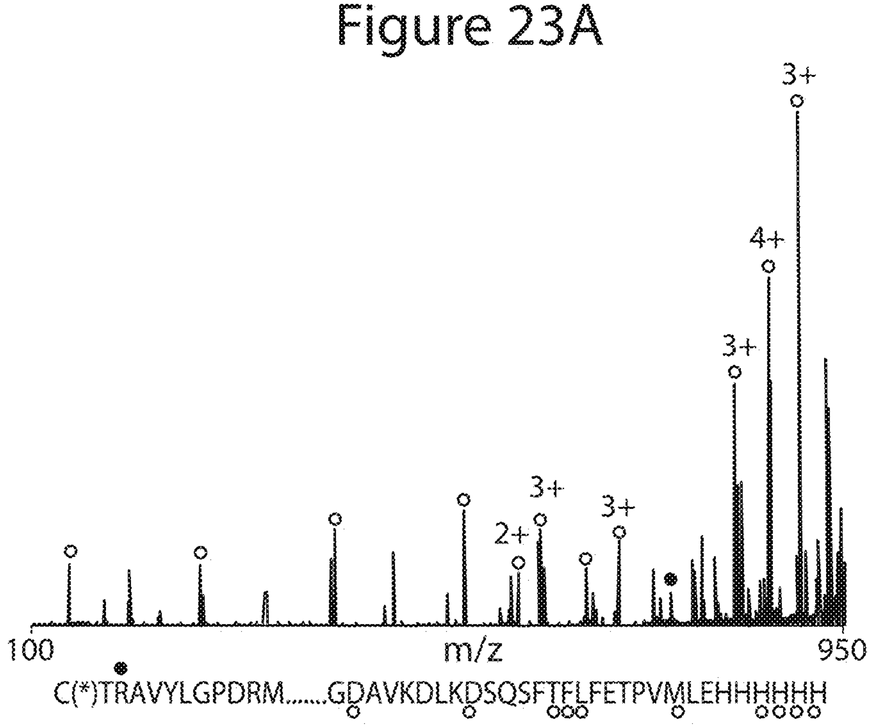
(FIG. 23B) Top-down MS/MS of BSH treated with 10 fold excess of compound 7. Ions of type c and z are indicated with red and green glyphs respectively. Ion c3 indicates that modification is on the N-terminus Cys2 residue.

The mechanism of inhibition of 7. The *B. theta* BSH contains two cysteine residues, Cys2 and Cys67 was also investigated. Analysis of an apo crystal structure of this enzyme revealed that both the cysteine residues are pointed towards the active site (PDB 3HBC). To confirm that 7 is a covalent inhibitor that modifies Cys2, purified *B. theta* BSH was incubated with an excess of this molecule. Analysis by mass spectrometry revealed a mass shift consistent with the addition of a single molecule of 7, confirming formation of a covalent bond (FIG. 23). Subsequent top-down mass spectrometry analysis identified Cys2 as the modified residue (FIG. 23).

The structure of the *B. theta* BSH, first in its apo form to 2.7 Å resolution and then covalently bound to 7 to 3.5 Å resolution was then determined (Table 5) (PDB 6UFY and 6UH4, respectively).

TABLE 5

Data collection and refinement statistics (molecular replacement)

| | BSH | BSH-Compound |
|---|---|---|
| Data collection | | |
| Space group | $P\,2_1\,2_1\,2_1$ | $P\,2_1\,2_1\,2$ |
| Cell dimensions | | |
| a, b, c (Å) | 84.88, 92.32, 194.25 | 98.58, 99.52, 162.12 |
| α, β, γ (°) | 90, 90, 90 | 90, 90, 90 |
| Resolution (Å) | 46.16-2.70 (2.80- 2.70)* | 47.57-3.50 (3.63-3.50) |
| $R_{merge}$ | 0.3686 (2.097) | 0.1394 (1.989) |
| I / σI | 4.28 (0.93) | 7.84 (0.86) |
| Completeness (%) | 91.08 (92.25) | 97.00 (95.32) |
| Redundancy | 4.6 (4.6) | 5.0 (5.2) |
| Refinement | | |
| Resolution (Å) | 46.16-2.70 | 47.57-3.50 |
| No. reflections | 38657 | 20032 |
| $R_{work}$ / $R_{free}$ | 0.2561 / 0.2982 | 0.2436 / 0.2932 |
| No. atoms | 10561 | 10249 |
| Protein | 10319 | 10221 |
| Ligand/ion | — | 28 |
| Water | 242 | — |
| B-factors | 34.45 | 187.80 |
| Protein | 34.56 | 187.69 |
| Ligand/ion | — | 230.31 |
| Water | 29.96 | — |
| R.m.s. deviations | | |
| Bond lengths (Å) | 0.002 | 0.002 |
| Bond angles (°) | 0.51 | 0.46 |

*Highest-resolution shell is shown in parentheses.
Each data set was collected using a single crystal.

Figure 24A:
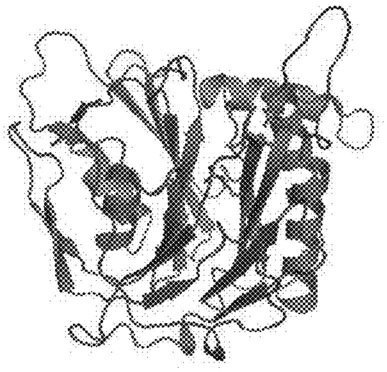
FIG. 24 shows Apo and co-crystal structures of *B. theta* BSH. X-ray structure of *B. theta* BSH apoprotein (FIG. 24A) superimposed on the X-ray structure of *B. theta* BSH covalently bound to compound 7 (FIG. 24B). The BSHs (apo in magenta, co-crystal structure in cyan) are shown in ribbon representation, with indicated side chains (magenta or cyan, respectively, with heteroatoms in CPK colors) rendered as sticks. Compound 7 (green, with heteroatoms in CPK colors) is rendered in stick form. Box (dashed lines) indicates loop (residues 127-138) that has repositioned in the co-crystal structure. Panels were prepared using PYMOL software (Schroedinger).
Figure 24B:
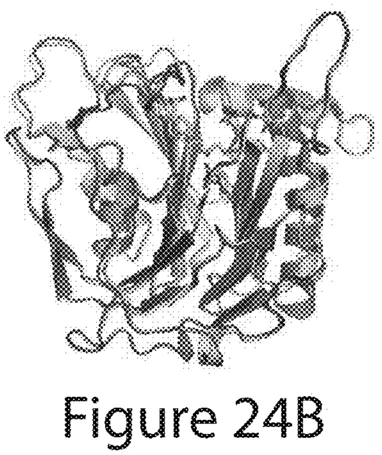
Figure 25A:
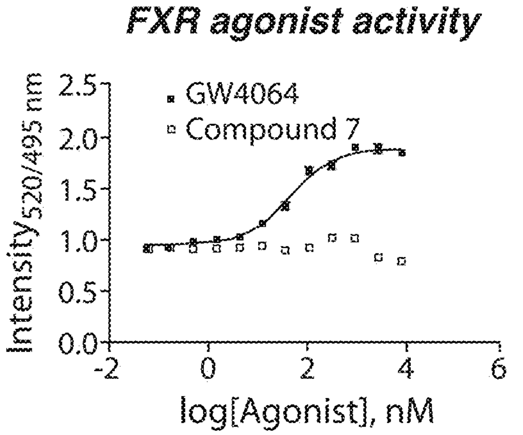
(FIG. 25A) Compound 7 is not an farnesoid X receptor (FXR) agonist as determined by an FXR coactivator recruitment assay. n=4 biological replicates per concentration.
Figure 25B:
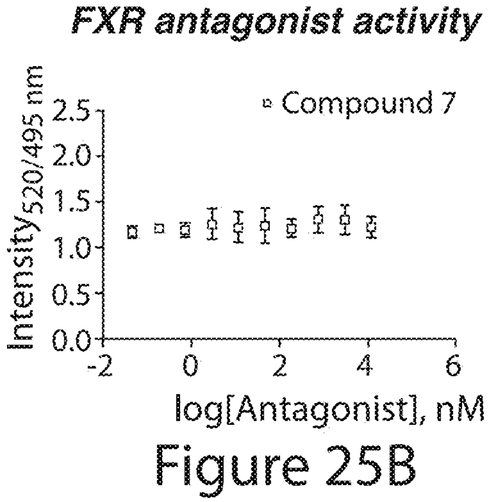
(FIG. 25B) FXR antagonist activity of compound 7 was evaluated in the presence of FXR agonist GW4064 at its EC50 value (50 nM, as determined in the corresponding agonist assay). n=4 biological replicates per concentration.
Figure 25C:
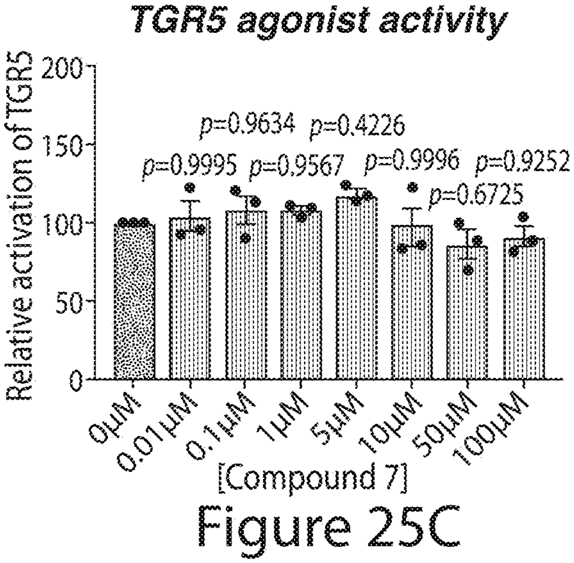
(FIG. 25C) Compound 7 is not a G protein-coupled bile acid receptor (GPBAR1/TGR5) agonist. Endogenous TGR5 agonist activity was measured by incubating Caco-2 cells with varying concentrations of 7 overnight. n=3 biological replicates per concentration, one-way ANOVA followed by Dunnett's multiple comparisons test.
Figure 25D:
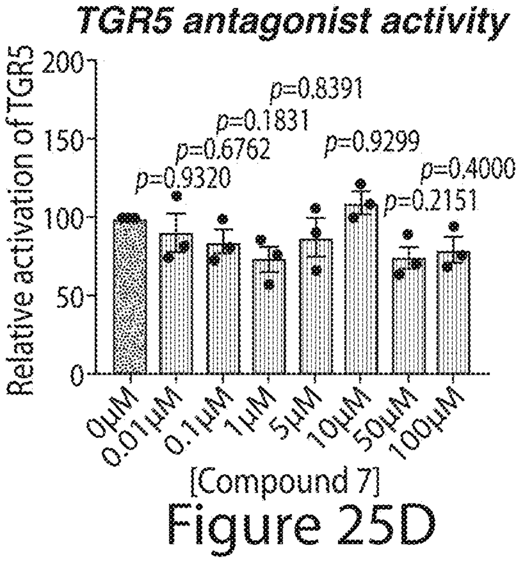
(FIG. 25D) Endogenous TGR5 antagonist activity was measured by incubating Caco-2 cells with varying concentrations of compound 7 overnight in the presence of 10 μM of the TGR5 agonist LCA. n=3 biological replicates per concentration, one-way ANOVA followed by Dunnett's multiple comparisons test.
Figure 25E:
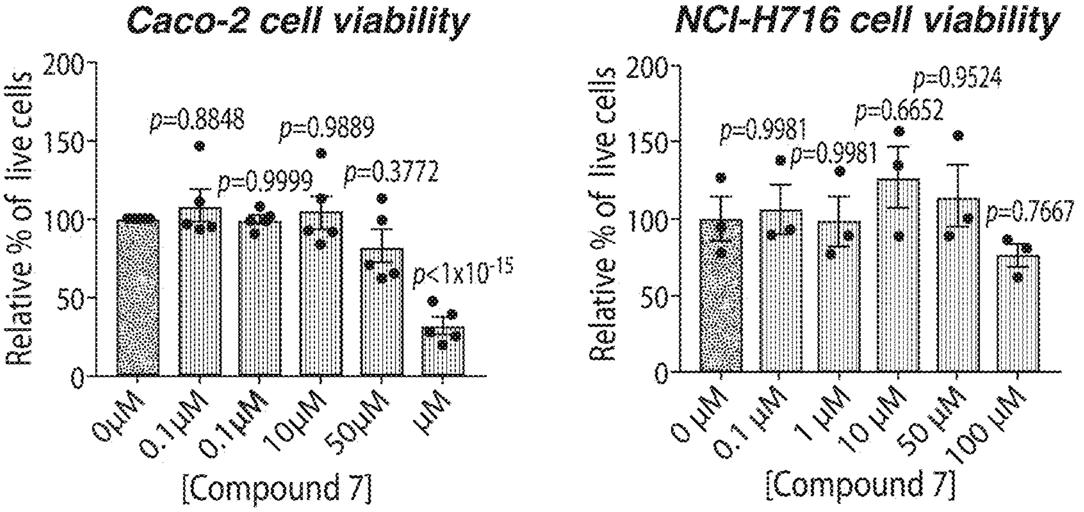
(FIG. 25E) Compound 7 did not display toxicity toward Caco-2 or NCI-H716 cells at concentrations up to 50 μM and 100 μM, respectively. n=5 and n=3 biological replicates per concentration, respectively, one-way ANOVA followed by Dunnett's multiple comparisons test. All data are presented as mean±SEM.

The structure of the BSH-inhibitor complex contains four copies of the protein in the asymmetric unit. The electron density map is best resolved in two of the four subunits, and electron density is clearly visible for the inhibitor in one of these subunits covalently attached to Cys2 (FIG. 3*a* and FIG. 3*b*). Comparison with the apo structure also suggests that there is a loop (residues 127-138) which repositions to clasp the inhibitor in the active site in a solvent-exposed channel (FIG. 24).

Figure 11A:
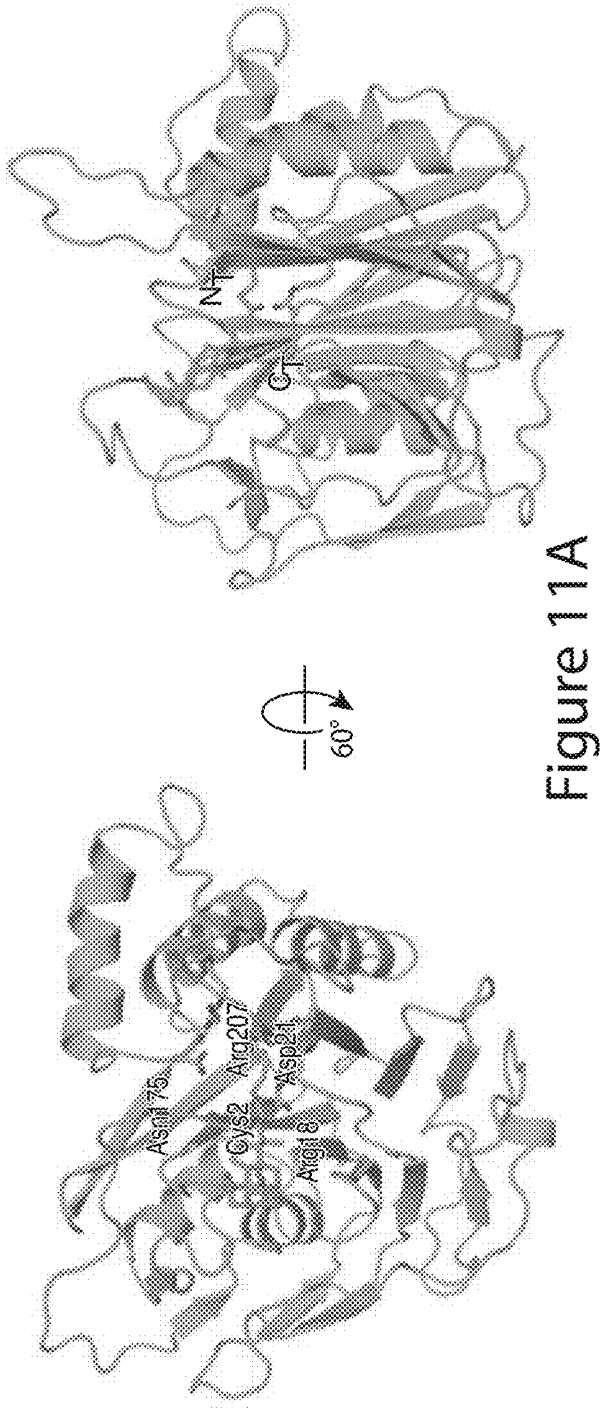
FIG. 11A shows X-ray structure of compound 7 bound to *B. theta* BSH. The BSH (cyan) is shown in ribbon representation, with indicated side chains (cyan, with heteroatoms in CPK colors) rendered as sticks.
Figure 11B:
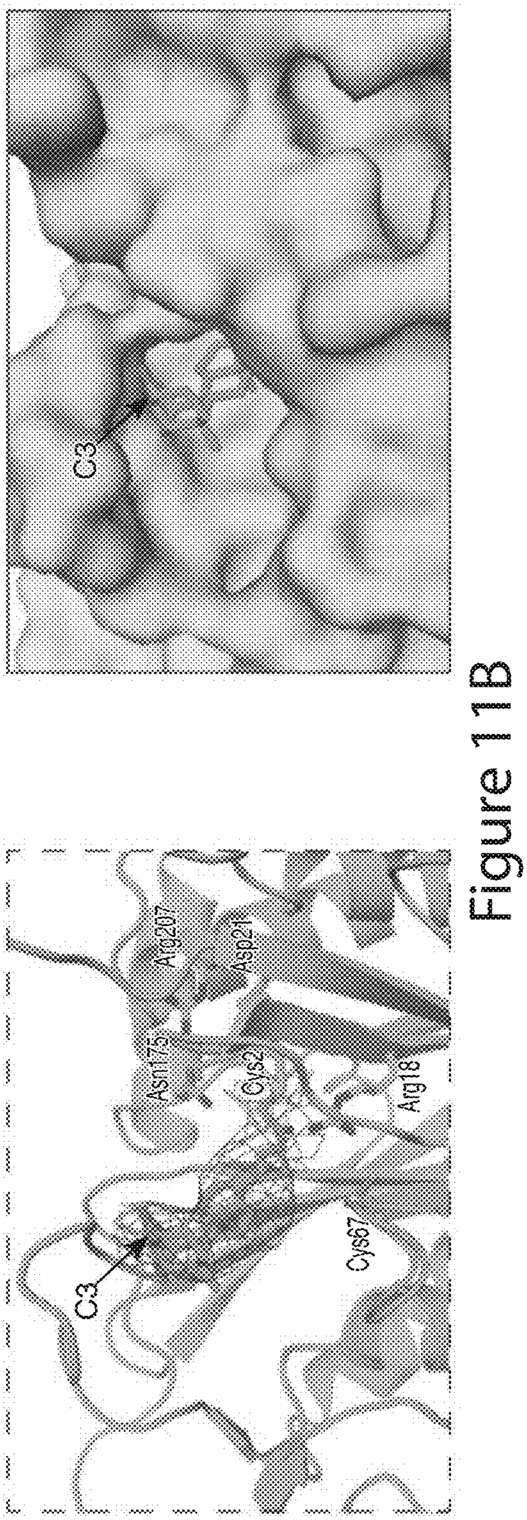
FIG. 11B shows a co-crystal structure of *B. theta* BSH and compound 7 shown in ribbon (left, with electron density of the compound shown as a blue net) and surface (right) representations. The A ring of 7, which includes the C3 hydroxyl group, is solvent-exposed. Panels a and b were prepared using PYMOL software (Schrödinger).

These data indicate that 7 selectively labels the *B. theta* BSH at Cys2. Furthermore, the co-crystal structure reveals that the C3-hydroxyl group is solvent-accessible, suggesting that this site might be amenable to further modification (FIG. 11*b*).

Example 7. Compound 7 Displays Minimal Off-Target Effects

Concerns have been raised that non-specific reactivity of covalent inhibitors could result in acute toxicity.[11] Bile acids are ligands for the farnesoid X receptor (FXR) and the G protein-coupled bile acid receptor 1 (TGR5).[2] An in vitro coactivator recruitment assay showed that 7 is neither an agonist nor an antagonist for FXR at physiologically relevant concentrations (FIG. 25).[31] Next, the effect of Compound 7 on TGR5 activation was evaluated in a human intestinal cell line (Caco-2). Compound 7 neither agonized nor antagonized TGR5 over the range of concentrations tested (FIG. 25). These results suggest that 7 does not induce off-target effects on either of these critical host receptors.

Figure 26:
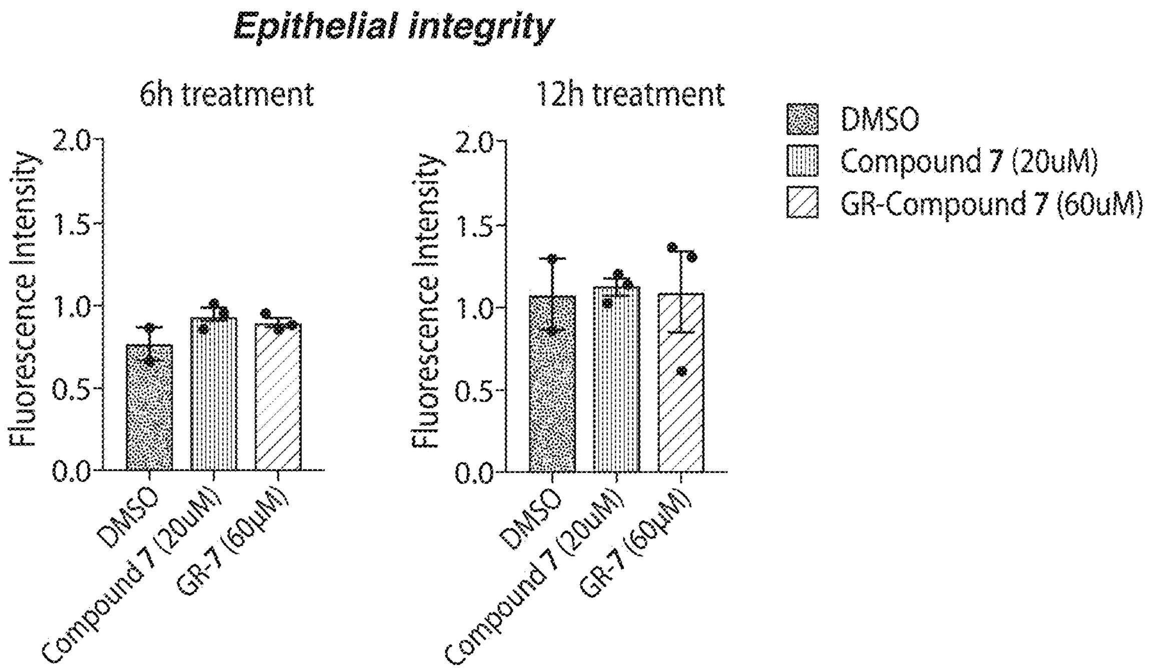
FIG. 26 shows neither compound 7 nor GR-7 significantly affected epithelial barrier integrity. Incubation of compound 7 or GR-7 with differentiated Caco-2 cells for 6 hours and 12 hours did not compromise epithelial monolayer integrity as measured by passive transport of 4 kDa FITC-dextran. n=2 biological replicates for DMSO control, n=3 biological replicates for inhibitor-treated conditions. All data are presented as mean±SEM
Figure 27A:
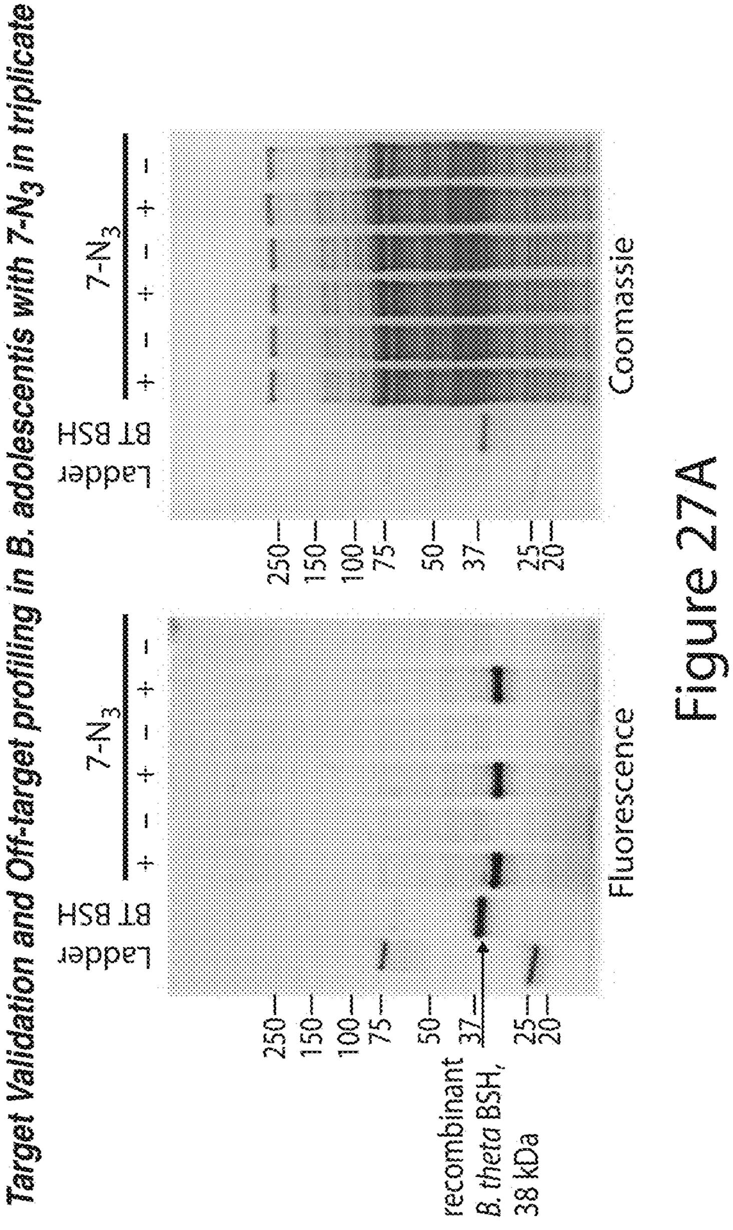
FIG. 27A shows compound 7-N labels *B. adolescentis* BSH with minimal off-target reactivity.
Figure 27B:
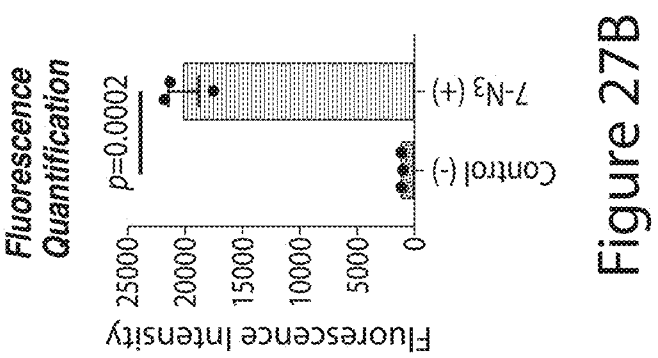
FIG. 27B shows fluorescence intensity of BSH bands were quantified. Two-tailed Student's t test. Data are presented as mean±SEM.
Figure 27C:
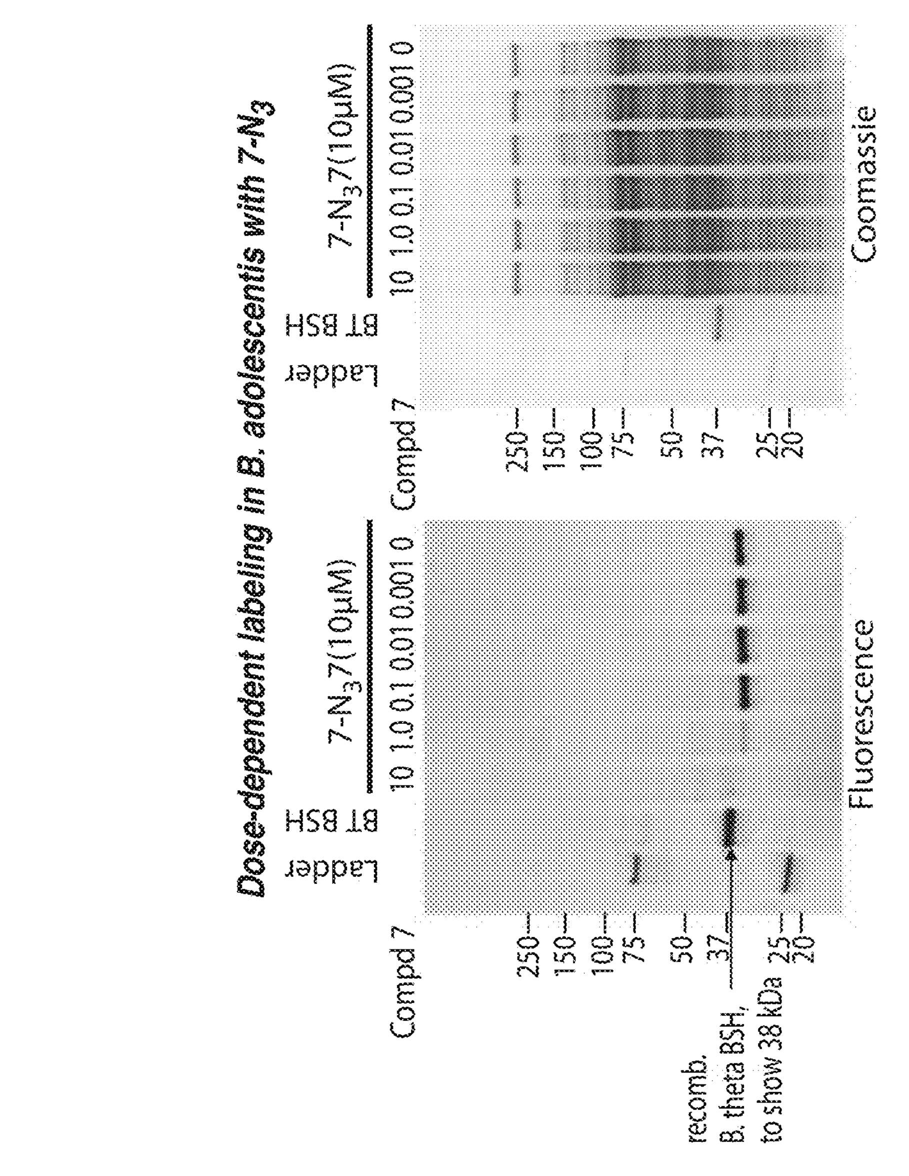
FIG. 27C shows full SDS-PAGE gel for the experiment described in FIG. 4H. *B. adolescentis* cultures were treated with decreasing concentrations of compound 7 for 1 hour and then treated with 10 μM compound 7-N for an additional hour. Dose-dependent labeling of BSH was observed with decreasing concentrations of compound 7. Experiment was repeated twice with similar results.
Figure 27D:
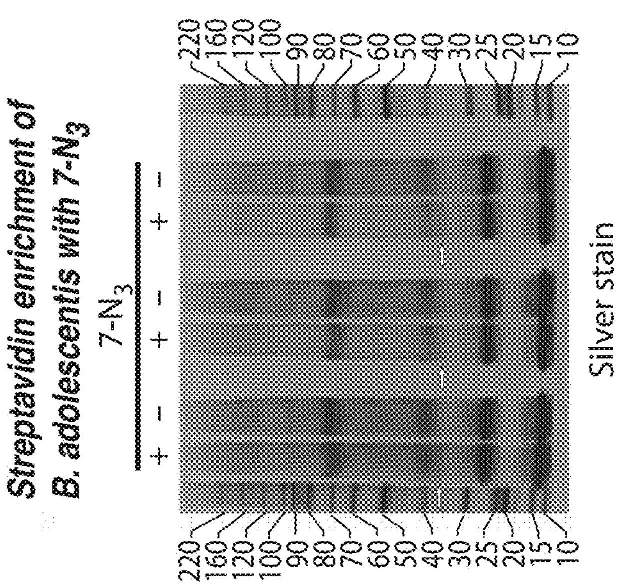
FIG. 27D shows silver stained gel for the experiment described in FIG. 4G performed in biological triplicate.

Bile acids are also known to be toxic due to their detergent properties.[1,33] The toxicity of this compound against human intestinal cells (Caco-2 and NCI-H716) was also tested. No resultant toxicity was observed when these cells were incubated with up to 50 μM or 100 μM of compound 7, respectively (FIG. 25). Because the $IC_{50}$ values of 7 range from 237 to 1070 nM, these results suggest that it should be possible to achieve an effective, non-toxic in vivo dose. To test the effect of compound 7 on epithelial integrity, Caco-2 cells were differentiated in transwell inserts into a polarized monolayer with tight intercellular junctions.[34] Compound 7 was incubated in the apical chamber of the transwells, and epithelial integrity was measured by passive diffusion of 4 kDa FITC-dextran. No significant increase in fluorescence was observed in 7-treated cells compared to control-treated cells, indicating that 7 did not compromise epithelial monolayer integrity (FIG. 26).

Figure 12A:
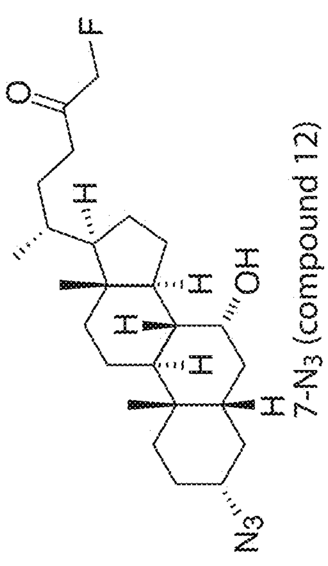
FIG. 12A shows structure of 'clickable' 7, 7-N3 (12), for on- and off-target studies.
Figure 12B:
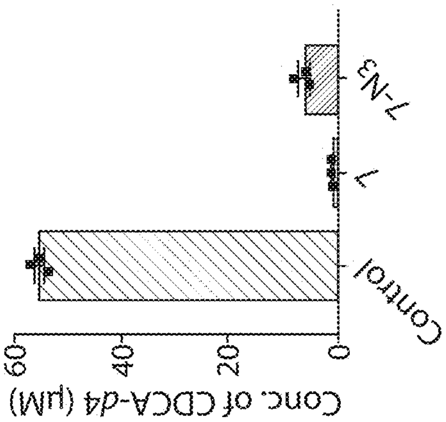
FIG. 12B shows 7-$N_3$ displayed significant BSH inhibition in conventional mouse feces, showing that this probe retained its function as a BSH inhibitor.
Figure 12C:
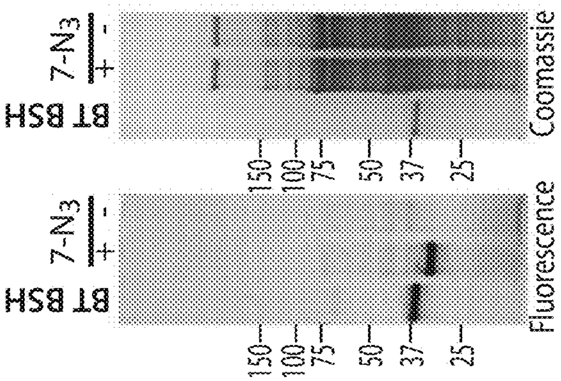
FIG. 12C shows treatment of *B. adolescentis* L-32 culture with 7-N3 for 1 hour followed by cell lysis, click reaction with Fluor 488-alkyne, and visualization using in-gel fluorescence revealed labeling of only one protein ~35 kDa in size, the mass of the annotated *B. adolescentis* BSH.
Figure 12F:
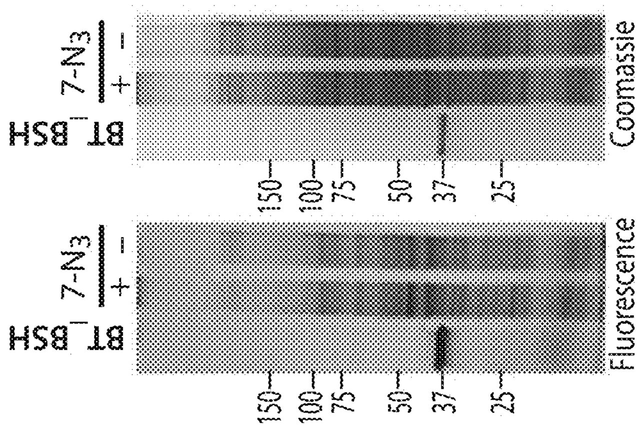
FIG. 12F shows one-hour treatment of NCI-H716 intestinal cells with 7-N3 followed by click reaction with Fluor 488-alkyne and visualization by in-gel fluorescence resulted in no significant labeling of proteins compared to control-treated cells. For (FIGS. 12B, 12C, 12D, and 12F), n=3 biological replicates per condition. For (FIG. 12B), data is presented as mean±SEM.
Figure 12E:
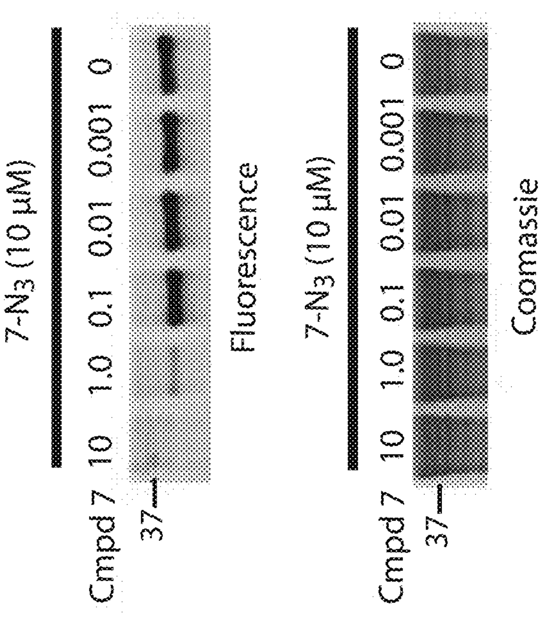
FIG. 12E shows the treatment of *B. adolescentis* cultures with decreasing concentrations of compound 7 followed by treatment with 10 QM 7-N3 and click reaction with Fluor 488-alkyne resulted in a dose-dependent increase in fluorescence labeling of annotated *B. adolescentis* BSH.
Figure 12D:
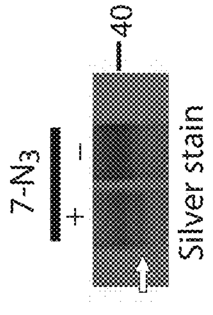
FIG. 12D shows lysate from the treatment of *B. adolescentis* cultures with 7-$N_3$ was reacted with desthiobiotin-alkyne, resolved by SDS-PAGE, and visualized by silver-staining. Arrow indicates a band in the probe-treated sample at the predicted molecular weight (~35 kDa) of BSH.

It is important to understand the proteome-wide reactivity of 7.35 To assess target engagement and off-target interactions of compound 7, a 'clickable' version of this inhibitor was synthesized by appending an α-azido moiety[36] to 7 at the solvent-exposed C3 position to generate 7-$N_3$ (compound 12, FIG. 26*a*). Like 7, 7-$N_3$ potently inhibited BSH activity in mouse feces (FIG. 26*b*). These results demonstrate that azide substitution did not significantly perturb the BSH inhibitory activity of this molecule. To study on- and off-target effects in bacterial cells, cultures of *B. adolescentis* L2-32 were treated for 1 hour with 10 μM of 7-$N_3$, a concentration at which 7 inhibited BSHs in bacterial culture (FIG. 17). Lysed bacterial supernatants were then reacted with Fluor 488-alkyne under copper catalyzed azide-alkyne cycloaddition conditions, and proteins were visualized by in-gel fluorescence. Only one fluorescent band was visible at a mass of ~35 kDa, the predicted mass of the annotated *B. adolescentis* BSH (FIGS. 12*c* and 27). To identify this protein, be clarified lysate was clicked with desthiobiotin-alkyne and performed streptavidin pulldown. Bound proteins from control and treated samples were resolved by SDS-PAGE and visualized by silver-staining (FIGS. 12*d* and 27). A single silver-stained band at the predicted molecular weight (~35 kDa) of BSH was observed. This band along with the corresponding region of the control lane was excised, digested both with trypsin, and performed LC-MS/MS. BSH was identified in the gel bands with high confidence, and a semi-quantitative analysis of these data indicated a 4.5-fold enrichment in 7-$N_3$-versus vehicle-treated bacterial cultures.

To assess off-target binding across the bacterial proteome, streptavidin bead-bound proteins isolated from treated and control bacterial cultures was digested. Label-free LC-MS/MS analysis identified BSH as 3.6-fold enriched in probe-treated cultures. No other proteins exceeded a 2-fold enrichment threshold across biological triplicate experiments. Competition of 7 with 7-$N_3$ showed dose-dependent labeling of the annotated *B. adolescentis* BSH (FIGS. 12*e* and 27), further confirming on-target activity of 7.

Figure 28:
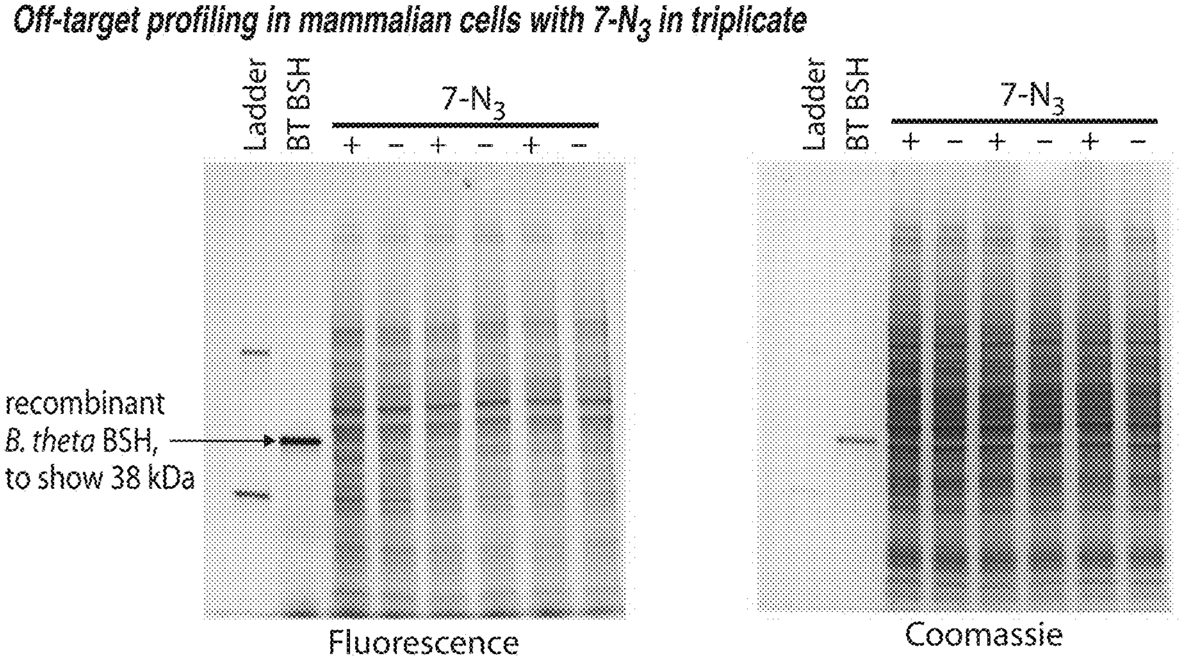
FIG. 28 shows 7-$N_3$ displayed minimal off-target labeling in mammalian cells. SDS-PAGE gel for the experiment described in FIG. 4I performed in biological triplicate (i.e., treatment of NCI-H716 cells with 10 μM 7-N3 for 1 hour followed by click reaction with Fluor 488-alkyne).

The off-target effects of compound 7 in mammalian intestinal cells (NCI-H716) were profiled. These cells were also treated with 7-$N_3$ and processed in the same manner as the bacterial cells. Click reaction with Fluor 488-alkyne showed no enrichment of any band by in-gel fluorescence (FIGS. 12*f* and 28). No proteins were enriched (>2-fold) in probe-treated lysates based on label-free LC-MS/MS analysis. Collectively, our data demonstrate on-target BSH binding of 7 and limited off-target activity against other bacterial proteins or mammalian proteins in intestinal cells.

Example 8. Single Dose of 7 Inhibits BSH Activity In Vivo

Figure 13A:
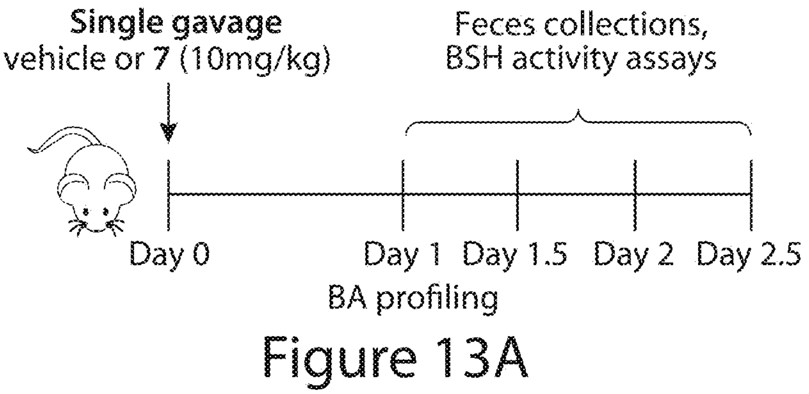
FIGS. 13A to 13C shows treatment of conventional mice with a single dose of compound 7 resulted in recoverable inhibition of BSH activity and a shift toward conjugated bile acids. n=4 mice per group, Student's t test.
Figure 13B:
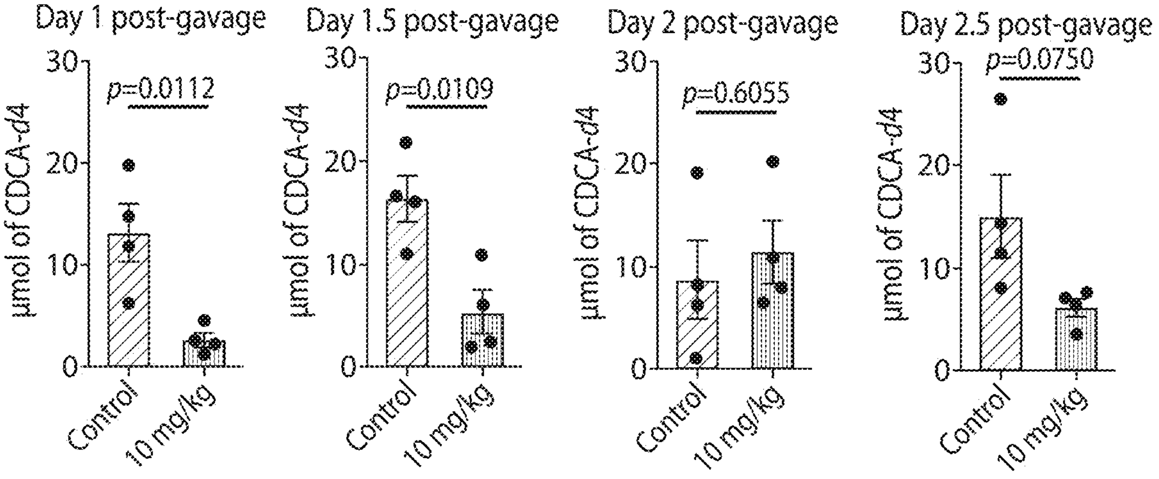
Figure 13C:
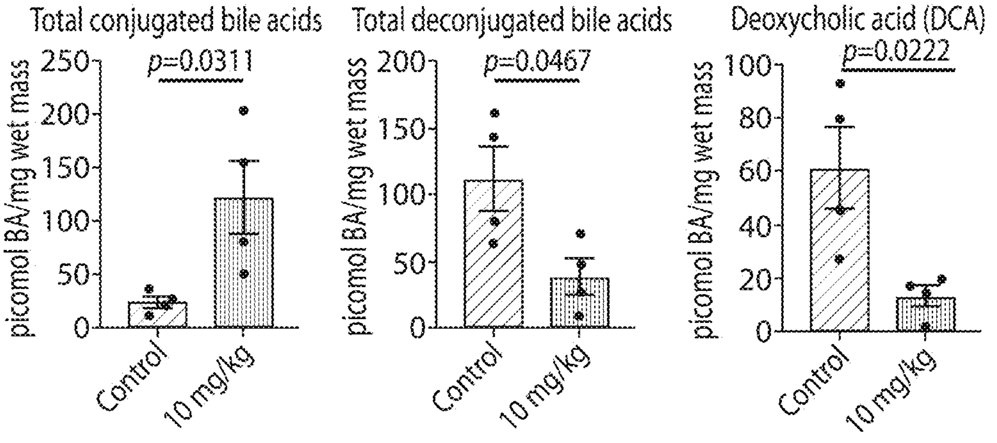
Figure 13D:
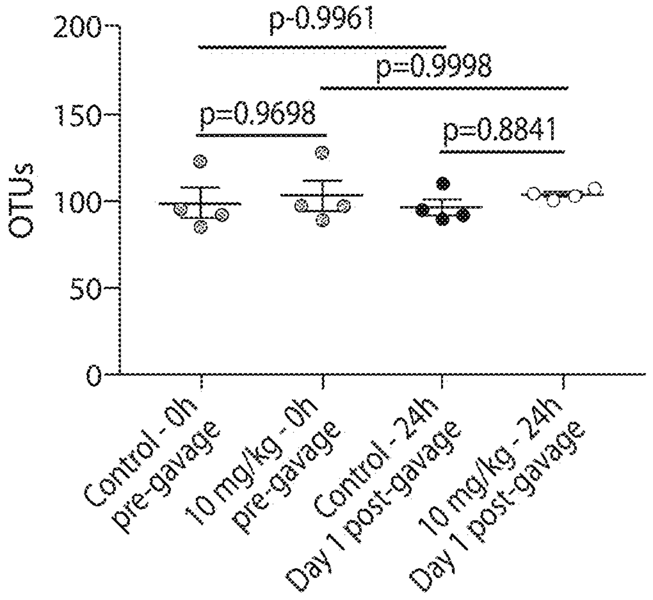
FIG. 13D shows bacterial OTUs (operational taxonomic units) did not differ between the inhibitor- and vehicle-treated groups 1 day post-gavage. n=4 mice per group, one-way ANOVA followed by Tukey's multiple comparisons test.

C57BL/6 mice were gavaged with a single dose of either 7 (10 mg/kg, see Online Methods for dose calculation) or vehicle control, and BSH activity in feces was monitored over time in half-day increments (FIG. 13*a*). A significant decrease in BSH activity in feces 1 day and 1.5 days post-gavage was observed, while at subsequent timepoints, BSH activity recovered (FIG. 13*b*) as well as a significant increase in fecal conjugated bile acids and a decrease in deconjugated bile acids 1 day-post gavage (FIG. 13*c*). 16S rDNA sequencing and plating of fecal samples from these mice indicated that compound 7 did not significantly affect gut bacterial OTUs, biomass, or community composition (FIGS. 13*d* and 28). Taken together, our results indicate that one dose of 7 can inhibit gut bacterial BSH activity and modulate the bile acid pool in vivo while not significantly affecting the gut bacterial community.

Example 9. Proof of Concept of Gut Restriction of 7

Figure 13E:
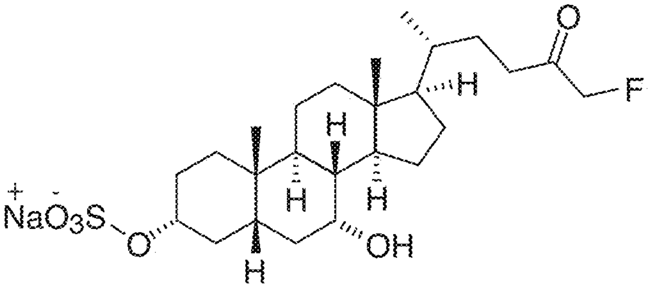
FIG. 13E shows structure of gut-restricted compound 7 (GR-7, 13).

To further minimize the likelihood that 7 would induce off-target effects, ideally, this molecule would be confined to the GI tract. A 3-sulfated variant (gut-restricted 7 or GR-7, compound 13, FIGS. 11*b*, 13*e*) was synthesized.

Figure 13F:
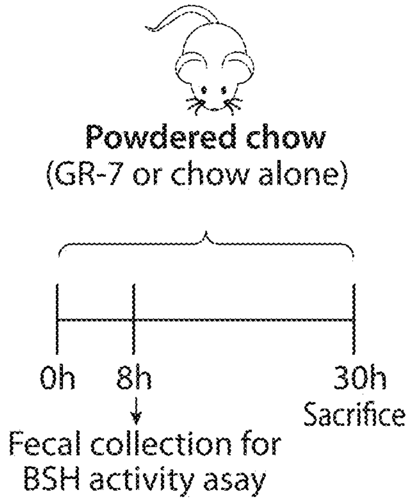
FIG. 13F shows design of proof-of-concept in vivo study with GR-7. Adult male C57BL/6 mice were fed powdered chow containing 0.09% (w/w) GR-7 or powdered chow alone for 30 hours. Fecal pellets were collected 8 hours post-diet change. n=10 mice per group.
Figure 13G:
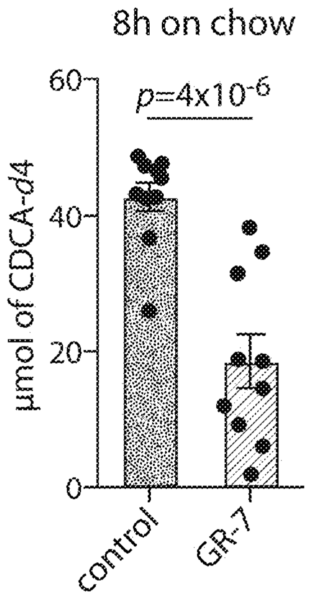
FIG. 13G shows resuspended fresh feces (20 mg/mL) from inhibitor- or control-treated mice were incubated with substrate (GCDCA-d4, 100 μM) for 25 min and formation of product was quantified by UPLC-MS. Significant inhibition of BSH activity was observed in the feces of GR-7-treated compared to control-treated mice. Student's t test. n=10 mice per group, two-tailed Student's t test.
Figure 13H:
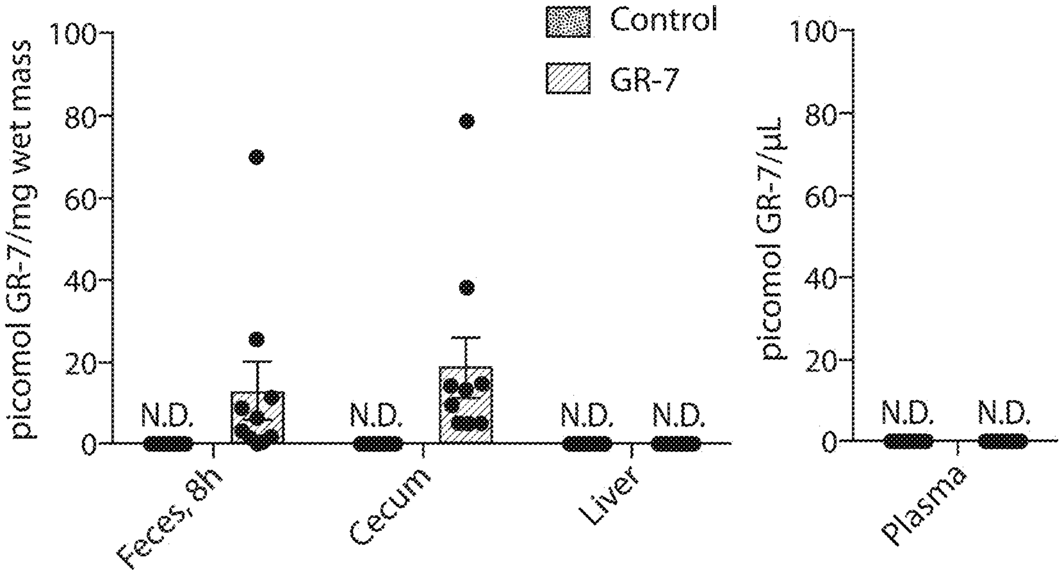
FIG. 13H shows quantification of GR-7 in tissues and plasma. Inhibitor was detected in feces 8 hours post-diet change and in cecal contents at sacrifice. No GR-7 was detected in the liver or plasma. N.D.=not detected. n=10 mice per group. All data are presented as mean±SEM.
Figure 14A:
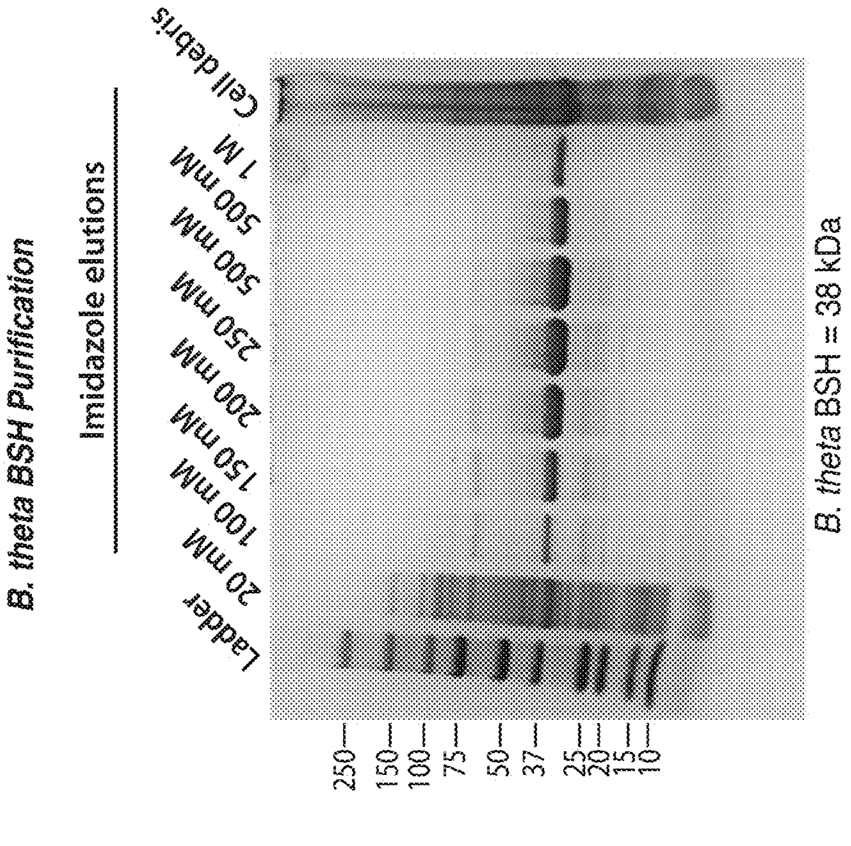
(FIG. 14A) SDS-PAGE of *B. theta* BSH purification. Experiment was repeated seven times with similar results.
Figure 14B:
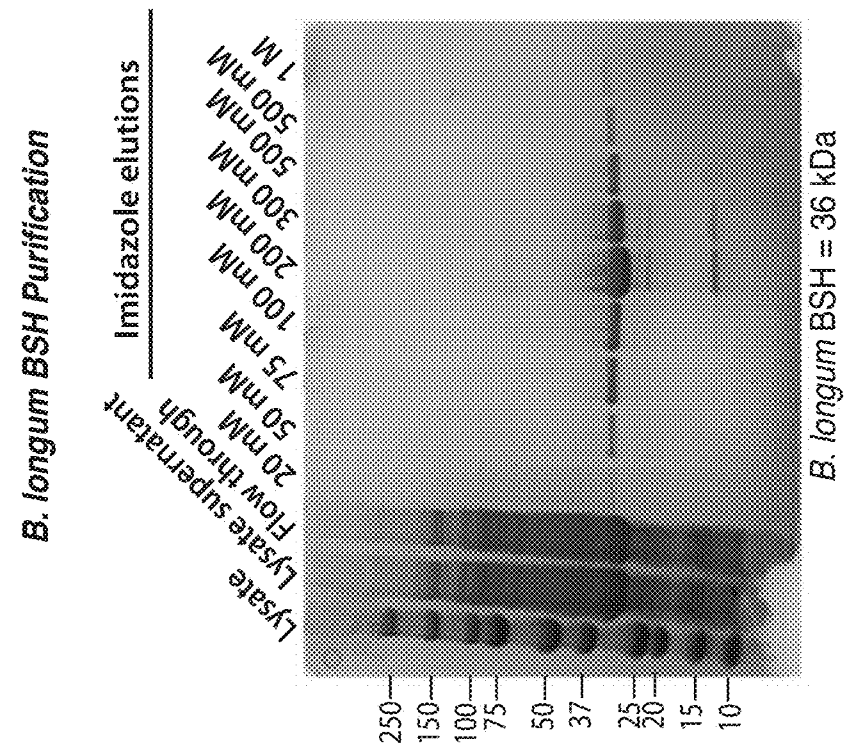
(FIG. 14B) SDS-PAGE of *B. longum* BSH purification. Michaelis-Menten analysis of BSH kinetic data. Rate vs substrate concentration curves for *B. theta* BSH (FIG. 14C) and *B. longum* BSH (FIG. 14D).
Figure 14C:
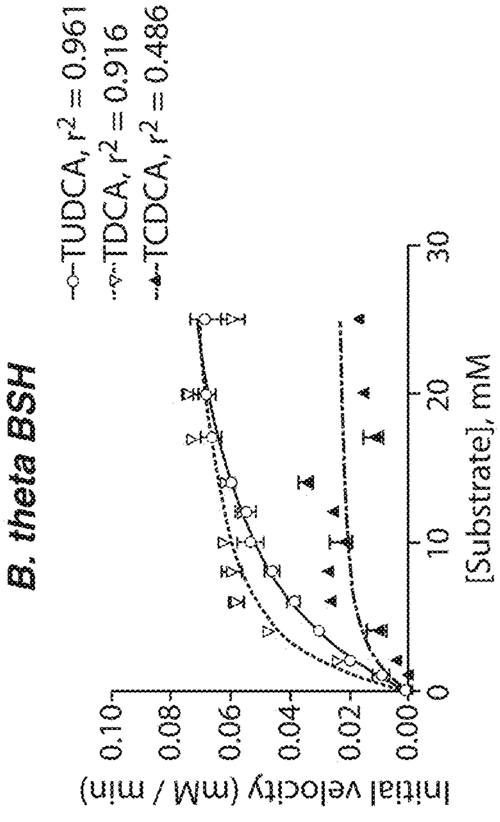
FIG. 14 shows purification and kinetic characterization of BSHs.
Figure 14D:
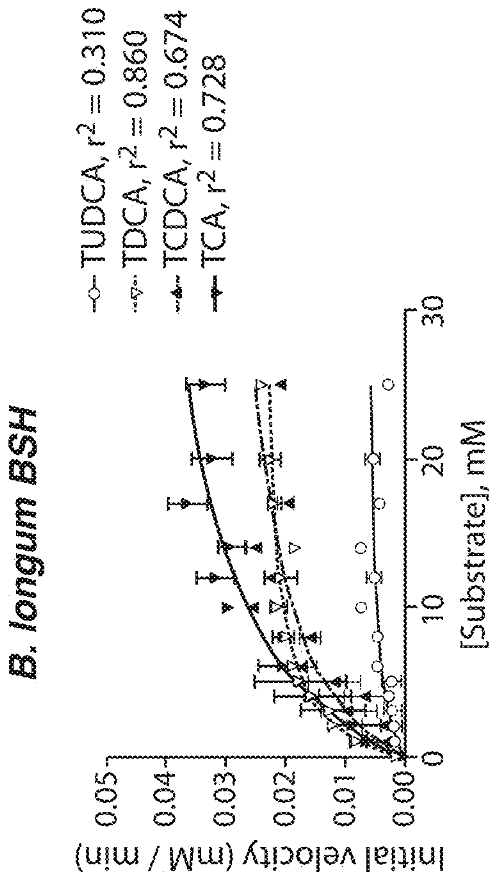
Figure 29A:
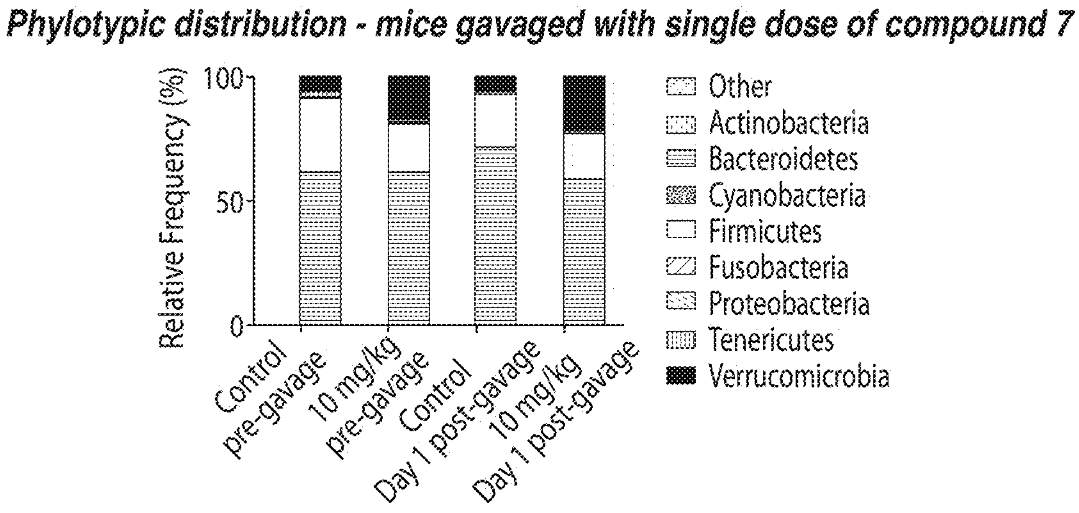
(FIG. 29A) Average relative abundance of microbiota at the phylum level by taxon-based analyses, n=4 mice group.
Figure 29B:
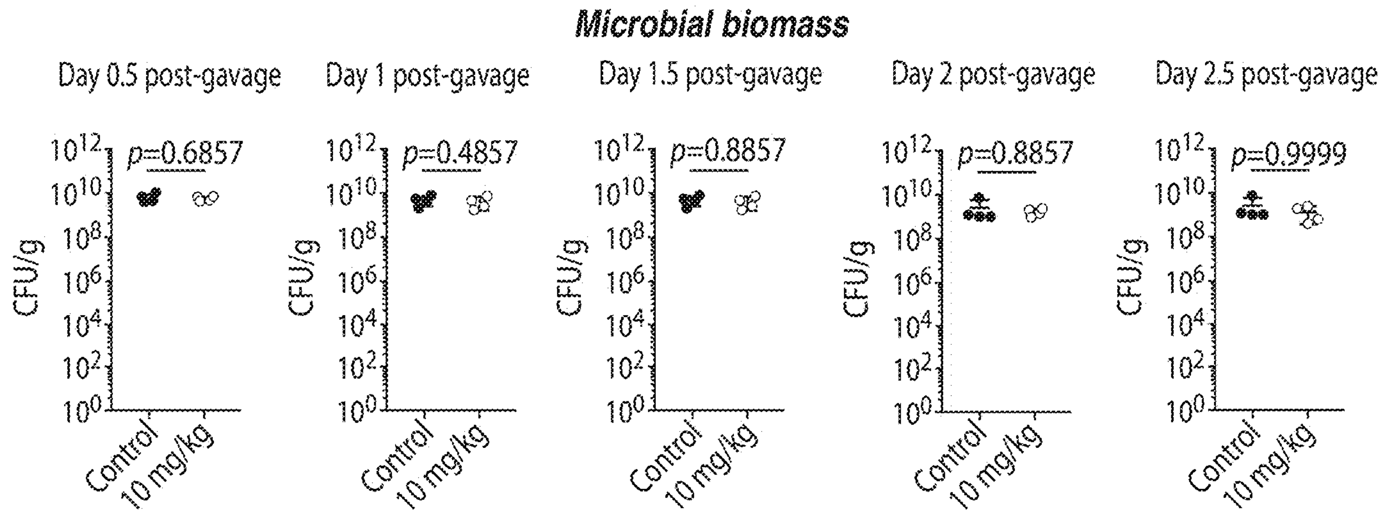
(FIG. 29B) CFU/g did not differ between the inhibitor- and vehicle-treated groups 0.5, 1,1.5, 2, or 2.5 days post-gavage. n=4 mice per group, two-tailed Mann-Whitney test. All data are presented as mean±SEM.
Figure 30A:
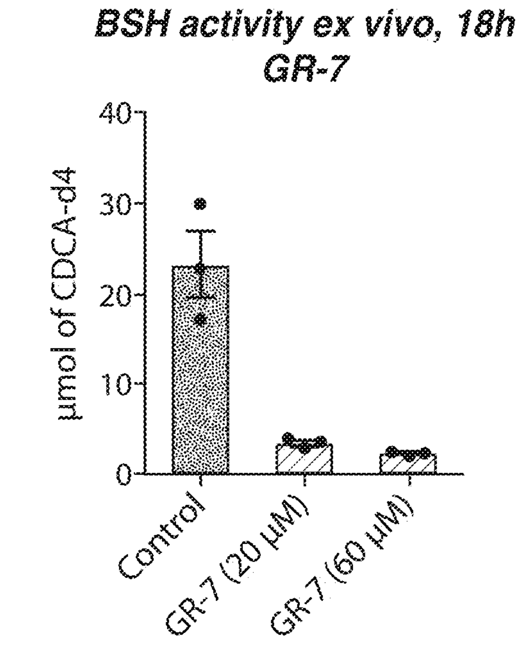
(FIG. 30A) GR-7 inhibited BSH activity in a fecal slurry. Freshly collected feces from conventional mice were resuspended in PBS (1 mg/mL) and incubated with 20 μM or 60 μM of GR-7 for 30 mins. Glycochenodeoxycholic acid-d4 (GCDCA-d4, 100 μM) was added as substrate and formation of product was determined by UPLC-MS after 18 hours. Assays were performed in biological triplicate.
Figure 30B:
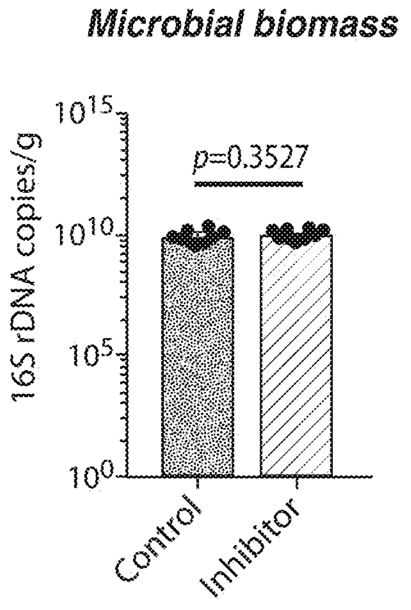
(FIG. 30B) 16S rDNA copies/g in cecal contents 30 hours post-diet change. Microbial biomass did not differ between the inhibitor- and vehicle-treated groups. Two-tailed Mann-Whitney test. n=10 mice per group. All data are presented as mean±SEM.

Evaluation of GR-7 in mouse feces revealed that GR-7 remains a potent pan-BSH inhibitor (FIG. 29). C57BL/6 mice were fed with either powdered chow containing 0.09% GR-7 (w/w) for 1 day or powdered chow alone (FIG. 13*f*). Significant inhibition of the BSH activity was observed in the feces of inhibitor-treated mice 8 hours post-diet change (FIG. 13*g*). GR-7 in feces collected at 8 h was detected, demonstrating that the inhibitor was being excreted at a rate consistent with mouse colonic transit time.[38] 20 picomol/mg wet mass was detected (~20 μM) of this compound in cecal contents (mean value, FIG. 13*h*). This concentration was effective at BSH inhibition in the mouse feces assay and lower than the toxicity threshold of 100 μM for 7 (FIGS. 24 and 29). Moreover, GR-7 (60 μM) did not affect epithelial barrier integrity of Caco-2 cells, suggesting that this compound is relatively non-toxic (FIG. 25). GR-7 also did not affect microbial biomass (FIG. 29). GR-7 was not detected in the serum and liver of inhibitor-treated mice (FIG. 5*h*). Collectively, these results provide proof of concept that 7 can be chemically modified to minimize absorption, and when fed in chow, a gut-restricted 7 derivative can inhibit BSH activity.

Example 10. Compound Synthesis

General: All anhydrous reactions were run under a positive pressure of argon or nitrogen. Anhydrous methylene chloride (DCM) and tetrahydrofuran (THF) were purchased from Sigma Aldrich. Silica gel column chromatography was performed using 60 Å silica gel (230-400 mesh). NMR spectra recorded in CDCl3 used residual chloroform or TMS as the internal reference.

Scheme 2. Synthesis of compounds 1 and 5.

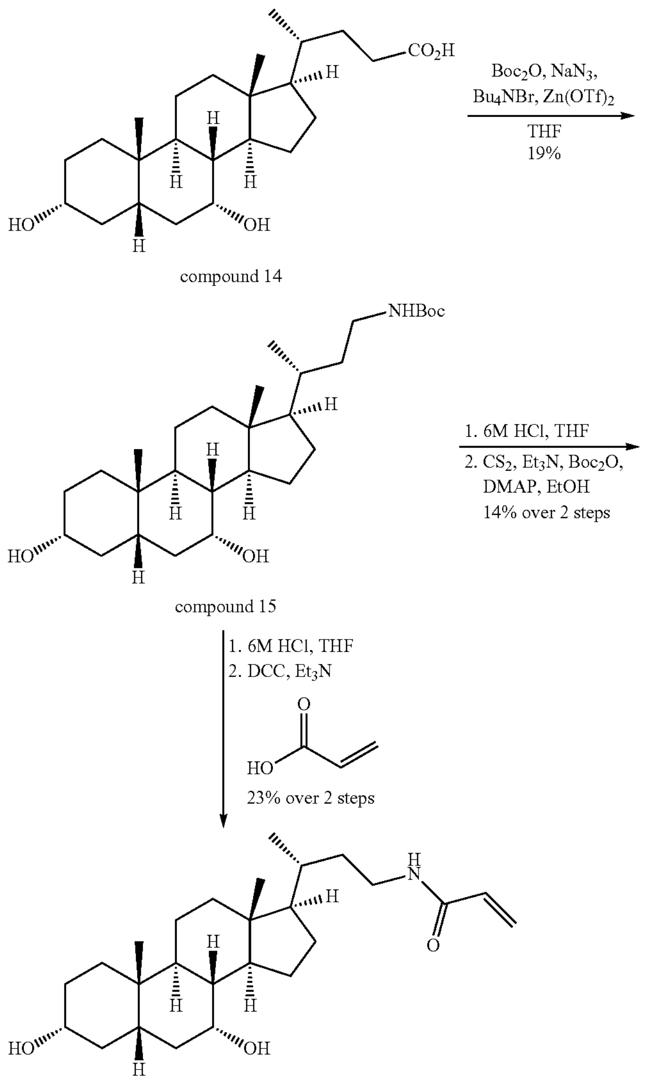

compound 14 compound 15 compound 1 compound 5

Compound 1

Step 1. To a solution of chenodeoxycholic acid (0.5 g, 1.27 mmol), sodium azide (0.29 g, 4.44 mmol), tetrabutylammonium bromide (61.0 mg, 0.19 mmol) and zinc trifluoromethanesulfonate (18.0 mg, 0.05 mmol) in 4.3 mL anhydrous THE at 40° C. was added di-tert-butyl dicarbonate (0.3 g, 1.40 mmol) and the mixture was heated overnight. The mixture was cooled to room temperature (rt) and quenched with 10 mL of 10% sodium nitrite and then diluted with 10 mL ethyl acetate. The organic layer was separated and the aqueous layer was extracted with ethyl acetate (2×10 mL). The combined organic layers where then dried over magnesium sulfate, filtered and concentrated on the rotovap. The crude compound was then purified by silica gel chromatography (80% ethyl acetate/20% hexanes) to provide compound 15 (0.11 g, 19%) as a white foam.

Step 2. To the Boc amine 15 (0.97 g, 2.09 mmol) in 4 mL THF, 1 mL of 6M HCl was added and the mixture was refluxed for 45 mins. The mixture was then cooled to rt and concentrated on the rotovap. The aqueous solution was then resuspended in 10 mL ethyl acetate and basified to pH 10 with 1M sodium hydroxide. The organic layer was separated and the aqueous layer was extracted with ethyl acetate (2×10 mL). The combined organic layers where then dried over sodium sulfate, filtered and concentrated to provide the free amine (0.51 g, 67%) which was used in the subsequent steps without further purification.

Step 3. A literature reported protocol was followed for the final step of the synthesis (*Tetrahedron Lett.*, 2008, 49, 3117-3119).

Briefly, to the amine (0.24 g, 0.66 mmol) in 2 mL ethanol, carbon disulphide (0.40 ml, 6.6 mmol) and trimethylamine (0.1 mL, 0.66 mmol) were added and the mixture was stirred at rt for 1 h. The solution was then cooled to 0° C. and di-tert-butyl dicarbonate (0.14 g, 0.66 mmol) and DMAP (4.0 mg, 0.03 mmol) were added and the resulting mixture was stirred at 0° C. for 10 mins. The mixture was then warmed to rt and stirred for 10 mins following which it was concentrated on the rotovap. The crude compound was then purified by silica gel chromatography (75% ethyl acetate/25% hexanes) to provide the compound 1 (20.0 mg, 20%) as a clear oil.

Compound 1. TLC (Ethyl acetate:Hexanes, 85:15 v/v): Rf=0.5; $^{1}H$ NMR (400 MHz, CDCl3): δ 3.83 (s, 1H), 3.57-3.41 (m, 3H), 2.18 (q, J=12.4 Hz, 1H), 1.99-1.79 (m, 7H), 1.71-1.64 (m, 3H), 1.57-1.11 (m, 14H), 1.00-0.81 (m, 7H), 0.67 (s, 3H); $^{13}C$ NMR (100 MHz, CDCl3): δ71.97, 68.50, 68.42, 55.85, 50.44, 42.80, 42.75, 41.44, 39.88, 39.60, 39.38, 36.13, 35.30, 35.03, 34.69, 33.49, 32.82, 30.66, 28.25, 23.67, 22.75, 20.56, 18.20, 11.73; HRMS (n/z): $[M-2H2O+H]^+$ calcd. for $C_{24}H_{39}NO_2S$, 370.2568; found, 370.2543.

Compound 5

Step 1. The free amine was synthesized as per the conditions in step 2 for compound 1.

Step 2. The acid (12.0 mg, 0.16 mmol) was dissolved in 1.65 mL anhydrous DCM followed by the addition of the coupling agent N,N'-dicyclohexylcarbodiimide (DCC) (42.0 mg, 0.20 mmol) and trimethylamine (76 μL, 0.55 mmol). The mixture was stirred at rt for 30 mins and then the free amine (50.0 mg, 0.14 mmol) dissolved in 1.4 mL DCM was added to the above mixture. The resulting solution was stirred at rt for 3 h. The mixture was then partitioned using 5 mL of 1M HCl and 5 mL DCM. The organic layer was separated and the aqueous layer was extracted with DCM (2×10 mL). The combined organic layers where then dried over sodium sulfate, filtered and concentrated. The crude compound was then purified by silica gel chromatography (90% ethyl acetate/10% hexanes) to provide the compound 5 (20.0 mg, 33%) as a clear oil.

Compound 5. TLC (Ethyl acetate:Hexanes, 80:20 v/v): $R_f$=0.12; $^{1}H$ NMR (400 MHz, $CDCl_3$): δ 6.27 (dd, J=16.8, 1.2 Hz, 1H), 6.07 (dd, J=16.8, 10.4 Hz, 1H), 5.62 (dd, J=10.4, 1.2 Hz, 1H), 5.45 (br s, 1H), 3.85-3.84 (m, 1H), 3.50-3.37 (m, 2H), 3.31-3.22 (m, 1H), 2.20 (q, J=12.8 Hz, 1H), 2.01-1.79 (m, 5H), 1.73-1.10 (m, 19H), 1.01-0.94 (m, 4H), 0.90 (s, 3H), 0.66 (s, 3H); $^{13}C$ NMR (100 MHz, $CDCl_3$): δ 155.54, 130.95, 126.14, 72.00, 68.51, 55.97, 50.45, 42.73, 41.46, 39.91, 39.61, 39.42, 37.24, 35.76, 35.30, 35.03, 34.61, 34.07, 32.83, 30.68, 28.35, 23.69, 22.75, 20.55, 18.67, 11.73; HRMS (n/z): $[M-2H2O+H]^+$ calcd. for $C_{26}H_{43}NO_3$, 382.3110; found, 382.3082.

Scheme 3. Synthesis of the common C-24 aldehyde intermediate 17.

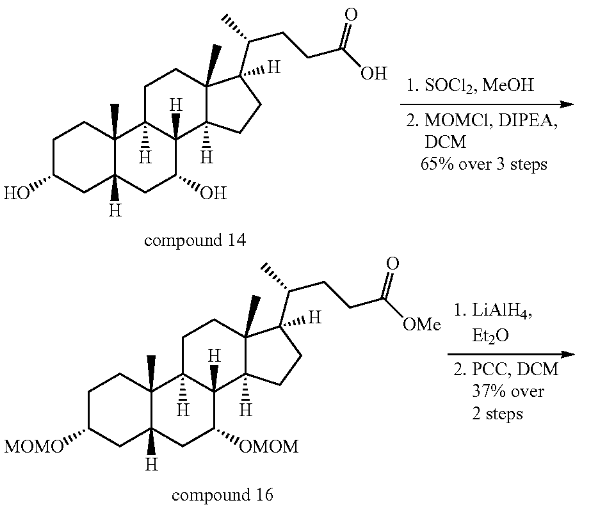

compound 14 compound 16

-continued

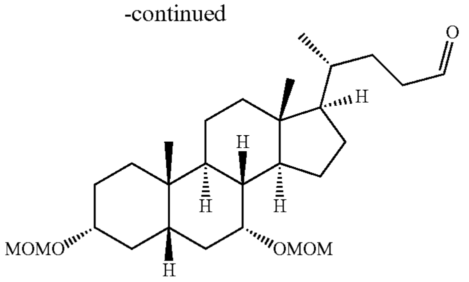

compound 17

Step 1. To chenodeoxycholic acid (20.0 g, 50.8 mmol) suspended in 100 mL methanol at 0° C., thionyl chloride (4.0 mL, 55.9 mmol) was added dropwise. The reaction was warmed to rt and stirred for 3 h. The reaction was quenched by the addition of 100 mL saturated sodium bicarbonate. The resulting mixture was then concentrated on the rotovap. The residue was partitioned between aqueous layer and 50 mL ethyl acetate. The organic layer was separated and the aqueous layer was extracted with ethyl acetate (2×50 mL). The combined organic layers where then dried over sodium sulfate, filtered and concentrated on the rotovap. The crude compound was then purified by silica gel chromatography (60% ethyl acetate/40% hexanes) to provide the methyl ester (20.6 g, quant.) as a white foam.

Step 2. The methyl ester (1.6 g, 3.93 mmol) was dissolved in 8 mL of anhydrous DCM and cooled to 0° C. under nitrogen. To this solution, N,N-diisopropylethylamine (1.4 mL, 11.79 mmol) was added followed by the slow addition of methoxymethyl chloride (1.2 mL, 11.79 mmol). The reaction mixture was then warmed to rt and stirred for 3 h. The reaction was quenched with the addition of 10 mL saturated sodium bicarbonate. The organic layer was separated and the aqueous layer was extracted with DCM (2×10 mL). The combined organic layers were then dried over sodium sulfate, filtered and concentrated. The crude compound was then purified by silica gel chromatography (25% ethyl acetate/75% hexanes) to provide the pure product 16 (1.26 g, 65%) as a white foam.

Step 3. The protected methyl ester 16 (1.73 g, 3.49 mmol) was dissolved in 14 mL anhydrous diethyl ether and cooled to 0° C. under nitrogen. LiAlH4 (0.27, 6.99 mmol) was added in portions to the above solution. The mixture was allowed to stir at 0° C. for 2 h and then quenched by the slow addition of 14 mL of Rochelle's salt. The organic layer was separated and the aqueous layer was extracted with ethyl acetate (2×15 mL). The combined organic layers were then dried over magnesium sulfate, filtered and concentrated. The crude compound was then purified by silica gel chromatography (30% ethyl acetate/70% hexanes) to provide the pure C-24 alcohol (0.80 g, 50%) as a clear oil.

Step 4. To a suspension of pyridinium chlorochromate (1.42 g, 6.57 mmol) and silica gel (1.42 g) in 8 mL DCM at 0° C., C-24 alcohol (1.9 g, 4.06 mmol) dissolved in another 8 mL DCM was added slowly. The resulting solution was then stirred at rt for 2 h. The reaction mixture was then filtered through a bed of celite and the residue was concentrated to provide the crude aldehyde S4. The crude compound was then purified by silica gel chromatography (20% ethyl acetate/80% hexanes) to provide pure aldehyde 17 (1.39 g, 74%) as a clear oil.

Scheme 4. Synthesis of compounds 2-4 and 6.

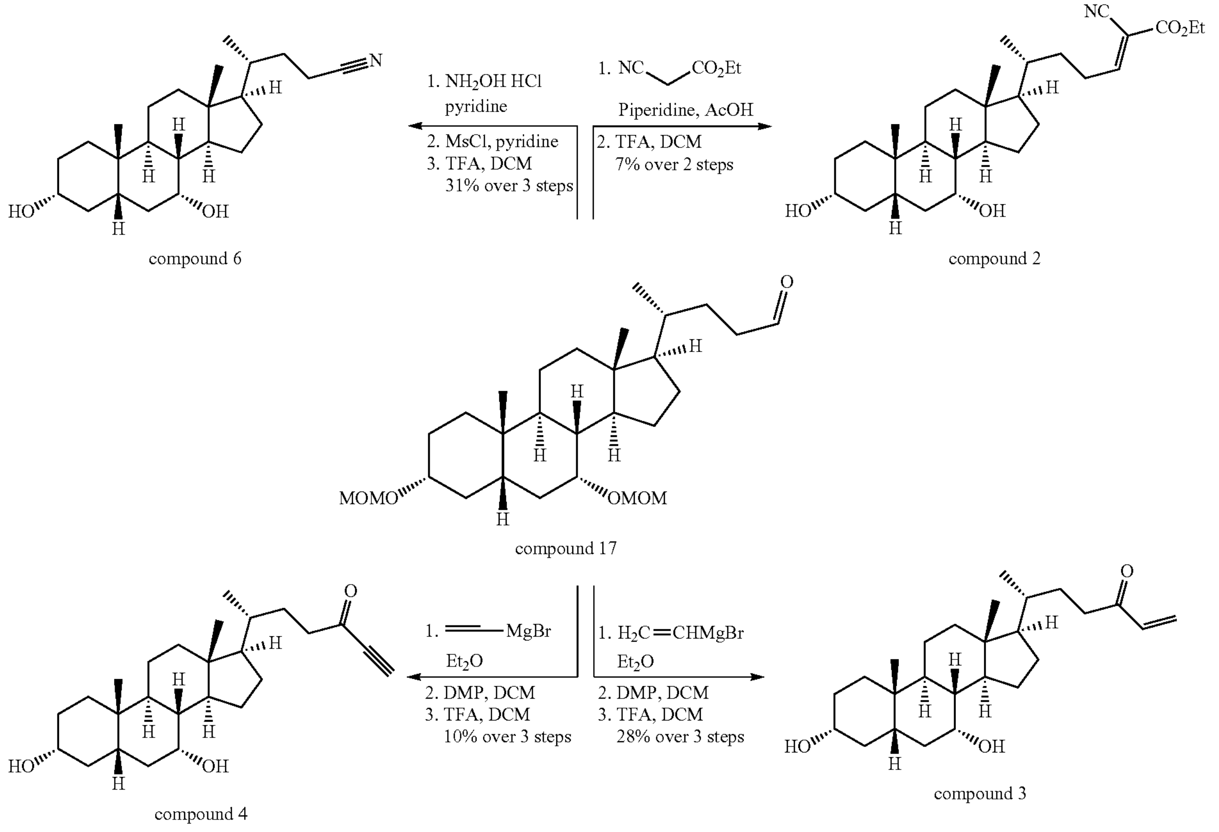

compound 6 compound 2 compound 17 compound 4 compound 3

Compound 2.

Step 1. A literature reported protocol was followed for this step of the synthesis (*J. Med. Chem.,* 2005, 48, 3026-3035). To the aldehyde 17 (0.12 g, 0.28 mmol) and ethyl 2-cyano-acrylate (35.0 mg, 0.30 mmol) at 0° C., acetic acid (17 μL, 0.28 mmol) and piperidine (28 μL, 0.28 mmol) were added. The mixture was then stirred at rt overnight. The residue was then diluted with 5 mL DCM and washed with 5 mL of 1M HCL. The organic layer was separated and the aqueous layer was extracted with DCM (2×10 mL). The combined organic layers were then dried over sodium sulfate, filtered and concentrated. The crude compound was then purified by silica gel chromatography (30% ethyl acetate/70% hexanes) to provide the condensed intermediate (40.0 mg, 29%) as a clear oil.

Step 2. To the condensed product (50.0 mg, 0.09 mmol) in 1 mL DCM, 0.2 mL trifluoroacetic acid was added and the reaction mixture was stirred at 0° C. for 1 h. The mixture was then cooled to rt, diluted with 5 mL DCM and quenched slowly with 5 mL saturated sodium bicarbonate solution. The organic layer was separated and the aqueous layer was extracted with DCM (2×10 mL). The combined organic layers were then dried over sodium sulfate, filtered and concentrated. The crude compound was then purified by silica gel chromatography (60% ethyl acetate/40% hexanes) to provide the target compound 2 (10.0 mg, 24%) as a mixture of diastereomers which was used in the screen without further purification.

Compound 2. TLC (Ethyl acetate:Hexanes, 70:30 v/v): $R_f$=0.43; $^1H$ NMR (400 MHz, $CDCl_3$): δ 7.64 (t, J=8.0 Hz, 1H), 4.31 (q, J=7.2 Hz, 2H), 3.85 (s, 1H), 3.50-3.44 (m, 1H), 2.63-2.43 (m, 2H), 2.20 (q, J=12.8 Hz, 1H), 1.99-1.11 (m, 26H), 1.02-0.98 (m, 4H), 0.91 (s, 4H), 0.66 (s, 3H); $^{13}C$ NMR (100 MHz, $CDCl_3$): Because this compound was isolated as a mixture of diastereomers, C13 peak assignment was not performed. HRMS (m/z): $[M+Na]^+$ calcd. for $C_{29}H_{45}NO_4$, 494.3246; found, 494.3233.

Compound 3.

Step 1. In a flame dried flask, the aldehyde 17 (0.50 g, 1.07 mmol) was dissolved in 4.3 mL diethyl ether under nitrogen. Vinylmagnesium bromide (1.6 mL, 1.60 mmol) was then added slowly to the above solution at 0° C. The mixture was stirred at rt overnight. The reaction was quenched by the addition of 5 mL 1M HCl and diluted with 10 mL ethyl acetate.

The organic layer was separated and the aqueous layer was extracted with ethyl acetate (2×10 mL). The combined organic layers were then dried over magnesium sulfate, filtered and concentrated. The crude compound was then purified by silica gel chromatography (30% ethyl acetate/70% hexanes) to provide the alcohol as a mixture of diastereomers (0.40 g, 77%).

Step 2 and 3. Compound 3, was synthesized following Steps 2 and 3 as described above for compound 4. The overall yield is reported on the reaction scheme.

Compound 3. TLC (Ethyl acetate:Hexanes, 60:40 v/v): Rf=0.34; $^1H$ NMR (400 MHz, $CDCl_3$): δ 6.35 (dd, J=18.0, 10.8 Hz, 1H), 6.21 (dd, J=17.6, 1.2 Hz, 1H), 5.89 (dd, J=10.4, 0.8 Hz, 1H), 3.86-3.85 (m, 1H), 3.50-3.43 (m, 1H), 2.65-2.57 (m, 1H), 2.54-2.46 (m, 1H), 2.20 (q, J=12.8 Hz, 1H), 2.01-1.11 (m, 22H), 1.02-0.91 (m, 9H), 0.66 (s, 3H); $^{13}$C NMR (100 MHz, $CDCl_3$): δ 201.43, 136.57, 127.77, 72.01, 68.53, 55.78, 50.46, 42.70, 41.47, 39.91, 39.62, 39.42, 36.51, 35.35, 35.31, 35.04, 34.60, 32.84, 30.67, 30.02, 28.15, 23.71, 22.75, 20.57, 18.47, 11.77; HRMS (m/z): $[M-2H_2O+H]^+$ calcd. for $C_{26}H_{42}O_3$, 367.3001; found, 367.2985.

Compound 4.

Step 1. In a flame dried flask, the aldehyde 17 (0.20 g, 0.65 mmol) was dissolved in 1.5 mL diethyl ether under nitrogen. Ethynylmagnesium bromide (1.2 mL, 0.97 mmol) was then added slowly to the above solution at 0° C. The mixture was stirred at rt overnight. The reaction was quenched by the addition of 2 mL 1M HCl and diluted with 10 mL ethyl acetate. The organic layer was separated and the aqueous layer was extracted with ethyl acetate (2×10 mL). The combined organic layers were then dried over magnesium sulfate, filtered and concentrated. The crude compound was then purified by silica gel chromatography (30% ethyl acetate/70% hexanes) to provide the alcohol as a mixture of diastereomers (0.12 g, 57%).

Step 2. To the alcohol (0.12 g, 0.24 mmol) in 2.5 mL anhydrous DCM at 0° C., Dess-Martin periodinane (1.1 mL, 0.37 mmol) was added slowly. The reaction mixture was then stirred at rt until the reaction was complete by TLC. Upon consumption of the starting material, the reaction was quenched by the addition of 3 mL saturated sodium thiosulfate solution and 3 mL saturated sodium bicarbonate solution. The organic layer was separated and the aqueous layer was extracted with DCM (2×10 mL). The combined organic layers were then dried over sodium sulfate, filtered and concentrated. The crude compound was then purified by to provide the product (60.0 mg, 50%) as a clear oil.

Step 3. To the protected compound (20.0 mg, 0.04 mmol) in 1.0 mL DCM, trifluoroacetic acid (12 μL, 0.15 mmol) was added and the reaction mixture was stirred at 0° C. for 1 h. The mixture was then cooled to rt, diluted with 5 mL DCM and quenched slowly with 5 mL saturated sodium bicarbonate solution. The organic layer was separated and the aqueous layer was extracted with DCM (2×10 mL). The combined organic layers were then dried over sodium sulfate, filtered and concentrated. The crude compound was then purified by silica gel chromatography (50% ethyl acetate/50% hexanes) to provide the target compound 4 (5.5 mg, 34%) as a clear oil.

Compound 4. TLC (Ethyl acetate:Hexanes, 60:40 v/v): $R_f$=0.28; $^1$H NMR (400 MHz, $CDCl_3$): δ 3.86-3.85 (m, 1H), 3.50-3.43 (m, 1H), 3.20 (s, 1H), 2.66-2.48 (m, 2H), 2.20 (q, J=12.8 Hz, 1H), 2.02-1.80 (m, 6H), 1.73-1.11 (m, 18H), 1.02-0.91 (m, 7H), 0.66 (s, 3H); $^{13}$C NMR (100 MHz, $CDCl_3$): δ 187.87, 78.23, 72.00, 68.52, 55.71, 50.46, 42.72, 42.44, 41.46, 39.91, 39.60, 39.42, 35.30, 35.14, 35.03, 35.02, 34.63, 32.83, 30.67, 29.73, 28.11, 23.69, 22.75, 20.56, 18.33, 11.76; HRMS (m/z): $[M-2H_2O+H]^+$ calcd. for $C_{26}H_{40}O_3$, 365.2844; found, 365.2827.

Compound 6.

Step 1. To the aldehyde 17 (0.50 g, 1.07 mmol) in 4 mL anhydrous pyridine, hydroxylamine hydrochloride (0.37 g, 5.37 mmol) was added and the reaction mixture was stirred at rt for 4 h. The mixture was then diluted with 20 mL DCM and washed with 20 mL 1M HCl. The organic layer was separated and the aqueous layer was extracted with DCM (2×20 mL). The combined organic layers were then dried over sodium sulfate, filtered and concentrated to provide the crude oxime which was used in the subsequent step without further purification.

Step 2. To the oxime (0.38 g, 0.79 mmol) in 4 mL pyridine, methanesulfonyl chloride (92 μL, 1.19 mmol) was added at 0° C. The reaction mixture was warmed to rt and stirred for 18 h after which the mixture was diluted with 20 mL DCM and washed with 20 mL 1M HCl. The organic layer was separated and the aqueous layer was extracted with DCM (2×20 mL). The combined organic layers were then dried over sodium sulfate, filtered and concentrated to provide the crude oxime which was purified using silica gel chromatography (20% ethyl acetate/80% hexanes) to provide the pure bis-MOM protected nitrile (0.16 g, 44% yield over two steps). Step 3. To the protected nitrile (70.0 mg, 0.15 mmol) in 1.5 mL tetrahydrofuran (THF), 50% HBr (100 μL, 0.61 mmol) was added and the reaction mixture was heated at 50° C. for 1 h. The mixture was then cooled to rt and diluted with 5 mL ethyl acetate and then quenched slowly with 5 mL saturated sodium bicarbonate solution. The organic layer was separated and the aqueous layer was extracted with ethyl acetate (2×20 mL). The combined organic layers were then dried over magnesium sulfate, filtered and concentrated. The crude compound was then purified by silica gel chromatography to provide the target compound 6 (40.0 mg, 71%) as a white solid.

Compound 6. TLC (Ethyl acetate:Hexanes, 60:40 v/v): Rf=0.2; $^1$H NMR (400 MHz, $CDCl_3$): δ 3.843-3.836 (m, 1H), 3.49-3.41 (m, 1H), 2.40-2.15 (m, 3H), 2.00-1.80 (m, 6H), 1.72-1.63 (m, 3H), 1.55-1.11 (m, 15H), 1.01-0.90 (m, 7H), 0.67 (s, 3H); $^{13}$C NMR (100 MHz, $CDCl_3$): δ 120.17, 71.94, 68.42, 55.54, 50.42, 42.77, 41.44, 39.86, 39.59, 39.36, 35.30, 35.17, 35.02, 34.71, 32.81, 31.51, 30.65, 28.15, 23.65, 22.74, 20.55, 17.86, 14.25, 11.77; HRMS (m/z): $[M-2H_2O+H]^+$ calcd. for $C_{24}H_{39}NO_2$, 338.2848; found, 338.2828.magnesium benzyl fluoromalonate coupling reagent was synthesized according to a reported protocol: James T Palmer. Process for Forming a Fluoromethyl Ketone. 5,210,272, May 11, 1993.

Step 1. To the protected methyl ester 16 (6.4 g, 12.95 mmol) in 26 mL methanol, 28 mL 1M NaOH was added and the resulting solution was heated to 60° C. overnight. The mixture was then concentrated on the rotovap and resuspended in 30 mL each of 1M HCl and DCM. The organic layer was separated and the aqueous layer was extracted with DCM (2×30 mL). The combined organic layers were then dried over sodium sulfate, filtered and concentrated to provide the acid 18 (5.7 g, 91%) as a white foam, which was used in subsequent reactions without further purification.

Step 2. To the C-24 acid 18 (1.60 g, 3.33 mmol) in 6.5 mL of anhydrous THF, 1'-carbonyldiimidazole (CDI) (0.7 g, 4.33 mmol) was added and stirred at rt for 1 h. The magnesium benzyl fluoromalonate (1.20 g, 2.68 mmol) was suspended in 6.5 mL anhydrous THF and the above solution was added dropwise and the resulting mixture was stirred at rt for 18 h. The reaction was quenched by the addition of 10 mL of 1M HCl and concentrated on the rotovap. The residue was then partitioned using 10 mL DCM and 10 mL water. The organic layer was separated and the aqueous layer was extracted with DCM (2×10 mL). The combined organic layers were then dried over sodium sulfate, filtered and concentrated. The crude compound was then purified by silica gel chromatography (20% ethyl acetate/80% hexanes) to provide the pure compound 19 (1.36 g, 66%) as a white foam.

Step 3. The compound 19 (1.0 g, 1.63 mmol) and palladium on carbon (8.6 mg, 0.08 mmol) were suspended in 82 mL methanol. The flask for vacuumed and replaced with a hydrogen balloon. The reaction mixture was stirred at rt for 3 h. The solution was then filtered through a celite bed and the filtrate was concentrated to provide the bis-MOM protected fluoromethyl ketone (0.74 g, 96%).

Step 4. To the bis-MOM fluoromethyl ketone compound (0.74 g, 1.56 mmol) dissolved in 15.6 mL THF, 48% HBr (1.10 mL, 6.24 mmol) was added and the resulting solution was heated at 50° C. for 1 h. The mixture was cooled to rt and then quenched by slow addition of 20 mL saturated sodium bicarbonate solution. The biphasic solution was then concentrated on the rotovap and the resulting residue was partitioned using 20 mL DCM and 20 mL water. The organic layer was separated and the aqueous layer was extracted with DCM (2×20 mL). The combined organic layers were then dried over sodium sulfate, filtered and concentrated. The crude compound was then purified by silica gel chromatography (40% ethyl acetate/60% hexanes to 60% ethyl acetate/40% hexanes) to provide the pure compound 7 (0.18 g, 29%) as a white foam.

Compound 7. TLC (Ethyl acetate:Hexanes, 70:30 v/v): $R_f$=0.36; $^1$H NMR (400 MHz, $CDCl_3$): δ 4.79 (d, J=48.0 Hz, 1H), 3.85 (s, 1H), 3.50-3.44 (m, 1H), 2.60-2.44 (m, 2H), 2.20 (q. J=13.2 Hz, 1H), 2.00-1.11 (m, 26H), 1.02-0.88 (m, 6H), 0.66 (s, 3H); $^{13}$C NMR (100 MHz, $CDCl_3$): δ 207.62 (d, J=19.2 Hz), 84.91 (d, J=184.2), 71.98, 68.49, 55.70, 50.45, 42.69, 41.47, 39.88, 39.61, 39.41, 35.31, 35.24, 35.11, 35.03, 34.63, 32.83, 30.66, 28.67 (d, J=1.7 Hz), 28.12, 23.68, 22.74, 20.56, 18.38, 11.76; HRMS (m/z): $[M-2H_2O+H]^+$ calcd. for $C_{25}H_{41}FO_3$, 373.2907; found, 373.2888.

Scheme 5. Synthesis of Compound 9

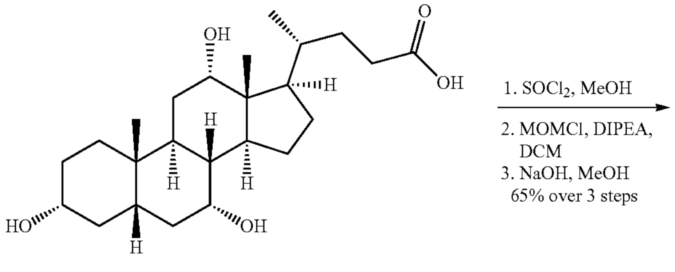

compound 20

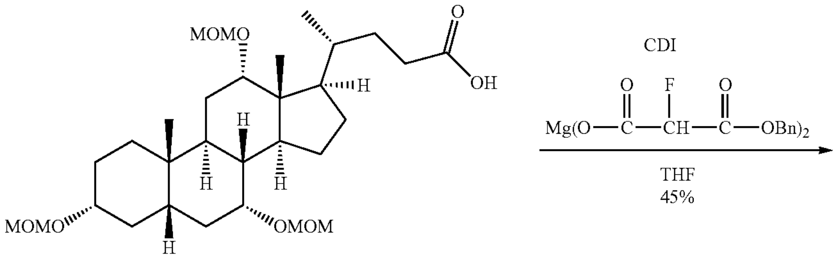

compound 21

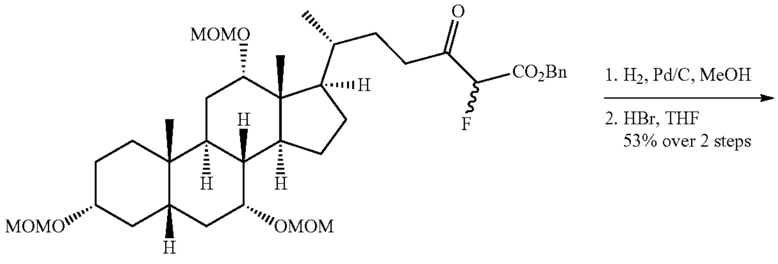

compound 22

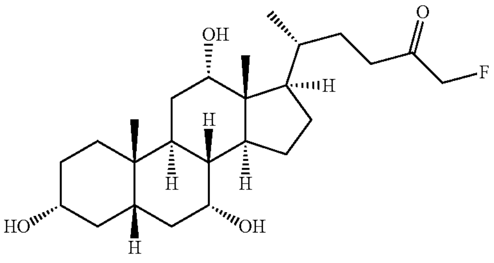

compound 9

Compound 9 was synthesized from cholic acid (20) as per the procedure described above for compound 7. Yields for the synthesis of compound 9 are listed in the scheme above.

Compound 9. TLC (100% Ethyl acetate): Rf=0.12; $^1H$ NMR (400 MHz, $CDCl_3$): δ 4.80 (d, J=47.6 Hz, 1H), 3.96 (s, 1H), 3.85 (s, 1H), 3.48-3.41 (m, 1H), 2.63-2.43 (m, 2H), 2.27-1.25 (m, 24H), 1.17-1.07 (m, 1H), 1.02-0.94 (m, 4H), 0.89 (s, 3H), 0.68 (s, 3H); $^{13}C$ NMR (100 MHz, $CDCl_3$): δ 207.61 (d, J=19.0 Hz), 84.92 (d, J=184.2 Hz), 72.98, 71.92, 68.41, 46.97, 46.47, 41.82, 41.43, 39.65, 39.53, 35.21, 35.12, 35.07, 34.70, 34.63, 30.47, 28.60 (d, J=1.5 Hz), 28.29, 27.43, 26.52, 23.18, 22.48, 17.44, 12.50; HRMS (m/z): $[M-2H_2O+H]^+$ calcd. for $C_{25}H_{41}FO_4$, 371.2750; found, 371.2725.

Scheme 6. Synthesis of compound 8.

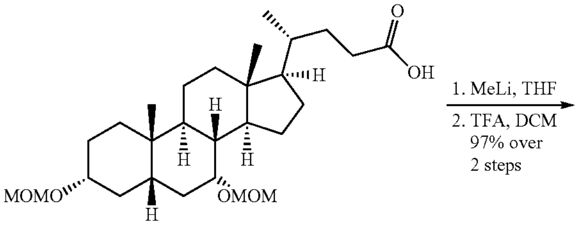

compound 18

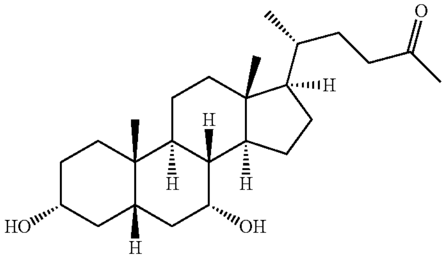

compound 8

Step 1. In a flame dried flask, the C-24 acid 18 (0.36 g, 0.75 mmol) was dissolved in 7.5 mL anhydrous THF and cooled to −5° C. Methyllithium (1.35 mL, 2.24 mmol) was then added dropwise and the reaction was stirred at −5° C. for 1 h. The reaction was quenched with 8 mL water and concentrated on the rotovap. The residue was then partitioned using ethyl acetate and water. The organic layer was separated and the aqueous layer was extracted with ethyl acetate (2×10 mL). The combined organic layers were then dried over sodium sulfate, filtered and concentrated. The crude compound was then purified by silica gel chromatography (30% ethyl acetate/70% hexanes) to provide the pure compound (0.15 g, 42%) as a white foam.

Step 2. Compound 8, was synthesized following step 3 as described above for compound 4. The overall yield is reported on the reaction scheme.

Compound 8. TLC (Ethyl acetate:Hexanes, 30:70 v/v): Rf=0.1; $^1H$ NMR (400 MHz, $CDCl_3$): δ 3.844-3.837 (m, 1H), 3.49-3.41 (m, 1H), 2.49-2.13 (m, 5H), 2.00-1.59 (m, 9H), 1.52-1.05 (m, 16H), 1.01-0.90 (m, 7H), 0.65 (s, 3H); $^{13}C$ NMR (100 MHz, $CDCl_3$): δ 209.66, 71.99, 68.50, 55.78, 50.45, 42.67, 41.47, 40.58, 39.88, 39.41, 35.31, 35.25, 35.03, 34.62, 32.83, 30.65, 29.87, 29.77, 28.15, 23.69, 22.75, 20.56, 18.41, 11.76 (one carbon overlapping with $CDCl_3$); HRMS (n/z): $[M-2H_2O+H]^+$ calcd. for $C_{25}H_{42}O_3$, 355.3001; found, 355.2980.

Scheme 7. Synthesis of compound 7-$N_3$ (12).

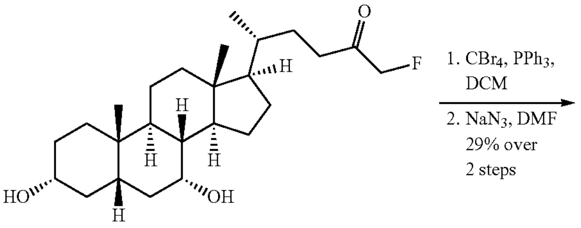

compound 7

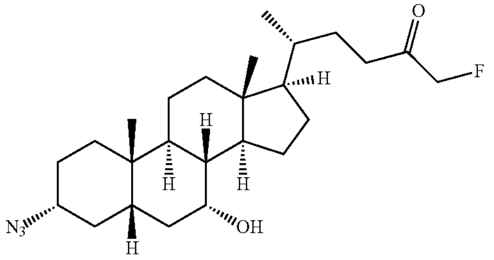

compound 7-$N_3$ (12)

Step 1. To compound 7 (20.0 mg, 0.05 mmol) in 1 mL anhydrous DCM, triphenylphosphine (16.0 mg, 0.06 mmol) and carbon tetrabromide (21.0 mg, 0.06 mmol) were added and the reaction was stirred at rt for 18 h. The reaction was concentrated on the rotovap. The crude compound was then purified by silica gel chromatography (20% ethyl acetate/80% hexanes) to provide the pure bromide (15.0 mg, 65%) as a white powder.

Step 2. C-3 bromo compound (15.0 mg, 0.03 mmol), was dissolved in 0.5 mL DMF followed by the addition of sodium azide (4.1 mg, 0.06 mmol). The reaction mixture was heated at 100° C. for 1 h. The mixture was concentrated on the rotovap and partitioned using saturated solution of sodium bicarbonate and ethyl acetate (5 mL each). The organic layer was separated and the aqueous layer was extracted with ethyl acetate (2×5 mL). The combined organic layers were then dried over sodium sulfate, filtered and concentrated. The crude compound was then purified by silica gel chromatography (20% ethyl acetate/80% hexanes) to provide the pure compound 7-$N_3$ (6.0 mg, 44%) as a white powder. The overall yield is reported on the reaction scheme.

Compound 7-$N_3$ (12). TLC (Ethyl acetate:Hexanes, 30:70 v/v): Rf=0.56; $^1H$ NMR (400 MHz, $CDCl_3$): δ 4.81 (d, J=38.4 Hz, 2H), 3.87 (s, 1H), 3.20-3.13 (m, 1H), 2.63-2.45 (m, 2H), 2.37 (q, J=10.4 Hz, 1H), 2.06-1.62 (m, 9H), 1.53-1.14 (m, 14H), 1.04-0.90 (m, 7H), 0.69-0.65 (m, 3H); $^{13}C$ NMR (125 MHz, DMSO-$d_6$): δ 209.29 (d, J=15.0 Hz), 87.90 (d, J=178.8 Hz), 69.15, 63.79, 58.48, 53.07, 45.04, 44.50, 43.56, 38.15, 38.11, 37.90, 37.80, 37.58, 36.88, 35.36, 31.46, 30.83, 29.57, 26.21, 25.74, 23.35, 21.44, 14.80 (one carbon signal may overlap with DMSO); HRMS (m/z): $[M+Na]^+$ calcd. for $C_{25}H_{40}FN_3O_2$, 456.3002; found, 456.2985.

Scheme 8. Synthesis of gut-restricted 7.

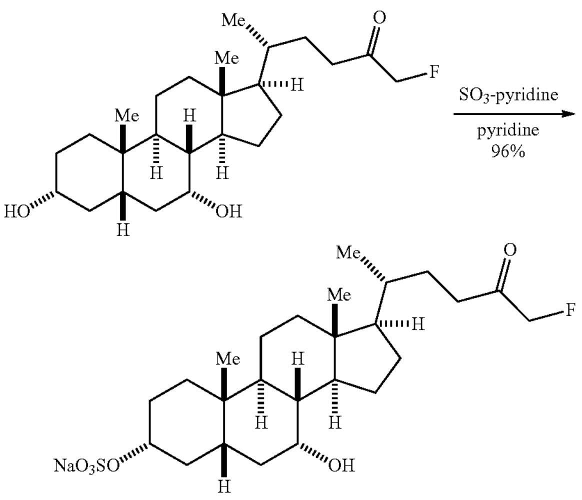

Gut restricted 7 (GR-7)
(i.e., Compound 13)

To compound 7 (60.0 mg, 0.15 mmol) dissolved in 4 mL pyridine, $SO_3$.pyridine (70.1 g, 0.44 mmol) was added and the resulting solution was stirred at rt for 18 h. The reaction mixture was concentrated on a rotovap. The resulting slurry was resuspended in 10:1 dichloromethane:methanol (10 mL) and washed with 10 mL saturated solution of sodium bicarbonate. The organic layer was separated and the aqueous layer was extracted with 10:1 dichloromethane:methanol (10 mL). The combined organic layer was re-subjected to the above extraction process. The obtained organic layer was dried over sodium sulfate, filtered and concentrated. The crude compound was then purified by silica gel chromatography (80% dichloromethane/20% methanol) to provide pure GR-7 (69.0 mg, 96%) as a white powder.

GR-7 (compound 13). TLC (Dichloromethane:Methanol, 80:20 v/v): Rf=0.39; $^1$H NMR (400 MHz, $CD_3OD$): δ 4.91 (d, J=47.6 Hz, 2H), 4.17-4.10 (m, 1H), 3.78 (d, J=1.2 Hz, 1H), 2.79 (br s, 0.4H), 2.59-2.37 (m, 3H), 2.00-1.70 (m, 9H), 1.56-0.93 (m, 20H), 0.69 (s, 3H); $^{13}$C NMR (100 MHz, $CD_3OD$): δ 207.69 (d, J=16.9 Hz), 84.50 (d, J=181.0 Hz), 79.30, 67.56, 55.74, 50.06, 42.22, 41.85, 39.56, 39.31, 36.32, 35.24, 35.03, 34.71, 34.38, 34.01, 32.57, 28.57, 27.776, 27.64, 23.18, 21.84, 20.35, 17.48, 10.70; HRMS (m/z): $[M-H]^-$ calcd. for $C_{25}H_{40}FO_6S$, 487.2535; found, 487.2532.

REFERENCES (1) Frank, D. N.; St Amand, A. L.; Feldman, R. A.; Boedeker, E. C.; Harpaz, N.; Pace, N. R. Molecular-Phylogenetic Characterization of Microbial Community Imbalances in Human Inflammatory Bowel Diseases. PNAS 2007, 104 (34), 13780-13785.

(2) Moore, W. E.; Moore, L. H. Intestinal Floras of Populations That Have a High Risk of Colon Cancer. Appl. Environ. Microbiol. 1995, 61 (9), 3202-3207.

(3) Sandler, R. H.; Finegold, S. M.; Bolte, E. R.; Buchanan, C. P.; Maxwell, A. P.; Väisänen, M.-L.; Nelson, M. N.; Wexler, H. M. Short-Term Benefit From Oral Vancomycin Treatment of Regressive-Onset Autism. Journal of Child Neurology 2016, 15 (7), 429-435.

(4) Turnbaugh, P. J.; Ley, R. E.; Mahowald, M. A.; Magrini, V.; Mardis, E. R.; Gordon, J. I. An Obesity-Associated Gut Microbiome with Increased Capacity for Energy Harvest. Nature 2006, 444 (7122), 1027-1031.

(5) Ridaura, V. K.; Faith, J. J.; Rey, F. E.; Cheng, J.; Duncan, A. E.; Kau, A. L.; Griffin, N. W.; Lombard, V.; Henrissat, B.; Bain, J. R.; et al. Gut Microbiota From Twins Discordant for Obesity Modulate Metabolism in Mice. Science 2013, 341 (6150), 1241214-1241214.

(6) Ivanov, I. I.; Atarashi, K.; Manel, N.; Brodie, E. L.; Shima, T.; Karaoz, U.; Wei, D.; Goldfarb, K. C.; Santee, C. A.; Lynch, S. V.; et al. Induction of Intestinal Th17 Cells by Segmented Filamentous Bacteria. Cell 2009, 139 (3), 485-498.

(7) Atarashi, K.; Tanoue, T.; Oshima, K.; Suda, W.; Nagano, Y.; Nishikawa, H.; Fukuda, S.; Saito, T.; Narushima, S.; Hase, K.; et al. Treg Induction by a Rationally Selected Mixture of Clostridia Strains From the Human Microbiota. Nature 2013, 500 (7461), 232-236.

(8) Sampson, T. R.; Debelius, J. W.; Thron, T.; Janssen, S.; Shastri, G. G.; Ilhan, Z. E.; Challis, C.; Schretter, C. E.; Rocha, S.; Gradinaru, V.; et al. Gut Microbiota Regulate Motor Deficits and Neuroinflammation in a Model of Parkinson's Disease. Cell 2016, 167 (6), 1469-1480.e12.

(9) Backhed, F.; Manchester, J. K.; Semenkovich, C. F.; Gordon, J. I. Mechanisms Underlying the Resistance to Diet-Induced Obesity in Germ-Free Mice. PNAS 2007, 104 (3), 979-984.

(10) Spiljar, M.; Merkler, D.; Trajkovski, M. The Immune System Bridges the Gut Microbiota with Systemic Energy Homeostasis: Focus on TLRs, Mucosal Barrier, and SCFAs. Front Immunol 2017, 8, 1353.

(11) Thaiss, C. A.; Zmora, N.; Levy, M.; Elinav, E. The Microbiome and Innate Immunity. Nature 2016, 535 (7610), 65-74.

(12) Diaz Heijtz, R.; Wang, S.; Anuar, F.; Qian, Y.; Björkholm, B.; Samuelsson, A.; Hibberd, M. L.; Forssberg, H.; Pettersson, S. Normal Gut Microbiota Modulates Brain Development and Behavior. Proc. Natl. Acad. Sci. U.S.A. 2011, 108 (7), 3047-3052.

(13) Wallace, B. D.; Wang, H.; Lane, K. T.; Scott, J. E.; Orans, J.; Koo, J. S.; Venkatesh, M.; Jobin, C.; Yeh, L.-A.; Mani, S.; et al. Alleviating Cancer Drug Toxicity by Inhibiting a Bacterial Enzyme. Science 2010, 330 (6005), 831-835.

(14) Roberts, A. B.; Gu, X.; Buffa, J. A.; Hurd, A. G.; Wang, Z.; Zhu, W.; Gupta, N.; Skye, S. M.; Cody, D. B.; Levison, B. S.; et al. Development of a Gut Microbe-Targeted Nonlethal Therapeutic to Inhibit Thrombosis Potential. Nat. Med. 2018, 24 (9), 1407-1417.

(15) Donia, M. S.; Fischbach, M. A. HUMAN MICROBIOTA. Small Molecules From the Human Microbiota. Science 2015, 349 (6246), 1254766-1254766.

(16) Ridlon, J. M.; Kang, D.-J.; Hylemon, P. B. Bile Salt Biotransformations by Human Intestinal Bacteria. J. Lipid Res. 2006, 47 (2), 241-259.

(17) Hamilton, J. P.; Xie, G.; Raufman, J.-P.; Hogan, S.; Griffin, T. L.; Packard, C. A.; Chatfield, D. A.; Hagey, L. R.; Steinbach, J. H.; Hofmann, A. F. Human Cecal Bile Acids: Concentration and Spectrum. Am. J. Physiol. Gastrointest. Liver Physiol. 2007, 293 (1), G256-G263.

(18) Fiorucci, S.; Distrutti, E. Bile Acid-Activated Receptors, Intestinal Microbiota, and the Treatment of Metabolic Disorders. Trends Mol Med 2015, 21 (11), 702-714.

(19) Katsuma, S.; Hirasawa, A.; Tsujimoto, G. Bile Acids Promote Glucagon-Like Peptide-1 Secretion Through TGR5 in a Murine Enteroendocrine Cell Line STC-1. Biochem. Biophys. Res. Commun. 2005, 329 (1), 386-390.

(20) Makishima, M.; Lu, T. T.; Xie, W.; Whitfield, G. K.; Domoto, H.; Evans, R. M.; Haussler, M. R.; Mangelsdorf, D. J. Vitamin D Receptor as an Intestinal Bile Acid Sensor. Science 2002, 296 (5571), 1313-1316.

(21) Staudinger, J. L.; Goodwin, B.; Jones, S. A.; Hawkins-Brown, D.; MacKenzie, K. I.; LaTour, A.; Liu, Y.; Klaassen, C. D.; Brown, K. K.; Reinhard, J.; et al. The Nuclear Receptor PXR Is a Lithocholic Acid Sensor That Protects Against Liver Toxicity. PNAS 2001, 98 (6), 3369-3374.

(22) Song, C.; Hiipakka, R. A.; Liao, S. Selective Activation of Liver X Receptor Alpha by 6alpha-Hydroxy Bile Acids and Analogs. Steroids 2000, 65 (8), 423-427.

(23) Modica, S.; Gadaleta, R. M.; Moschetta, A. Deciphering the Nuclear Bile Acid Receptor FXR Paradigm. Nucl Recept Signal 2010, 8, e005.

(24) Vavassori, P.; Mencarelli, A.; Renga, B.; Distrutti, E.; Fiorucci, S. The Bile Acid Receptor FXR Is a Modulator of Intestinal Innate Immunity. J. Immunol. 2009, 183 (10), 6251-6261.

(25) Pols, T. W. H.; Puchner, T.; Korkmaz, H. I.; Vos, M.; Soeters, M. R.; de Vries, C. J. M. Lithocholic Acid Controls Adaptive Immune Responses by Inhibition of Th1 Activation Through the Vitamin D Receptor. PLOS ONE 2017, 12 (5), e0176715.

(26) Begley, M.; Hill, C.; Gahan, C. G. M. Bile Salt Hydrolase Activity in Probiotics. Appl. Environ. Microbiol. 2006, 72 (3), 1729-1738.

(27) Chiang, J. Y. Recent Advances in Understanding Bile Acid Homeostasis. F1000Res 2017, 6, 2029.

(28) Sayin, S. I.; Wahlström, A.; Felin, J.; Jantti, S.; Marschall, H.-U.; Bamberg, K.; Angelin, B.; Hyötyläinen, T.; Orešič, M.; Backhed, F. Gut Microbiota Regulates Bile Acid Metabolism by Reducing the Levels of Tauro-Beta-Muricholic Acid, a Naturally Occurring FXR Antagonist. Cell Metab. 2013, 17 (2), 225-235.

(29) Song, Z.; Cai, Y.; Lao, X.; Wang, X.; Lin, X.; Cui, Y.; Kalavagunta, P. K.; Liao, J.; Jin, L.; Shang, J.; et al. Taxonomic Profiling and Populational Patterns of Bacterial Bile Salt Hydrolase (BSH) Genes Based on Worldwide Human Gut Microbiome. Microbiome 2019, 7 (1), 9.

(30) Strelow, J. M. A Perspective on the Kinetics of Covalent and Irreversible Inhibition. SLAS Discov 2017, 22 (1), 3-20.

(31) Rossocha, M.; Schultz-Heienbrok, R.; Moeller, von, H.; Coleman, J. P.; Saenger, W. Conjugated Bile Acid Hydrolase Is a Tetrameric N-Terminal Thiol Hydrolase with Specific Recognition of Its Cholyl but Not of Its Tauryl Product. Biochem. 2005, 44 (15), 5739-5748.

(32) Huijghebaert, S. M.; Hofmann, A. F. Influence of the Amino Acid Moiety on Deconjugation of Bile Acid Amidates by Cholylglycine Hydrolase or Human Fecal Cultures. J. Lipid Res. 1986, 27 (7), 742-752.

(33) Yao, L.; Seaton, S. C.; Ndousse-Fetter, S.; Adhikari, A. A.; DiBenedetto, N.; Mina, A. I.; Banks, A. S.; Bry, L.; Devlin, A. S. A Selective Gut Bacterial Bile Salt Hydrolase Alters Host Metabolism. eLife 2018, 7, 675.

(34) Liu, Q.; Sabnis, Y.; Zhao, Z.; Zhang, T.; Buhrlage, S. J.; Jones, L. H.; Gray, N. S. Developing Irreversible Inhibitors of the Protein Kinase Cysteinome. Chemistry & Biology 2013, 20 (2), 146-159.

(35) Gehringer, M.; Laufer, S. A. Emerging and Re-Emerging Warheads for Targeted Covalent Inhibitors: Applications in Medicinal Chemistry and Chemical Biology. Journal of Medicinal Chemistry 2019, acs.jmedchem.8b01153.

(36) Lewis, S. M.; Li, Y.; Catalano, M. J.; Laciak, A. R.; Singh, H.; Seiner, D. R.; Reilly, T. J.; Tanner, J. J.; Gates, K. S. Inactivation of Protein Tyrosine Phosphatases by Dietary Isothiocyanates. Bioorganic & Medicinal Chemistry Letters 2015, 25 (20), 4549-4552.

(37) Wilson, A. J.; Kerns, J. K.; Callahan, J. F.; Moody, C. J. Keap Calm, and Carry on Covalently. Journal of Medicinal Chemistry 2013, 56 (19), 7463-7476.

(38) Cross, J. V.; Foss, F. W.; Rady, J. M.; Macdonald, T. L.; Templeton, D. J. The Isothiocyanate Class of Bioactive Nutrients Covalently Inhibit the MEKK1 Protein Kinase. BMC Cancer 2007, 7 (1), 183.

(39) Serafimova, I. M.; Pufall, M. A.; Krishnan, S.; Duda, K.; Cohen, M. S.; Maglathlin, R. L.; McFarland, J. M.; Miller, R. M.; Frödin, M.; Taunton, J. Reversible Targeting of Noncatalytic Cysteines with Chemically Tuned Electrophiles. Nature Chemical Biology 2012, 8 (5), 471-476.

(40) Mi, L.; Xiao, Z.; Hood, B. L.; Dakshanamurthy, S.; Wang, X.; Govind, S.; Conrads, T. P.; Veenstra, T. D.; Chung, F.-L. Covalent Binding to Tubulin by Isothiocyanates. a Mechanism of Cell Growth Arrest and Apoptosis. J. Biol. Chem. 2008, 283 (32), 22136-22146.

(41) Henise, J. C.; Taunton, J. Irreversible Nek2 Kinase Inhibitors with Cellular Activity. Journal of Medicinal Chemistry 2011, 54 (12), 4133-4146.

(42) Xie, T.; Lim, S. M.; Westover, K. D.; Dodge, M. E.; Ercan, D.; Ficarro, S. B.; Udayakumar, D.; Gurbani, D.; Tae, H. S.; Riddle, S. M.; et al. Pharmacological Targeting of the Pseudokinase Her3. Nature Chemical Biology 2014, 10 (12), 1006-1012.

(43) Quintás-Cardama, A.; Kantarjian, H.; Cortes, J.; Verstovsek, S. Janus Kinase Inhibitors for the Treatment of Myeloproliferative Neoplasias and Beyond. Nature Reviews Drug Discovery 2011, 10 (2), 127-140.

(44) Gehringer, M.; Forster, M.; Laufer, S. A. Solution-Phase Parallel Synthesis of Ruxolitinib-Derived Janus Kinase Inhibitors via Copper-Catalyzed Azide-Alkyne Cycloaddition. ACS Comb Sci 2015, 17 (1), 5-10.

(45) Cohen, M. S.; Zhang, C.; Shokat, K. M.; Taunton, J. Structural Bioinformatics-Based Design of Selective, Irreversible Kinase Inhibitors. Science 2005, 308 (5726), 1318-1321.

(46) Yang, W.; Guastella, J.; Huang, J.-C.; Wang, Y.; Zhang, L.; Xue, D.; Tran, M.; Woodward, R.; Kasibhatla, S.; Tseng, B.; et al. MX1013, a Dipeptide Caspase Inhibitor with Potent in Vivo Antiapoptotic Activity. Br. J. Pharmacol. 2003, 140 (2), 402-412.

(47) Angliker, H.; Wikstrom, P.; Rauber, P.; Shaw, E. The Synthesis of Lysylfluoromethanes and Their Properties as Inhibitors of Trypsin, Plasmin and Cathepsin B. Biochem. J. 1987, 241 (3), 871-875.

(48) Garland, M.; Babin, B. M.; Miyashita, S.-I.; Loscher, S.; Shen, Y.; Dong, M.; Bogyo, M. Covalent Modifiers of Botulinum Neurotoxin Counteract Toxin Persistence. ACS Chem. Biol. 2019, 14 (1), 76-87.

(49) Miller, R. M.; Taunton, J. Targeting Protein Kinases with Selective and Semipromiscuous Covalent Inhibitors. Meth. Enzymol. 2014, 548, 93-116.

(50) Lebel, H.; Leogane, O. Boc-Protected Amines via a Mild and Efficient One-Pot Curtius Rearrangement. Org. Lett. 2005, 7 (19), 4107-4110.

(51) Palmer, J. T.; Inc, P. Process for Forming a Fluoromethyl Ketone. 1994.

(52) Dong, Z.; Lee, B. H. Bile Salt Hydrolases: Structure and Function, Substrate Preference, and Inhibitor Development. Protein Sci. 2018, 27 (10), 1742-1754.
(53) Wang, Z.; Zeng, X.; Mo, Y.; Smith, K.; Guo, Y.; Lin, J. Identification and Characterization of a Bile Salt Hydrolase From *Lactobacillus Salivarius* for Development of Novel Alternatives to Antibiotic Growth Promoters. Appl. Environ. Microbiol. 2012, 78 (24), 8795-8802.
(54) Tanaka, H.; Hashiba, H.; Kok, J.; Mierau, I. Bile Salt Hydrolase of *Bifidobacterium Longum*-Biochemical and Genetic Characterization. Appl. Environ. Microbiol. 2000, 66 (6), 2502-2512.
(55) Chand, D.; Panigrahi, P.; Varshney, N.; Ramasamy, S.; Suresh, C. G. Structure and Function of a Highly Active Bile Salt Hydrolase (BSH) From *Enterococcus Faecalis* and Post-Translational Processing of BSH Enzymes. Biochim Biophys Acta Proteins Proteom 2018, 1866 (4), 507-518.
(56) Stellwag, E. J.; Hylemon, P. B. Purification and Characterization of Bile Salt Hydrolase From *Bacteroides Fragilis* Subsp. *Fragilis*. Biochimica et Biophysica Acta (BBA)—Enzymology 1976, 452 (1), 165-176.
(57) Kawamoto, K.; Horibe, I.; Uchida, K. Purification and Characterization of a New Hydrolase for Conjugated Bile Acids, Chenodeoxycholyltaurine Hydrolase, From *Bacteroides* Vulgatus. J. Biochem. 1989, 106 (6), 1049-1053.
(58) Coleman, J. P.; Hudson, L. L. Cloning and Characterization of a Conjugated Bile Acid Hydrolase Gene From *Clostridium Perfringens*. Appl. Environ. Microbiol. 1995, 61 (7), 2514-2520.
(59) Smith, K.; Zeng, X.; Lin, J. Discovery of Bile Salt Hydrolase Inhibitors Using an Efficient High-Throughput Screening System. PLOS ONE 2014, 9 (1), e85344.
(60) Hofmann, A. F. The Function of Bile Salts in Fat Absorption. the Solvent Properties of Dilute Micellar Solutions of Conjugated Bile Acids. Biochem. J. 1963, 89 (1), 57-68.
(61) Kraal, L.; Abubucker, S.; Kota, K.; Fischbach, M. A.; Mitreva, M. The Prevalence of Species and Strains in the Human Microbiome: a Resource for Experimental Efforts. PLOS ONE 2014, 9 (5), e97279.
(62) Li, F.; Jiang, C.; Krausz, K. W.; Li, Y.; Albert, I.; Hao, H.; Fabre, K. M.; Mitchell, J. B.; Patterson, A. D.; Gonzalez, F. J. Microbiome Remodelling Leads to Inhibition of Intestinal Farnesoid X Receptor Signalling and Decreased Obesity. Nat Commun 2013, 4, 2384.
(63) Joyce, S. A.; MacSharry, J.; Casey, P. G.; Kinsella, M.; Murphy, E. F.; Shanahan, F.; Hill, C.; Gahan, C. G. M. Regulation of Host Weight Gain and Lipid Metabolism by Bacterial Bile Acid Modification in the Gut. Proc. Natl. Acad. Sci. U.S.A. 2014, 111 (20), 7421-7426.
(64) Ma, C.; Han, M.; Heinrich, B.; Fu, Q.; Zhang, Q.; Sandhu, M.; Agdashian, D.; Terabe, M.; Berzofsky, J. A.; Fako, V.; et al. Gut Microbiome-Mediated Bile Acid Metabolism Regulates Liver Cancer via NKT Cells. Science 2018, 360 (6391), eaan5931.
(65) Xie, C.; Jiang, C.; Shi, J.; Gao, X.; Sun, D.; Sun, L.; Wang, T.; Takahashi, S.; Anitha, M.; Krausz, K. W.; et al. An Intestinal Farnesoid X Receptor-Ceramide Signaling Axis Modulates Hepatic Gluconeogenesis in Mice. Diabetes 2017, 66 (3), 613-626.
(66) Sun, L.; Xie, C.; Wang, G.; Wu, Y.; Wu, Q.; Wang, X.; Liu, J.; Deng, Y.; Xia, J.; Chen, B.; et al. Gut Microbiota and Intestinal FXR Mediate the Clinical Benefits of Metformin. Nat. Med. 2018, 24 (12), 1919-1929.

EQUIVALENTS AND SCOPE

All patents and other publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents are based on the information available to the applicants and do not constitute any admission as to the correctness of the dates or contents of these documents.

The singular terms "a," "an," and "the" include plural referents unless context clearly indicates otherwise. Similarly, the word "or" is intended to include "and" unless the context clearly indicates otherwise. Although methods and materials similar or equivalent to those provided herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

Unless otherwise explained, all technical and scientific terms used herein have the same meaning as commonly understood by one of ordinary skill in the art to which this disclosure belongs.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

FORMULA (I)

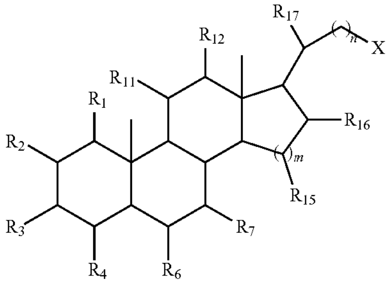

or a pharmaceutically acceptable salt thereof, wherein:

n is 1,2, 3, 4, 5, 6, 7, 8, 9, or 10;

m is 1;

X is —C(O)$CH_2$F;

$R_1$, $R_2$, $R_4$, $R_6$, $R_{11}$, $R_{15}$, and $R_{16}$ are H;

$R_{17}$ is unsubstituted $C_1$-$C_6$ alkyl;

$R_3$, $R_7$, and $R_{12}$ are each independently H, substituted or unsubstituted alkyl, substituted or unsubstituted heteroalkyl, —$OR_{18}$, —$N(R_{18})_2$, —$SR_{18}$, halogen, —CN, —$CO_2H$, —$CO_2R_{18}$, —$NO_2$, —$ONO_2$, —$SO_3H$, —$OSO_3H$, —$NR_{18}SO_3H$, —$PO_3H_2$, —$OSO_2R_{18}$, —$SO_2N(R_{18})_2$, —$OSO_2N(R_{18})_2$, —$NR_{18}SO_2R_{18}$, or —$SO_2N(R_{18})_2$; and each $R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

2. The compound of claim 1, or a pharmaceutically acceptable salt thereof, wherein $R_3$ is —$OR_{18}$ or —$OSO_3H$; $R_7$ is —$OR_{18}$; and $R_{12}$ is H or —$OR_{18}$.

3. The compound of claim 1, or a pharmaceutically acceptable salt thereof, wherein the compound is of Formula (XVI):

FORMULA (XVI)

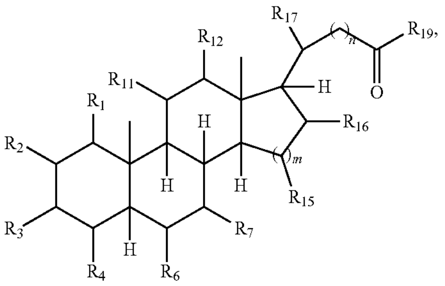

wherein $R_{19}$ is —$CH_2$F.

4. The compound of claim 1, wherein the compound is of the formula:

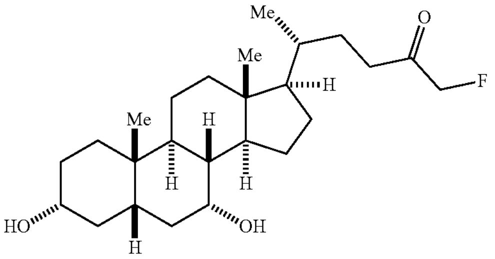

or

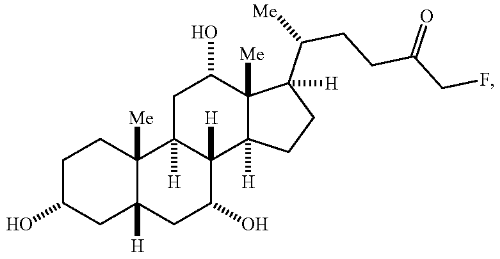

or a pharmaceutically acceptable salt thereof.

5. The compound of claim 1, wherein the compound is of the Formula (I-e'):

(I-e')

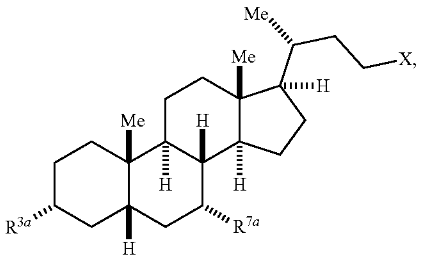

or a pharmaceutically acceptable salt thereof, wherein:

$R^{3a}$ and $R^{7a}$ are independently selected from the group consisting of —$OR_{18}$, —$SO_3H$, —$OSO_3H$, —$PO_3H_2$, —$OPO_3H_2$, —$OSO_2R_{18}$, and —$SO_2N(R_{18})_2$, wherein each $R_{18}$ is independently H or substituted or unsubstituted alkyl.

6. The compound of claim 5, wherein the compound is of the formula:

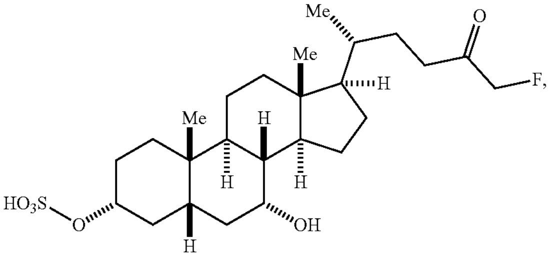

or a pharmaceutically acceptable salt thereof.

7. The compound of claim 1, wherein the compound is of the Formula (I-f'):

(I-f')

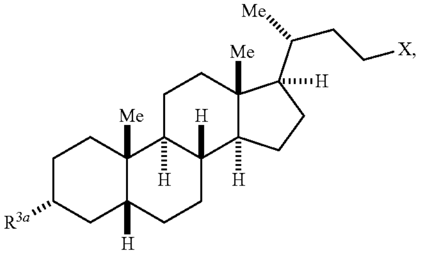

or a pharmaceutically acceptable salt thereof, wherein:

$R^{3a}$ is selected from the group consisting of —$OR_{18}$, —$SO_3H$, —$OSO_3H$, —$PO_3H_2$, —$OPO_3H_2$, —$OSO_2R_{18}$, and —$SO_2N(R_{18})_2$, wherein each $R_{18}$ is independently H or substituted or unsubstituted alkyl.

8. The compound of claim 7, wherein the compound is of the Formula (I-f'') or Formula (I-f'''):

(I-f'')

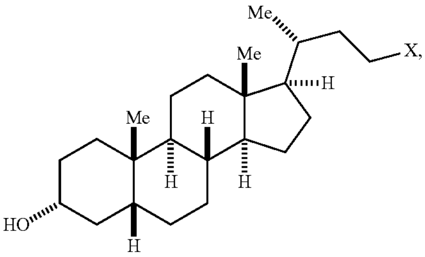

or

-continued (I-f''')

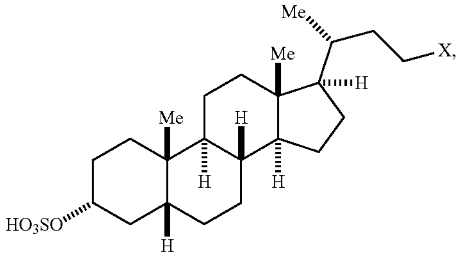

or a pharmaceutically acceptable salt thereof.

9. A pharmaceutical composition comprising a compound of claim 1, or a pharmaceutically acceptable salt thereof, and a pharmaceutically acceptable carrier or excipient.

10. The pharmaceutical composition of claim 9, wherein the carrier or excipient restricts delivery of the compound to gastrointestinal tract.

11. A method for inhibiting a bile salt hydrolase (BSH), the method comprising contacting a BSH with a compound of claim 1, or a pharmaceutically acceptable salt thereof; or a pharmaceutical composition thereof.

12. A method of modulating bile acids in a subject, the method comprising: administering to the subject in need thereof a therapeutically effective amount of a compound of claim 1, or a pharmaceutically acceptable salt thereof; or a pharmaceutical composition thereof.

13. The method of claim 12, wherein the subject is at risk of having or has cancer, a gastrointestinal disease, obesity, or an inflammatory disease.

14. The compound of claim 1, or a pharmaceutically acceptable salt thereof, wherein the compound is of Formula (XVII):

FORMULA (XVII)

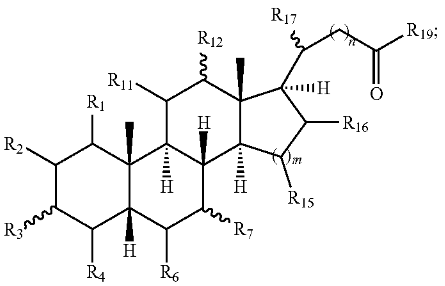

wherein $R_{19}$ is —$CH_2F$.

15. The compound of claim 1, or a pharmaceutically acceptable salt thereof, wherein the compound is of Formula (XVIII):
FORMULA (XVIII)
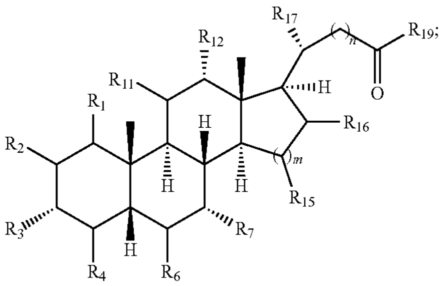
wherein $R_{19}$ is —$CH_2F$.
* * * * *